US006991775B2

(12) United States Patent
Koerner et al.

(10) Patent No.: US 6,991,775 B2
(45) Date of Patent: Jan. 31, 2006

(54) PEPTIDE-BASED MULTIMERIC TARGETED CONTRAST AGENTS

(75) Inventors: Steffi K. Koerner, Somerville, MA (US); Andrew Kolodziej, Winchester, MA (US); Thomas J. McMurry, Winchester, MA (US); Shrikumar Nair, Lexington, MA (US); Alexander L. Nivorozhkin, West Roxbury, MA (US); Wei-Chuan Sun, Acton, MA (US); Xifang Wang, Belmont, MA (US)

(73) Assignee: Epix Medical, Inc., Cambridge, MA (US)

( * ) Notice: Subject to any disclaimer, the term of this patent is extended or adjusted under 35 U.S.C. 154(b) by 0 days.

(21) Appl. No.: 10/209,172

(22) Filed: Jul. 30, 2002

(65) Prior Publication Data

US 2003/0216320 A1 Nov. 20, 2003

Related U.S. Application Data

(60) Provisional application No. 60/308,721, filed on Jul. 30, 2001.

(51) Int. Cl.
  A61K 51/00 (2006.01)
  A61M 36/14 (2006.01)

(52) U.S. Cl. .................. 424/1.69; 424/1.11; 424/1.65; 424/1.37; 530/330

(58) Field of Classification Search ............... 424/1.11, 424/1.65, 1.69, 1.37, 9.3, 9.4, 9.5, 9.6, 9.7, 424/9.8; 530/300, 327, 328, 329, 330; 514/2; 536/23.1; 435/7.1
See application file for complete search history.

(56) References Cited

U.S. PATENT DOCUMENTS

| | | | |
|---|---|---|---|
| 4,622,420 A | 11/1986 | Meares et al. | |
| 4,659,839 A | 4/1987 | Nicolotti et al. | |
| 4,678,667 A | 7/1987 | Meares et al. | |
| 4,831,175 A | 5/1989 | Gansow et al. | |
| 4,880,008 A | 11/1989 | Lauffer | |
| 4,897,255 A | 1/1990 | Fritzberg et al. | |
| 5,099,069 A | 3/1992 | Gansow et al. | |
| 5,223,409 A | 6/1993 | Ladner et al. | |
| 5,246,692 A | 9/1993 | Gansow et al. | |
| 5,492,892 A | * 2/1996 | Andersen et al. | ............. 514/13 |
| 5,637,759 A | 6/1997 | Hearst et al. | |
| 5,641,878 A | 6/1997 | Dandliker et al. | |
| 6,001,809 A | 12/1999 | Thorsett et al. | |
| 6,207,858 B1 | 3/2001 | Chinn et al. | |
| 6,342,598 B1 | 1/2002 | Anelli et al. | |
| 6,517,814 B2 | 2/2003 | Liu | |
| 6,652,834 B2 | 11/2003 | Anelli et al. | |

FOREIGN PATENT DOCUMENTS

| | | |
|---|---|---|
| EP | 329 363 | 2/1989 |
| EP | 0 515 313 B1 | 8/2000 |
| WO | WO 93/17719 | 9/1993 |
| WO | WO 95/19187 | 7/1995 |
| WO | WO 96/01644 | 1/1996 |
| WO | WO 96/23524 | 8/1996 |
| WO | WO 96/23526 | 8/1996 |
| WO | WO 96/36361 | 11/1996 |
| WO | WO 97/13490 | 4/1997 |
| WO | WO 97/14804 | 4/1997 |
| WO | WO 98/45331 | 10/1998 |
| WO | WO 01/08712 | 2/2001 |
| WO | WO 01/09188 | 2/2001 |
| WO | WO01/30398 | 3/2001 |

OTHER PUBLICATIONS

Caravan et al., "Gadolinium(III) Chelates as MRI Contrast Agents: Structure, Dynamics, and Applications," *Chem. Rev.*, 1999, 99:2293–2352.

Lauffer, "Paramagnetic Metal Complexes as Water Proton Relaxation Agents for NMR Imaging: Theory and Design," *Chem. Rev.*, 1987, 87:901–927.

Alavi et al., "Radiolabeled Antifibrin Antibody in the Detection of Venous Thrombosis: Preliminary Results," *Radiology*, 1990, 175:79–85.

Alexander et al., "Intracranial Black–Blood MR Angiography with High–Resolution 3D Fast Spin Echo," *Machine Resonance in Medicine*, 1998, 40(2):298–310.

Bautovich et al., "Detection of Deep Venous Thrombi and Pulmonary Embolus with Technetium–99m–DD–3B6/22 Anti–fibrin Monoclonal Antibody Fab' Fragment," *J. Nucl. Med.*, 1994, 35:195–202.

Edelman et al., "Extracranial Carotid Arteries: Evaluation with "Black Blood" MR Angiography," *Radiology*, 1990, 177(1):45–50.

Harker et al., "Role of Platelets and Thrombosis in Mechanisms of Acute Occlusion and Restenosis After Angioplasty," *Am. J. Cardiology*, 1987, 60:20B–28B.

Hermans et al., "Fibrin: Structure and Interactions," *Semin. Thromb. Hemost.*, 1982, 8:11–24.

Kakkar et al., "I–Labelled Fibrinogen Test Adapted for Routine Screening for Deep–Vein Thrombosis," *Lancet*, 1970, 1:540–542.

Knight et al., "Fragment $E_1$ Labeled with I–123 in the Detection of Venous Thrombosis," *Radiology*, 1985, 156:509–514.

Lanza et al., "High–Frequency Ultrasonic Detections of Thrombi and A Targeted Contrast System," *Ultrasound in Med. & Bio.*, 1997, 23(6):863–870.

Moskowitz and Budzynski, "The (DD)E Complex is Maintained by a Composite Fibrin Polymerization Site," *Biochemistry*, 1994, 33:12937–12944.

(Continued)

*Primary Examiner*—Dameron L. Jones
(74) *Attorney, Agent, or Firm*—Fish & Richardson P.C.P.A.

(57) ABSTRACT

Peptides and peptide-targeted multimeric contrast agents are described, as well as methods of making and using the contrast agents.

17 Claims, 9 Drawing Sheets

OTHER PUBLICATIONS

Muto et al., "Initial Clinical Experience with Tc–99m P280, a Synthetic Peptide Useful for Imaging Thrombi and Pulmonary Emboli," *Radiology*, 1993, 189(suppl.): 303.

Nielson et al., "Cysteine Residue Periodicity is a Conserved Structural Feature of Variable Surface Proteins from *Paramecium tetraurelia*," *J. Mol. Biol.*, 1991, 222:835–841.

Olexa et al., "Structure of Fragment E Species from Human Cross–Linked Fibrin," *Biochemistry*, 1981, 20:6139–6145.

Palabrica et al., "Thrombus imaging in a primate model with antibodies specific for an external membrane protein of activated platelets," *Proc. Natl. Acad. Sci. USA*, 1989, 86:1036–1040.

Redenbach et al., "A set of ordered cosmids and a detailed genetic and physical map for the 8 Mb *Streptomyces coelicolor* A3(2) chromosome," *Mol. Microbiol.*, 1996, 21:77–96.

Rosebrough et al., "Thrombus Imaging: A Comparison of Radiolabeled GC4 and T2G1s Fibrin–Specific Monoclonal Antibodies," *J. Nucl. Med.*, 1990, 31:1048–1054.

Spraggon et al., "Crystal structures of fragment D from human fibrinogen and its crosslinked counterpart from fibrin," *Nature*, 1997, 389:455–462.

Thakur et al., "Indium–111 Labeled Platelets: Studies on Preparation and Evaluation of In Vitro and In Vivo Functions," *Throm. Res.*, 1976, 9:345–357.

GenBank Accession No. T05787.

GenBank Accession No. T34584.

Restriction Requirement mailed Jul. 22, 2004 in co–pending U.S. Appl. No. 10/209,183.

Preliminary Amendment and Response to Restriction Requirement mailed Feb. 23, 2004 in co–pending U.S. Appl. No. 10/209,183.

Aime et al., "Synthesis, Characterization, and $1/T_1$ NMRD Profiles of Gadolinium(III) Complexes of Monoamide Derivatives of DOTA–like Ligands. X–ray Structure of the 10–[2–[[2–Hydroxy–1–(hydroxymethyl)ethyl]amino]–1–[(phenylmethoxy)methyl]–2–oxo–ethyl]–1, 4,7,10–tetraazacyclododecane–1,4,7–triacetic Acid–Gadolinium(III) Complex," *Inorg. Chem.*, 1992, 31:2422–2428.

Aime et al., "Multinuclear and Multifrequency NMR study of gadolinium(III) complexes with bis–amide derivatives of ethylenedioxydiethylene–dinitrilotetraacetic acid," *J. Chem. Soc. Dalton Trans.*, 2000, pp. 3435–3440.

Amedio Jr. et al., "A Practical Manufacturing Synthesis of 1–(R)–Hydroxymethyl–DPTA: An Important Intermediate in the Synthesis of MRI Contrast Agents," *Synthetic Communications*, 1999, 29(14):2377–2391.

Amedio Jr. et al., "Preparation of N,N–BIS[2–[N',N'–BBIS (Tert–Butoxycarbonyl) Methyl]–Amino]Ethyl–L–Aspartic Acid: An Intermediate in the Synthesis of MRI Contrast Agents," *Synthetic Communications*, 2000, 30(20):3755–3763.

Augustijns et al., "Peptidyl Dipeptidase A–Catalyzed Metabolism of Delta Sleep–Inducing Peptide in Bovine Brain Microvessel Endothelial Cells: A Cell Culture Model of the Blood Brain Barrier," *Biochem. Biophys. Res. Comm.*, 1995, 210(3):987–994.

Bakker et al., "In Vivo Application of [$^{111}$In–DTPA–D–PHE$^1$]–Octreotide for Detection of Somatostatin Receptor–Positive Tumors in Rats," *Life Sciences*, 1991, 49:1593–1601.

Bligh et al., "Neutral Gadolinium(III) Complexes of Bulky Octadenate dtpa Derivatives as Potential Contrast Agents for Magnetic Resonance Imaging," *Polyhedron*, 1995, 14(4)567–569.

Bulte et al., "Dysproium–DOTA–PAMAM Dendrimers as Macromolecular T2 Contrast Agents," *Invest. Radiol.*, 1998, 33(11):841–845.

Collen et al., "Thrombolysis with Human Extrinsic (Tissue–Type) Plasminogen Activator in Rabbits with Experimental Jugular Vein Thrombosis," *J. Clin. Invest.*, 1983, 71:368–376.

Deacon et al., "Degradation of Glucagon–Like Peptide–1 by Human Plasma in Vitro Yields an N–Terminally Truncated Peptide That Is a Major Endogenous Metabolite in Vivo," *J. Clin. Endocrinol.*, 1995, 80(3):952–957.

Kellar et al., "Magnetic Field Dependence of Solvent Proton Relaxation by Solute Dysprosium(III) Complexes," *Invest. Radiol.*, 1998, 33(11):835–840.

Kojima et al., "Bioimaging of Nitric Oxide with Fluorescent Indicators Based on the Rhodamine Chromophore," *Anal. Chem.*, 2001, 73:1967–1973.

Kolc, "Amino Acids and Peptides. LXXXIX. Synthesis of $_L$–4–Azalysine, $_D$–4–Azalysine, and $_L$–4–Analysine–[6–$^{14}$C]," *Coll. Czech. Chem. Commun.*, 1969, 34:630–634.

Konings et al., "Gadolinium Complexation by a New DTPA–Amide Ligand. Amide Oxygen Coordination," *Inorg. Chem.*, 1990, 29:1488–1491.

Krieter et al., "In Vivo Metabolism of Atrial Natriuretic Peptide: Identification of Plasma Metabolites and Enzymes Responsible for Their Generation," *J. Pharmacol. Exp. Ther.*, 1989, 249(2):411–417.

Liu et al., "Labeling a Hydrazino Nicotinamide–Modified Cyclic Iib/IIIa Receptor Antagonist with $^{99m}$Tc Using Aminocaroboxylates as Coligands," *Bioconjugate Chem.*, 1996, 7:63–71.

Martin et al., "Gadolinium(III) Di– and Tetrachelates Designed for in Vivo Noncovalent Complexation with Plasma Proteins: A Novel Molecular Design for Blood Pool MRI Contrast Enhancing Agents," *Bioconjugate Chem.*, 1995, 6:616–623.

Mühler and Hochlaus, "Metabolism of Dynorphin A 1–13 in Human Blood and Plasma," *Pharm. Res.*, 1995, 12(8):1165–1170.

Mühler et al., "Interspecies comparison of in vitro plasma degradation of dynorphin A 1–13," *Pharmazie*, 1996, 51(8):581–585.

Muller et al., "Physicochemical Characterization of MS–325, a New Gadolinium Complex, by Multinuclear Relaxometry," *Eur. J. Inorg. Chem.*, 1999, pp. 1949–1955.

Mühler et al., "Assessment of Complex Peptide Degradation Pathways via Structured Multicompartmental Modeling Approaches: The Metabolism of Dynorphin A1–13 and Related Fragments in Human Plasma," *J. Pharm. Sci.*, 1999, 88(9):938–944.

Murphey et al., "Metabolism of Bradykinin in Vivo in Humans: Identification of BK1–5 as a Stable Plasma Peptide Metabolite," *J. Pharmacol. Exp. Ther.*, 2000, 294:263–269.

Murru et al., "Luminescence Behaviour of Stable Europium and Terbium Complexes of Tetraaza Phosphinates: Efficient Through–space Energy Transfer from Phenyl to Terbium," *J. Chem. Soc. Chem. Commun.*, 1993, pp. 1116–1118.

Muto et al., "Detecting Deep Venous Thrombosis with Technetium–99m–Labeled Synthetic Peptide P280," *J. Nucl. Med.*, 1995, 36(8):1384–1391.

Oefner et al., "High–Resolution Liquid Chromatography of Fluorescent Dye–Labeled Nucleic Acids," *Analytical Biochem.,* 1994, 223:39–46.

Pearson et al., "Somatostatin Receptor–Binding Peptides Labeled with Technetium–99m: Chemistry and Initial Biological Studies," *J. Med. Chem.,* 1996, 39:1361–1371.

Powell et al. "Peptide Stability in Drug Development. II. Effect of Single Amino Acid Substitution and Glycosylation on Peptide Reactivity in Human Serum," *Pharm. Res.,* 1993, 10(9):1268–1273.

Powell et al., "Structural and Dynamic Parameters Obtained from $^{17}O$ NMR, EPR, and NMRD Studies of Monomeric and Dimeric $Gd^{3+}$ Complexes of Interest in Magnetic Resonance Imaging: An Integrated and Theoretically Self–Consistent Approach," *J. Am. Chem. Soc.,* 1996, 118:9333–9346.

Ramachandran et al., "New Multimeric Magnetic Resonance Imaging Agents," *Invest. Radiol.,* 1998, 33(11):779–797.

Reubi et al., "Unsulfated DTPA– and DOTA–CCK analogs as specific high–affinity ligands for CCK–B receptor–expressing human and rat tissues in vitro and in vivo," *Eur. J. Nucl. Med.,* 1998, 25(5):481–490.

Solomon et al., "Focal Infection Imaging Using an In–III Labeled Antagonist Chemotactic Peptide," *J. Nucl. Med.,* 1994, 35(5):45P, Abstract No. 172.

Stall et al., "Rearrangement and expression of endogenous immunoglobin genes occur in many murine B cells expressing transgenic membrane IgM," *Proc. Natl. Acad. Sci. USA,* 1988, 85:3546–3550.

Tóth et al., "The Role of Water Exchange in Attaining Maximum Relaxivities for Dendrimeric MRI Contrast Agents," *Chem. Eur. J.,* 1996, 2(12):1607–1615.

Tóth et al. "Tuning water–exchange rates on (carboxymethyl) iminobis–(ethylenenitrilo)tetraacetate(dtpa)–type gadolinium (III) complexes," *J. Chem. Soc., Dalton Trans.,* 1997, pp. 1587–1594.

Tóth et al., "Direct assessment of water exchange on a Gd(III) chelate bound to a protein," *J. Biol. Inorg. Chem.,* 1998, 3:606–613.

Uggeri et al., "Novel Contrast Agents for Magnetic Resonance Imaging. Synthesis and Characterization of the Ligand BOPTA and Its Ln(III) Complexes (Ln=Gd, La, Lu). X–ray Structure of Disodium (TPS–9–145337286–C–S)–[4–Carboxy–5,8,11–tris (carboxymethyl)–1–phenyl–2–oxa–5,8, 11–triazatridecan–13–oato(5–)]gadolinate (2–) in a Mixture with Its Enantiomer," *Inorg. Chem.,* 1995, 34:633–642.

Weinmann et al. "A New Lipophilic Gadolinium Chelate as a Tissue–Specific Contrast Medium for MRI," *Magn. Reson. Med.,* 1991, 22:233–237.

Wettergren et al. "Amidated and non–amidated glucagon–like peptide–1 (GLP–1): non–pancreatic effects (cephalic phase acid secretion) and stability in plasma in humans," *Reg. Peptides,* 998, 77:83–87.

Zhao et al., "Oxidation of Primary Alcohols to Carboxylic Acids with Sodium Chlorite Catalyzed by TEMPO and Bleach," *J. Org. Chem.,* 1999, 64:2564–2566.

\* cited by examiner

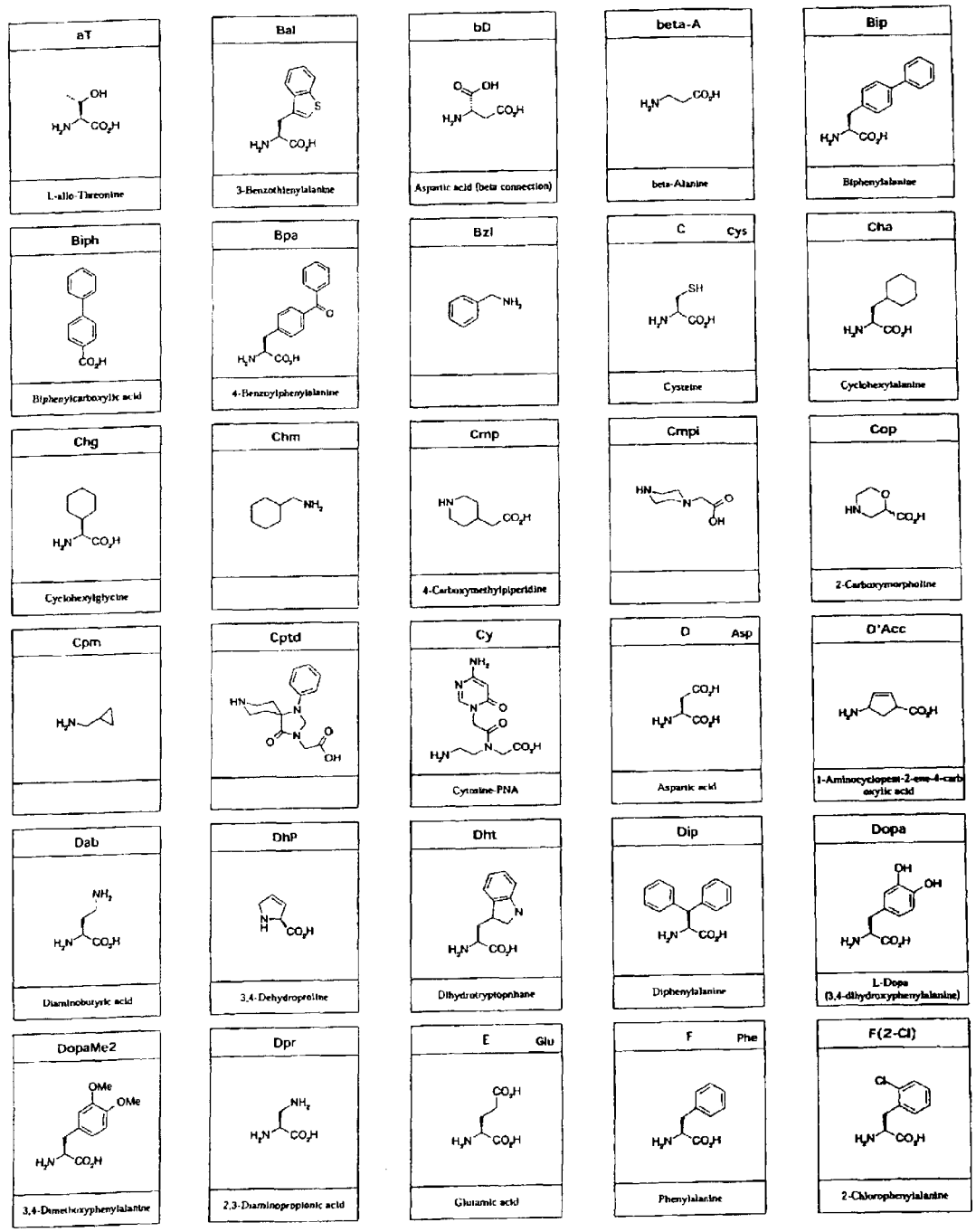

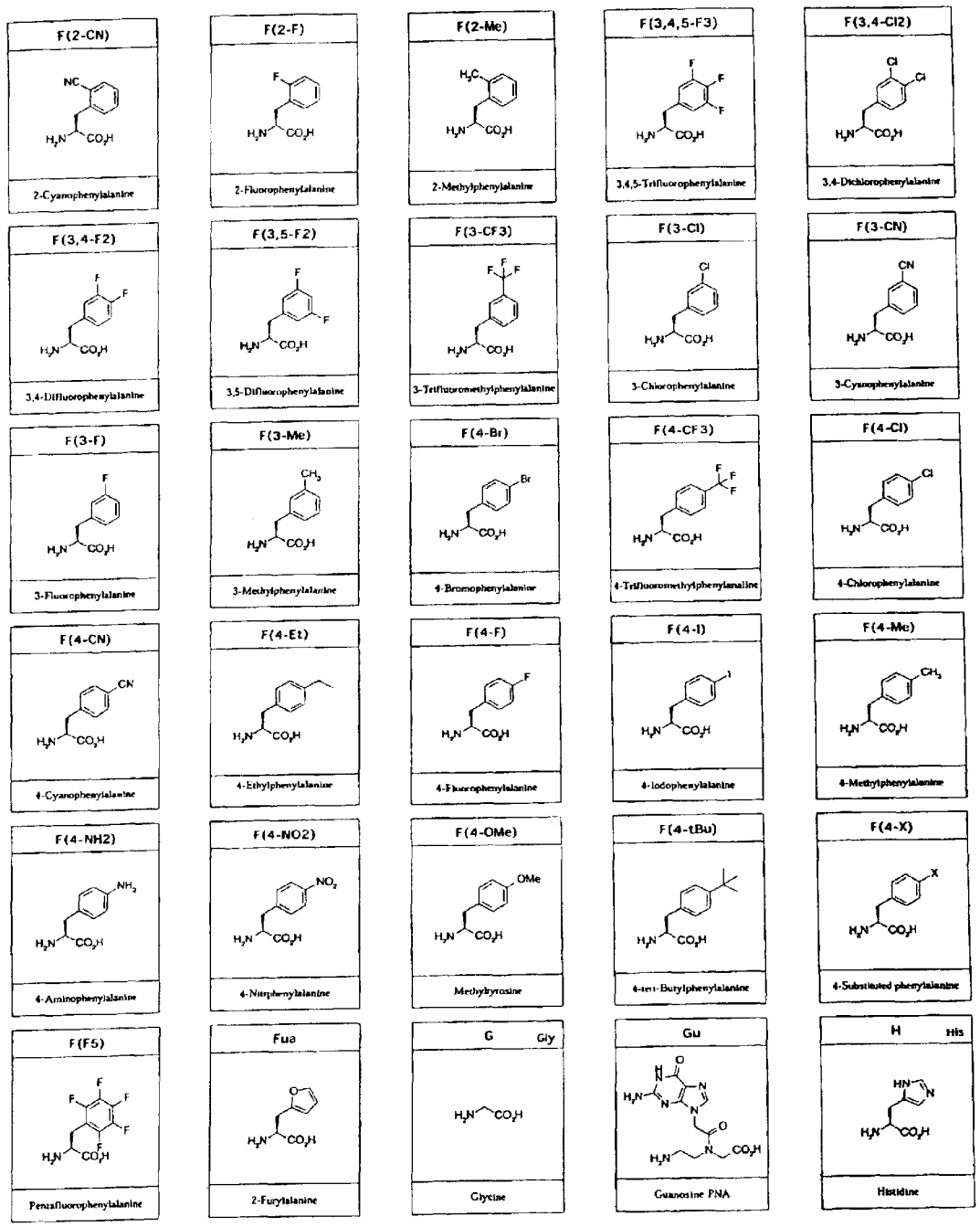

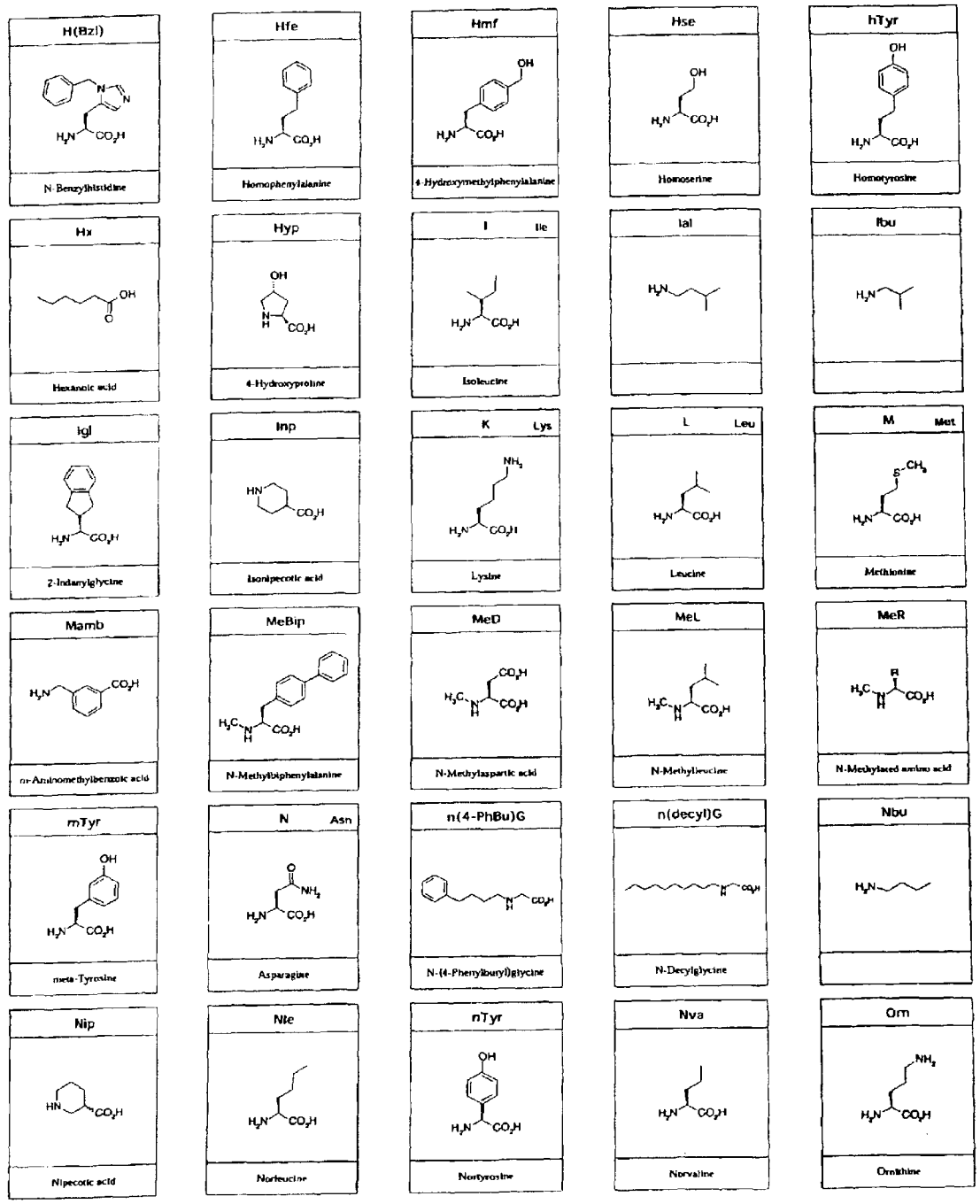

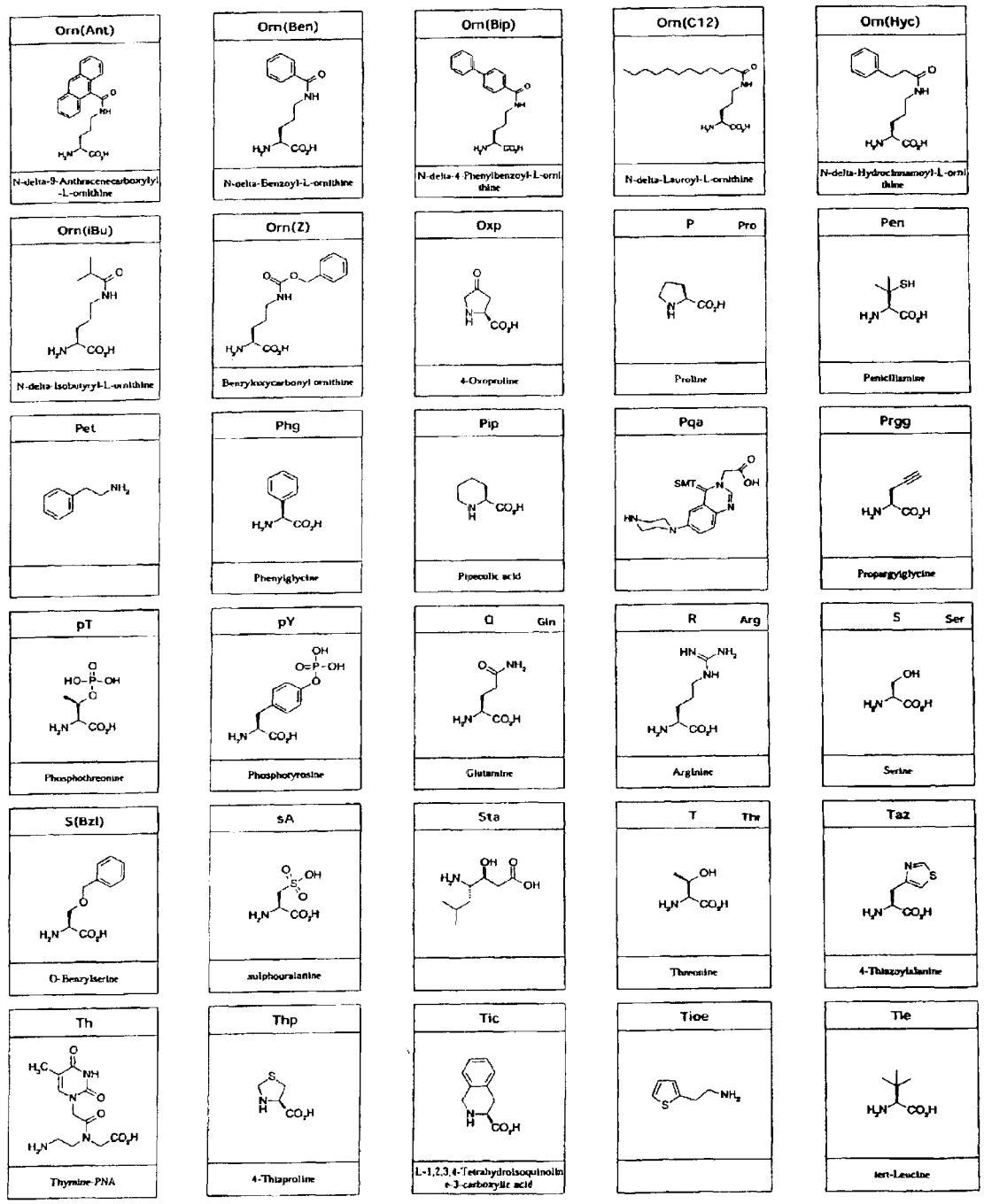

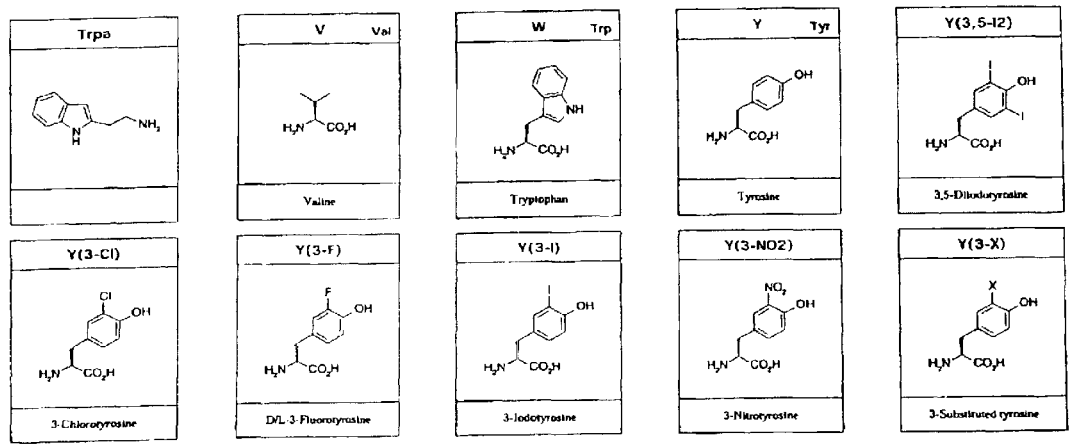

A

B

```
                           SEQUENCE LISTING

<160> NUMBER OF SEQ ID NOS: 27

<210> SEQ ID NO 1
<211> LENGTH: 4
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 1
<223> OTHER INFORMATION: Xaa = Pro or a non-natural derivative thereof
<220> FEATURE:
<221> NAME/KEY: VARIANT
<222> LOCATION: 2
<223> OTHER INFORMATION: Xaa = Tyr or a non-natural derivative thereof
<220> FEATURE:
<221> NAME/KEY: VARIANT
<222> LOCATION: 3
<223> OTHER INFORMATION: Xaa = Gly or Asp, or a non-natural derivative
      of Gly or Asp
<220> FEATURE:
<221> NAME/KEY: VARIANT
<222> LOCATION: 4
<223> OTHER INFORMATION: Xaa = Leu or a non-natural derivative thereof

<400> SEQUENCE: 1

Xaa Xaa Xaa Xaa
 1

<210> SEQ ID NO 2
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 1
<223> OTHER INFORMATION: Xaa = Trp, Tyr, Phe, Ser, nTyr, dW, dF,
      F(3/4*), Y(3*), or a non-natural derivative thereof
<220> FEATURE:
<221> NAME/KEY: VARIANT
<222> LOCATION: 2
<223> OTHER INFORMATION: Xaa = Glu, His, dGlu, Ser, or a non-natural
      derivative thereof
<220> FEATURE:
<221> NAME/KEY: VARIANT
<222> LOCATION: 4
<223> OTHER INFORMATION: Xaa = Pro or a non-natural derivative thereof
<220> FEATURE:
<221> NAME/KEY: VARIANT
<222> LOCATION: 5
<223> OTHER INFORMATION: Xaa = Tyr or a non-natural derivative thereof
<220> FEATURE:
<221> NAME/KEY: VARIANT
<222> LOCATION: 6
<223> OTHER INFORMATION: Xaa = Gly or Asp
<220> FEATURE:
<221> NAME/KEY: VARIANT
```

```
<222> LOCATION: 9
<223> OTHER INFORMATION: Xaa = His, Phe, Tyr, or Trp
<220> FEATURE:
<221> NAME/KEY: VARIANT
<222> LOCATION: 10
<223> OTHER INFORMATION: Xaa = Ile, Leu, Val, Asn, F(3/4*), or a
      non-natural derivative thereof
<220> FEATURE:
<221> NAME/KEY: VARIANT
<222> LOCATION: 11
<223> OTHER INFORMATION: Xaa = Asn, Gln, Ile, Leu, Val, or absent

<400> SEQUENCE: 2

Xaa Xaa Cys Xaa Xaa Xaa Leu Cys Xaa Xaa Xaa
 1               5                  10

<210> SEQ ID NO 3
<211> LENGTH: 6
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 2
<223> OTHER INFORMATION: Xaa = Pro or 4-hydroxyproline
<220> FEATURE:
<221> NAME/KEY: VARIANT
<222> LOCATION: 3
<223> OTHER INFORMATION: Xaa = Tyr or a non-natural derivative of
      tyrosine
<220> FEATURE:
<221> NAME/KEY: VARIANT
<222> LOCATION: 4
<223> OTHER INFORMATION: Xaa = Gly or Asp

<400> SEQUENCE: 3

Cys Xaa Xaa Xaa Leu Cys
 1               5

<210> SEQ ID NO 4
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 4

Trp Glu Cys Xaa Xaa Gly Leu Cys Trp Ile Gln
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine
```

```
<400> SEQUENCE: 5

Tyr Glu Cys Xaa Xaa Gly Leu Cys Tyr Ile Gln
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 6

Tyr Glu Cys Xaa Xaa Gly Leu Cys Trp Ile Gln
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 7

Trp Glu Cys Xaa Xaa Gly Leu Cys Tyr Ile Gln
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 8

Trp Glu Cys Xaa Xaa Asp Leu Cys Trp Ile Gln
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
```

```
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 9

Tyr Glu Cys Xaa Xaa Asp Leu Cys Tyr Ile Gln
 1               5                  10

<210> SEQ ID NO 10
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 10

Tyr Glu Cys Xaa Xaa Asp Leu Cys Trp Ile Gln
 1               5                  10

<210> SEQ ID NO 11
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 11

Trp Glu Cys Xaa Xaa Asp Leu Cys Tyr Ile Gln
 1               5                  10

<210> SEQ ID NO 12
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 1
<223> OTHER INFORMATION: Xaa = 4-methoxyphenylalanine
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 12

Xaa His Cys Xaa Xaa Asp Leu Cys His Ile Leu
 1               5                  10
```

```
<210> SEQ ID NO 13
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 13

Tyr His Cys Xaa Xaa Gly Leu Cys Trp Ile Gln
 1               5                  10

<210> SEQ ID NO 14
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 5
<223> OTHER INFORMATION: Xaa = meta-chlorotyrosine

<400> SEQUENCE: 14

Trp Glu Cys Pro Xaa Gly Leu Cys Trp Ile Gln
 1               5                  10

<210> SEQ ID NO 15
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline

<400> SEQUENCE: 15

Trp Glu Cys Xaa Tyr Gly Leu Cys Trp Ile Gln
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 4
<223> OTHER INFORMATION: Xaa = 4-hydroxyproline
<220> FEATURE:
<221> NAME/KEY: MOD_RES
<222> LOCATION: 5
<223> OTHER INFORMATION: Xaa = meta-chlorotyrosine

<400> SEQUENCE: 16

Phe His Cys Xaa Xaa Asp Leu Cys His Ile Leu
 1               5                  10

<210> SEQ ID NO 17
<211> LENGTH: 8
<212> TYPE: PRT
```

```
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 8
<223> OTHER INFORMATION: Xaa = n(decyl)Gly, n(4-PhBu)Gly, MeLeu,
      Phe(4*), Phe(3-Me), Phe(3,4-difluoro), Tyr(3, 5-di-iodo), or
      MeLeu

<400> SEQUENCE: 17

Cys Asp Tyr Tyr Gly Thr Cys Xaa
1               5

<210> SEQ ID NO 18
<211> LENGTH: 9
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 8
<223> OTHER INFORMATION: Xaa = n(decyl)Gly, n(4-PhBu)Gly, MeLeu,
      Phe(4*), Phe(3-Me), Phe(3,4-difluoro), Tyr(3,5-di-iodo), or
      MeLeu
<220> FEATURE:
<221> NAME/KEY: VARIANT
<222> LOCATION: 9
<223> OTHER INFORMATION: Xaa = Asp, dAsp, beta-Asp, Me-Asp, or dCys

<400> SEQUENCE: 18

Cys Asp Tyr Tyr Gly Thr Cys Xaa Xaa
1               5

<210> SEQ ID NO 19
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 10
<223> OTHER INFORMATION: Xaa = n(Decyl)Gly

<400> SEQUENCE: 19

Leu Pro Cys Asp Tyr Tyr Gly Thr Cys Xaa Asp
1               5                   10

<210> SEQ ID NO 20
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 10
<223> OTHER INFORMATION: Xaa = n(Decyl)Gly

<400> SEQUENCE: 20

Leu Pro Cys Asp Tyr Tyr Gly Thr Cys Xaa Asp
1               5                   10

<210> SEQ ID NO 21
<211> LENGTH: 11
<212> TYPE: PRT
<213> ORGANISM: Artificial Sequence
<220> FEATURE:
<223> OTHER INFORMATION: synthetically generated peptide
```

-continued

```
<220> FEATURE:
<221> NAME/KEY: MOD_RES
<222> LOCATION: 10
<223> OTHER INFORMATION: Xaa = biphenylalanine

<400> SEQUENCE: 21

Leu Pro Cys Asp Tyr Tyr Gly Thr Cys Xaa Asp
1               5                   10

<210> SEQ ID NO 22
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 10
<223> OTHER INFORMATION: Xaa = biphenylalanine

<400> SEQUENCE: 22

Leu Pro Cys Asp Tyr Tyr Gly Thr Cys Xaa Asp
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 10
<223> OTHER INFORMATION: Xaa = methyl-leucine

<400> SEQUENCE: 23

Leu Pro Cys Asp Tyr Tyr Gly Thr Cys Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 10
<223> OTHER INFORMATION: Xaa = methyl-leucine

<400> SEQUENCE: 24

Leu Pro Cys Asp Tyr Tyr Gly Thr Cys Xaa
1               5                   10

<210> SEQ ID NO 25
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: MOD_RES
<222> LOCATION: 10
<223> OTHER INFORMATION: Xaa = methyl-biphenylalanine

<400> SEQUENCE: 25

Leu Pro Cys Asp Tyr Tyr Gly Thr Cys Xaa Asp
1               5                   10
```

```
-continued

<210> SEQ ID NO 26
<211> LENGTH: 11
<212> TYPE: PRT
<213> ORGANISM: Artificial Sequence
<220> FEATURE:
<223> OTHER INFORMATION: synthetically generated peptide
<220> FEATURE:
<221> NAME/KEY: VARIANT
<222> LOCATION: 1
<223> OTHER INFORMATION: Xaa = any natural or non-natural amino acid
<220> FEATURE:
<221> NAME/KEY: VARIANT
<222> LOCATION: 2
<223> OTHER INFORMATION: Xaa = Pro or a non-natural derivative thereof
<220> FEATURE:
<221> NAME/KEY: VARIANT
<222> LOCATION: 10
<223> OTHER INFORMATION: Xaa = n(decyl)Gly, n(4-PhBu)Gly, MeLeu,
     Phe(4*), Phe(3-Me), Phe(3,4-difluoro), Tyr(3, 5-di-iodo), or
     MeLeu
<220> FEATURE:
<221> NAME/KEY: VARIANT
<222> LOCATION: 11
<223> OTHER INFORMATION: Xaa = Asp, dAsp, beta-Asp, or Me-Asp

<400> SEQUENCE: 26

Xaa Xaa Cys Asp Tyr Tyr Gly Thr Cys Xaa Xaa
1               5                   10

<210> SEQ ID NO 27
<211> LENGTH: 12
<212> TYPE: PRT
<213> ORGANISM: Artificial Sequence
<220> FEATURE:
<223> OTHER INFORMATION: synthetically generated peptide

<400> SEQUENCE: 27

Gln Trp Glu Cys Pro Tyr Gly Leu Cys Trp Ile Gln
1               5                   10
```

PEPTIDE-BASED MULTIMERIC TARGETED CONTRAST AGENTS

RELATED APPLICATION DATA

This application claims priority from U.S. Provisional Application Ser. No. 60/308,721, filed Jul. 30, 2001, and is related to co-pending U.S. application Ser. No. 10/209,183, filed Jul. 30, 2002, both of which are incorporated herein in their entirety.

TECHNICAL FIELD

This invention relates to contrast agents for diagnostic imaging, and more particularly to peptide-targeted, multimeric contrast agents, wherein a peptide functions as a targeting group and a point of attachment for one or more chelates at both the amino and carboxy termini of the peptide.

BACKGROUND

Diagnostic imaging techniques, such as magnetic resonance imaging (MRI), X-ray, nuclear radiopharmaceutical imaging, ultraviolet-visible-infrared light imaging, and ultrasound, have been used in medical diagnosis for a number of years. Contrast media additionally have been used to improve or increase the resolution of the image or to provide specific diagnostic information.

To be effective, the contrast media must interfere with the wavelength of electromagnetic radiation used in the imaging technique, alter the physical properties of tissue to yield an altered signal, or, as in the case of radiopharmaceuticals, provide the source of radiation itself. MRI and optical methods are unique among imaging modalities in that they yield complex signals that are sensitive to the chemical environment. While the signal from X-ray or radionuclide agents remains the same whether agents are free in plasma, bound to proteins or other targets, or trapped inside bone, certain contrast agents for MRI and optical imaging will have different signal characteristics in differing physiological environments. It is important that the contrast agent be sufficiently sensitive and present at high enough concentration so that signal changes can be observed.

Complexes between gadolinium or other paramagnetic ions and organic ligands are widely used to enhance and improve MRI contrast. Gadolinium complexes increase contrast by increasing the nuclear magnetic relaxation rates of protons found in the water molecules that are accessible to the contrast agents during MRI (Caravan, P., et al., *R. B. Chem. Rev.* 99, 2293 (1999)). The relaxation rate of the protons in these water molecules increases relative to protons in other water molecules that are not accessible to the contrast agent. This change in relaxation rate leads to improved contrast of the images. In addition, this increase in relaxivity within a specific population of water molecule protons can result in an ability to collect more image data in a given amount of time. This in turn results in an improved signal to noise ratio.

Imaging may also be performed using light, in which case an optical dye is chosen to provide signal. In particular, light in the 600–1300 nm (visible to near-infrared) range passes relatively easily through biological tissues and can be used for imaging purposes. The light that is transmitted through, or scattered by, reflected, or re-emitted (fluorescence), is detected and an image generated. Changes in the absorbance, reflectance, or fluorescence characteristics of a dye, including an increase or decrease in the number of absorbance peaks or a change in their wavelength maxima, may occur upon binding to a biological target, thus providing additional tissue contrast. In some situations, for example the diagnosis of disease close to the body surface, UV or visible light may also be used.

A need persists for contrast agents that can deliver sufficient concentrations of the imaging moiety to the target to improve the sensitivity of the imaging process as well as contrast agents that have a sufficient half-life in vivo.

SUMMARY

The invention is based on peptides and peptide-targeted multimeric contrast agents for MR, optical, and radionuclide imaging, wherein a single peptide can function both as a targeting group and a point of attachment for one or more chelates at both the N- and C-termini, either directly or via an optional intervening linker. Surprisingly, contrast agents of the invention maintain binding affinity for biological targets such as fibrin and high relaxivity. Agents of the invention have a sufficient half-life following in vivo administration such that effective imaging studies can be performed.

In one aspect, the invention features purified peptides that include the amino acid sequence: P*-Y*-$X_1$*-L* (SEQ ID NO:1), wherein P* is a proline or a non-natural derivative thereof, Y* is a tyrosine or a non-natural derivative thereof; $X_1$* is G or D or a non-natural derivative of G or D; L* is a leucine or a non-natural derivative thereof; and wherein at least one of P*, Y*, $X_1$*, and L* is a non-natural derivative of the respective amino acid. $X_1$* can be G or D and L* can be leucine. In some embodiments, P* is proline or 4-hydroxyproline, and Y* is tyrosine or a non-natural derivative of tyrosine substituted at the 3 position with a moiety selected from the group consisting of F, Cl, Br, I, and $NO_2$. Compounds of the invention can include such peptides linked to a thrombolytic agent.

In another aspect, the invention features purified peptides that include the amino acid sequence $X_1$-$X_2$-C-P*-Y*-$X_3$-L-C-$X_4$-$X_5$-$X_6$ (SEQ ID NO:2), wherein: P* is a proline or a non-natural derivative thereof; Y* is a tyrosine or a non-natural derivative thereof; $X_1$ is selected from the group consisting of W, Y, F, S, Bip, Hx, Dpr, Cy, Gu, Ad, Hfe, 3-Pal, 4-Pal, DopaMe2, nTyr, dW, dF, F(3/4*), and Y(3*), wherein F(3/4*) is a phenylalanine substituted at either the 3 or the 4 position with a moiety selected from the group consisting of $CH_3$, $CF_3$, $NH_2$, $CH_2NH_2$, CN, F, Cl, Br, I, Et, and OMe, and wherein Y(3*) is a tyrosine substituted at the 3 position with a moiety selected from the group consisting of F, Cl, Br, I, and $NO_2$; $X_2$ is selected from the group consisting of E, H, dE, S, H(Bzl), 2-Pal, Dpr, and Th; $X_3$ is selected from the group consisting of G and D; $X_4$ is selected from the group consisting of H, F, Y, and W; $X_5$ is selected from the group consisting of I, L, V, N, Bpa, Bal, Hfe, Nle, Tle, Nval, Phg, Cha, Taz, Fua, Th, 4-Pal, and F(3/4*), wherein F(3/4*) is a phenylalanine substituted at either the 3 or the 4 position with a moiety selected from the group consisting of $CF_3$, Et, iPr, and OMe; $X_6$ is selected from the group consisting of N, Q, I, L, and V, or $X_6$ is not present; and wherein at least one of $X_1$, $X_2$, $X_5$, P*, and Y* is a non-natural derivative of an amino acid. For example, P* can be proline or 4-hydroxyproline, and Y* can be tyrosine or a non-natural derivative of tyrosine substituted at the 3 position with a moiety selected from the group consisting of F, Cl, Br, I, and $NO_2$. The purified peptides can be capable of forming a disulfide bond under non-reducing conditions and can have specific binding affinity for fibrin. In some embodiments, the peptides include a disulfide bond. Compounds of the invention can include such peptides linked to a thrombolytic agent.

The invention also features purified peptides having an amino acid sequence selected from the group consisting of W-dE-C-P(4-OH)-Y(3-Cl)-G-L-C-W-I-Q (SEQ ID NO:4), Y-dE-C-P(4-OH)-Y(3-Cl)-G-L-C-Y-I-Q (SEQ ID NO:5), Y-dE-C-P(4-OH)-Y(3-Cl)-G-L-C-W-I-Q (SEQ ID NO:6), W-dE-C-P(4-OH)-Y(3-Cl)-G-L-C-Y-I-Q (SEQ ID NO:7), W-dE-C-P(4-OH)-Y(3-Cl)-D-L-C-W-I-Q (SEQ ID NO:8), Y-dE-C-P(4-OH)-Y(3-Cl)-D-L-C-Y-I-Q (SEQ ID NO:9), Y-dE-C-P(4-OH)-Y(3-Cl)-D-L-C-W-I-Q (SEQ ID NO:10), W-dE-C-P(4-OH)-Y(3-Cl)-D-L-C-Y-I-Q (SEQ ID NO:11), F(4-OMe)-H-C-P(4-OH)-Y(3-Cl)-D-L-C-H-I-L (SEQ ID NO:12), Y-H-C-P(4-OH)-Y(3-Cl)-G-L-C-W-I-Q (SEQ ID NO:13), W-dE-C-P-Y(3-Cl)-G-L-C-W-I-Q (SEQ ID NO:14), W-dE-C-P(4-OH)-Y-G-L-C-W-I-Q (SEQ ID NO:15), and F-H-C-P-(4-OH)-Y(3-Cl)-D-L-C-H-I-L (SEQ ID NO:16). The peptides can be capable of forming a disulfide bond under non-reducing conditions, and in some embodiments, the peptides include a disulfide bond. The peptides can have specific binding affinity for fibrin. Compounds of the invention can include such peptides linked to a thrombolytic agent.

In some embodiments, P* is proline; Y* is tyrosine; $X_1$ is selected from the group consisting of W, Y, F, S, Bip, Hx, Dpr, Cy, Gu, Ad, Hfe, 3-Pal, 4-Pal, DopaMe2, nTyr, dW, dF, F(3/4*), and Y(3*), wherein F3/4* is a phenylalanine substituted at either the 3 or the 4 position with a moiety selected from the group consisting of $CH_3$, $CF_3$, $NH_2$, $CH_2NH_2$, CN, F, Cl, Br, I, Et, and OMe, and wherein Y3* is a tyrosine substituted at the 3 position with a moiety selected from the group consisting of F, Cl, Br, I, and $NO_2$; $X_2$ is selected from the group consisting of dE, H(Bzl), 2-Pal, Dpr, and Th; $X_3$ is selected from the group consisting of G and D; $X_4$ is selected from the group consisting of H, F, Y, and W; $X_5$ is selected from the group consisting of I, L, V, N, Bpa, Bal, Hfe, Nle, Tle, nVal, Phg, Cha, Taz, Fua, Th, 4-Pal, and F(3/4*), wherein F3/4* is a phenylalanine substituted at either the 3 or the 4 position with a moiety selected from the group consisting of $CF_3$, Et, iPr, and Ome, wherein at least one of X1, X2, or X5 is a non-natural amino acid derivative; and $X_6$ is selected from the group consisting of N, Q, I, L, and V, or $X_6$ is not present. Such peptides can be capable of forming a disulfide bond under non-reducing conditions, and in some embodiments, the peptides include a disulfide bond. The peptides can have specific binding affinity for fibrin.

In other embodiments, the invention features purified peptides that include the amino acid sequence: C-P*-Y*-$X_1$-L-C (SEQ ID NO:3), wherein $X_1$ is G or D, P* is proline or its non-natural derivative 4-hydroxyproline; and Y* is tyrosine or a non-natural derivative of tyrosine substituted at the 3 position with a moiety selected from the group consisting of F, Cl, Br, I, and $NO_2$; provided that at least one of P* or Y* is a non-natural derivative of the respective amino acid. The purified peptides can be capable of forming a disulfide bond under non-reducing conditions and can have specific binding affinity for fibrin. In some embodiments, the peptides include a disulfide bond. Compounds of the invention can include such peptides linked to a thrombolytic agent.

The invention also features purified peptides that include the amino acid sequence: C-D-Y-Y-G-T-C-$X_{10}$ (SEQ ID. NO:17), wherein $X_{10}$ is selected from the group consisting of n(decyl)G, n(4-PhBu)G, MeL, Bpa, Bip, Me-Bip, F(4*), F(3-Me), F(3, 4-difluoro), Amh, Hfe, Y(3,5-di-iodo), Pff, 1Nal, d1Nal, and MeL, wherein F(4*) is a phenylalanine substituted at the 4 position with a moiety selected from the group consisting of Et, $CF_3$, I, and iPr. Purified peptides can include the amino acid sequence C-D-Y-Y-G-T-C-$X_{10}$-$X_{11}$ (SEQ ID. NO:18), wherein $X_{11}$ is selected from the group consisting of D, dD, βD, Inp, Nip, Me-D, dC, Cop, and Cmp. For example, a peptide can have the follow amino acid sequences: L-P-C-D-Y-Y-G-T-C-n(Decyl)G-dD (SEQ ID NO:19), L-P-C-D-Y-Y-G-T-C-n(Decyl)G-D (SEQ ID NO:20), L-P-C-D-Y-Y-G-T-C-Bip-D (SEQ ID NO:21), L-P-C-D-Y-Y-G-T-C-Bip-dD (SEQ ID NO:22), L-P-C-D-Y-Y-G-T-C-MeL-Inp (SEQ ID NO:23), L-P-C-D-Y-Y-G-T-C-MeL-Cmp (SEQ ID NO:24), or L-P-C-D-Y-Y-G-T-C-MeBip-D (SEQ ID NO:25). The purified peptides can be capable of forming a disulfide bond under non-reducing conditions and can have specific binding affinity for fibrin. In some embodiments, the peptides include a disulfide bond. Compounds of the invention can include such peptides linked to a thrombolytic agent.

In another aspect, the invention features a method of making an MR imaging agent. The method includes reacting a peptide having an N-terminal amine functional group with a linker-subunit moiety to form a modified peptide having both a C-terminal amine functional group and N-terminal amine functional group; covalently attaching a linker moiety to the C-terminal amine functional group and to the N-terminal amine functional group to form a precursor MR imaging agent; and converting the precursor MR imaging agent to the MR imaging agent. The linker-subunit moiety can be selected from the group consisting of:

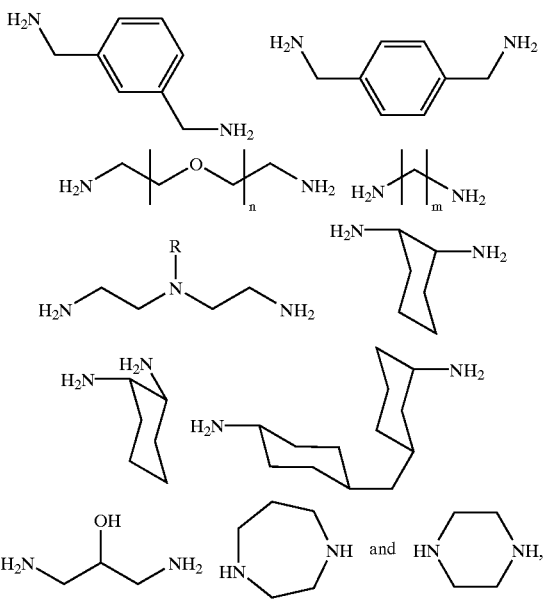

wherein n is an integer from 1 to 4; m is an integer selected 1 to 12; and R is an aliphatic or aromatic group. The linker moiety can be selected from the group consisting of:

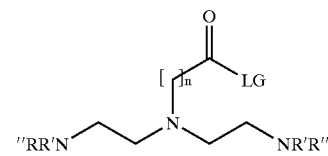

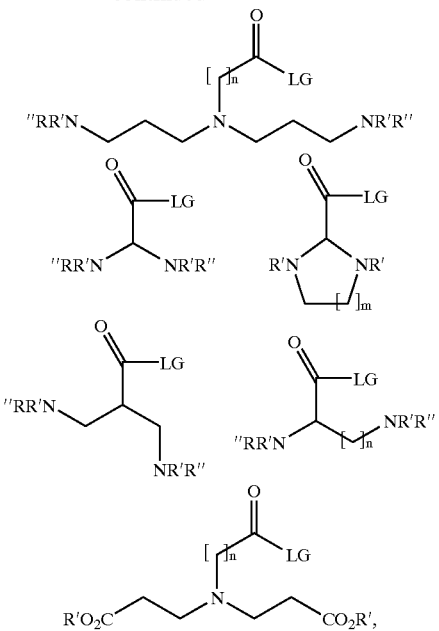

wherein m is an integer from 1 to 4; n is an integer from 0 to 4; LG is a leaving group; and R' and R" independently are selected from the group consisting of hydrogen and a chemical protecting group.

The linker moiety also can be selected from the group consisting of:

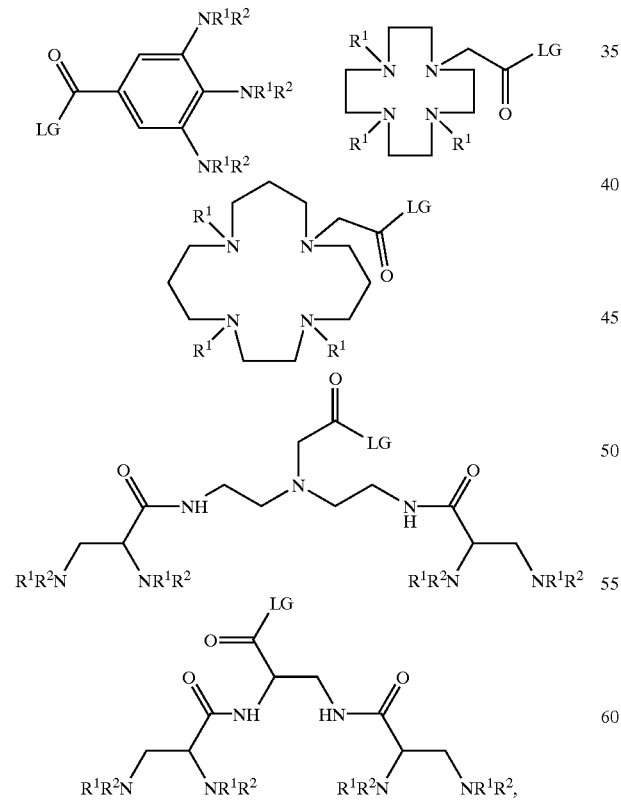

wherein LG is a leaving group; and $R^1$ and $R^2$ independently are selected from the group consisting of hydrogen and a chemical protecting group. The LG can be selected from the group consisting of —OH, activated ester, halide, and anhydride. The activated ester can be selected from the group consisting of pentafluorophenol (Pfp), N-hydroxysuccinimide (NHS), N-Hydroxysulfosuccinimide Sodium Salt (NHSS), 2-Thioxothiazolidin-1yl, and hydroxybenzotriazole (OBT). The halide can be selected from the group consisting of F, Cl, Br, and I. The chemical protecting group can be selected from the group consisting of Boc, Fmoc, CBZ, t-butyl, benzyl, and allyl.

Converting the precursor MR imaging agent to the MR imaging agent can include reacting the precursor imaging agent with a precursor chelate moiety to form a covalent bond between the precursor chelate moiety and the linker moiety of the precursor MR imaging agent, the precursor chelate moiety comprising a plurality of carboxylate precursor groups, the carboxylate precursor groups capable of being transformed into carboxylate moieties; transforming a plurality of the carboxylate precursor groups of the bound precursor chelate moiety to a plurality of carboxylate moieties, the carboxylate moieties capable of complexing a paramagnetic metal ion; and complexing a paramagnetic metal ion to the plurality of carboxylate moieties to produce the MR imaging agent. The precursor chelate moiety can be selected from the group consisting of:

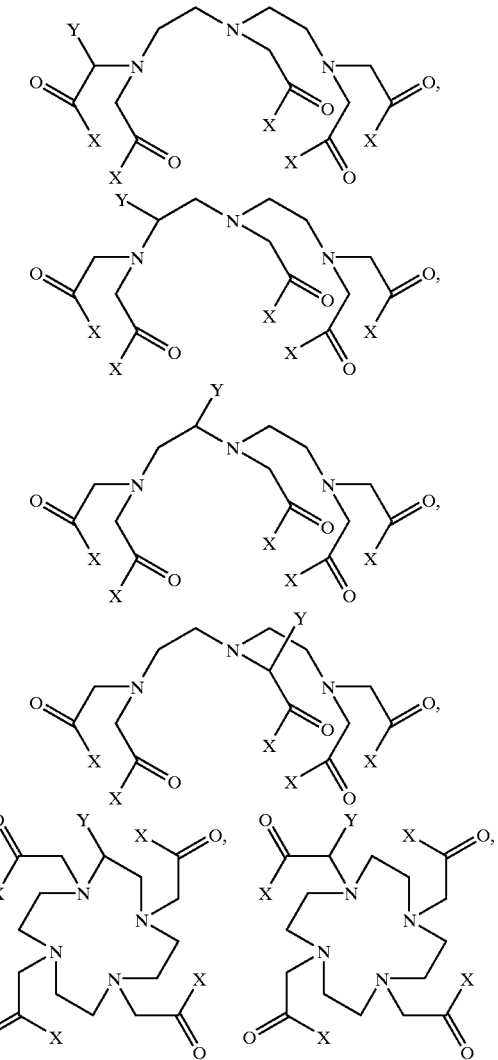

-continued

[chemical structures]

wherein Y is a synthetic moiety capable of forming a covalent bond with the attached linker moiety, and wherein each X, independently, is an O⁻ or an O⁺ precursor so that X, upon conversion to O⁻, is capable of forming a carboxylate moiety with its adjacent carbonyl, and $R^1$ is an uncharged chemical moiety, an aliphatic, alkyl group, or cycloalkyl group, or uncharged substituted versions thereof. The synthetic moiety can be selected from the group consisting of a carboxylic acid, activated ester, acid halide, anhydride, alkyl halide, isocyanate, and isothiocyanate, and wherein the O⁻ precursor is selected from the group consisting of —OH, -OMe, OEt, OtBu, Obenzyl, and O-allyl.

The precursor chelate moiety also can be selected from the group consisting of:

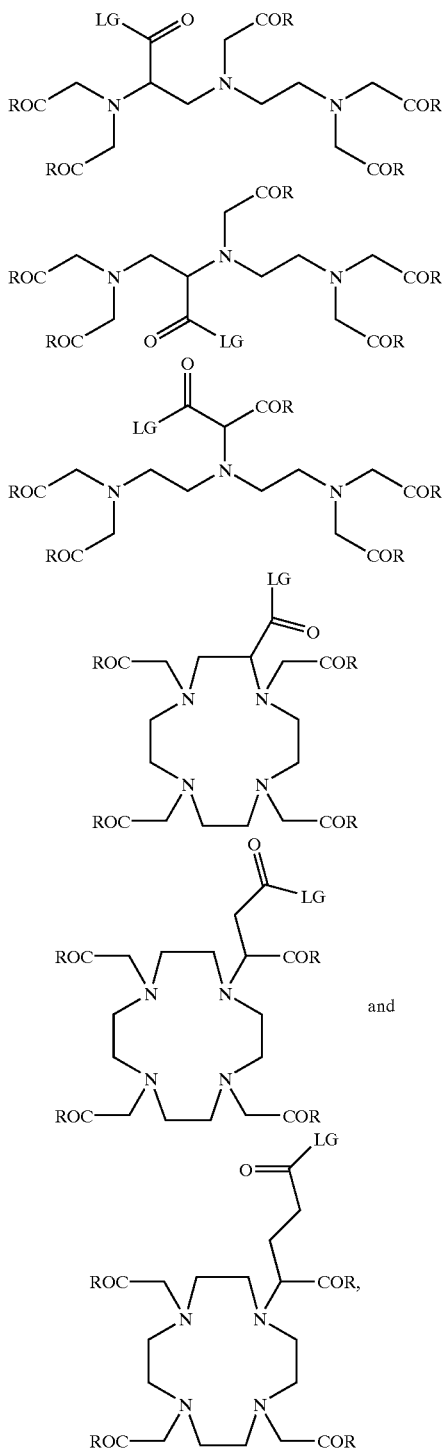

wherein LG is a leaving group selected from the group consisting of —OH, activated ester, halide, and anhydride, and wherein each R, independently, is an O⁻ or an O⁺ precursor selected from the group consisting of OH, —O-Me, O-Et, O-tBu, O-benzyl, and O-allyl, so that R, upon conversion to O⁻, is capable of forming a carboxylate moiety with its adjacent carbonyl.

The precursor chelate moiety also can be selected from the group consisting of:
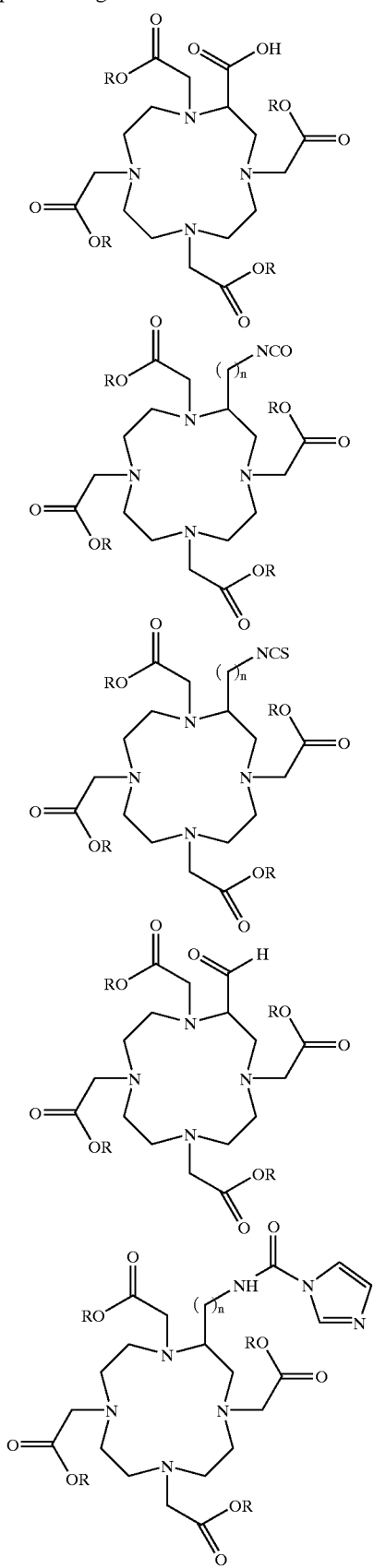
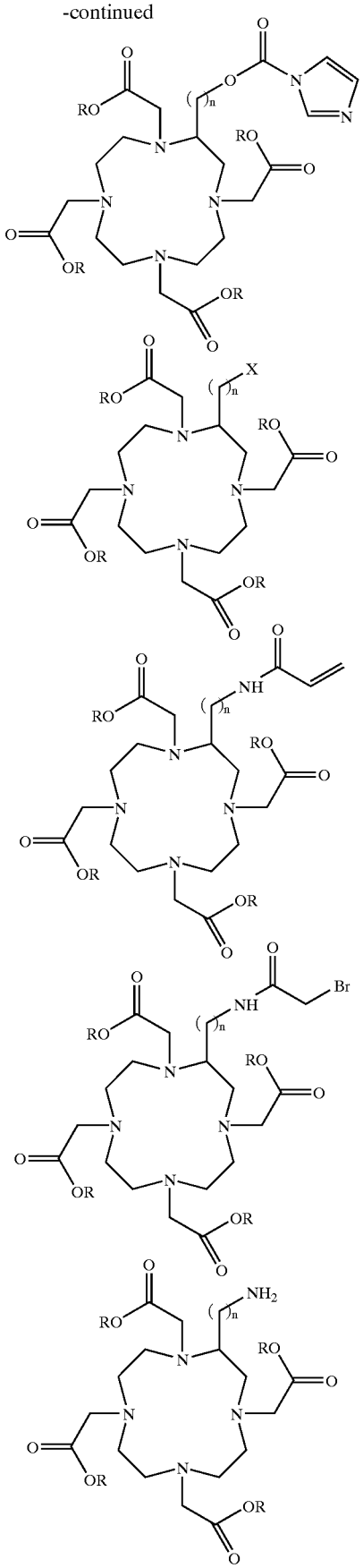

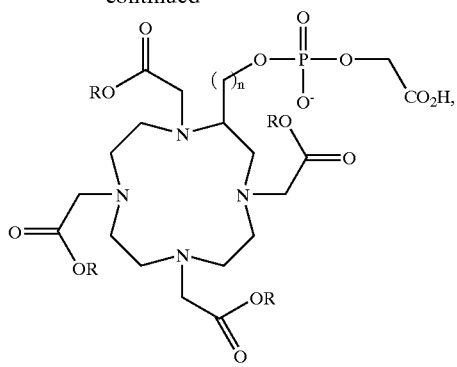
wherein n is an integer from 1 to 4; R is selected from the group consisting of a negative charge and a negative charge precursor capable of being transformed into a negative charge; and X is a chemical leaving group selected from the group consisting of —Cl, —Br, —I, -MsO, -TsO, and -TfO.
The precursor chelate moiety can be selected from the group consisting of:
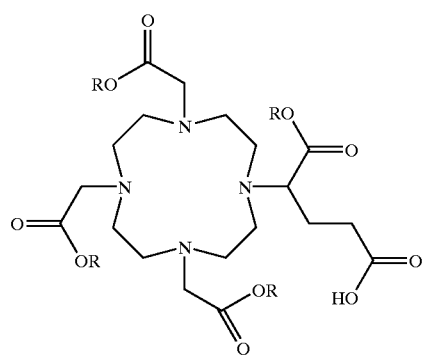
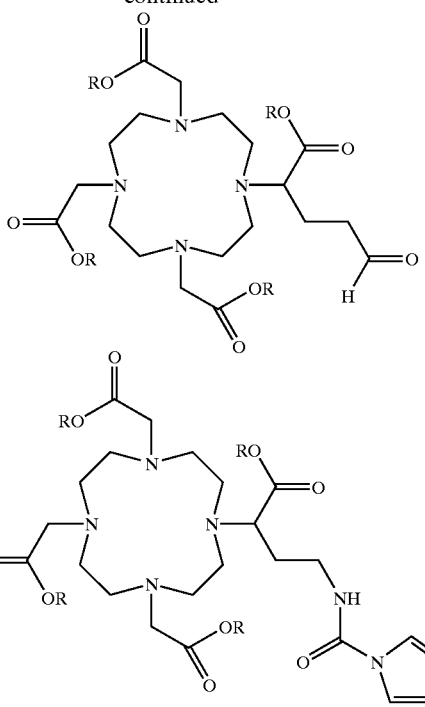
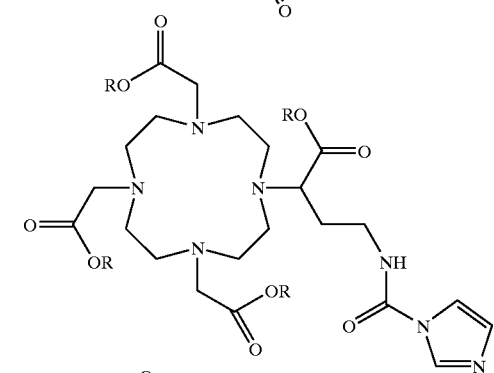
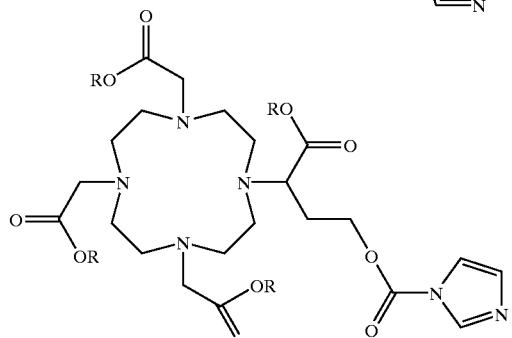
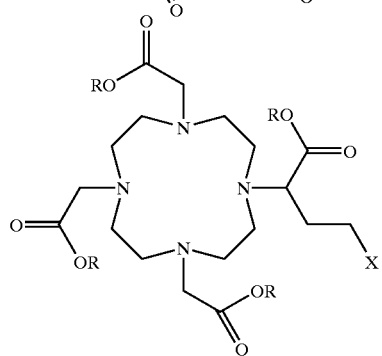
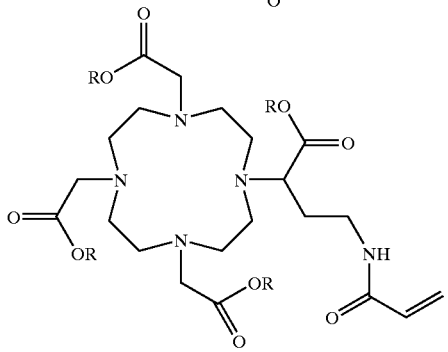

-continued

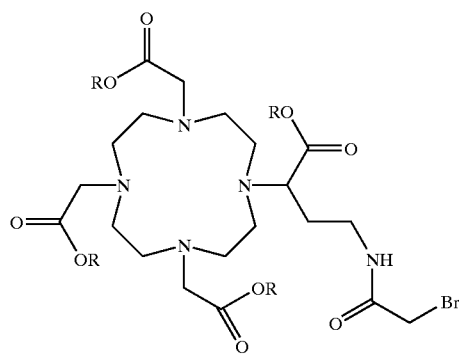

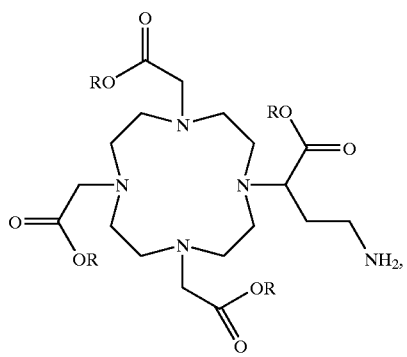

wherein R is selected from the group consisting of a negative charge and a negative charge precursor capable of being transformed into a negative charge; and X is a chemical leaving group selected from the group consisting of —Cl, —Br, —I, -MsO, -TsO, and -TfO. The negative charge precursor is selected from the group consisting of —H, -Me, -Et, -t-Bu, -benzyl, and -allyl.

In some embodiments, the linker moiety can be covalently conjugated to a precursor chelate moiety, the covalent conjugate comprising a plurality of carboxylate precursor groups, the carboxylate precursor groups capable of being transformed into carboxylate moieties. Converting the precursor MRI imaging agent to the MR imaging agent can include transforming a plurality of the covalent conjugate's carboxylate precursor groups into carboxylate moieties, the carboxylate moieties capable of complexing a paramagnetic metal ion; and complexing a paramagnetic metal ion to the plurality of carboxylate moieties to result in the MR imaging agent. The paramagnetic metal ion can be selected from the group consisting of: Gd(III), Fe(III), Mn(II and III), Cr(III), Cu(II), Dy(III), Tb(III and IV), Ho(III), Er(III), Pr(III), Eu(II) and Eu(III). Gd(III) is a particularly useful paramagnetic ion.

The covalent conjugate can be selected from the group consisting of:

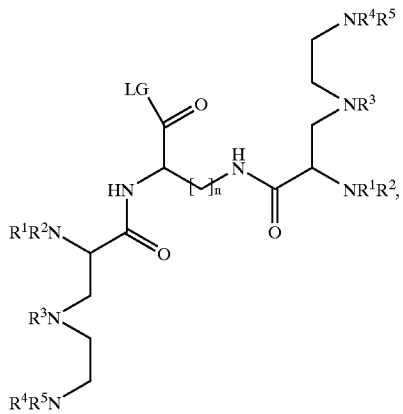

and

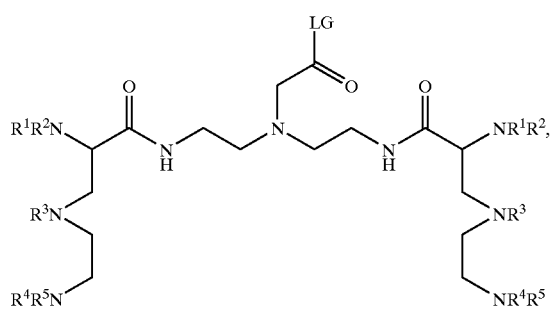

wherein n is an integer from 1 to 4; LG is a leaving group selected from the group consisting of —OH, activated ester, halide, and anhydride; and $R^1$, $R^2$, $R^3$, $R^4$, and $R^5$ are independently selected from the group consisting of an acetate moiety, a -Me, -Et, or -t-Bu protected acetate moiety, an acetamide moiety, and an acetoxy moiety.

The covalent conjugate also can be selected from the group consisting of:

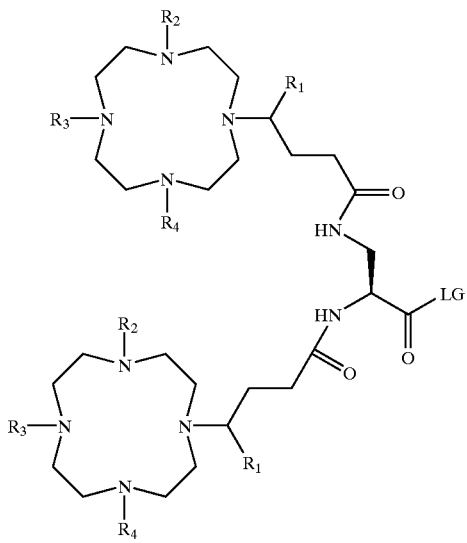

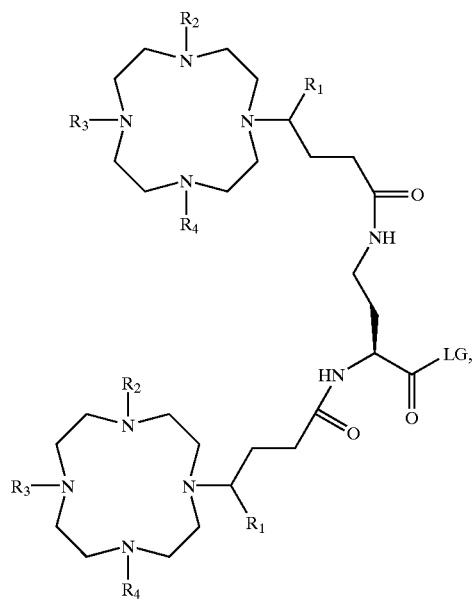

wherein LG is a leaving group selected from the group consisting of —OH, activated ester, halide, and anhydride; and $R^1$, $R^2$, $R^3$, and $R^4$ are selected from the group consisting of an acetate moiety, a -Me, -Et, or -t-Bu protected acetate moiety, an acetamide moiety, and an acetoxy moiety.

The covalent conjugate can be selected from the group consisting of:

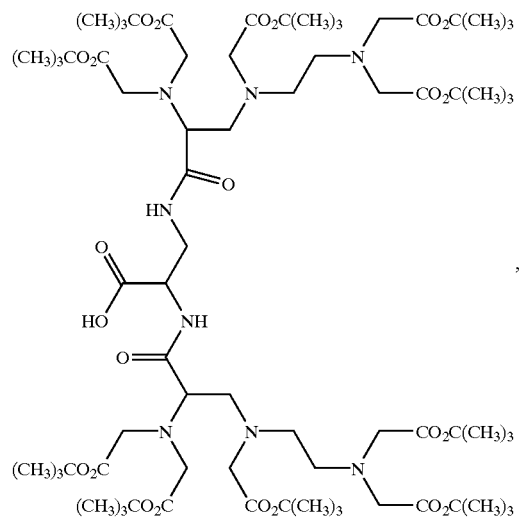

, and

The covalent conjugate also can be selected from the group consisting of:

17
-continued

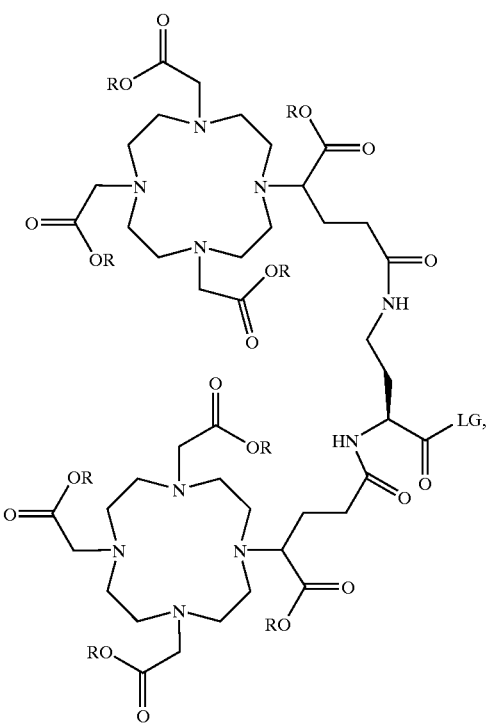

wherein:

R is a -tBu group, LG is a leaving group selected from the group consisting of —OH, activated ester, halide, and anhydride.

Methods of the invention further can include, before covalently attaching a linker moiety to the C- and N-terminal amine functional groups, reacting a linker-subunit with the N-terminal amine functional group of the peptide to produce a derivatized N-terminal amine functional group of the peptide. The linker-subunit can be selected from the group consisting of:

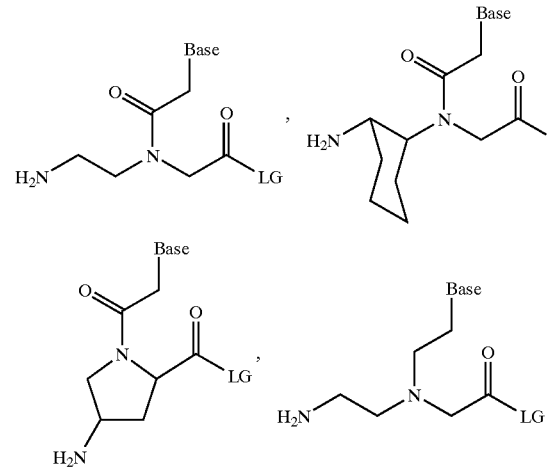

18
-continued

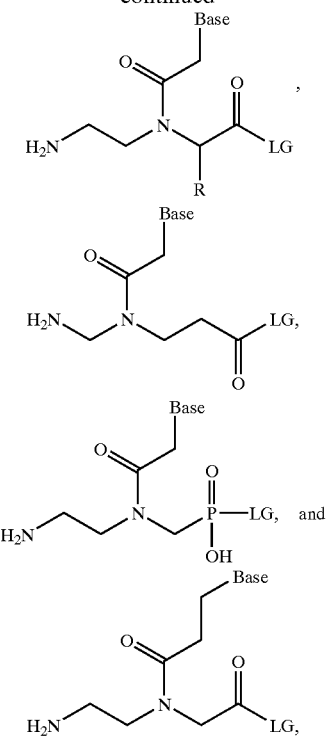

wherein Base is selected from the group consisting of adenosine, guanosine, thymine, and cytosine; LG is a leaving group selected from the group consisting of OH, activated ester, halide, and anhydride; and R is an aliphatic or aromatic moiety. The linker-subunit also can be selected from the group consisting of:

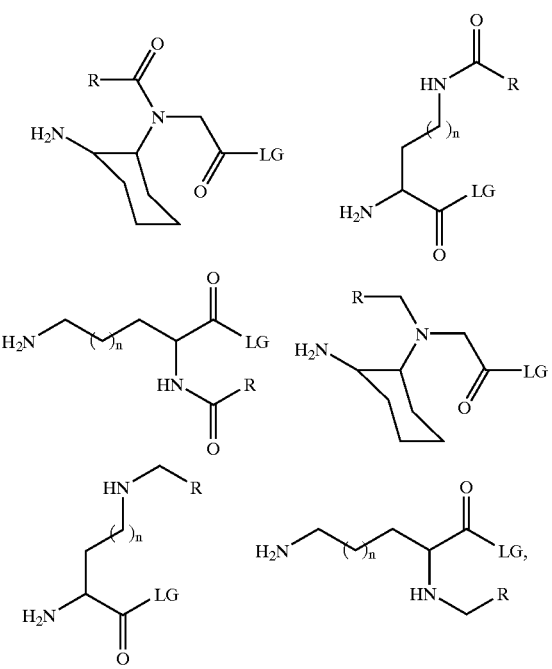

wherein n is independently an integer from 0 to 3; R is an aliphatic or aromatic group; and LG is a leaving group selected from the group consisting of: OH, activated ester, halide, and anhydride.

The linker-subunit also can be selected from the group consisting of:

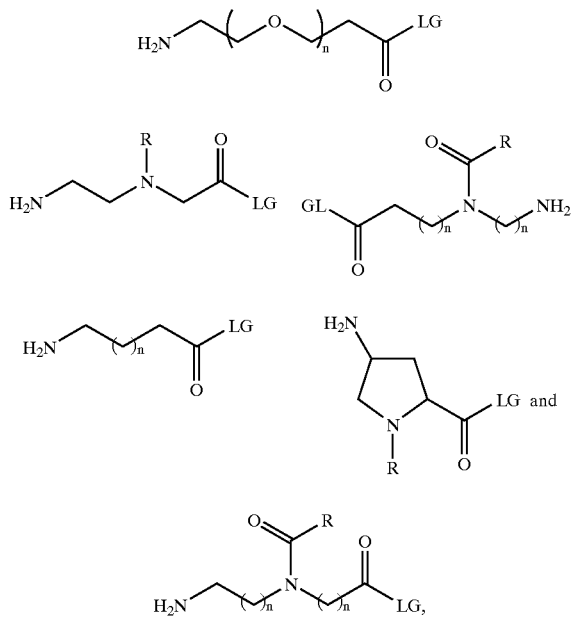

wherein n is independently 1 or 2; R is an aliphatic or aromatic group; and LG is a leaving group selected from the group consisting of: OH, activated ester, halide, and anhydride.

In another aspect, the invention features a method of making a MR imaging agent. The method includes covalently binding an amino acid residue to a linker-subunit moiety to form a C-terminal end of a peptide, wherein the linker-subunit moiety is covalently attached to a resin; synthesizing a peptide on the resin from the covalently bound C-terminal end to an N-terminal residue of the peptide, the N-terminal residue comprising an N-terminal amine functional group; cleaving the peptide from the resin to produce a peptide having a C-terminal amine functional group; covalently attaching a linker moiety to the peptide's C-terminal amine functional group and N-terminal amine functional group to form a precursor MR imaging agent; and converting the precursor MR imaging agent to the MR imaging agent. The method further can include before cleaving the peptide from the resin, covalently attaching a linker-subunit moiety to the N-terminal amino functional group to produce a derivatized N-terminal amine functional group. The linker moiety can be covalently conjugated to a precursor chelate moiety, the covalent conjugate comprising a plurality of carboxylate precursor groups, the carboxylate precursor groups capable of being transformed into carboxylate moieties.

Converting the precursor MR imaging agent to the MR imaging agent can include reacting the precursor MR imaging agent with a precursor chelate moiety to form a covalent bond between the precursor chelate moiety and the linker moiety of the precursor MR imaging agent, the precursor chelate moiety comprising a plurality of carboxylate precursor groups, the carboxylate precursor groups capable of being transformed into carboxylate moieties; transforming a plurality of the carboxylate precursor groups of the bound precursor chelate moiety to a plurality of carboxylate moieties, the carboxylate moieties capable of complexing a paramagnetic metal ion; and complexing a paramagnetic metal ion to the plurality of carboxylate moieties to produce the MR imaging agent.

Converting the precursor MRI imaging agent to the MR imaging agent also can include transforming a plurality of the covalent conjugate's carboxylate precursor groups into carboxylate moieties, the carboxylate moieties capable of complexing a paramagnetic metal ion; and complexing a paramagnetic metal ion to the plurality of carboxylate moieties to result in the MR imaging agent. The paramagnetic metal ion can be selected from the group consisting of: Gd(III), Fe(III), Mn(II and III), Cr(III), Cu(II), Dy(III), Tb(III and IV), Ho(III), Er(III), Pr(III), Eu(II) and Eu(III). Gd(III) is a particularly useful paramagnetic metal ion.

In another aspect, the invention features a method of making a MR imaging agent that includes reacting a peptide having a C-terminal carboxylate functional group with a linker-subunit moiety to form a modified peptide having both a C-terminal carboxylate functional group and an N-terminal carboxylate functional group; covalently attaching a linker moiety to both the N-terminal and C-terminal carboxylate functional groups of the modified peptide to form a precursor MR imaging agent; and converting the precursor MR imaging agent to the MR imaging agent. The linker-subunit moiety can be selected from the group consisting of:

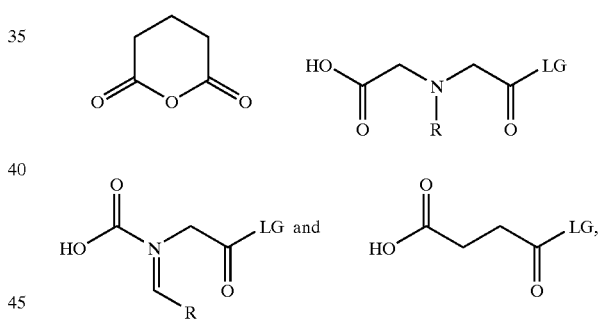

wherein LG is a leaving group selected from the group consisting of OH, activated ester, halide, and anhydride; and R is an aromatic or aliphatic group. The linker moiety also can be selected from the group consisting of:

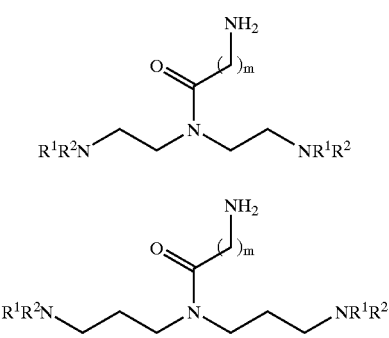

-continued

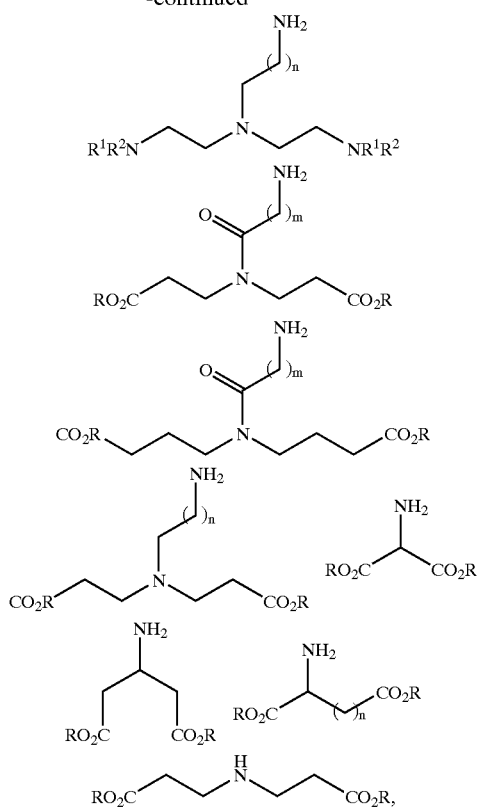

wherein m is an integer from 1 to 4; n is an integer from 0 to 4; R is independently selected from the group consisting of —H, -Me, -Et, -Bz, and -tBu; and $R^1$ and $R^2$ are independently selected from a hydrogen or a chemical protecting group.

The linker moiety can be selected from the group consisting of:

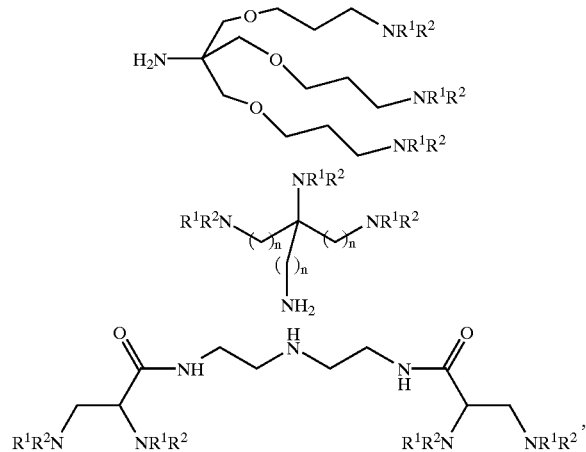

wherein $R^1$ and $R^2$ are selected independently from the group consisting of hydrogen and a chemical protecting group, the chemical protecting group selected from the group consisting of: Boc, Fmoc, CBZ, t-butyl, benzyl, and allyl.

Converting the precursor MR imaging agent to the MR imaging agent also can include reacting the precursor MR imaging agent with a precursor chelate moiety in order to form a covalent bond between the linker moiety of the precursor MR imaging agent and the precursor chelate moiety, the precursor chelate moiety comprising a plurality of carboxylate precursor groups, the carboxylate precursor groups capable of being transformed into carboxylate moieties; transforming a plurality of the carboxylate precursor groups of the bound precursor chelate moiety to a plurality of carboxylate moieties, the carboxylate moieties capable of complexing a paramagnetic metal ion; and complexing a paramagnetic metal ion to the plurality of carboxylate moieties to produce the MR imaging agent. The linker moiety can be covalently conjugated to a precursor chelate moiety, the covalent conjugate comprising a plurality of carboxylate precursor groups, the carboxylate precursor groups capable of being transformed into carboxylate moieties.

Converting the precursor MR imaging agent to the MR imaging agent also can include transforming a plurality of the covalent conjugate's carboxylate precursor groups into carboxylate moieties, the carboxylate moieties capable of complexing a paramagnetic metal ion; and complexing a paramagnetic metal ion to the plurality of carboxylate moieties to produce the MR imaging agent.

A covalent conjugate can be selected from the group consisting of:

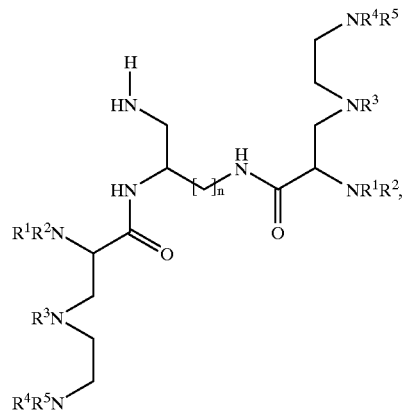

and

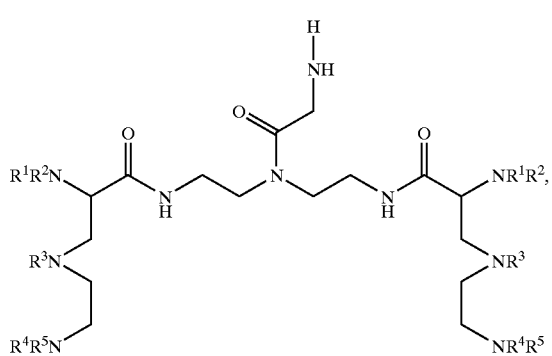

wherein n is an integer from 1 to 4; and $R^1$, $R^2$, $R^3$, $R^4$, and $R^5$ are independently selected from the group consisting of an acetate moiety, a -Me, -Et, or -t-Bu protected acetate moiety, an acetamide moiety, and an acetoxy moiety. The covalent conjugate can be:

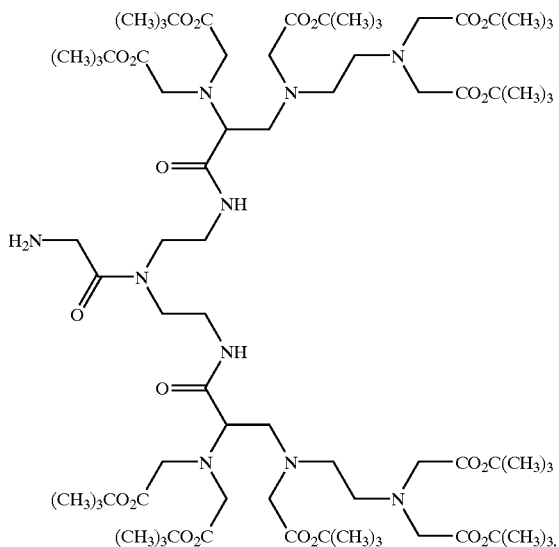

Converting the precursor MR imaging agent to the MR imaging agent also can include reacting the precursor imaging agent with a chelate moiety, wherein the chelate moiety contains a paramagnetic metal ion, to form a covalent bond between the chelate moiety and the linker moiety of the precursor MR imaging agent to produce the MR imaging agent. Suitable paramagnetic metal ions are described above.

In yet another aspect, the invention features a contrast agent that includes a metal chelate complex at a —$CO_2R$ and NHR termini of a biopolymer (e.g., a peptide), wherein R is independently selected from the group consisting of hydrogen, alkyl, aliphatic, and a leaving group. The contrast agent can include two metal chelate complexes at the $CO_2R$ and NHR termini of the biopolymer. The biopolymer can have a specific binding affinity for fibrin. The peptide can be capable of forming a disulfide bond under non-reducing conditions, and in some embodiments, includes a disulfide bond. A contrast agent can have the formula:

wherein Chelate represents a metal chelate complex; Linker represents a linker moiety; Linker-subunit represents a linker-subunit moiety; m is independently an integer from 1 to 10; p is independently an integer from 0 to 5; s is independently 0 or 1; $R^1$ is an amino acid side chain or a derivative thereof; and $R^2$ is independently a hydrogen or an aliphatic group. A contrast agent also can have a structure of any one of structures 4–55.

In another aspect, the invention features a method for altering the stability of a peptide, the peptide having an N-terminal amine functional group. The method includes reacting the peptide with a linker-subunit moiety to form a peptide having a C-terminal amine functional group; and covalently attaching a linker moiety to the peptide's C-terminal amine functional group and N-terminal amine functional group to form a modified peptide. The method further can include reacting the modified peptide with a capping moiety to form a covalent bond between the capping moiety and the linker moiety of the modified peptide. The method also can include reacting the modified peptide with a precursor chelate moiety to form a covalent bond between the precursor chelate moiety and the linker moiety of the modified peptide, the precursor chelate moiety comprising a plurality of carboxylate precursor groups, the carboxylate precursor groups capable of being transformed into carboxylate moieties. After transforming a plurality of the carboxylate precursor groups of the bound precursor chelate moiety to a plurality of carboxylate moieties, the carboxylate moieties capable of complexing a paramagnetic metal ion; a paramagnetic metal ion can be complexed to the plurality of carboxylate moieties. The method further can include assaying the stability of the modified peptide or assaying the stability of the unmodified peptide and comparing the stability of said modified peptide to the stability of the unmodified peptide. Stability of the modified peptide can be improved relative to the stability of the unmodified peptide (e.g., improved 10-fold, 20-fold, or 30-fold relative to the stability of the unmodified peptide). Stability can be assayed using a rat liver homogenate assay.

In another aspect, the invention features a modified peptide having the structure:

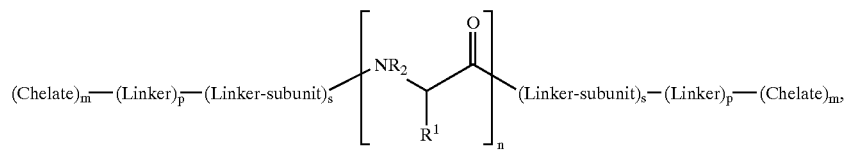

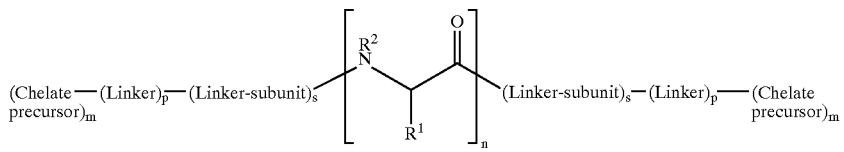

wherein Chelate precursor represents a chelate precursor moiety; Linker represents a linker moiety; Linker-subunit represents a linker-subunit moiety; m is independently an integer from 1 to 10; p is independently an integer from 0 to 5;

s is independently 0 or 1; $R^1$ is an amino acid side chain or a derivative thereof; and $R^2$ is selected from the group consisting of H and an aliphatic group.

In yet another aspect, the invention features a modified peptide having the structure:

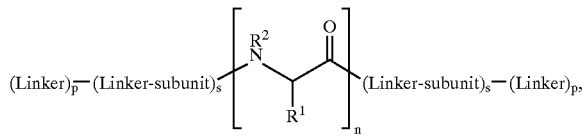

wherein Linker represents a linker moiety; Linker-subunit represents a linker-subunit moiety; p is independently an integer from 0 to 5; s is independently 0 or 1; $R^1$ is an amino acid side chain or a derivative thereof; and $R^2$ is selected from the group consisting of H and an aliphatic group.

Method of making an MR imaging agent also are featured that include reacting a peptide having an N-terminal amine functional group with a linker-subunit moiety to form a modified peptide having an amine functional group on both its N-terminus and C-terminus, or reacting a peptide having a C-terminal carboxylate functional group with a linker-subunit moiety to form a modified peptide having a carboxylate functional group on both its C-terminus and N-terminus; and converting the modified peptide to the MR imaging agent. Converting the modified peptide to the MR imaging agent can include covalently attaching a chelate moiety to the modified peptide, wherein the chelate moiety contains a paramagnetic metal ion, to produce the MR imaging agent. Converting the modified peptide to the MR imaging agent also can include covalently linking a linker moiety to a chelate moiety to form a covalent conjugate, wherein the chelate moiety contains a paramagnetic metal ion; and reacting the covalent conjugate with the modified peptide to form the MR imaging agent. Suitable paramagnetic ions are described above.

In another aspect, the invention features a method of making an MR imaging agent that includes covalently binding an amino acid residue to a linker-subunit moiety to form a C-terminal end of a peptide, wherein the linker-subunit moiety is covalently attached to a resin; synthesizing a peptide on the resin from the covalently bound C-terminal end to an N-terminal residue of the peptide, the N-terminal residue comprising an N-terminal amine functional group; cleaving the peptide from the resin to produce a C-terminal amine functional group of the modified peptide; converting the modified peptide to the MR imaging agent. Converting the modified peptide to the MR imaging agent can include covalently attaching a chelate moiety to the modified peptide, wherein the chelate moiety contains a paramagnetic metal ion, to produce the MR imaging agent. Converting the modified peptide to the MR imaging agent also can include covalently linking a linker moiety to a chelate moiety to form a covalent conjugate, wherein the chelate moiety contains a paramagnetic metal ion; and reacting the covalent conjugate with the modified peptide to form the MR imaging agent. Suitable paramagnetic ions are described above.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Definitions

Figure 1:
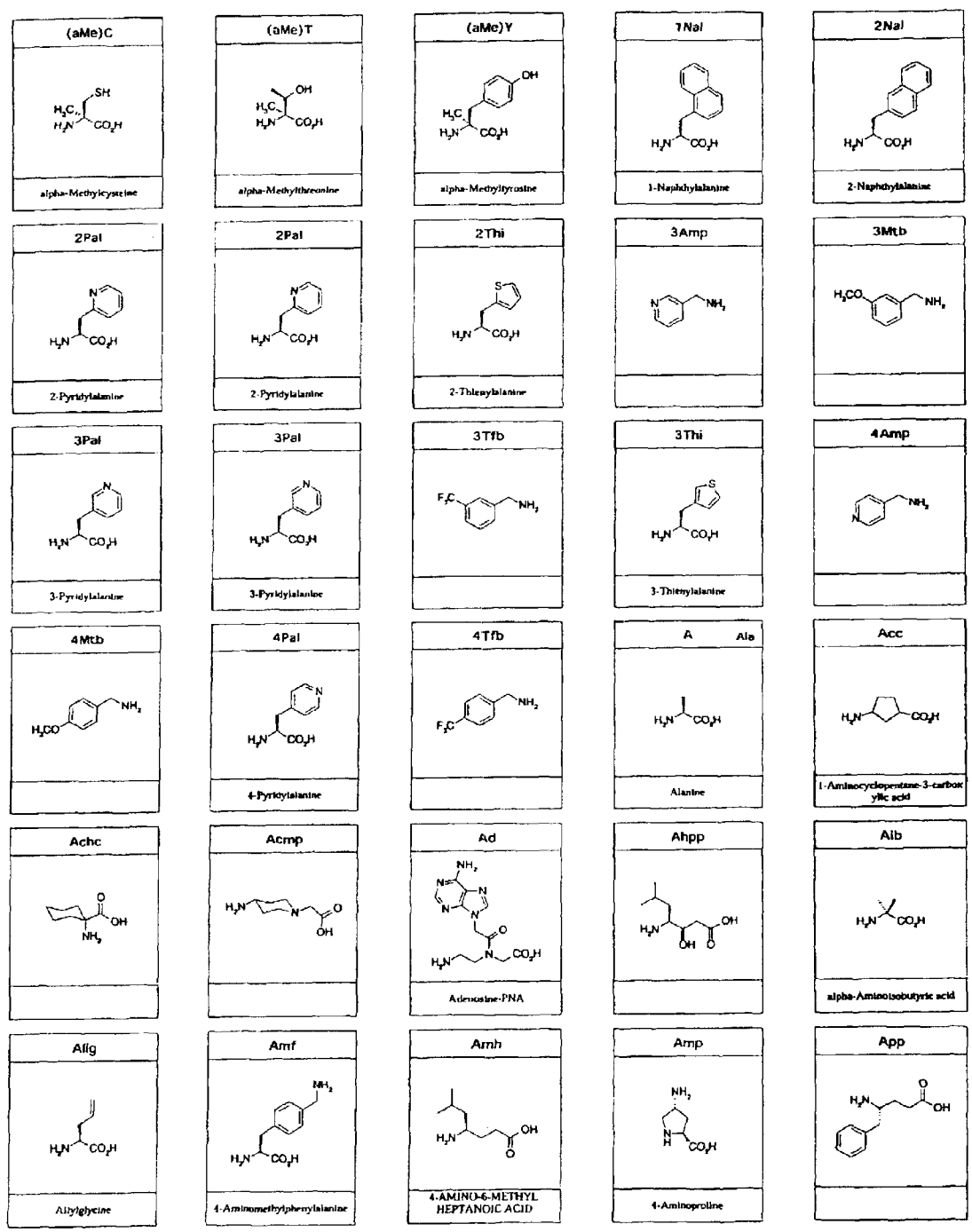
FIG. 1 provides the chemical structures of non-natural amino acids.

Commonly used chemical abbreviations that are not explicitly defined in this disclosure may be found in The American Chemical Society Style Guide, Second Edition; American Chemical Society, Washington, D.C. (1997), "2001 Guidelines for Authors" J. Org. Chem. 66(1), 24A (2001), "A Short Guide to Abbreviations and Their Use in Peptide Science" J. Peptide. Sci. 5, 465–471 (1999).

For the purposes of this application, the term "chemical protecting group" or "protecting group" means any chemical moiety temporarily covalently bound to a molecule throughout one or more synthetic chemistry steps in a reaction sequence to prevent undesirable reactions. Common protecting group strategies are described in "Protecting Groups in Organic Synthesis, Third Ed." by P. Wuts and T. Greene,© 1999 John Wiley & Sons, Inc.

For the purposes of this application, the term "leaving group" means any chemical moiety that is displaced by a nucleophile in a nucleophilic substitution or sequence of addition-elimination reactions. A molecule comprising a leaving group may be isolated or it may be formed in situ as a transient intermediate in a chemical reaction.

For the purposes of this application, the term "aliphatic" describes any acyclic or cyclic, saturated or unsaturated, branched or unbranched carbon compound, excluding aromatic compounds.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3–8 carbon atoms in their ring structure, and more preferably have 5 or 6 carbons in the ring structure. The term $C_1$–$C_6$ includes alkyl groups containing 1 to 6 carbon atoms.

Moreover, the term "alkyl" includes both "unsubstituted alkyls" and "substituted alkyls," the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "arylalkyl" moiety is an alkyl substituted with an aryl (e.g., phenylmethyl (benzyl)). The term "alkyl" also includes the side chains of natural and unnatural amino acids. The term "n-alkyl" means a straight chain (i.e., unbranched) unsubstituted alkyl group.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$–$C_6$ for straight chain, $C_3$–$C_6$ for branched chain). Likewise, cycloalkenyl groups may have from 3–8 carbon atoms in their ring structure, and more preferably have 5 or 6 carbons in the ring structure. The term $C_2$–$C_6$ includes alkenyl groups containing 2 to 6 carbon atoms.

Moreover, the term alkenyl includes both "unsubstituted alkenyls" and "substituted alkenyls," the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond and two carbon atoms. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

In general, the term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, such as naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heterocycles," "heteroaryls," or "heteroaromatics." An aryl group may be substituted at one or more ring positions with substituents.

For the purposes of this application, "DTPA" refers to a chemical compound comprising a substructure composed of diethylenetriamine, wherein the two primary amines are each covalently attached to two acetyl groups and the secondary amine has one acetyl group covalently attached according to the following formula:

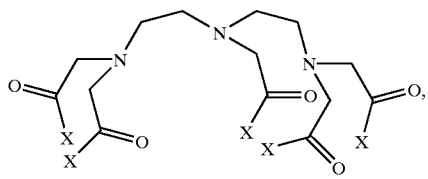

wherein X is a heteroatom electron-donating group capable of coordinating a metal cation, preferably O⁻, OH, $NH_2$, $OPO_3^{2-}$, or NHR, or OR wherein R is any aliphatic group. When each X group is tert-butoxy (tBu), the structure may be referred to as "DTPE" ("E" for ester).

For the purposes of this application, "DOTA" refers to a chemical compound comprising a substructure composed of 1,4,7,11-tetraazacyclododecane, wherein the amines each have one acetyl group covalently attached according to the following formula:

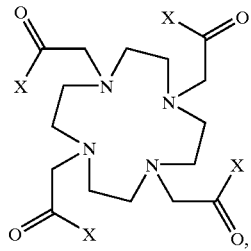

wherein X is defined above.

For the purposes of this application, "NOTA" refers to a chemical compound comprising a substructure composed of 1,4,7-triazacyclononane, wherein the amines each have one acetyl group covalently attached according to the following formula:

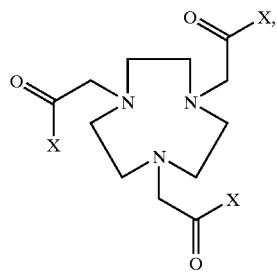

wherein X is defined above.

For the purposes of this application, "DO3A" refers to a chemical compound comprising a substructure composed of 1,4,7,11-tetraazacyclododecane, wherein three of the four amines each have one acetyl group covalently attached and the other amine has a substituent having neutral charge according to the following formula:

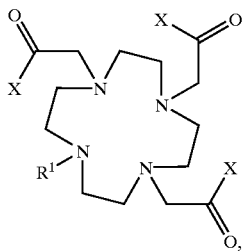

wherein X is defined above and $R^1$ is an uncharged chemical moiety, preferably hydrogen, any aliphatic, alkyl group, or cycloalkyl group, and uncharged derivatives thereof. The preferred chelate "HP"-DO3A has $R^1$=—$CH_2$(CHOH)$CH_3$.

In each of the four structures above, the carbon atoms of the indicated ethylenes may be referred to as "backbone" carbons. The designation "bbDTPA" may be used to refer to the location of a chemical bond to a DTPA molecule ("bb" for "back bone"). Note that as used herein, bb(CO)DTPA-Gd means a C═O moiety bound to an ethylene backbone carbon atom of DTPA.

The terms "chelating ligand," "chelating moiety," and "chelate moiety" may be used to refer to any polydentate ligand which is capable of coordinating a metal ion, including DTPA (and DTPE), DOTA, DO3A, or NOTA molecule, or any other suitable polydentate chelating ligand as is further defined herein, that is either coordinating a metal ion or is capable of doing so, either directly or after removal of protecting groups, or is a reagent, with or without suitable protecting groups, that is used in the synthesis of a contrast agent and comprises substantially all of the atoms that ultimately will coordinate the metal ion of the final metal complex. The term "chelate" refers to the actual metal-ligand complex, and it is understood that the polydentate ligand will eventually be coordinated to a medically useful metal ion.

The term "specific binding affinity" as used herein, refers to the capacity of a contrast agent to be taken up by, retained by, or bound to a particular biological component to a greater degree than other components. Contrast agents that have this property are said to be "targeted" to the "target" component. Contrast agents that lack this property are said to be "non-specific" or "non-targeted" agents. The specific binding affinity of a binding group for a target is expressed in terms of the equilibrium dissociation constant "Kd."

The term "relaxivity" as used herein, refers to the increase in either of the MRI quantities 1/T1 or 1/T2 per millimolar (mM) concentration of paramagnetic ion or contrast agent, which quantities may be different if the contrast agent contains a multiplicity of paramagnetic ions, wherein T1 is the longitudinal or spin-lattice, relaxation time, and T2 is the transverse or spin-spin relaxation time of water protons or other imaging or spectroscopic nuclei, including protons found in molecules other than water. Relaxivity is expressed in units of $mM^{-1}s^{-1}$.

The term "open coordination site" as used herein refers to a site on a metal ion that is generally occupied by a water or solvent molecule.

As used herein, the term "purified" refers to a peptide that has been separated from either naturally occurring organic molecules with which it normally associates or, for a chemically-synthesized peptide, separated from any other organic molecules present in the chemical synthesis. Typically, the polypeptide is considered "purified" when it is at least 70% (e.g., 70%, 80%, 90%, 95%, or 99%), by dry weight, free from any other proteins or organic molecules.

As used herein, the term "peptide" refers to a chain of amino acids that is about 2 to about 75 amino acids in length (e.g., 3 to 50 amino acids).

As used herein, the term "biopolymer" refers to a polymeric substance that is naturally formed in a biological system. Certain biopolymers can be constructed from a defined set of building subunits and with common functionalities linking the subunits, e.g., a peptide is usually constructed from a set of amino acids (both natural and non-natural) with amide bonds linking the subunits.

The term "multimer" for purposes herein is defined as a contrast agent or a subunit thereof comprising at least two covalently bonded chelates or synthetic precursors thereof.

As used herein, the term "natural" or "naturally occurring" amino acid refers to one of the twenty most common occurring amino acids. Natural amino acids modified to provide a label for detection purposes (e.g., radioactive labels, optical labels, or dyes) are considered to be natural amino acids. Natural amino acids are referred to by their standard one- or three-letter abbreviations.

The term "non-natural amino acid" or "non-natural" refers to any derivative of a natural amino acid including D forms, and β and γ amino acid derivatives. It is noted that certain amino acids, e.g., hydroxyproline, that are classified as a non-natural amino acid herein, may be found in nature within a certain organism or a particular protein.

The term "stable," as used herein, refers to compounds that possess stability sufficient to allow manufacture and which maintains the integrity of the compound for a sufficient period of time to be useful and safe for the purposes detailed herein. Typically, such compounds are stable at a temperature of 40° C. or less, in the absence of moisture or other chemically reactive conditions, for at least a week. Combinations of substituents and variables envisioned by this invention are only those that result in the formation of stable compounds.

The terms "target binding" and "binding" for purposes herein refer to non-covalent interactions of a contrast agent with a target. These non-covalent interactions are independent from one another and may be, inter alia, hydrophobic, hydrophilic, dipole-dipole, pi-stacking, hydrogen bonding, electrostatic associations, or Lewis acid-base interactions.

The term "capping moiety" refers to a chelate, organic dye, contrast agent, thrombolytic, or stabilizing moiety. Suitable stabilizing moieties are biologically inert, i.e., does not have biological activity.

Contrast Agents

In general, the present invention relates to MRI, optical, and radionuclide contrast agents that include a targeting polymer (e.g., peptide) in which both the N- and C-terminal amino acids are each conjugated, either directly or via an optional intervening linker-subunit and linker, to at least one chelate of a paramagnetic (for magnetic resonance imaging) or radioactive (for radionuclide imaging) metal ion or an optical dye (for optical imaging). As further exemplified herein, the linker or linker-subunit may be branched and therefore allow for multiple chelates or dyes to be attached to each end of the peptide, i.e. a multimer. The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration unless specifically designated otherwise. Although the specific compounds exemplified in this application may be depicted in a particular stereochemical configuration, compounds having either the opposite stereochemistry at any given chiral center or mixtures thereof are also envisioned. It should be understood that the compounds of this invention may adopt a variety of conformational and ionic forms in solution, in pharmaceutical compositions and in vivo. Although the depictions herein of specific preferred compounds of this invention are of particular conformations and ionic forms, the disclosure of the invention is not so limited.

Novel peptide-based multimers of the present invention offer several advantages as targeted contrast agents.

1. The compounds can deliver two or more capping moieties (e.g., chelates, organic dyes, or thrombolytics) to the target using a single targeting peptide so that sufficient improvement in the tissue contrast will be observed in part because of a meaningful concentration of the imaging moiety around the target.
2. The MRI contrast agents of this invention also exhibit a high relaxivity upon binding to the target due to the receptor induced magnetic enhancement (RIME) effect combined with the ability of the peptide to limit the local motion of individual chelates when bound to the target.
3. The compounds have a high affinity for one or more targets.
4. Since the compounds are relatively easy to synthesize according to the methods described herein and only one peptide per molecule is required, a multiplicity of metal ions or organic dyes may be delivered to a target more economically.

5. The compounds of the invention can have higher in vivo stability (i.e., longer half-lives) from diminished enzyme metabolism (e.g., decreased cleavage by peptidases).

These favorable features of peptide-based multimers according to the present invention make them useful targeted contrast agents.

The chemical structure of MRI and radionuclide contrast agents contemplated by the invention may be illustrated by the formula:

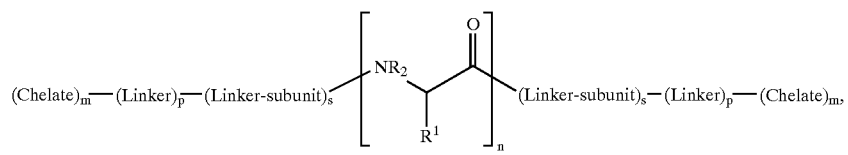

wherein for each m, independently, $1 \leq m \leq 10$, chelate represents a metal chelate complex, p is independently an integer from zero to five; s is independently one or zero; $R^1$ is any amino acid side chain including side chains of non-natural amino acids; $R^2$ is any aliphatic group or hydrogen; and n is an integer from 3 to 50 inclusive. Alternately, $R^1$ and $R^2$ may be taken together to form a ring structure (including proline and substituted versions thereof). Linkers, if present, may be different.

Metal ions preferred for MRI include those with atomic numbers 21–29, 39–47, or 57–83, and, more preferably, a paramagnetic form of a metal ion with atomic numbers 21–29, 42, 44, or 57–83. Particularly preferred paramagnetic metal ions are selected from the group consisting of Gd(III), Fe(III), Mn(II and III), Cr(III), Cu(II), Dy(III), Tb(III and IV), Ho(III), Er(III), Pr(III) and Eu(II and III). Gd(III) is particularly useful. Note that, as used herein, the term "Gd" is meant to convey the ionic form of the metal gadolinium; such an ionic form can be written as GD(III), GD3+, gado, etc., with no difference in ionic form contemplated.

For radionuclide imaging agents, radionuclides $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb, and $^{141}$Ce are particularly useful. Metal complexes with useful optical properties also have been described. See, Murru et al., *J. Chem. Soc. Chem. Comm.* 1993, 1116–1118. For optical imaging using chelates, lanthanide chelates such as La(III), Ce(III), Pr(III), Nd(III), Pn(III), Sm(III), Eu(III), Gd(III), Tb(III), Dy(III), Ho(III), Er(III), Tm(III), Yb(III) and Ln(III) are suitable. Eu(III) and Tb(III) are particularly useful.

Metal chelates should not dissociate to any significant degree during the imaging agent's passage through the body, including while bound to a target tissue. Significant release of free metal ions can result in toxicity, which would generally not be acceptable.

In one embodiment, with reference to the above structure of a contrast agent, m is 2, n, s, $R^1$, and $R^2$ are defined as above, and the Linker moiety comprises:

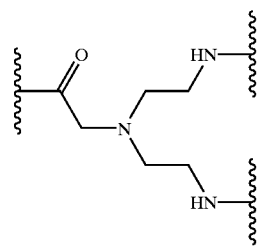

The "Chelate" is preferably bb(CO)DTPA.Gd.

In another embodiment, with reference to the above structure of a contrast agent, m is 2, n, s, $R^1$, and $R^2$ are defined as above, and the linker moiety comprises:

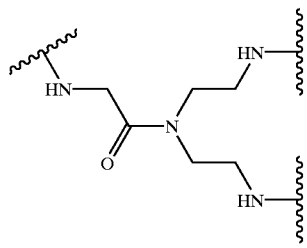

The "Chelate" moiety can be bb(CO)DTPA.Gd.

For the purposes of illustration, one contrast agent contemplated by the instant invention is presented below with the various subunits annotated:

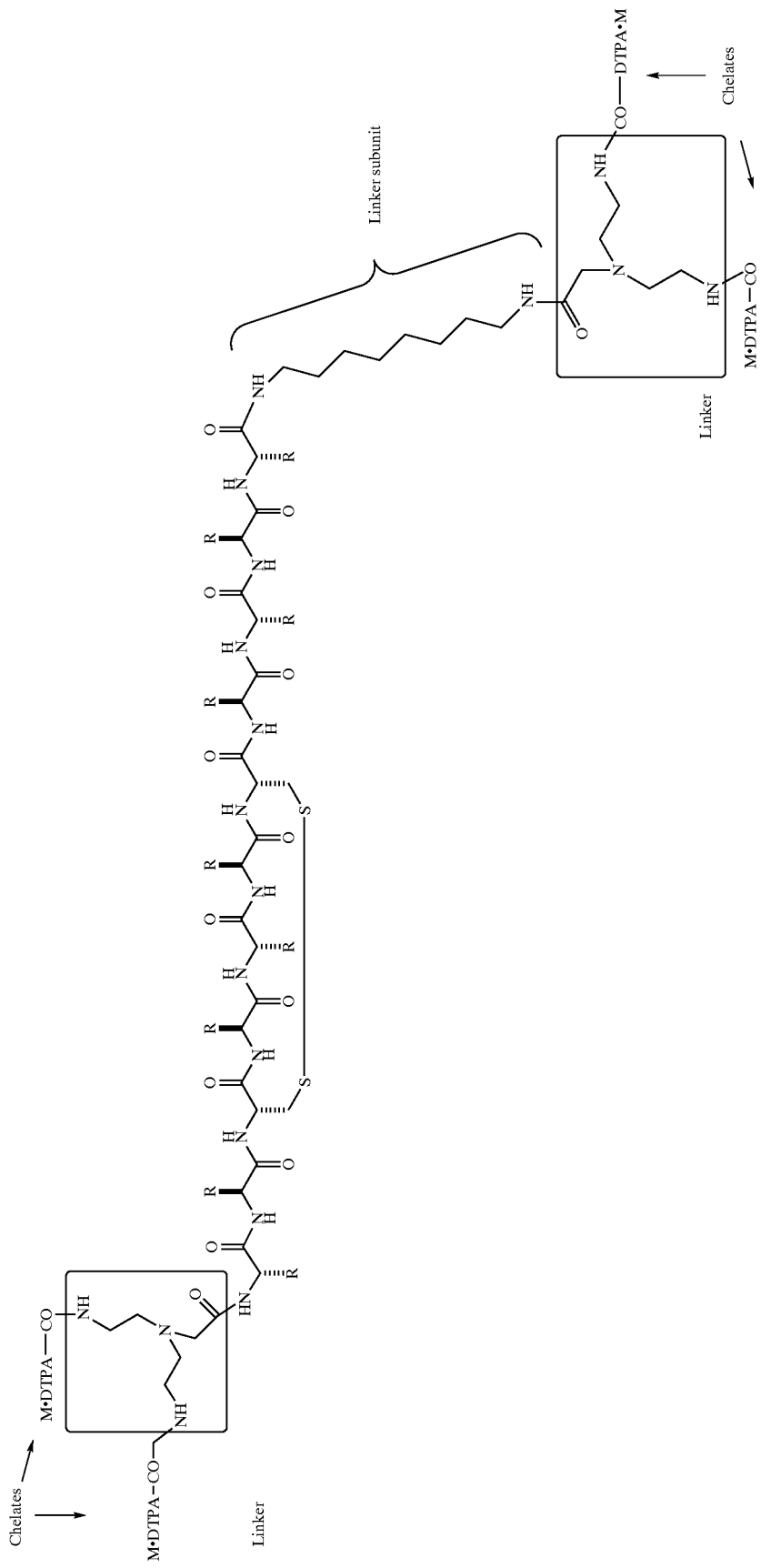

wherein R=amino acid side chains such that the peptide has affinity for a biological target, and m=metal ion (paramagnetic for MRI, radioactive for radionuclide imaging, and fluorescent, luminescent, or absorbant for optical imaging).

The chemical structure of optical contrast agents contemplated by the invention may be illustrated by the formula:

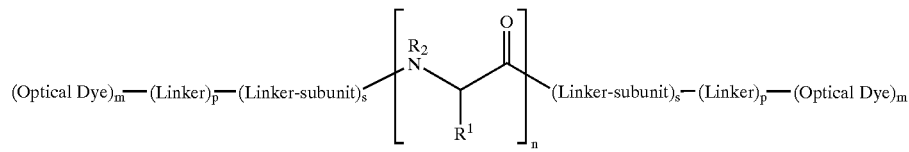

wherein $1 \leq m \leq 10$, p is independently an integer from zero to five, n is 3 to 50 inclusive, $R^1$ is any amino acid side chain including non-natural amino acid side chains, and $R^2$ is any aliphatic group or hydrogen. Alternatively, $R^1$ and $R^2$ taken together form a ring structure (including Pro and derivatives thereof. The N- and C-terminal amino acids of the peptide can be conjugated to the optical dye directly or via an optional linker (e.g., p=0 or 1). The linker moieties can be different.

The optical dye may be an organic dye or an appropriate metal chelate. Organic dyes suitable for optical imaging have been described and include, for example, fluorescent porphyrin and fluorescent phthalocyanines [see, e.g., U.S. Pat. No. 5,641,878], particulate materials [see, e.g., WO 96/23524], and polymethine dyes [see, e.g., WO 97/13490]. Commonly used optical organic dyes are fluorescein, rhodamine [see, e.g., Kojima H, et al., Anal. Chem. 73, 1967–1973 (2001)], tetramethylrhodamine [e.g., Anal. Biochem. 223, 39 (1994)], and Texas red [e.g., Proc. Natl. Acad. Sci. USA 85, 3546 (1988)]. Fluroscein and luminescent lanthanide chelates are particularly useful.

Targets and Target Binding Peptides

The peptide moiety of the contrast agents of the present invention can exhibit specific binding for a biological target and function as a point of attachment for one or more chelates at each terminus. In general, biological targets are present in a low (e.g., micromolar or less) concentration and are inefficiently imaged using existing monomeric gadolinium complex MRI contrast agents. The peptide-based multimeric MRI contrast agents according to the instant invention, however, provide a much higher concentration of the agent at the target as well as high relaxivity to make imaging of these targets possible. Similarly, the peptide-based multimeric radionuclide contrast agents of the invention may deliver more radionuclides to targets so that imaging can be further improved. While not being bound to a particular mechanism, it is thought that targeting creates an increased concentration of the imaging agent at the site to be imaged and increases the relaxivity of MRI contrast agents in the bound state through the RIME effect and also limits local chelate motion by rigidifying the bound peptide.

Targets for the contrast agents can be in any body compartment, cell, organ, or tissue or component thereof. Preferred targets are those that are of diagnostic and therapeutic relevance, i.e., those that are associated with disease states. Particularly preferred targets are those in association with body fluids, and particularly those in association with blood, plasma, lymph and fluids of the central nervous system. Other preferred targets are proteins and receptors that either exist in high concentration or have a large number of binding sites for certain ligands. Included among such target proteins are enzymes and glycoproteins.

Human serum albumin (HSA) and fibrin are useful targets for MRI contrast agents. For vascular blood pool imaging, serum albumin is a preferred target. Since HSA is present at high concentration in serum (approximately 0.6 mM) and binds a wide array of molecules with reasonably high affinity, it is a preferred target plasma protein for blood pool contrast agents. HSA is a particularly preferred target for cardiovascular imaging; see U.S. patent application Ser. No. 08/875,365, filed Jul. 24,1997, and WO 96/23526.

For imaging thrombi, fibrin is a preferred target because it is present in all clots and it can be targeted without interfering with the normal thrombolytic process. For additional details concerning target binding moieties that include fibrin-binding peptides, see PCT Patent Application WO 01/09188.

Other protein targets include, but are not limited to, alpha acid glycoprotein, fibrinogen, collagen, platelet GPIIb/IIIa receptor, chemotactic peptide receptor, somatostatin receptors, vasoactive intestinal peptides (VIP) receptor, bombesin/Gastrin release peptide receptor, and integrin receptors.

Suitable peptides for use in the invention include those capable of specifically binding to the targets identified above. Included among such peptides are RGD-containing peptides targeting platelet GPIIb/IIIa receptor for thrombus imaging, chemotactic peptides targeting white blood cells for infection/inflammation imaging, Octreotide and P-829 peptide targeting somastatin receptors for tumor imaging, vasoactive intestinal peptides (VIP) targeting VIP receptor for tumor imaging, bombesin analogs targeting bombesin/Gastrin release peptide receptor for tumor imaging, and RGD-containing peptides targeting the integrin $\alpha v\beta 3$ (vitronectin receptor) for tumor imaging.

In principle, any peptide with an affinity for a biological target may be used in a contrast agent of the invention. The peptide may be linear or cyclic. Ordinarily, insoluble lipophilic peptides are considered unsuitable for pharmacological use, but such peptides may be suitable according to the invention because addition of hydrophilic metal chelates to the two termini of the peptide may increase solubility. For ease of synthesis and cost considerations, it is preferred that the peptides have between 3 to 50 amino acids (e.g., 3 to 30, 3 to 20, 3 to 15, 5 to 30, 5 to 20, 5 to 15, 10 to 12 amino acids in length).

In the targeting peptides of the invention, a great variety of amino acids can be used. Suitable amino acids include natural and non-natural amino acids. Amino acids with many different protecting groups appropriate for immediate use in the solid phase synthesis of peptides are commercially available. In addition to the twenty most common naturally occurring amino acids, the following non-natural amino acids or amino acid derivatives may be constituents of the peptide targeting group of the invention (common abbreviations in parentheses, see FIG. 1): β-Alanine (β-Ala), γ-Aminobutyric Acid (GABA), 2-Aminobutyric Acid (2-Abu), α,β-Dehydro-2-aminobutyric Acid (Δ-Abu), 1-Aminocyclopropane-1-carboxylic Acid (ACPC), Aminoisobutyric Acid (Aib), 2-Amino-thiazoline-4-carboxylic Acid, 5-Aminovaleric Acid (5-Ava), 6-Aminohexanoic Acid (6-Ahx), 8-Aminooctanoic Acid (8-Aoc), 11-Aminoundecanoic Acid (11-Aun), 12-Aminododecanoic Acid (12-Ado), 2-Aminobenzoic Acid (2-Abz), 3-Aminobenzoic Acid (3-Abz), 4-Aminobenzoic Acid (4-Abz), 4-Amino-3-hydroxy-6-methylheptanoic Acid (Statine, Sta), Aminooxyacetic Acid (Aoa), 2-Aminotetraline-2-carboxylic Acid (Atc), 4-Amino-5-cyclohexyl-3-hydroxypentanoic Acid (ACHPA), para-Aminophenylalanine (4-NH2-Phe), Biphenylalanine (Bip), para-Bromophenylalanine (4-Br-Phe), ortho-Chlorophenylalanine (2-Cl-Phe), meta-Chlorophenylalanine (3-Cl-Phe), para-Chlorophenylalanine (4-Cl-Phe), meta-Chlorotyrosine (3-Cl-Tyr), para-Benzoylphenylalanine (Bpa), tert-Butylglycine (Tle), Cyclohexylalanine (Cha), Cyclohexylglycine (Chg), 2,3-Diaminopropionic Acid (Dpr), 2,4-Diaminobutyric Acid (Dbu), 3,4-Dichlorophenylalanine (3,4-Cl2-Phe), 3,4-Diflurorphenylalanine (3,4-F2-Phe), 3,5-Diiodotyrosine (3,5-I2-Tyr), ortho-Fluorophenylalanine (2-F-Phe), meta-Fluorophenylalanine (3-F-Phe), para-Fluorophenylalanine (4-F-Phe), meta-fluorotyrosine (3-F-Tyr), Homoserine (Hse), Homophenylalanine (Hfe), Homotyrosine (Htyr), 5-Hydroxytryptophan (5-OH-Trp), Hydroxyproline (Hyp), para-Iodophenylalanine (4-I-Phe), 3-Iodotyrosine (3-I-Tyr), Indoline-2-carboxylic Acid (Idc), Isonipecotic Acid (Inp), meta-methyltyrosine (3-Me-Tyr), 1-Naphthylalanine (1-Nal), 2 Naphthylalanine (2-Nal), para-Nitrophenylalanine (4-NO2-Phe), 3-Nitrotyrosine (3-NO2-Tyr), Norleucine (Nle), Norvaline (Nva), Ornithine (Orn), ortho-Phosphotyrosine (H2PO3-Tyr), Octahydroindole-2-carboxylic Acid (Oic), Penicillamine (Pen), Pentafluorophenylalanine (F5-Phe), Phenylglycine (Phg), Pipecolic Acid (Pip), Propargylglycine (Pra), Pyroglutamic Acid (pGlu), Sarcosine (Sar), Tetrahydroisoquinoline-3-carboxylic Acid (Tic), and Thiazolidine-4-carboxylic Acid (Thioproline, Th). Stereochemistry of amino acids may be designated by preceding the name or abbreviation with the designation "D" or "d" or "L" or "l" as appropriate. Additionally, αN-alkylated amino acids may be employed, as well as amino acids having amine-containing side chains (such as Lys and Orn) in which the amine has been acylated or alkylated.

Peptides of the invention can include the general formula $P^*$-$Y^*$-$X_1^*$-$L^*$ (SEQ ID NO:1), wherein $P^*$ is a proline or a non-natural derivative of proline, $Y^*$ is a tyrosine or a non-natural derivative thereof, $X_1^*$ is glycine or aspartic acid, or a non-natural derivative of glycine or aspartic acid, and $L^*$ is leucine or a non-natural derivative thereof. Typically, at least one of $P^*$, $Y^*$, $X_1^*$, or $L^*$ is a non-natural derivative of the respective amino acid. For example, $X_1^*$ can be glycine or aspartic acid, $L^*$ can be leucine, and at least one of $P^*$ or $Y^*$ can be a non-natural derivative, such as hydroxyproline or a tyrosine substituted at the 3 position with F, Cl, Br, I, or $NO_2$.

A peptide of the invention also can include the general formula $X_1$-$X_2$-C-$P^*$-$Y^*$-$X_3$-L-C-$X_4$-$X_5$-$X_6$ (SEQ ID NO:2), wherein $P^*$ is a proline or a non-natural derivative thereof, $Y^*$ is a tyrosine or a non-natural derivative thereof, $X_1$ is W, Y, F, S, Bip, Hx, Dpr, Cy, Gu, Ad, Hfe, 3-Pal, 4-Pal, DopaMe2, nTyr, dW, dF, F(3/4*), or Y(3*). F(3/4*) can be a phenylalanine substituted at either the 3 or the 4 position with a moiety such as $CH_3$, $CF_3$, $NH_2$, $CH_2NH_2$, CN, F, Cl, Br, I, Et, or Ome. Y(3*) can be a tyrosine substituted at the 3 position with a moiety such as F, Cl, Br, I, and $NO_2$. $X_2$ can be E, H, dE, S, H(Bzl), 2-Pal, Dpr, or Th; $X_3$ can be G or D; $X_4$ can be H, F, Y, or W; $X_5$ can be I, L, V, N, Bpa, Bal, Hfe, Nle, Tle, Nval, Phg, Cha, Taz, Fua, Th, 4-Pal, or F(3/4*), wherein F(3/4*) is a phenylalanine substituted at either the 3 or the 4 position with a moiety such as $CF_3$, Et, iPr, or OMe; $X_6$ can be N, Q, I, L, or V, or not present. Typically, at least one of $X_1$, $X_2$, $X_5$, $P^*$, and $Y^*$ is a non-natural derivative of an amino acid. For example, $P^*$ can be proline and $Y^*$ can be a non-natural derivative of tyrosine substituted at the 3 position with a moiety such as F, Cl, Br, I, or $NO_2$. Alternatively, $P^*$ can be a non-natural derivative of proline such as 4-hydroxyproline and $Y^*$ can be tyrosine. Such peptides can form a disulfide bond under non-reducing conditions.

Another example of a peptide that can bind fibrin includes the general formula C-$P^*$-$Y^*$-$X_1$-L-C (SEQ ID NO:3), wherein $X_1$ is G or D, $P^*$ is proline or its non-natural derivative 4-hydroxyproline; $Y^*$ is tyrosine or a non-natural derivative of tyrosine substituted at the 3 position with a moiety such as F, Cl, Br, I, or $NO_2$. Typically, at least one of $P^*$ or $Y^*$ is a non-natural derivative of the respective amino acid. For example, the peptide can have the following sequences: W-dE-C-P(4-OH)-Y(3-Cl)-G-L-C-W-I-Q (SEQ ID NO:4), Y-dE-C-P(4-OH)-Y(3-Cl)-G-L-C-Y-I-Q (SEQ ID NO:5), Y-dE-C-P(4-OH)-Y(3-Cl)-G-L-C-W-I-Q (SEQ ID NO:6), W-dE-C-P(4-OH)-Y(3-Cl)-G-L-C-Y-I-Q (SEQ ID NO:7), W-dE-C-P(4-OH)-Y(3-Cl)-D-L-C-W-I-Q (SEQ ID NO:8), Y-dE-C-P(4-OH)-Y(3-Cl)-D-L-C-Y-I-Q (SEQ ID NO:9), Y-dE-C-P(4-OH)-Y(3-Cl)-D-L-C-W-I-Q (SEQ ID NO:10), W-dE-C-P(4-OH)-Y(3-Cl)-D-L-C-Y-I-Q (SEQ ID NO:11), F(4-OMe)-H-C-P(4-OH)-Y(3-Cl)-D-L-C-H-I-L (SEQ ID NO:12), Y-H-C-P(4-OH)-Y(3-Cl)-G-L-C-W-I-Q (SEQ ID NO: 13), W-dE-C-P-Y(3-Cl)-G-L-C-W-I-Q (SEQ ID NO: 14), W-dE-C-P(4-OH)-Y-G-L-C-W-I-Q (SEQ ID NO: 15), or F-H-C-P-(4-OH)-Y(3-Cl)-D-L-C-H-I-L (SEQ ID NO:16). Such peptides can form disulfide bonds under non-reducing conditions.

According to standard synthesis methods such as those disclosed in WO 01/09188 or in WO 01/08712, peptides having the sequence set forth in Table 1 were synthesized (structure confirmed by mass spectrometry), cyclized, and assayed for affinity to the DD(E) fragment of fibrin. Each peptide was found to have a $Kd \leq 10$ μM ("-" indicates truncation).

TABLE 1

| Kd(μM) vs. DD(E) | $X_1$ | $X_2$ | C | P(4-OH) | $Y^*$ | $X_3$ | L | C | $X_4$ | $X_5$ | $X_6$ |
|---|---|---|---|---|---|---|---|---|---|---|---|
| ≤0.1 | F(4-OMe) | H | C | Hyp | Y(3-Cl) | D | L | C | H | I | L |
| ≤0.1 | F(4-OMe) | H | C | Hyp | Y(3-Cl) | D | L | C | H | I | |
| ≤0.1 | F(4-OMe) | H | C | Hyp | Y(3-I) | D | L | C | H | Bpa | |
| ≤0.1 | F | H | C | Hyp | Y(3-I) | D | L | C | H | Hfe | |
| ≤0.1 | F | H | C | Hyp | Y(3-I) | D | L | C | H | Bpa | |

TABLE 1-continued

| Kd(μM) vs. DD(E) | X₁ | X₂ | C | P(4-OH) | Y* | X₃ | L | C | X₄ | X₅ | X₆ |
|---|---|---|---|---|---|---|---|---|---|---|---|
| ≦0.1 | Y(3-Cl) | H | C | Hyp | Y(3-I) | D | L | C | H | I | |
| ≦0.1 | Y | D-E | C | Hyp | Y(3-Cl) | G | L | C | W | I | Q |
| ≦0.1 | F(4-OMe) | H | C | Hyp | Y(3-I) | D | L | C | H | I | L |
| ≦0.1 | F(4-OMe) | H(Bzl) | C | Hyp | Y(3-Cl) | D | L | C | H | Bpa | |
| ≦0.1 | F | H | C | Hyp | Y(3-Cl) | D | L | C | H | I | |
| ≦0.1 | F(4-OMe) | H | C | Hyp | Y(3-I) | D | L | C | H | I | |
| ≦0.1 | 3Pal | H | C | Hyp | Y(3-I) | D | L | C | H | I | |
| ≦0.1 | 4Pal | H | C | Hyp | Y(3-I) | D | L | C | H | I | |
| ≦0.1 | F(4-F) | H | C | Hyp | Y(3-I) | D | L | C | H | I | |
| ≦0.1 | Y(3-I) | H | C | Hyp | Y(3-I) | D | L | C | H | I | |
| ≦0.1 | F | H | C | Hyp | Y(3-I) | D | L | C | H | I | L |
| ≦0.1 | F(4-OMe) | H | C | Hyp | Y(3-Cl) | D | L | C | H | Bpa | L |
| ≦0.1 | F(4-OMe) | H | C | Hyp | Y(3-I) | D | L | C | H | Bpa | L |
| ≦0.1 | F | H(Bzl) | C | Hyp | Y(3-Cl) | D | L | C | H | I | L |
| ≦0.1 | 1Nal | H | C | Hyp | Y(3-I) | D | L | C | H | I | |
| ≦0.1 | MTyr | H | C | Hyp | Y(3-I) | D | L | C | H | I | |
| ≦0.1 | F(4-OMe) | H(Bzl) | C | Hyp | Y(3-I) | D | L | C | H | Bpa | |
| ≦0.1 | F(4-OMe) | H(Bzl) | C | Hyp | Y(3-Cl) | D | L | C | H | I | |
| ≦0.1 | F | H | C | Hyp | Y(3-I) | D | L | C | 3Pal | I | |
| ≦0.1 | F(4-I) | H | C | Hyp | Y(3-I) | D | L | C | H | I | |
| ≦0.1 | F(4-Br) | H | C | Hyp | Y(3-I) | D | L | C | H | I | |
| ≦0.1 | F(4-Me) | H | C | Hyp | Y(3-I) | D | L | C | H | I | |
| ≦0.1 | F(4-CF3) | H | C | Hyp | Y(3-I) | D | L | C | H | I | |
| ≦0.1 | F(4-CN) | H | C | Hyp | Y(3-I) | D | L | C | H | I | |
| ≦0.1 | Y(3-NO2) | H | C | Hyp | Y(3-I) | D | L | C | H | I | |
| ≦0.1 | Y(2-F) | H | C | Hyp | Y(3-I) | D | L | C | H | I | |
| ≦0.1 | F(4-CH2NH2) | H | C | Hyp | Y(3-I) | D | L | C | H | I | |
| ≦0.1 | F(4-NH2) | H | C | Hyp | Y(3-I) | D | L | C | H | I | |
| ≦0.1 | F(34-F2) | H | C | Hyp | Y(3-I) | D | L | C | H | I | |
| ≦0.1 | DopaMe2 | H | C | Hyp | Y(3-I) | D | L | C | H | I | |
| ≦0.1 | F(2-OMe) | H | C | Hyp | Y(3-I) | D | L | C | H | I | |
| ≦0.1 | F(3-Me) | H | C | Hyp | Y(3-I) | D | L | C | H | I | |
| ≦0.1 | F | H | C | Hyp | Y(3-I) | D | L | C | H | I | |
| ≦0.1 | F | H | C | Hyp | Y(3-I) | D | L | C | H | F(3-CF3) | |
| ≦0.1 | F(3-CF3) | H | C | Hyp | Y(3-I) | D | L | C | H | I | |
| ≦0.1 | F(3-OMe) | H | C | Hyp | Y(3-I) | D | L | C | H | I | |
| ≦0.1 | Hfe | H | C | Hyp | Y(3-I) | D | L | C | H | I | |
| ≦0.1 | nTyr | H | C | Hyp | Y(3-I) | D | L | C | H | I | |
| ≦0.1 | W | E | C | Hyp | Y(3-Cl) | G | L | C | W | I | Q |
| ≦0.1 | F | H | C | Hyp | Y(3-I) | D | L | C | H | I | L |
| ≦0.1 | F | H | C | Hyp | Y(3-Cl) | D | L | C | H | I | L |
| ≦0.1 | F(4-OMe) | H(Bzl) | C | Hyp | Y(3-Cl) | D | L | C | H | I | |
| ≦0.1 | F | H | C | Hyp | Y(3-I) | D | L | C | H | Nle | |
| ≦0.1 | F | H | C | Hyp | Y(3-I) | D | L | C | H | Tle | |
| ≦0.1 | F | H | C | Hyp | Y(3-I) | D | L | C | H | F(4-CF3) | |
| ≦0.1 | F | H | C | Hyp | Y(3-I) | D | L | C | H | Bip | |
| ≦0.1 | F | H | C | Hyp | Y(3-I) | D | L | C | H | F(4-Et) | |
| ≦0.1 | F | H | C | Hyp | Y(3-I) | D | L | C | H | F(4-OMe) | |
| ≦0.1 | F | H | C | Hyp | Y(3-I) | D | L | C | H | F(3-OMe) | |
| ≦0.1 | F(F5) | H | C | Hyp | Y(3-I) | D | L | C | H | I | |
| ≦0.1 | F | H | C | Hyp | Y(3-F) | D | L | C | H | I | L |
| ≦0.1 | W | E | C | Hyp | Y(3-Cl) | G | L | C | W | I | Q |
| ≦0.2 | T | D-E | C | Hyp | Y(3-Cl) | G | L | C | W | I | Q |
| ≦0.2 | F | H | C | P | Y(3-Cl) | D | L | C | H | I | L |
| ≦0.2 | Y(26-Me) | H | C | Hyp | Y(3-I) | D | L | C | H | I | |
| ≦0.2 | W | E | C | Hyp | Y(3-Cl) | G | L | C | H | I | Q |
| ≦0.2 | D-F | D-E | C | Hyp | Y(3-Cl) | G | L | C | W | I | Q |
| ≦0.2 | Y | E | C | Hyp | Y(3-Cl) | G | L | C | Y | I | Q |
| ≦0.2 | W | E | C | Hyp | Y(3-Cl) | G | L | C | F | I | Q |
| ≦0.2 | H | D-E | C | Hyp | Y(3-Cl) | G | L | C | W | I | Q |
| ≦0.2 | F | H | C | Hyp | Y(3-I) | D | L | C | H | I | L |
| ≦0.2 | W | E | C | P | Y | D | L | C | W | I | Q |
| ≦0.2 | F | H | C | Hyp | Y(3-I) | D | L | C | H | nVal | |
| ≦0.2 | F | H | C | Hyp | Y(3-I) | D | L | C | H | Phg | |
| ≦0.2 | F | H | C | Hyp | Y(3-I) | D | L | C | H | F(3-Me) | |
| ≦0.2 | F | H | C | Hyp | Y(3-I) | D | L | C | 4Pal | I | |
| ≦0.2 | S | D-E | C | Hyp | Y(3-Cl) | G | L | C | W | I | Q |
| ≦0.3 | W | E | C | Hyp | Y(3-Cl) | G | L | C | Y | I | Q |
| ≦0.3 | Y | E | C | Hyp | Y(3-Cl) | G | L | C | W | I | Q |
| ≦0.3 | F | D-E | C | Hyp | Y(3-Cl) | G | L | C | W | I | Q |
| ≦0.3 | F | H | C | P | Y | D | L | C | H | I | L |
| ≦0.3 | F | H | C | Hyp | Y(3-I) | D | L | C | H | I | L |
| ≦0.3 | F | H | C | Hyp | Y | D | L | C | H | Bpa | |
| ≦0.4 | F | H | C | Hyp | Y(3-Cl) | G | L | C | H | I | L |
| ≦0.4 | S(Bzl) | H | C | P | Y | D | L | C | H | I | L |

TABLE 1-continued

| Kd(μM) vs. DD(E) | X$_1$ | X$_2$ | C | P(4-OH) | Y* | X$_3$ | L | C | X$_4$ | X$_5$ | X$_6$ |
|---|---|---|---|---|---|---|---|---|---|---|---|
| ≦0.4 | H | E | C | Hyp | Y(3-Cl) | G | L | C | H | I | Q |
| ≦0.4 | F(4-OMe) | H | C | Hyp | Y | D | L | C | H | I | L |
| ≦0.4 | F | H | C | Hyp | Y(3-I) | D | L | C | Bpa | I | |
| ≦0.4 | Ad | H | C | Hyp | Y(3-I) | D | L | C | H | I | |
| ≦0.5 | F | H | C | Hyp | Y(3-Cl) | F | L | C | H | I | L |
| ≦0.5 | F | E | C | Hyp | Y(3-Cl) | G | L | C | W | I | Q |
| ≦0.5 | F | H | C | Hyp | Y(3-Cl) | 2-Nal | L | C | H | I | L |
| ≦0.5 | F | H | C | Hyp | Y | D | L | C | H | I | L |
| ≦0.5 | Hfe | H | C | Hyp | Y | D | L | C | H | I | L |
| ≦0.5 | Bip | H | C | Hyp | Y | D | L | C | H | I | L |
| ≦0.5 | W | E | C | P | Y | G | L | C | W | I | Q |
| ≦0.5 | F(4-OMe) | W | C | Hyp | Y(3-I) | D | L | C | H | I | |
| ≦0.5 | F | H | C | Hyp | Y(3-I) | D | L | C | 2Pal | I | |
| ≦0.5 | F | H | C | Hyp | Y(3-I) | D | L | C | Taz | I | |
| ≦0.5 | F | H | C | Hyp | Y(3-I) | D | L | C | Dht | I | |
| ≦0.5 | Gu | H | C | Hyp | Y(3-I) | D | L | C | H | I | |

A peptide also can have the general formula C-D-Y-Y-G-T-C-X$_{10}$ (SEQ ID. NO:17), wherein X$_{10}$ is n(decyl)G, n(4-PhBu)G, MeL, Bpa, Bip, Me-Bip, F(4*), F(3-Me), F(3,4-difluoro), Amh, Hfe, Y(3,5-di-iodo), Pff, 1Nal, d1Nal, or MeL, wherein F(4*) is a phenylalanine substituted at the 4 position with a moiety such as Et, CF$_3$, I, or iPr. In some embodiments, a peptide can include additional residues, X$_1$, P*, and/or X$_{11}$, to provide the general formula: C-D-Y-Y-G-T-C-X$_{10}$-X$_{11}$ (SEQ ID. NO:18) or X$_1$-P*-C-D-Y-Y-G-T-C-X$_{10}$-X$_{11}$ (SEQ ID. NO:26), wherein X$_1$ is any natural or non-natural amino acid, P* is proline or a non-natural derivative thereof, and X$_{11}$ is D, dD, βD, Inp, Nip, Me-D, Cop, or Cmp. For example, a peptide can have the sequence of L-P-C-D-Y-Y-G-T-C-n(Decyl)G-dD (SEQ ID NO:19), L-P-C-D-Y-Y-G-T-C-n(Decyl)G-D (SEQ ID NO:20), L-P-C-D-Y-Y-G-T-C-Bip-D (SEQ ID NO:21), L-P-C-D-Y-Y-G-T-C-Bip-dD (SEQ ID NO:22), L-P-C-D-Y-Y-G-T-C-MeL-Inp (SEQ ID NO:23), L-P-C-D-Y-Y-G-T-C-MeL-Cmp (SEQ ID NO:24), or L-P-C-D-Y-Y-G-T-C-MeBip-D (SEQ ID NO:25).

Peptides having the formula of SEQ ID NO:26 were synthesized (structure confirmed by mass spectrometry) according to standard synthesis methods, such as those disclosed in WO 01/09188 or in WO 01/08712, and assayed for affinity to the DD(E) fragment of fibrin. Each peptide was found to have a Kd≦10 μM (Table 2).

TABLE 2

| X$_{01}$ | X$_{10}$ | X$_{11}$ |
|---|---|---|
| L | n(Decyl)G | dD |
| L | n(Decyl)G | D |
| L | MeL | Inp |
| L | Bip | D |
| L | Bip | dD |
| L | Me-Bip | D |
| L | MeL | Cmp |
| L | Bip | D |
| L | L | D |
| Cha | Bip | D |

The ability of the peptides to bind a target such as HSA or fibrin can be assessed by known methodology. For example, affinity of the peptide for fibrin can be assessed using the DD(E) fragment of fibrin, which contains subunits of 55 kD (Fragment E) and 190 kD (Fragment DD). The DD(E) fragment can be biotinylated and immobilized via avidin to a solid substrate (e.g., a multi-well plate). Peptides can be incubated with the immobilized DD(E) fragment in a suitable buffer and binding detected using known methodology. See, for example, WO 01/09188.

N- and C-Terminus Linker-subunits and Linker

If present, linker-subunits and linkers are used to covalently attach capping moieties such as chelates, thrombolytics, and other groups to the two ends of a peptide. A linker-subunit moiety can (i) convert the functionality of either the C-terminus carboxylate to an amine functional group or the N-terminus amine to a carboxylate functional group; or (ii) provide a spacer moiety or group between the peptide terminus and the linker, if present, or capping group. In one embodiment, a peptide can be reacted with a linker-subunit to form a modified peptide having a C-terminal amine functional group and a N-terminal amine functional group. In another embodiment, a peptide can be reacted with a linker-subunit to form a modified peptide having a N-terminal carboxylate functional group and a C-terminal carboxylate functional group. In another embodiment, a peptide can be synthesized from a C-terminal linker-subunit that is bound to a resin, whereby upon cleaving the peptide from the resin, a peptide having a C-terminal amine functional group is produced. In still another embodiment, a linker-subunit can be used as a spacer group and not to change the terminus functional group. A linker-subunit may have multiple functional groups for attachment of linker moieties or capping moieties. Many types of reactions can be used, including acylation, reductive amination, nucleophilic displacement reactions, urea formation, thiourea formation, and chemoselective ligation in chemically conjugating the linker-subunit to the peptide, linker, and/or capping moieties. One advantage of using a linker-subunit is to create similar functional groups on the peptide, thereby facilitating subsequent synthesis.

The linker moiety can be used to covalently attach one or more capping moieties to the peptide terminus. The linker may be branched or unbranched and may comprise multiple functional groups for precursor chelate and chelate attachment. The chemical structure of the linker may affect the physical and pharmacological properties of the contrast agent, such as affinity, stability, blood half-life, relaxivity, and plasma protein binding. Linkers may be substituted with alkyl, aryl, alkenyl, or alkynyl groups. Linkers, if present, at each termini, typically are relatively small and rigid for MRI contrast agents. For example, a linker can have a molecular weight less than about 350 (e.g., less than about 200).

An example of a C-terminal linker-subunit moiety and a C- and N-terminal linker is

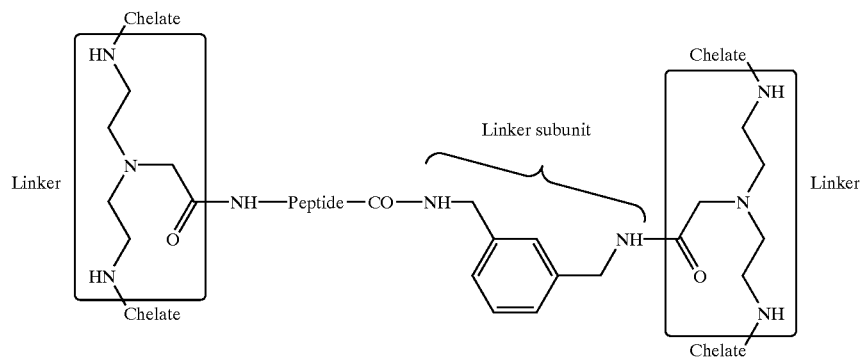

illustrated in the following structure:

The C-terminus carboxylate of a peptide may be converted to an amine functional group with a linker-subunit (e.g., a diamine synthon) to form a peptide having an amine functional group on each end of the peptide to which the remaining linker moiety can be attached. Examples of such peptides modified to have a C-terminal amine function group are:

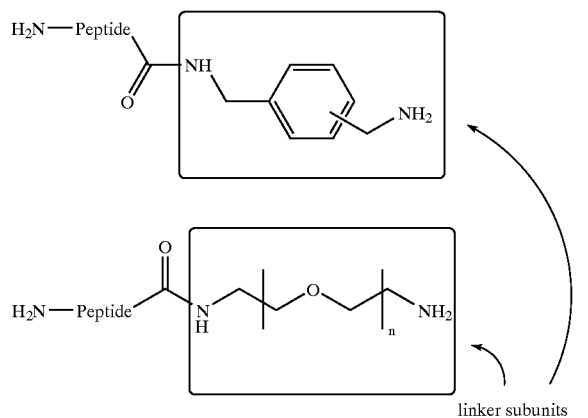

linker subunits

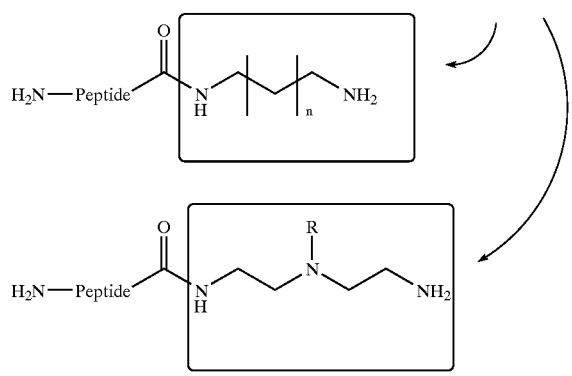

Wherein n=1 to 4.

Many diamine C-terminal linker-subunits can be conveniently derived from a solid phase resin:

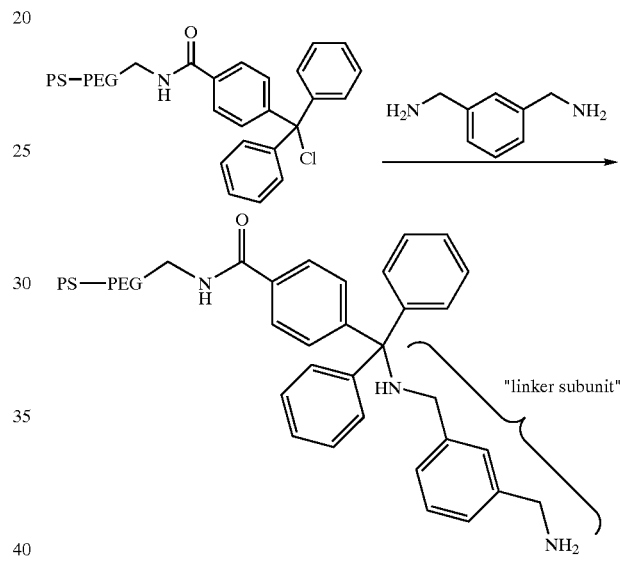

The following resins (R) are commercially available from Nova Biochem:

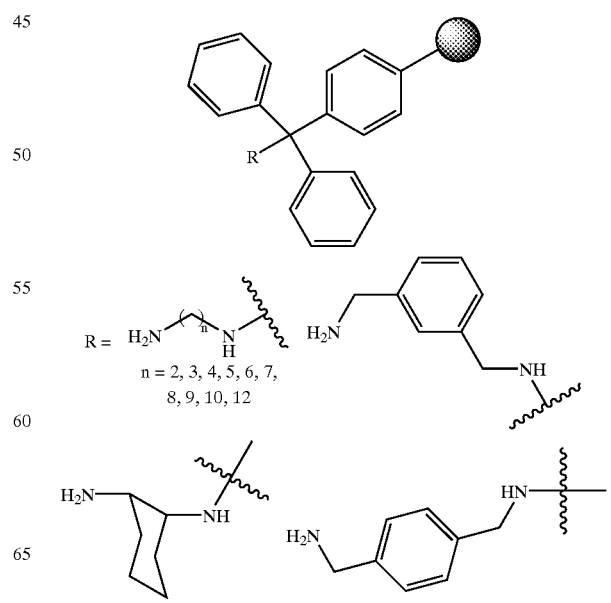

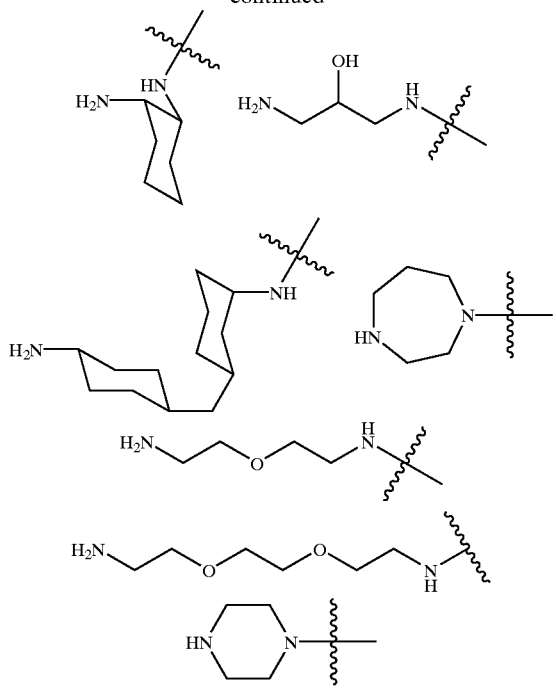

In some cases, the following linker-subunits may be employed as spacer groups at the N-terminal amine functional group:

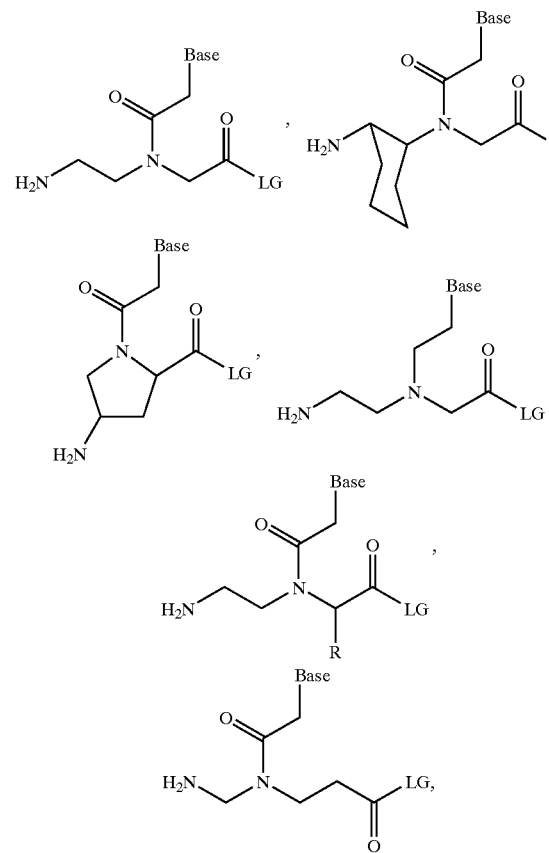

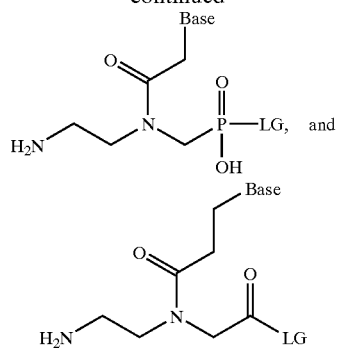

wherein "Base" is a purine or pyrimidine base ("Ad"= adenosine, "Gu"=guanosine, "T"=thymine, "Cy"=cytosine) and "LG" is a leaving group such as OH, activated ester, halide, or anhydride.

Additionally, αN-alkylated amino acids may be employed, as well as amino acids having amine-containing side chains (such as Lys and Orn) in which the amine has been acylated or alkylated as in the following examples:

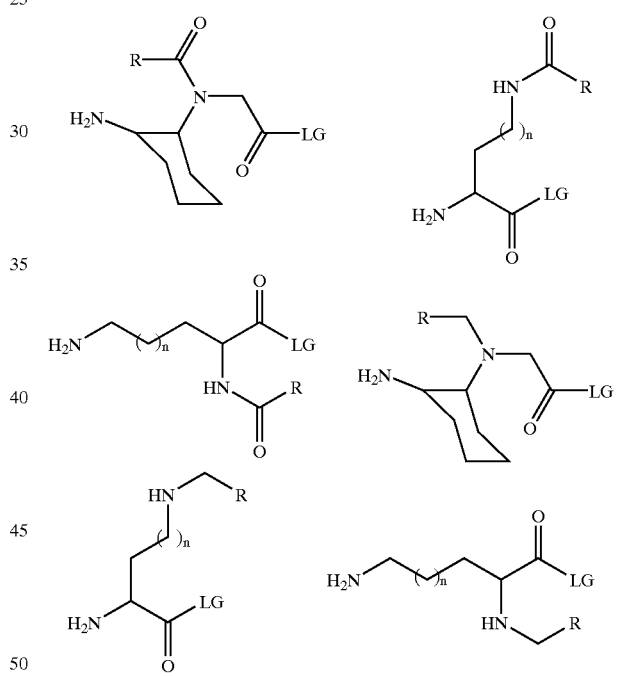

wherein n is an integer from 0 to 3, R is any aliphatic or aromatic group, and LG is a leaving group such as OH, activated ester, halide, and anhydride.

Still more linker-subunits include the following:

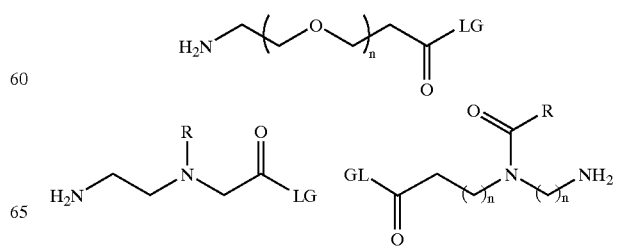

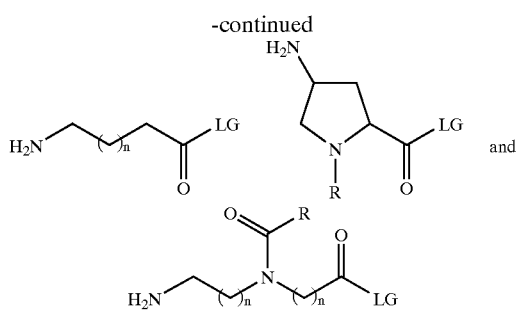

wherein n is independently 1 or 2, R is any aliphatic or aromatic group, and LG is a leaving group such as OH, activated ester, halide, and anhydride.

Examples of linker moieties that are useful when following an amide bond construction strategy in which a peptide molecule has two terminal amine groups include the following:

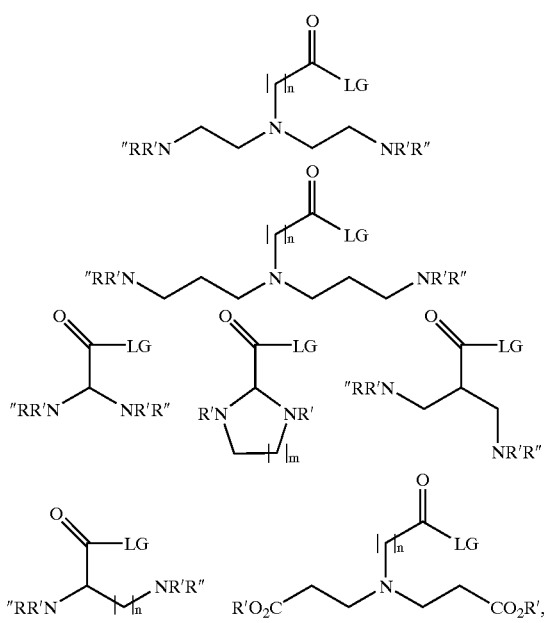

wherein each m is independently an integer from 1 to 4, n is independently an integer from 0 to 4 inclusive, LG is a leaving group, and R' or R" are independently hydrogen or a chemical protecting group.

A linker moiety also may have branch points for attachment of more than two chelates. For example, when following an amide bond formation strategy, a linker that includes a carbonyl with a leaving group LG (for example, a carboxylic acid or an activated ester) and three or more protected amines can be reacted with a peptide amine to create a molecule with three or more terminal amines. The following carbonyl-based linker reagents may be appropriate for introducing three or more amine functional groups:

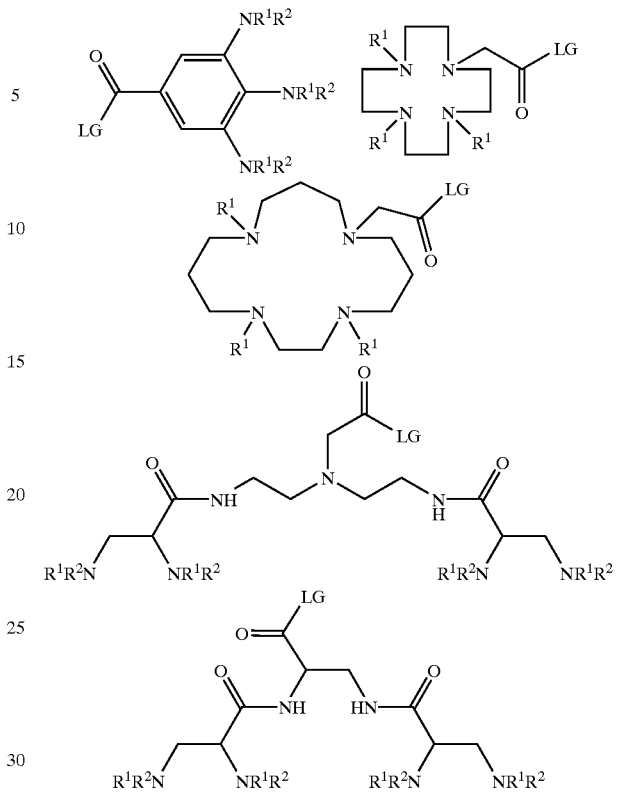

wherein LG is a leaving group (e.g., —OH, activated ester such as pentafluorophenol (Pfp), N-hydroxysuccinimide (NHS), N-hydroxysulfosuccinimide sodium salt (NHSS), 2-thioxothiazolidin-1yl, or hydroxybenzotriazole (HBT) and $R^1$ and $R^2$ are preferably independently hydrogen or a chemical protecting group (e.g., Boc, Fmoc, CBZ, t-butyl, benzyl, or allyl).

In other embodiments, an amine functional group at the N-terminus of a peptide may be converted to an N-terminus carboxylate functional group by reaction with a cyclic acid anhydride (linker-subunit moiety) thereby producing a modified peptide with a N-terminal carboxylate functional group:

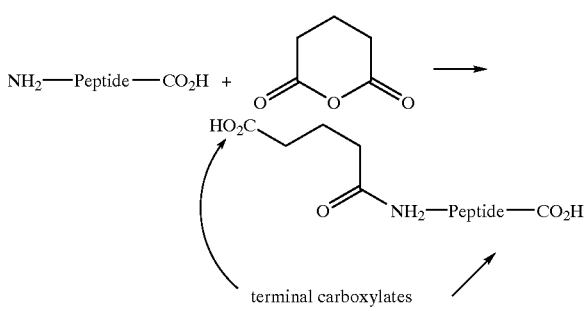

Examples of other linker-subunits that can be used to convert an N-terminal amine to a carboxylate functional group include:

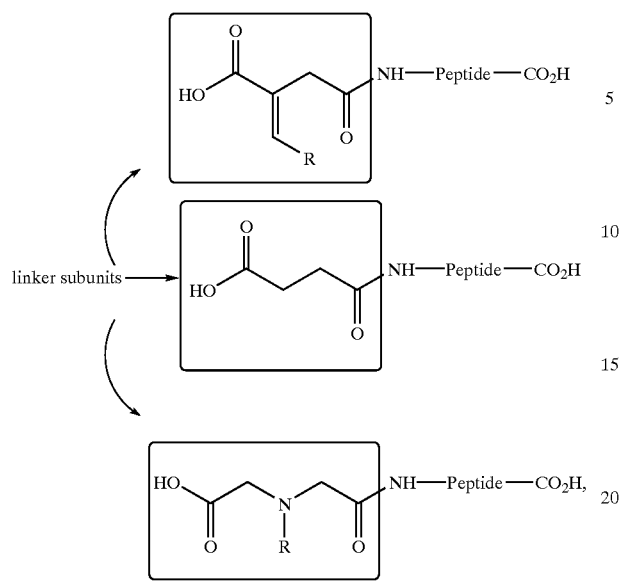

wherein R is any aliphatic or aromatic group.

Subsequently, both terminal carboxylates in the above examples may be simultaneously reacted with an amino group on a linker moiety as shown below to form a precursor MR imaging agent. In this example, the precursor MR imaging agent is a peptide molecule derivatized with linkers at both termini thru amide bonds:

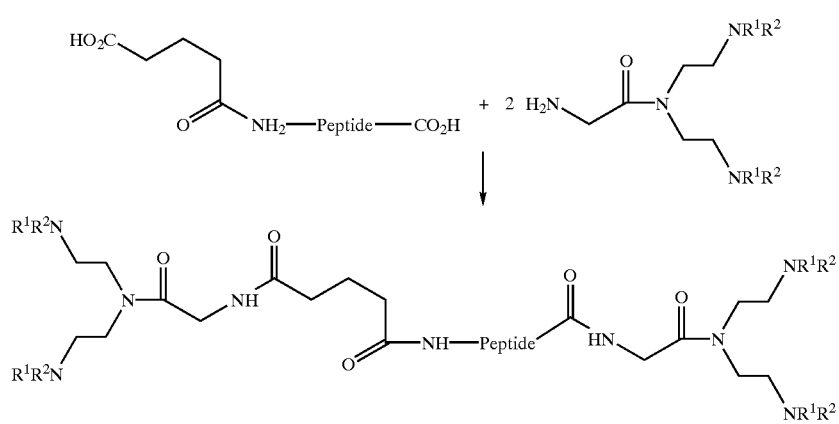

Specific examples of additional linker moieties useful for producing precursor MR imaging agents terminating with two carboxylates are:

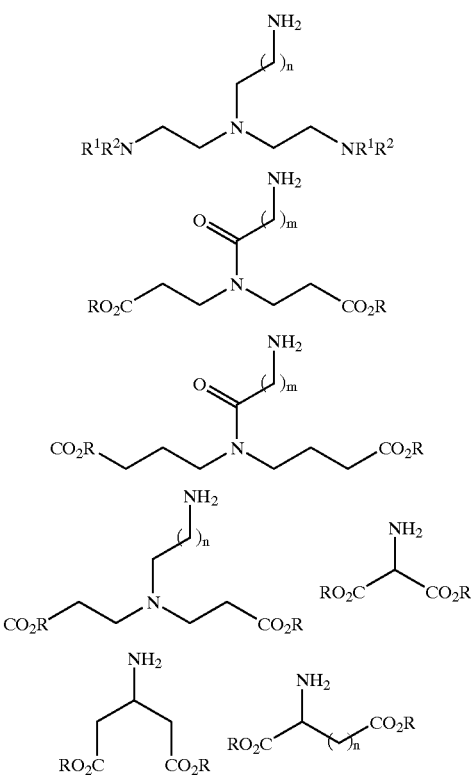

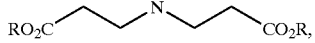

wherein each m is independently 1 to 4 inclusive, n is independently 0 to 4 inclusive (e.g., n=1 or 2), and R is hydrogen or an appropriate chemical protecting group, such as methyl, ethyl, benzyl, or t-butyl. In these examples, following attachment of the linker-subunits, the protecting groups can be removed and chelating or precursor chelating moieties can be attached through standard methods, for example, amide bond formation.

When following an amide bond construction strategy in which a peptide molecule is terminated with two carboxylates, the following linker reagents may be appropriate to introduce three or more amine functional groups:

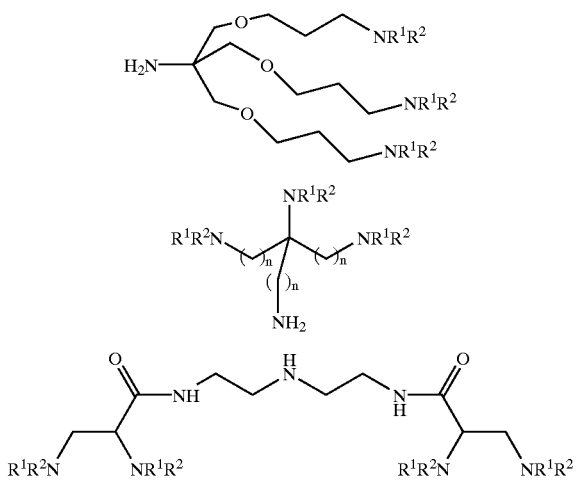

wherein $R^1$ and $R^2$ are independently hydrogen or a chemical protecting group such as OS, Boc, Fmoc, CBZ, tbutyl, benzyl, or allyl.

Linker strategies that involve formation of amide bonds are useful because they typically are compatible with the protecting groups on the peptide. As mentioned above, the peptide, linker, and linker-subunits may be covalently attached to each other by formation of other bond types (nucleophilic displacement, reductive amination and thio-urea formation, for example).

The linkers may also have effects on the properties of the contrast agents such as affinity, pharmacokinetic properties, stability in vivo, and relaxivity.

Alternatively, a covalent conjugate that includes both a linker moiety and a chelating or chelating precursor moiety can be reacted directly with a peptide with appropriate terminal functionality. One example of such a covalent conjugate capable of reacting with terminal carboxylate groups follows:

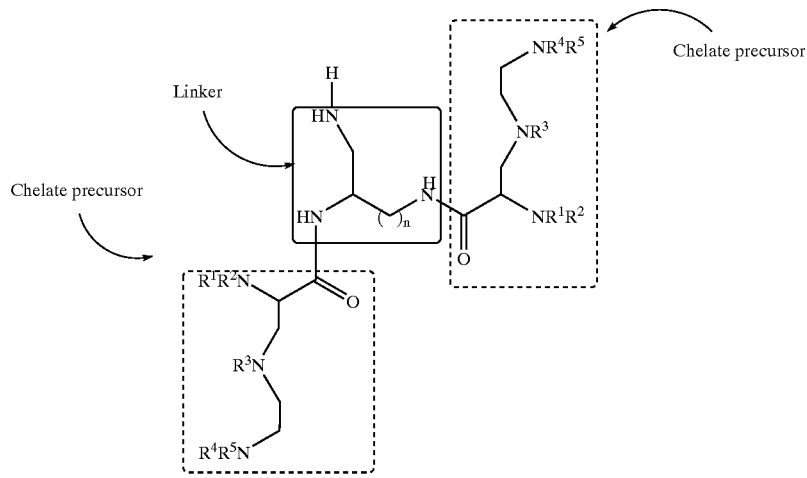

wherein n=1 to 4, and $R^1$, $R^2$, $R^3$, $R^4$, and $R^5$ are independently an acetate group, acetamide group, or an acetoxy group.

Another example of such a covalent conjugate has the following structure:

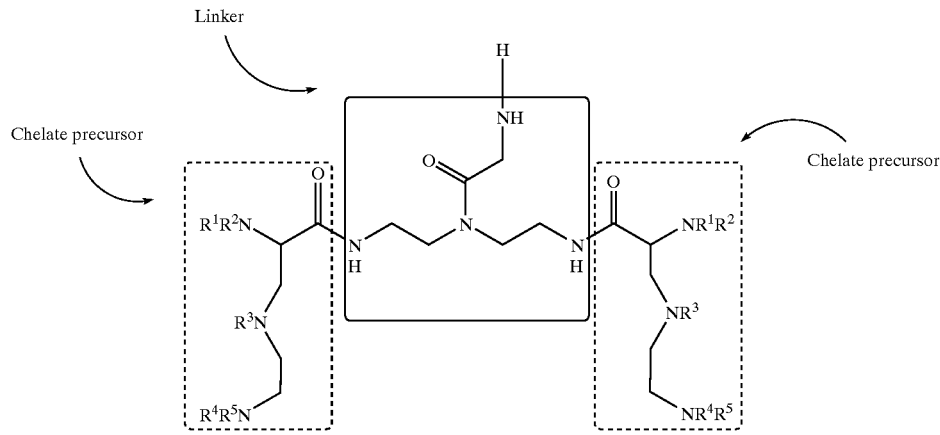

wherein $R^1$, $R^2$, $R^3$, $R^4$, and $R^5$ are independently an acetate group, acetamide group, or an acetoxy group.

An example of a covalent conjugate useful for converting a modified peptide with carboxylate functional groups at the two termini to a precursor imaging agent has the following structure:

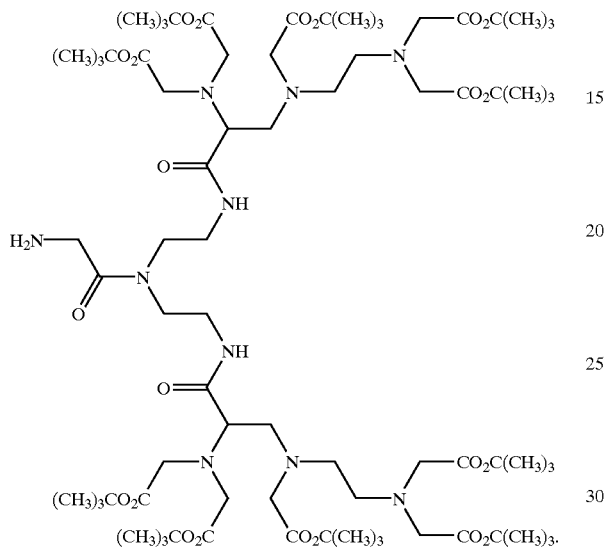

Examples of covalent conjugates capable of reacting with amine functional groups on a modified peptide are:

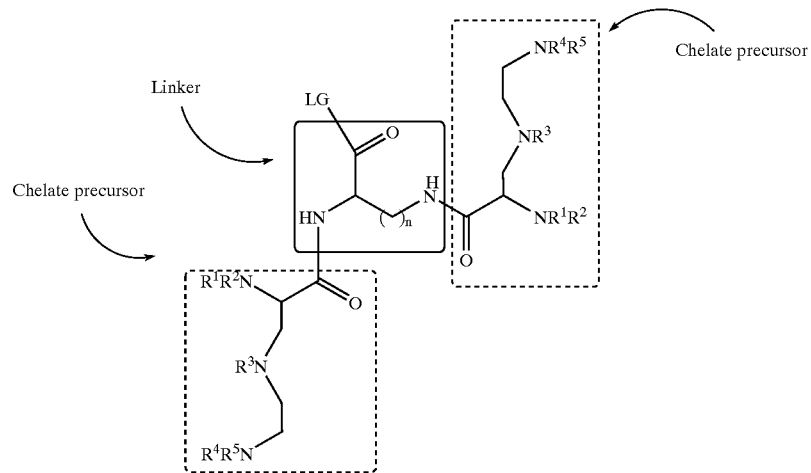

wherein LG is a leaving group, n=1 to 4, and $R^1$, $R^2$, $R^3$, $R^4$, and $R^5$ are independently an acetate group, acetamide group, or an acetoxy group, and

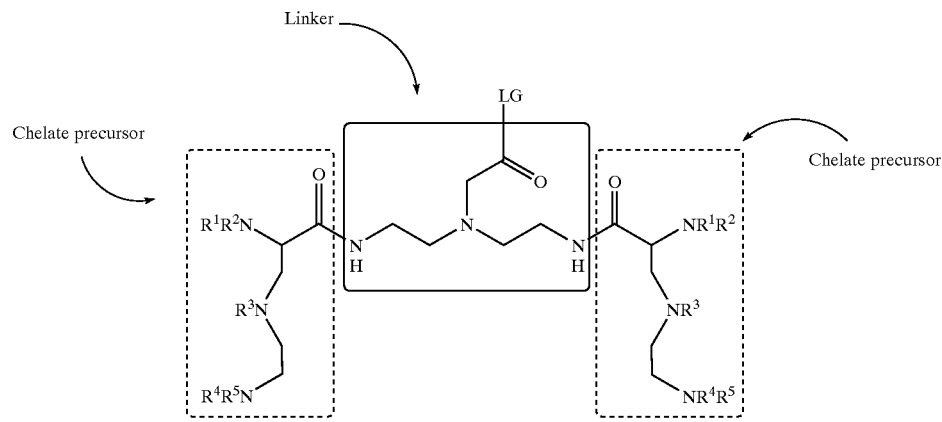

wherein LG is a leaving group, wherein $R^1$, $R^2$, $R^3$, $R^4$, and $R^5$ are independently an acetate group, acetamide group, or an acetoxy group.

A particularly useful covalent conjugate for synthesizing a multimer contrast agent has the following structure, hereinafter "Synthon #1":

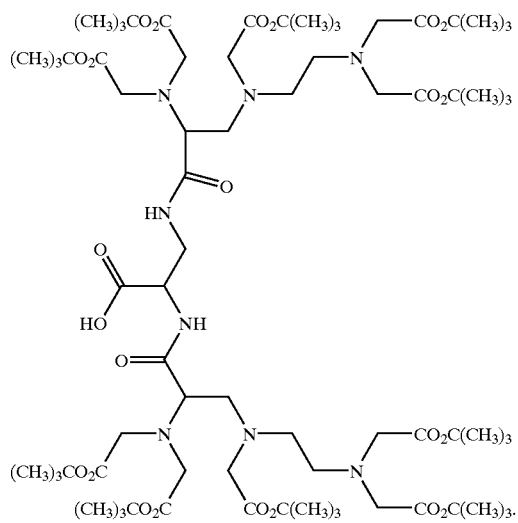

Another embodiment of a covalent conjugate useful for synthesizing a multimer has the following structure, hereinafter "Synthon #2":

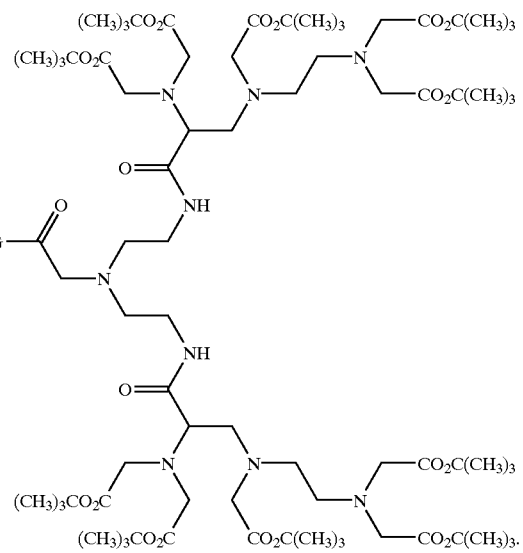

In the following example of an MRI contrast agent of the invention that includes a peptide as outlined above, the effect of the N-terminus linker on the relaxivity of MRI contrast agents is illustrated:

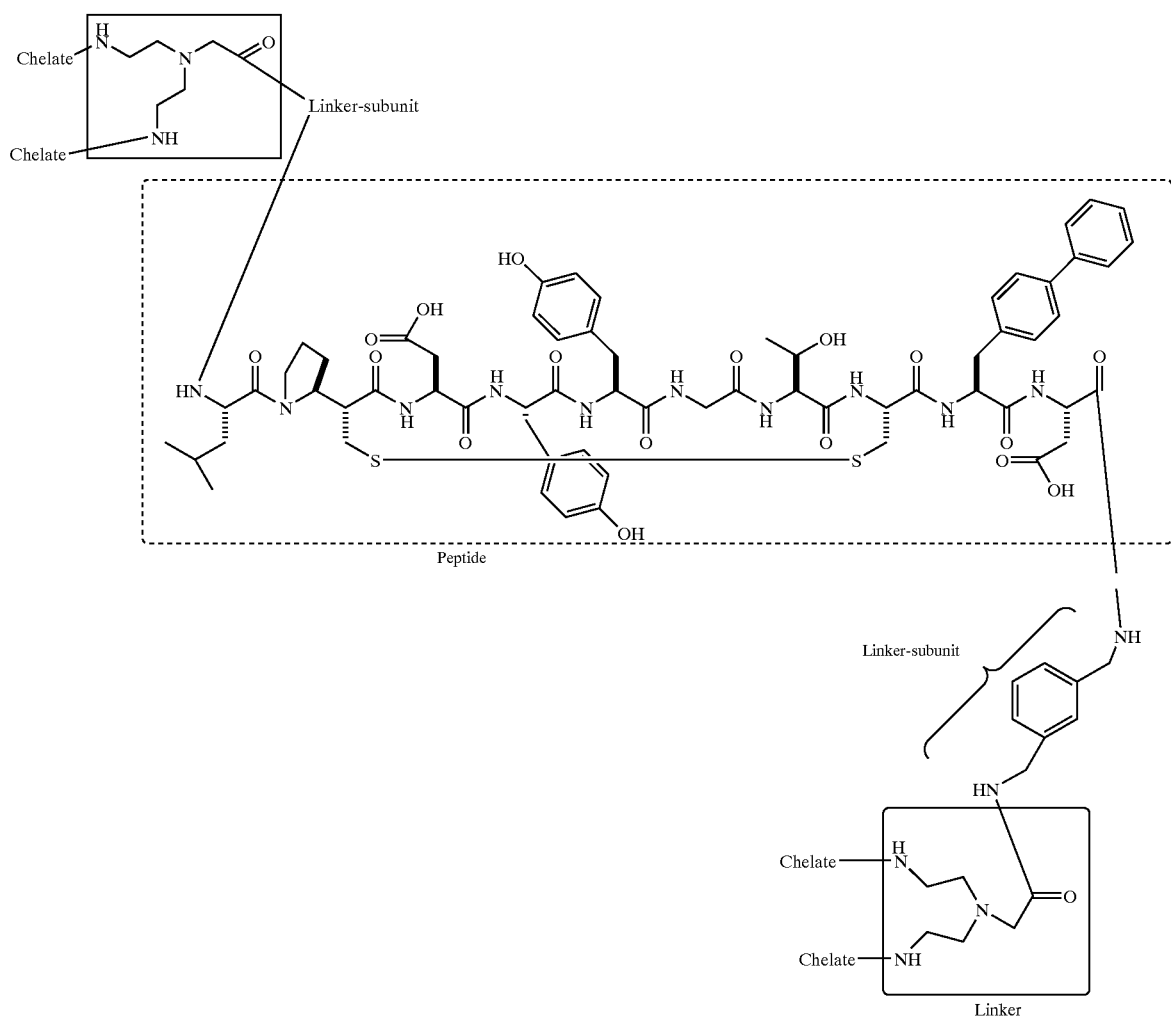
In this example, "chelate" refers to bb-DTPA-Gd(III).
The "Linker-subunit" above was varied with the following results (relaxivities per Gd(III) ion were determined at 20 MHz and 35° C., units are $mM^{-1}s^{-1}$):
| Fibrin Affinity | N-terminal Linker-subunit | Relaxivity PBS | Relaxivity Fibrin DD(E) (10 mg/mL) |
|---|---|---|---|
| Structure 15 Ki = 4.0 μM | 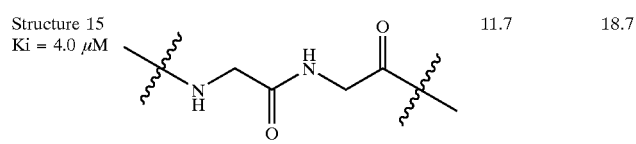 | 11.7 | 18.7 |

| Fibrin Affinity | N-terminal Linker-subunit | Relaxivity PBS | Relaxivity Fibrin DD(E) (10 mg/mL) |
|---|---|---|---|
| Structure 16 Ki = 3.4 μM | 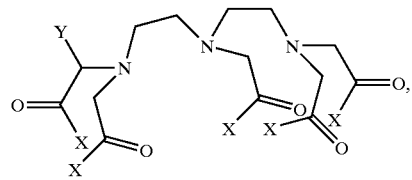 | 12.6 | 29.5 |
| Structure 32 Ki = 4.7 μM | (direct bond) | 12.5 | 21.6 |

As shown above, structures 15 and 16 are similar to 32 except for different N-terminal linker-subunits. The experimental results show that a linker can affect the relaxivity, as well as other characteristics of a contrast agent of the invention.

Chelating Moieties and Reagents

Chelating moieties are chelating ligands complexed with metal ions. These chelating moieties contain a synthetic moiety capable of forming a point of attachment to the linker, linker-subunit, and/or modified peptide. One or more chelating moieties may be covalently conjugated to the functional group at each terminus of the modified peptide. In one embodiment, the chelate is attached to a linker-subunit. In another embodiment, the chelate is attached to a linker moiety. In other embodiments, the chelate may be conjugated with a linker moiety to form a covalent conjugate before attaching the covalent conjugate to the modified peptide.

Precursor chelating moieties are chelating ligands that have not been complexed with metal ions. Chelating ligands may have protecting groups or may be precursors to chelating ligands. Precursor chelating moieties have a synthetic moiety capable of forming a point of attachment to the linker, linker-subunit, and/or modified peptide. Precursor chelating moieties can be converted into chelating moieties by complexing with a metal ion. One or more precursor chelate moieties may be covalently conjugated to the functional group at each terminus of the modified peptide. In one embodiment, the precursor chelate can be attached to a linker-subunit. In another embodiment, the precursor chelate is attached to a linker moiety. In other embodiments, the precursor chelate may be conjugated with a linker moiety to form a covalent conjugate before attaching the covalent conjugate to the modified peptide.

Precursor chelate moieties and chelate moieties according to the invention can have any of the following structures:

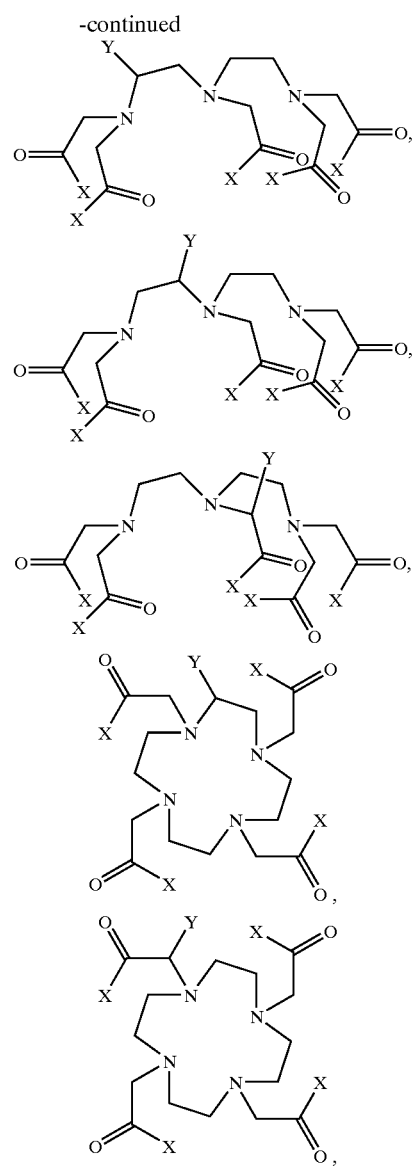

-continued

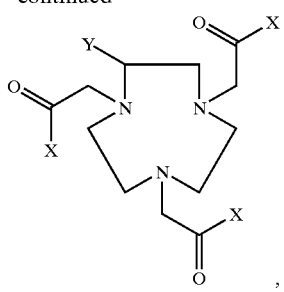,

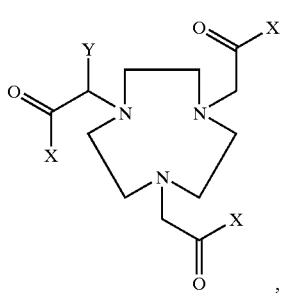,

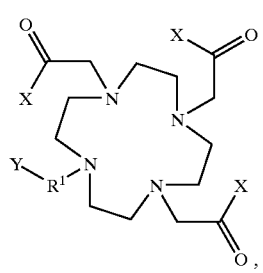,

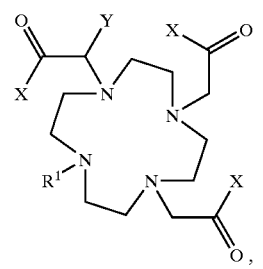,

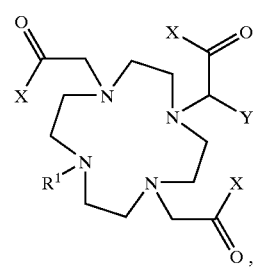,

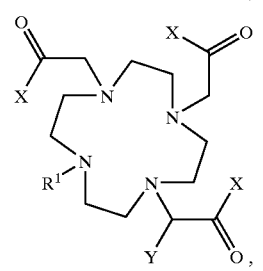,

-continued

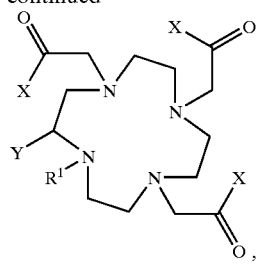,

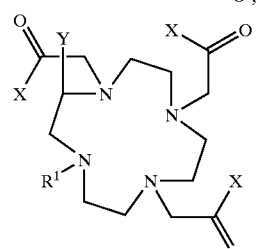,

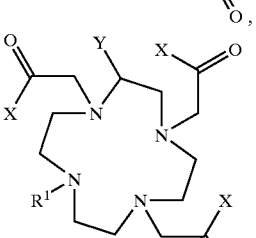, or

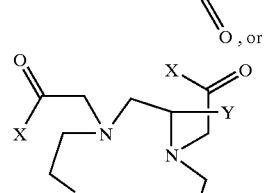, wherein X is a heteroatom electron-donating group capable of coordinating a metal cation, such as O⁻, OH, $NH_2$, $OPO_3^{2-}$, NHR, or OR, wherein R is any aliphatic group; $R^1$ is an uncharged chemical moiety, selected from hydrogen, any aliphatic, alkyl group, or cycloalkyl group, or uncharged substituted versions thereof (e.g. alcohols); and Y is a synthetic moiety (e.g., capable of forming a point of attachment, or being the point of attachment, to the functional group of the modified peptide, linker, and/or linker-subunit either directly or with an intervening carbonyl, methylene, methylene-oxygen, thiocarbonyl). Moieties with (chelate moiety) or without (precursor chelate moiety) a coordinated metal ion may be used.

A variety of chelating ligands may be used in contrast agents of the invention. Such chelating ligands include, but are not limited to, derivatives of DTPA, DOTA, NOTA, and DO3A. For MRI, metal chelates such as gadolinium diethylenetriaminepentaacetate (DTPA.Gd), gadolinium tetraamine 1,4,7,10-tetraazacyclododecane-N,N',N'',N'''-tetraacetate (DOTA.Gd) and gadolinium 1,4,7,10-tetraazacyclododecane-1,4,7-triacetate (DO3A.Gd) are particularly useful. Particularly useful chelates include bb(CO)DTPA.Gd. Other metals may be substituted for Gd(III) in MRI applications.

Examples of functionalized chelates that have been synthesized for the purpose of preparing multimeric chelates include pNCS-Bz-DTPA [Martin, V., et al. *Bioconjugate Chem.* 6,616–23, 1995] and Gd(4-NCS-phenyl)-aminocarbonylmethyl-DO3A [Ramachandran, R. et al., *Invest. Rad.* 1998, 33(11), 779–797]. For optimal relaxivity properties when bound to a target, it is frequently desirable to minimize chelate motion, and hence, a minimal number of covalent bonds linking the target to the chelating ligand are desirable. Below is an example of a reagent that includes a chelating ligand with a backbone carbonyl group for connecting to an amine functional group or a linker-subunit or linker, wherein "LG" is a leaving group (e.g., an activated ester) and R represents a group which may be easily cleaved to form O⁻ (-OtBu, e.g. a carboxylate ester) thereby forming a carboxylate with the neighboring carbonyl group:

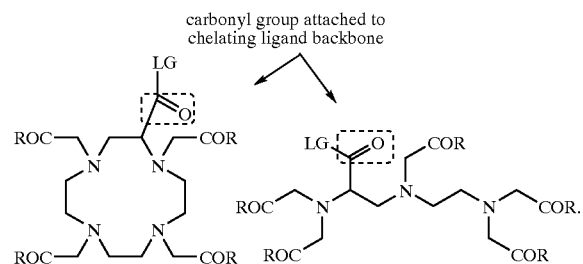

It has been found that the chemical motif of a carbonyl immediately adjacent to a chelating ligand constitutes a class of high relaxivity MRI contrast agents.

The present invention also relates to intermediates useful in the synthesis of contrast agents for MRI according to the following formulae:

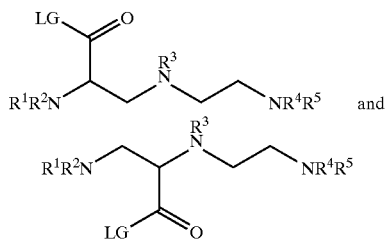

wherein, $R^1$, $R^2$, $R^3$, $R^4$, and $R^5$ may be any protected or unprotected acetyl ligand suitable for forming a chelate of a paramagnetic metal with an appropriate formation constant, including the following:

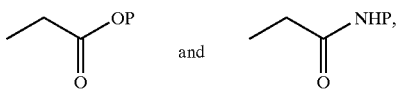

wherein P is any protecting group, including benzyl and tert-butyl groups. LG is a "leaving group" and represents —OH and ester forms thereof including, NHS esters, pentafluorophenol, and other activated esters.

In a particularly useful embodiment, LG is —OH, and $R^1$, $R^2$, $R^3$, $R^4$, and $R^5$ are $CH_2CO_2O^tBu$, hereinafter "Synthon #3", and has the following structure:

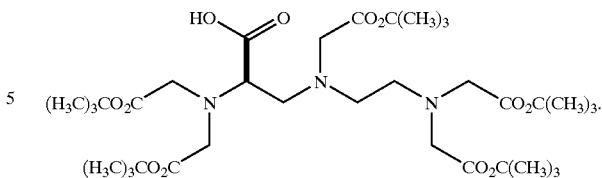

Alternatively, the following reagent may be used in the synthesis of contrast agents of the invention:

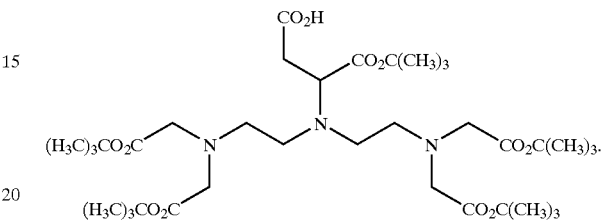

(vide *Syn. Comm.* 30, 3755 (2000).)

The present invention also provides methods of manufacturing compounds. In particular, a novel oxidation reaction permits the facile preparation of Synthon #3, a preferred embodiment of a chelating ligand. The synthesis of Synthon #3 can be achieved through two different synthetic routes, both commencing with hydroxymethyl-diethylenetriamine. One route involves a two synthetic step sequence (alkylation, followed by oxidation) and the other involves a six-step process (protection, oxidation, esterification, deprotection, alkylation and hydrogenolysis). Both produce Synthon #3 in high chemical and optical purity (vide Examples, below).

U.S. Pat. No. 5,637,759 discloses a synthesis of Synthon #1 from 2,3-diaminopropionic acid and aza-lysine by a selective hydrolysis protocol with sodium thiophenoxide. The method disclosed herein avoids the use of this toxic reagent.

Synthesis of Contrast Agents

Synthesis of the peptide-based contrast agents may be carried out in the following steps. First, a targeting peptide can be synthesized with or without a C-terminal linker-subunit, typically using solid phase peptide synthesis. For cyclic peptides described herein, a protected linear peptide may be cyclized in solution or on the resin. Unprotected peptide may also be cyclized in solution or on resin. A C-terminal linker-subunit may be conveniently derived from the solid phase synthesis resin and an N-terminus linker or N-terminal linker-subunit can be coupled to the peptide during the solid phase synthesis. Typically, following cyclization, the linker-subunit-chelate precursor moieties were coupled to the peptide. Protecting groups were removed to provide the ligand precursors, and then chelates were prepared. Radionuclide compounds of this invention were prepared from ligand precursors using commercially available radionuclides (for example, $^{99m}$Tc from Nycomed Amersham Boston cat. #RX-290195, $^{111}$In from NEN Life Science Products cat. #NEZ304, or [153]Gd from NEN Life Science Products cat. #NEZ142) by reaction in aqueous media, typically at pH 4–6 for 1 hour. In the case of optical contrast agents, an organic dye may be substituted for a chelate precursor.

Structure of Contrast Agents:
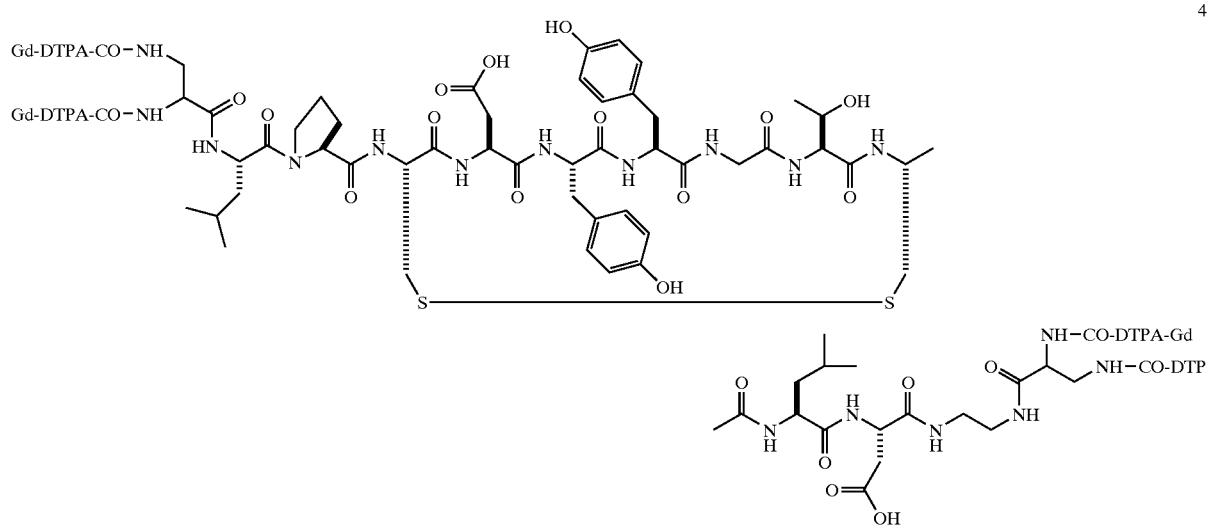
4
[synthesis is analogous to 32]
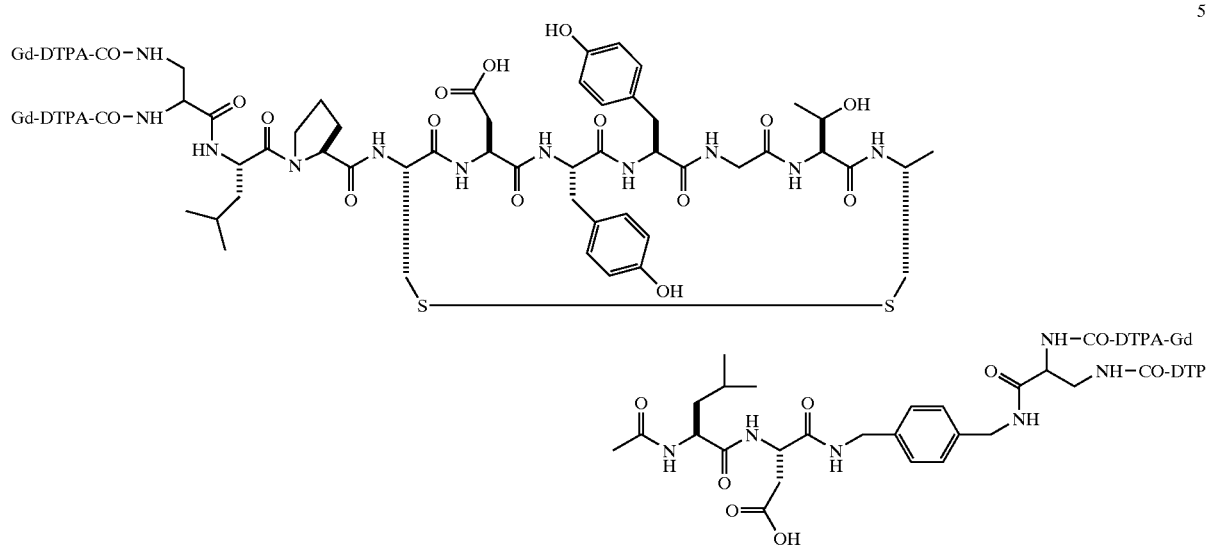
5
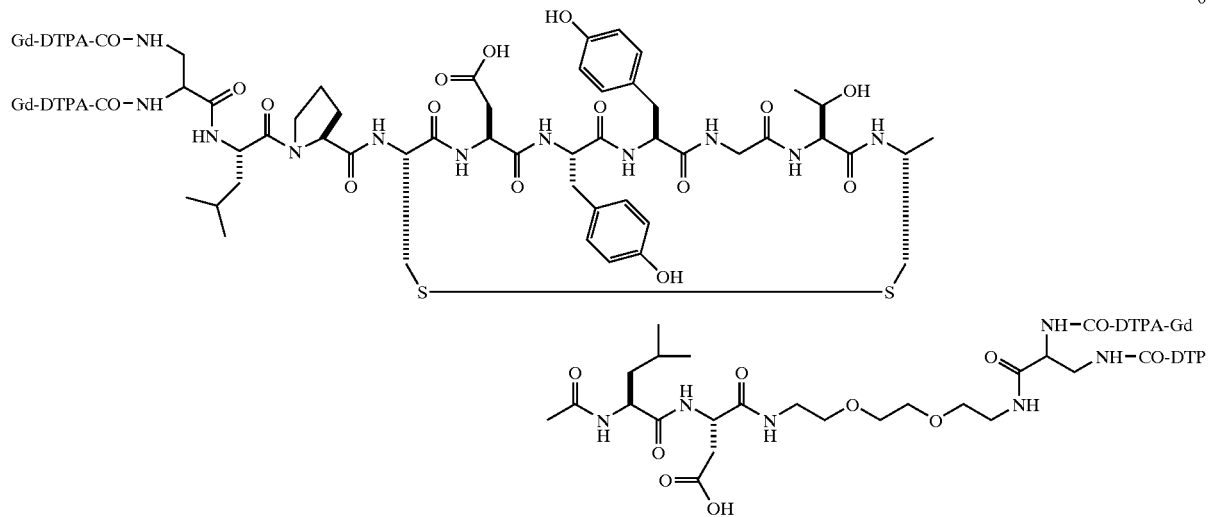
6

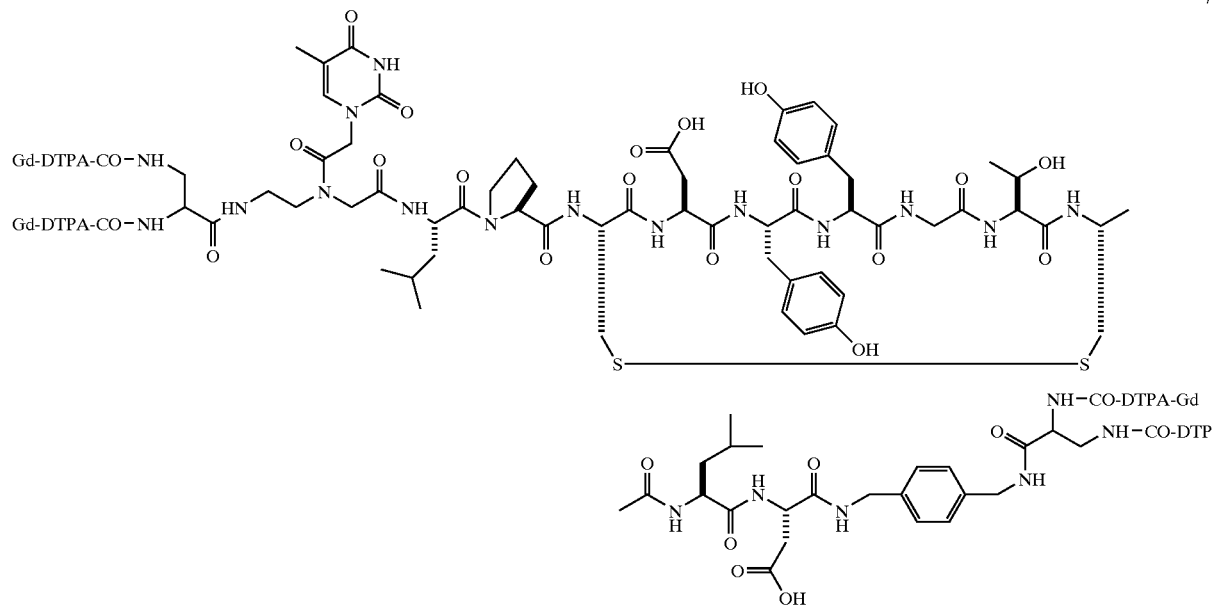
7
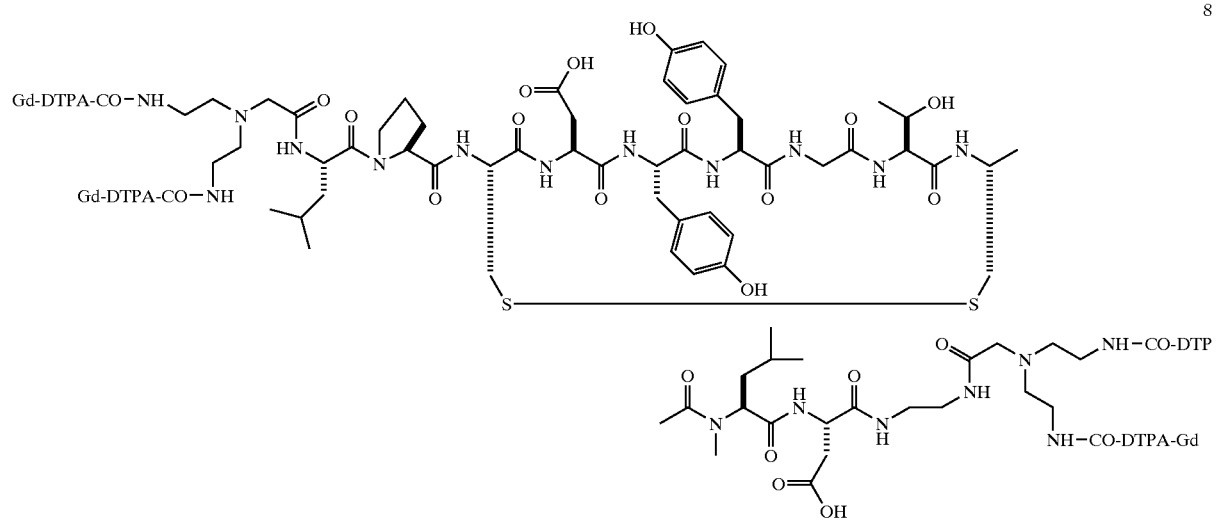
8
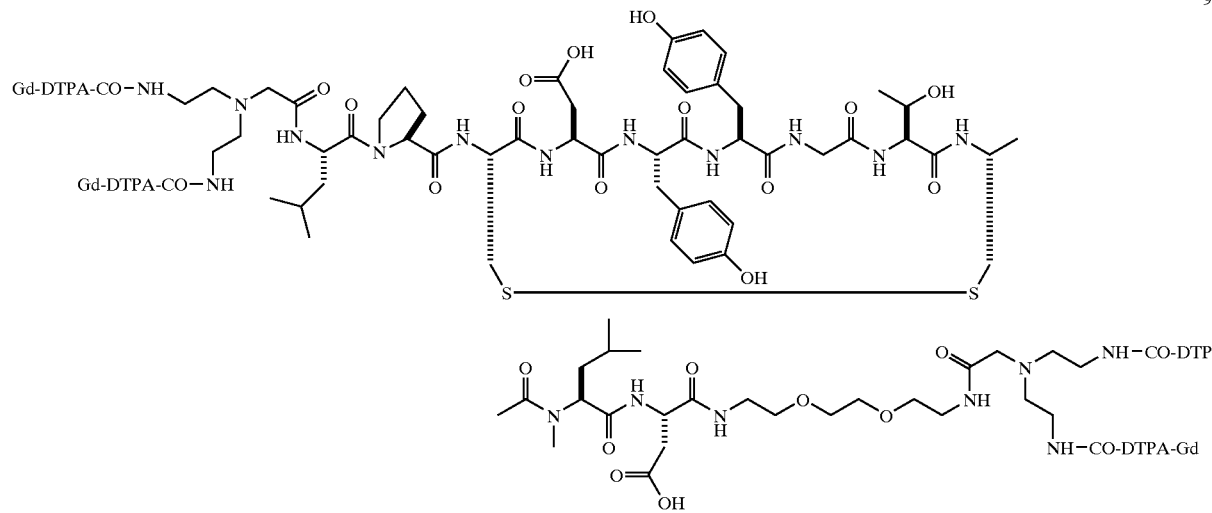
9

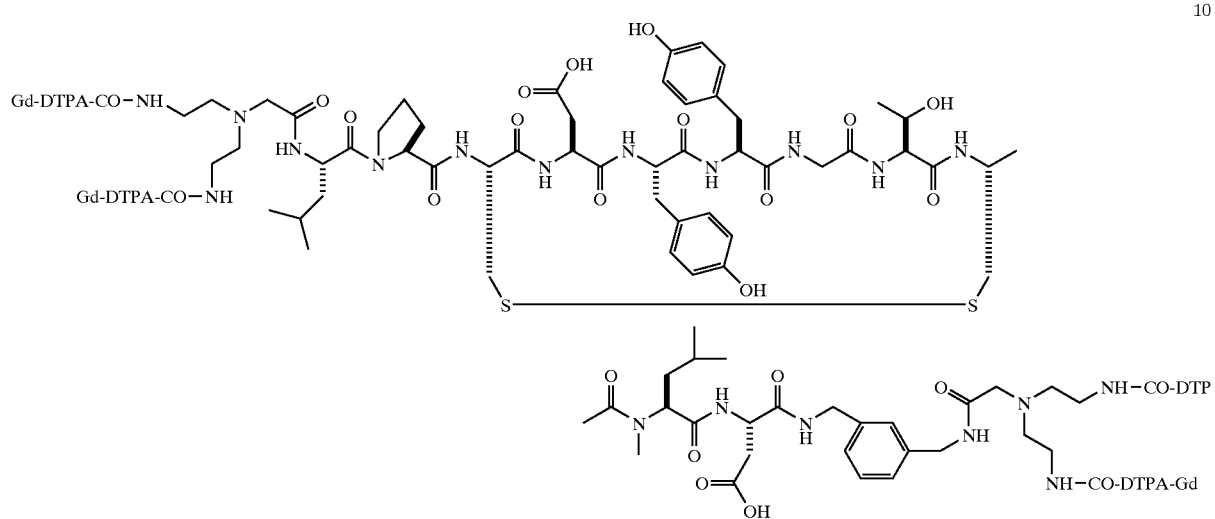
10
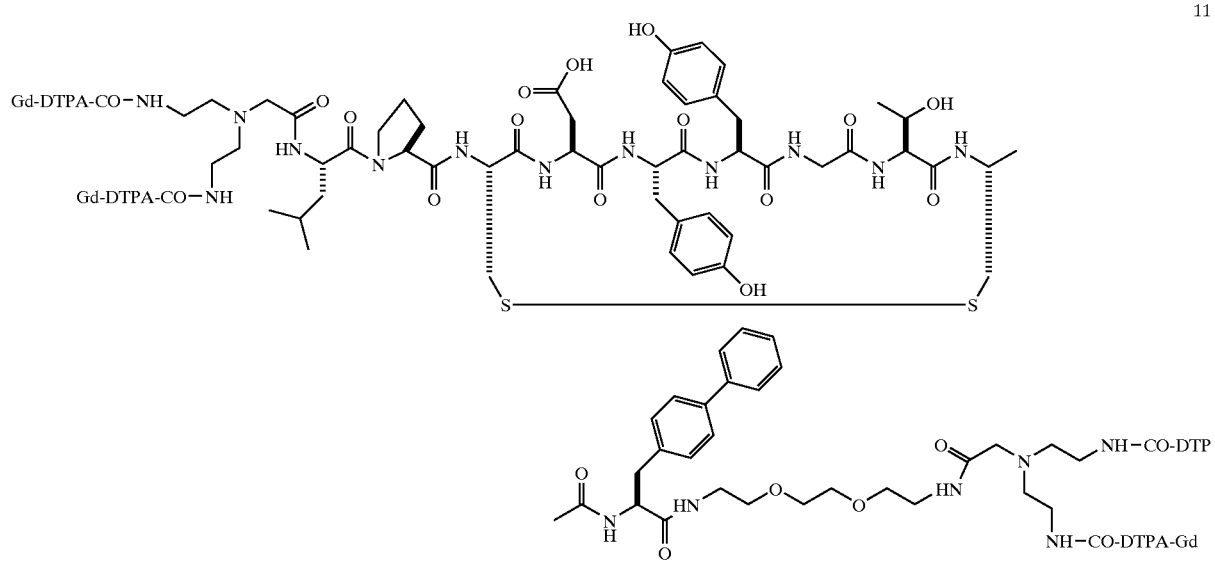
11
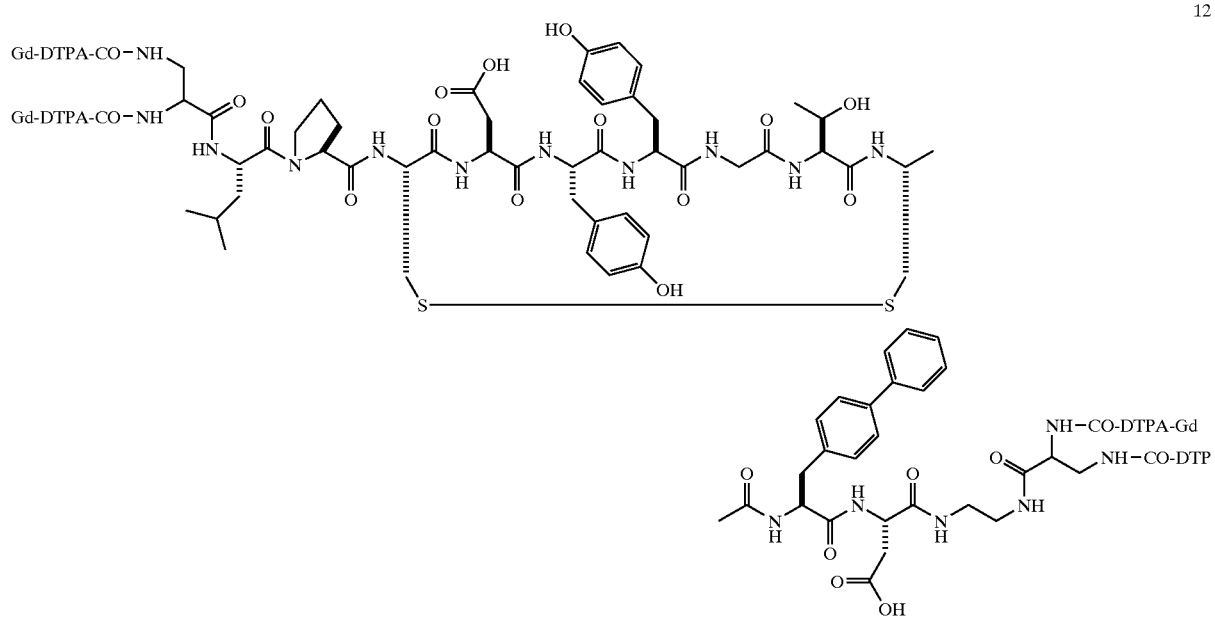
12

-continued
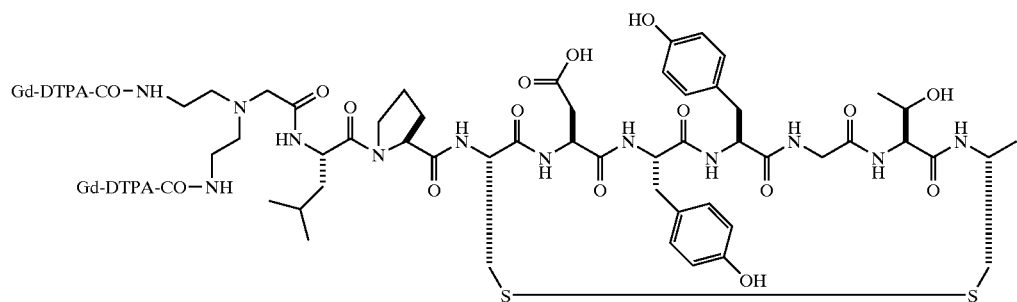
13
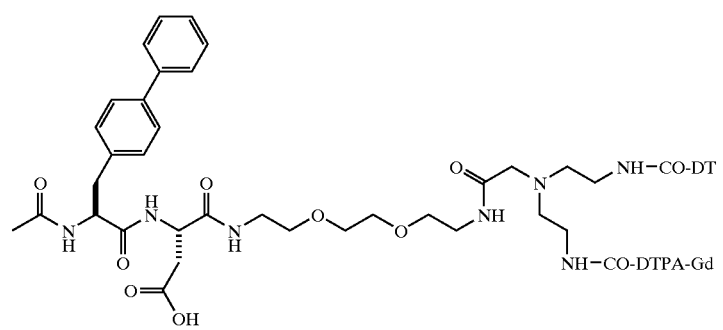
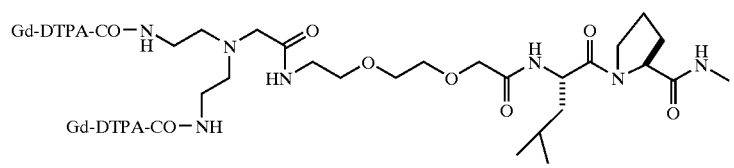
14
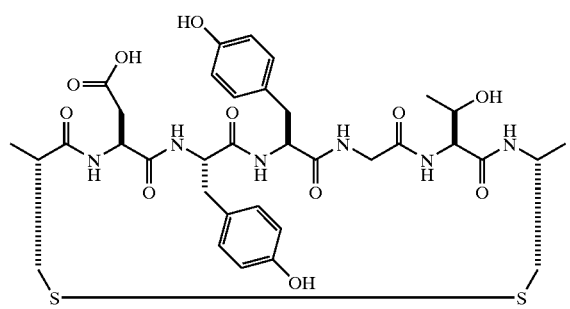
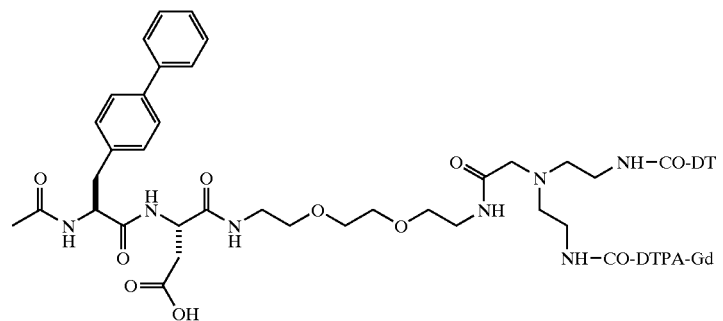

-continued
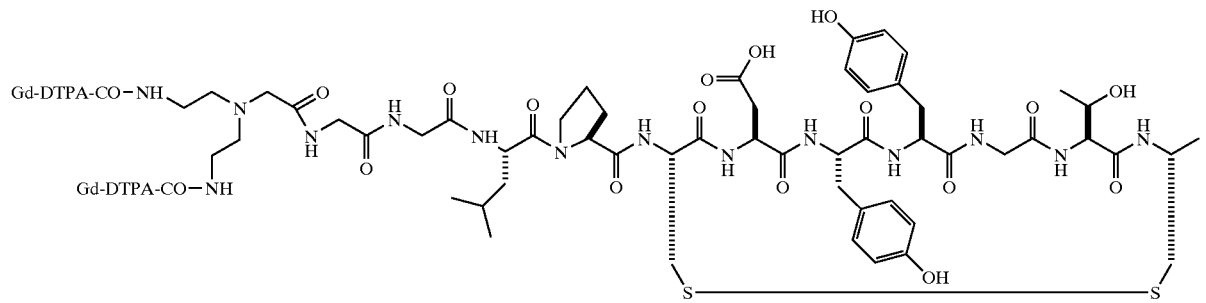
15
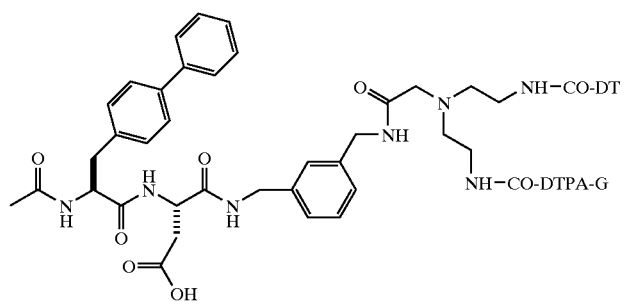
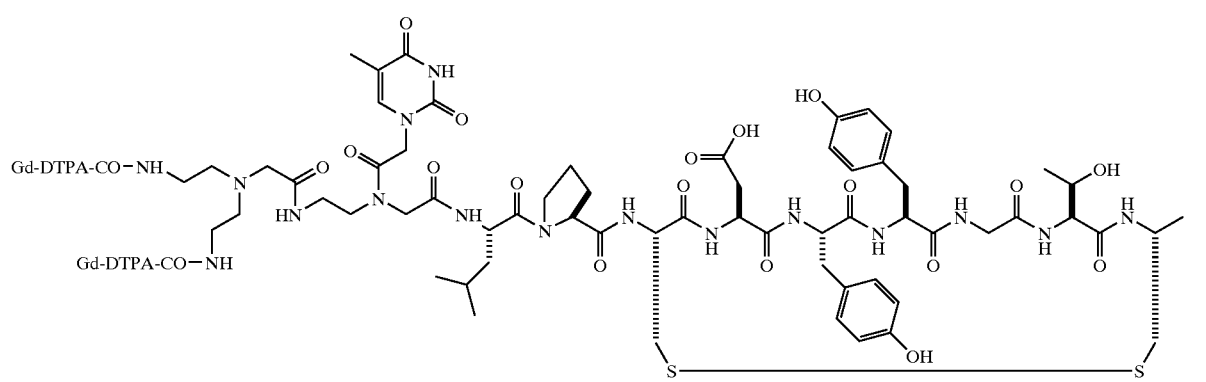
16
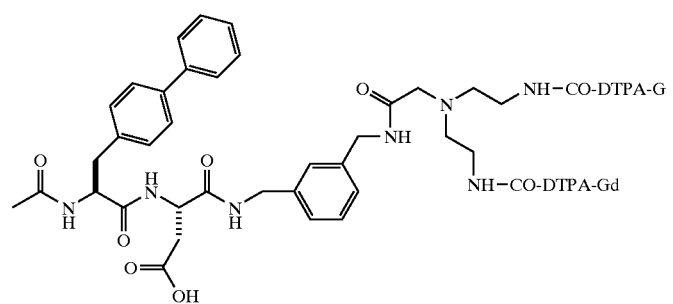
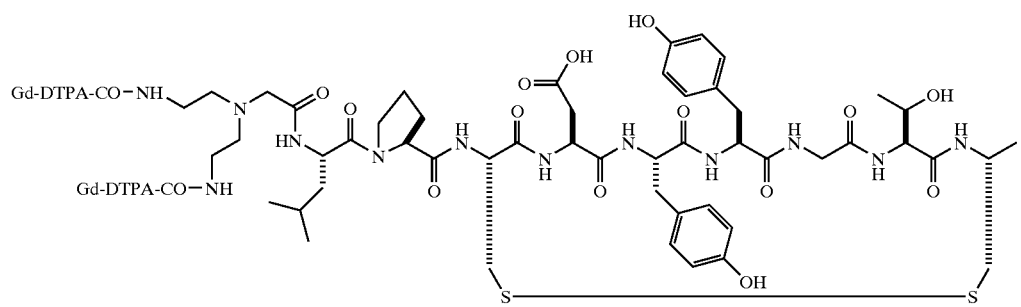
17

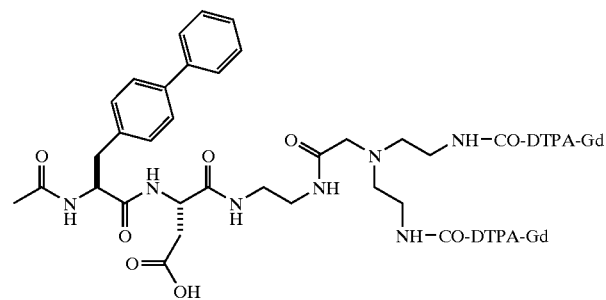
18
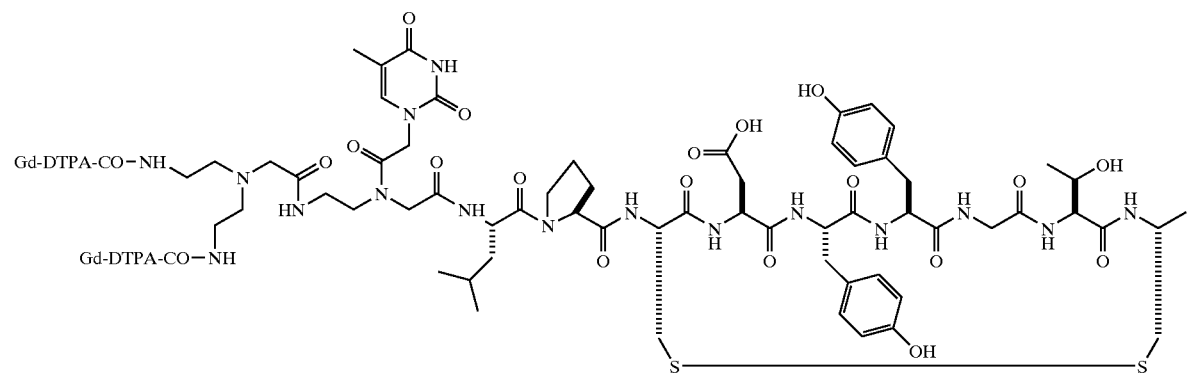
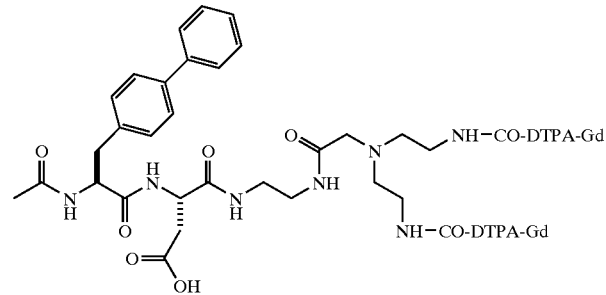
19
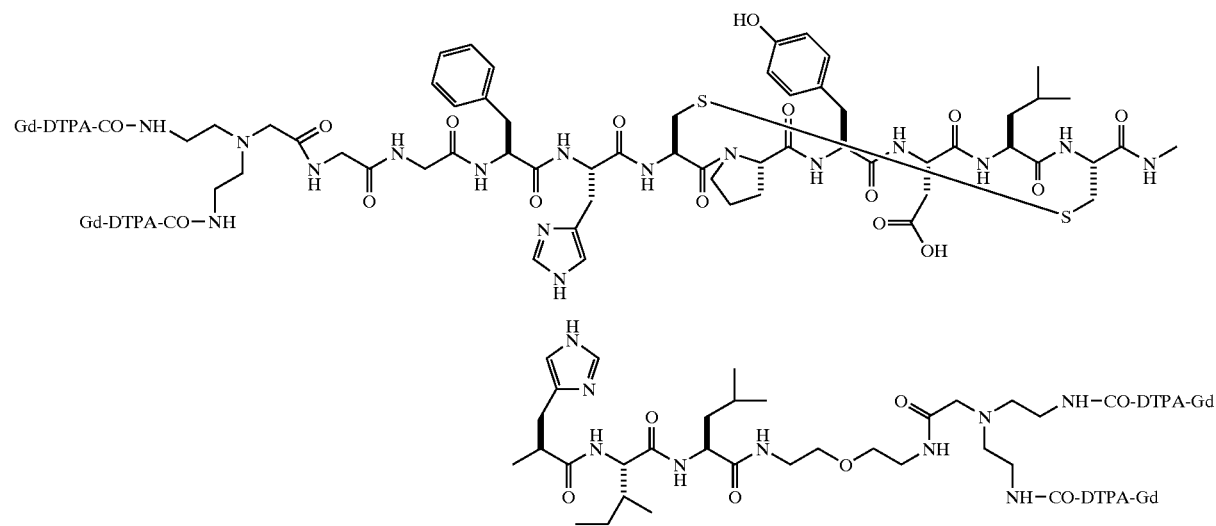

-continued
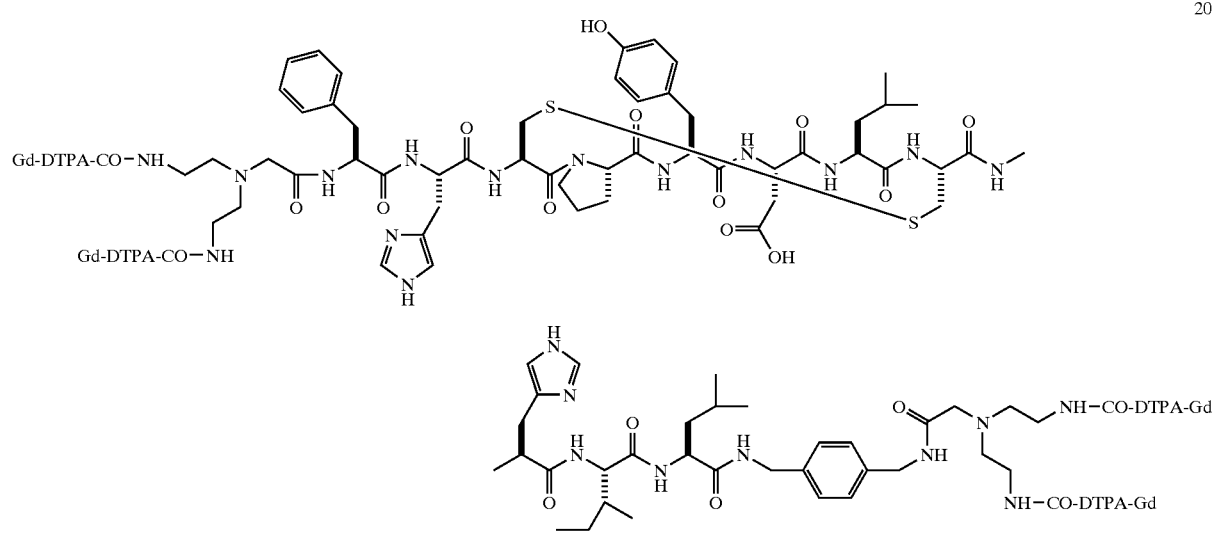
20
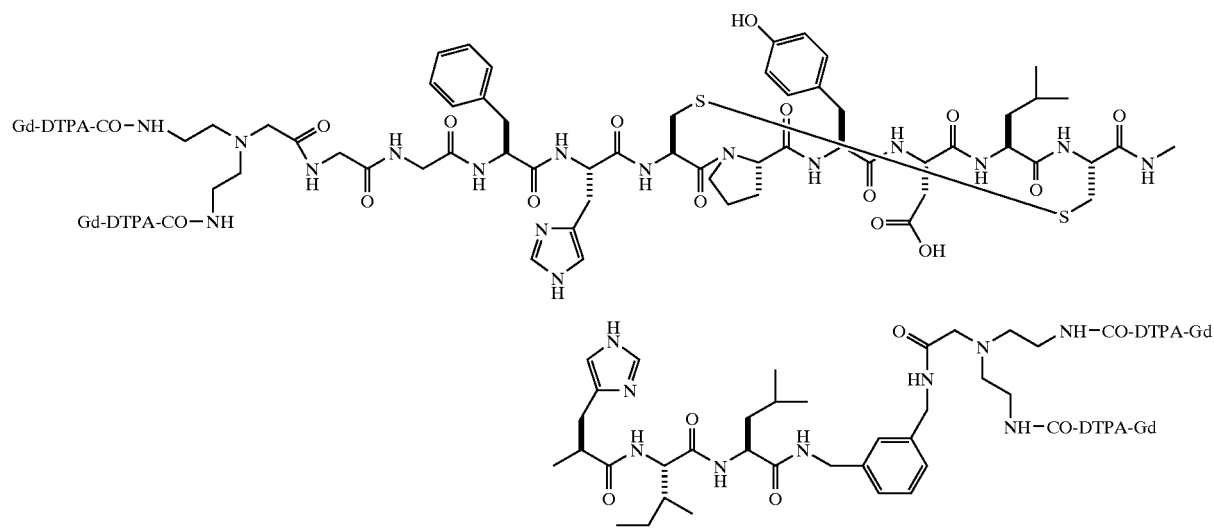
21
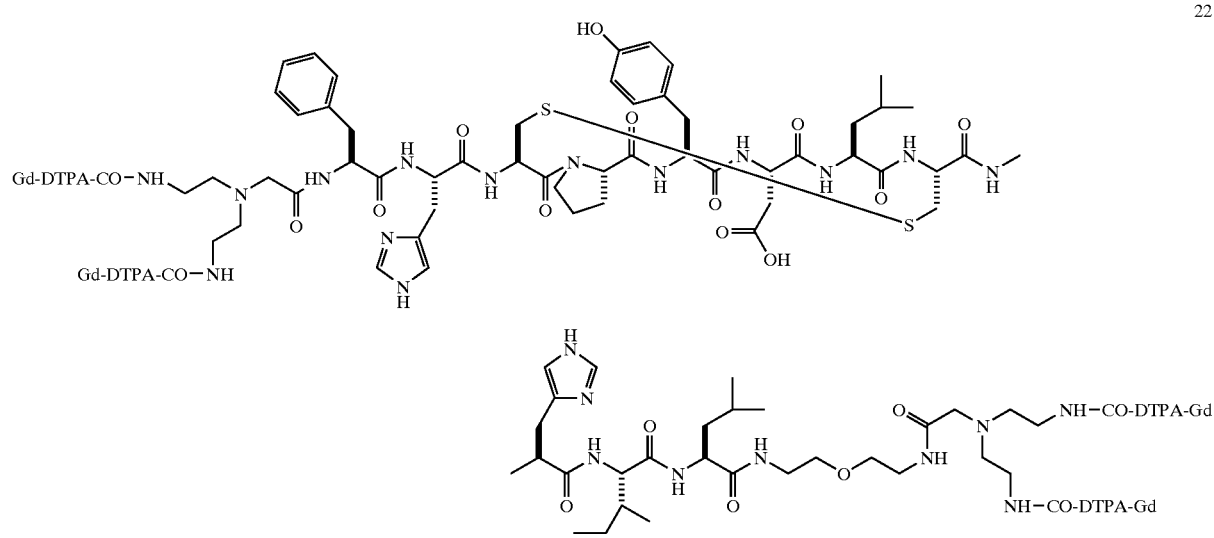
22

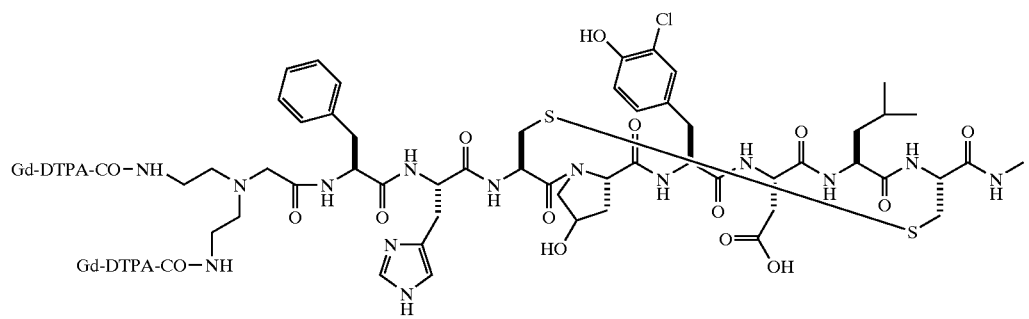
23
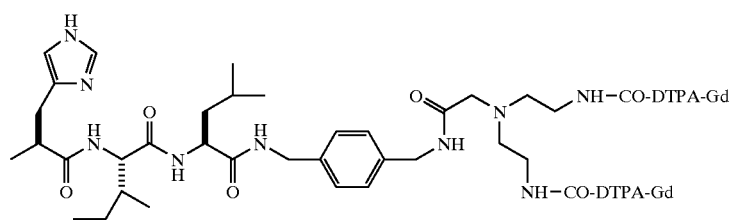
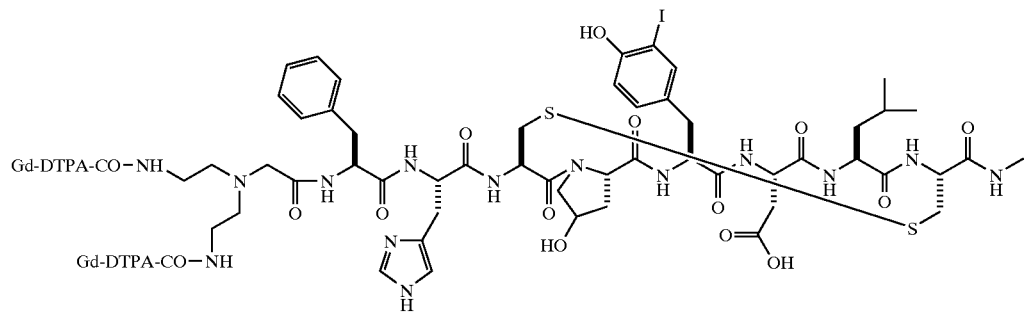
24
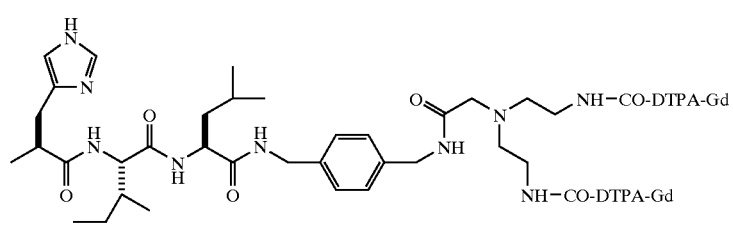
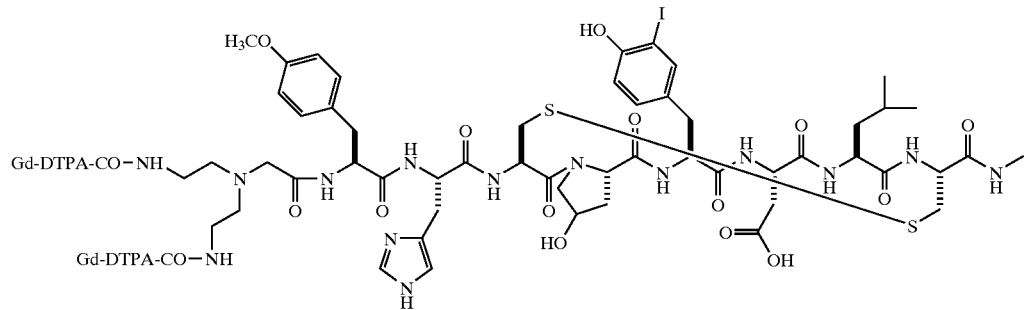
25
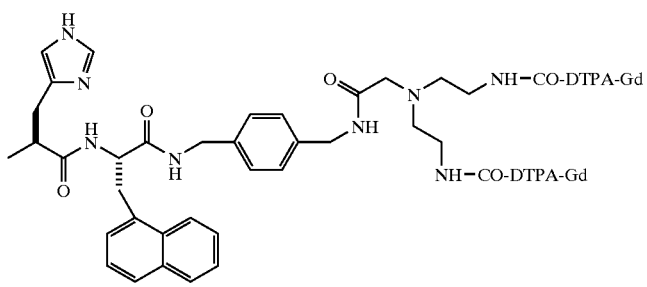

-continued
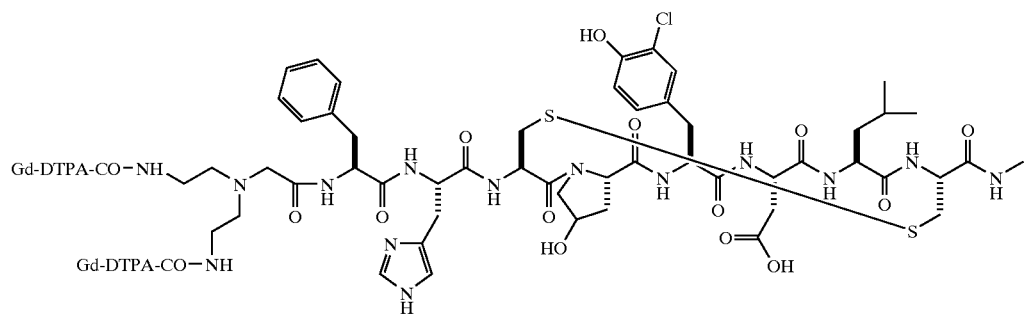
26
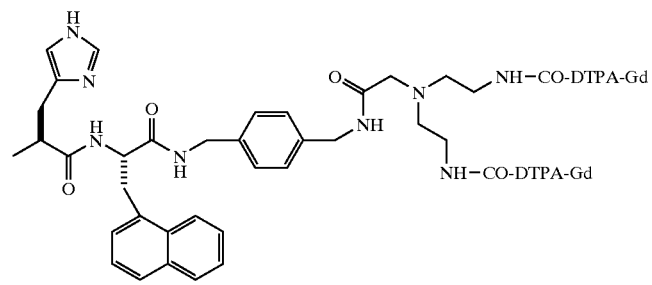
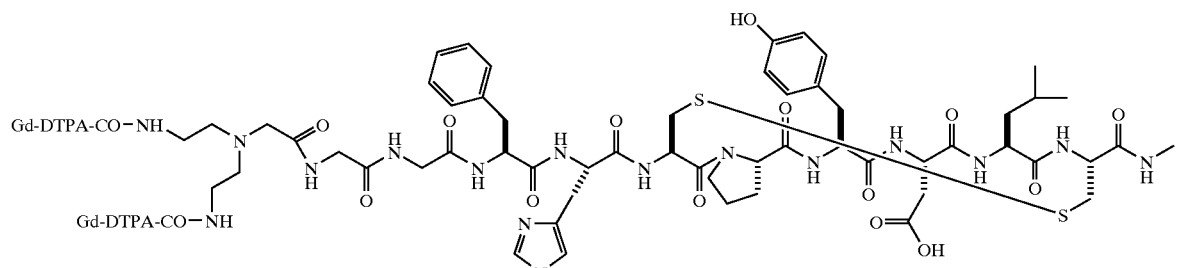
27
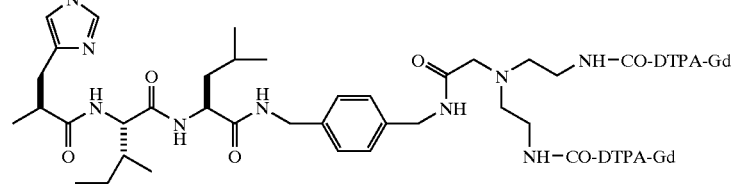
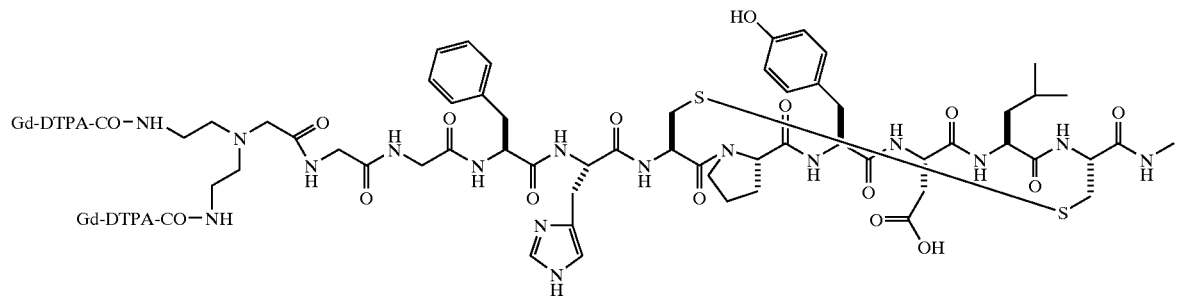
28
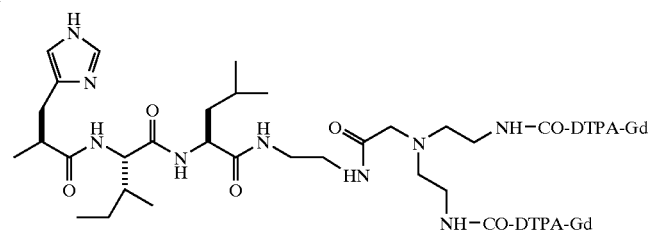

-continued
29
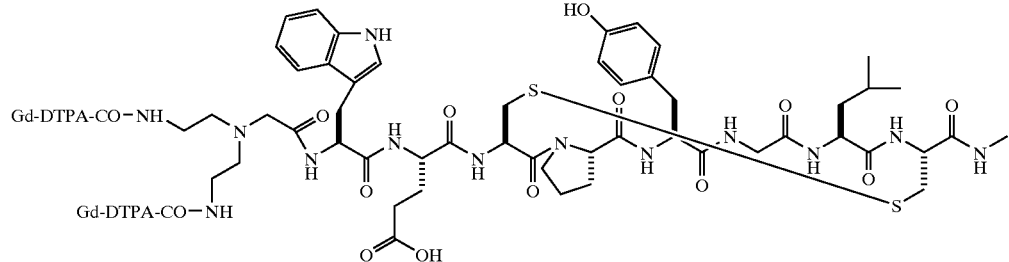
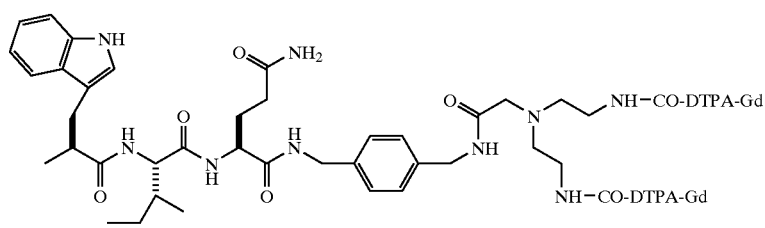
30
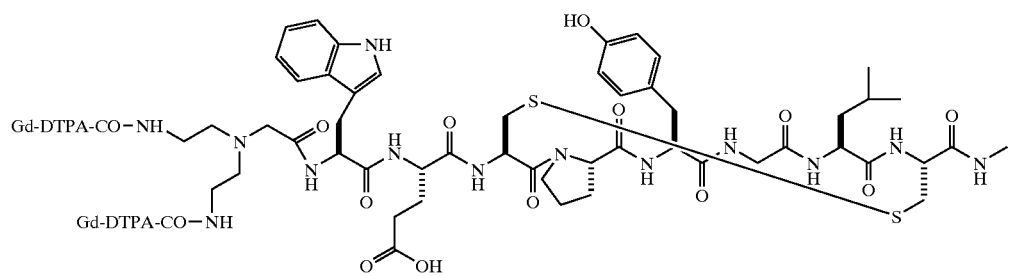
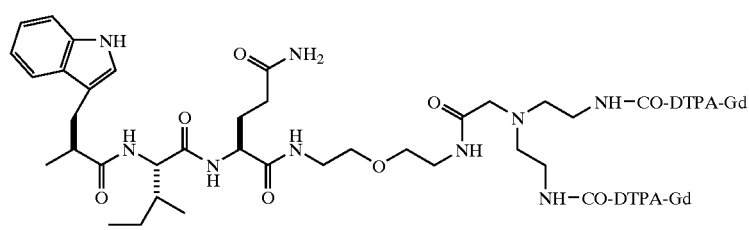
31
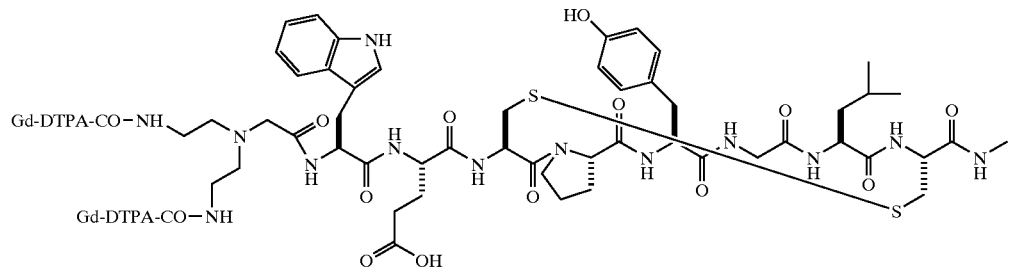
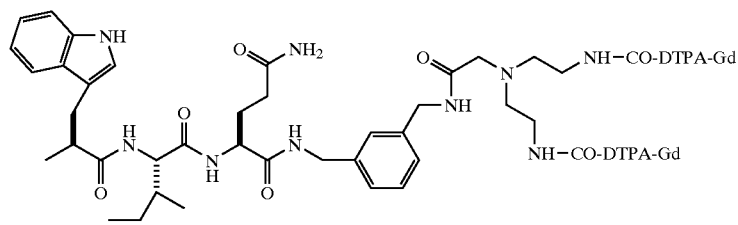

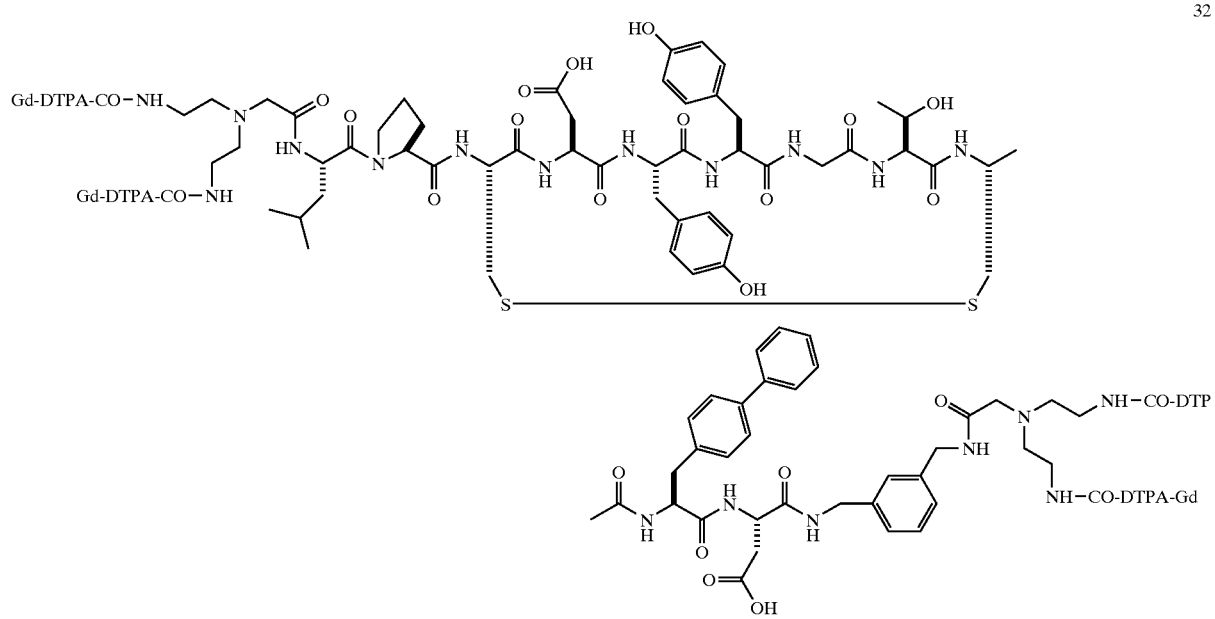
32
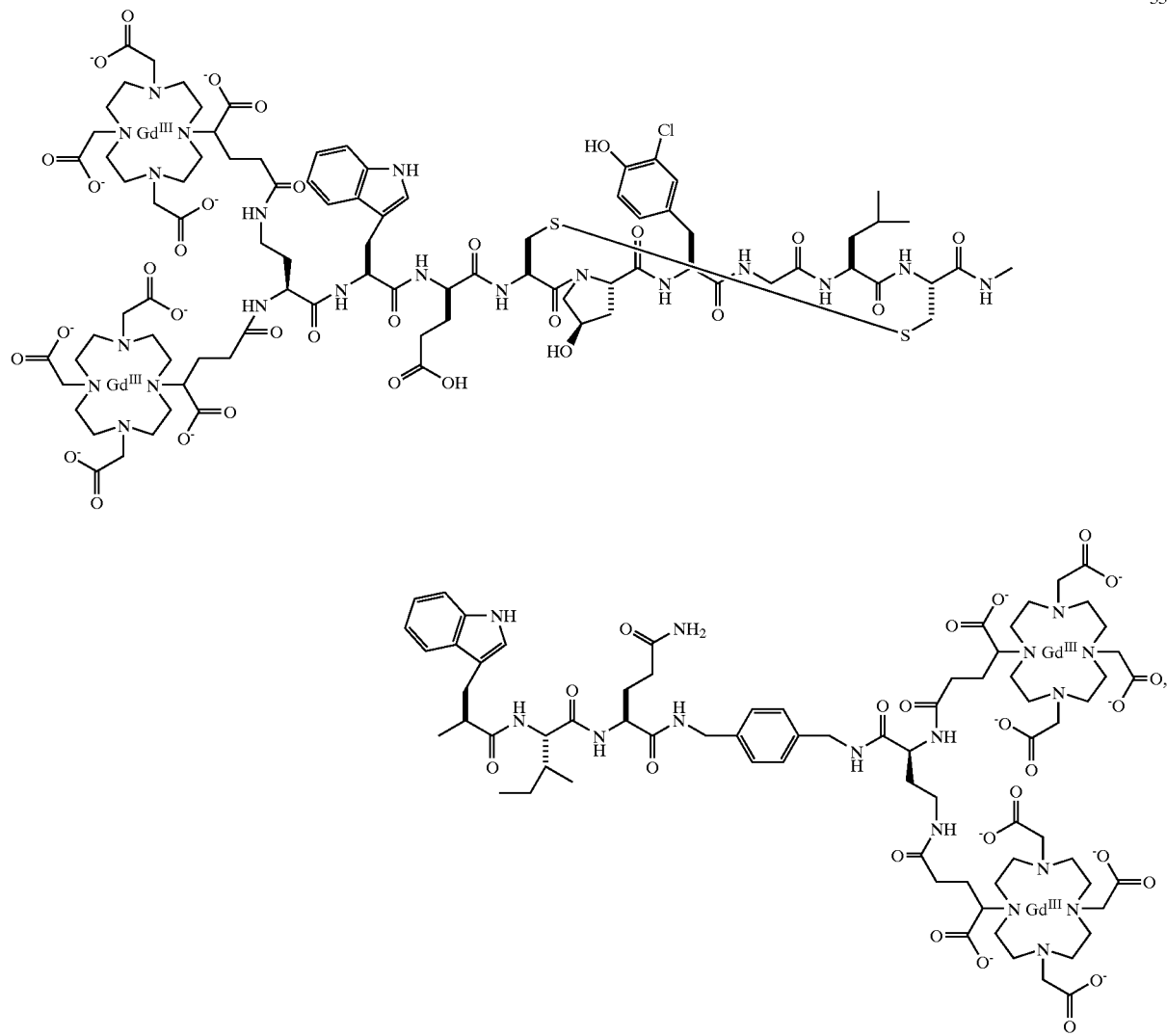
33

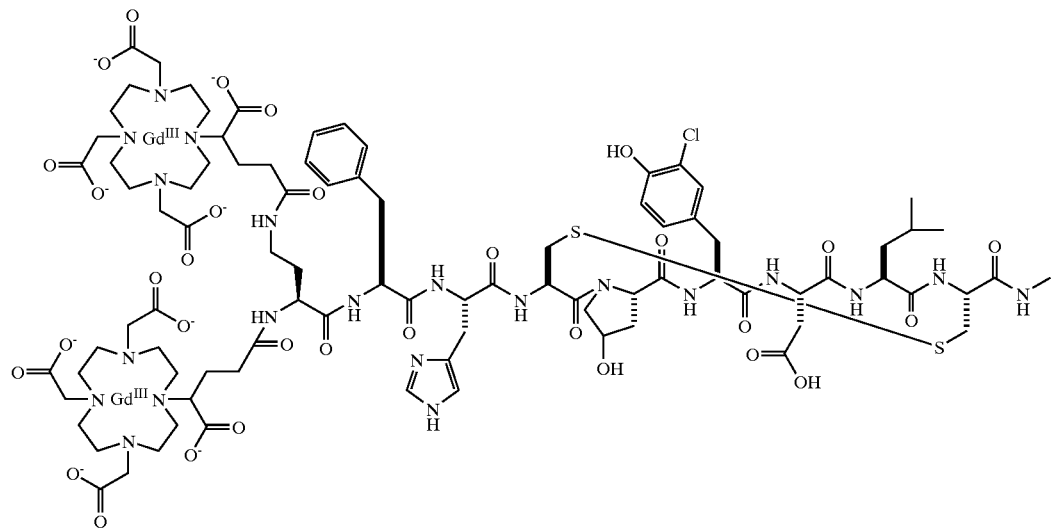
34
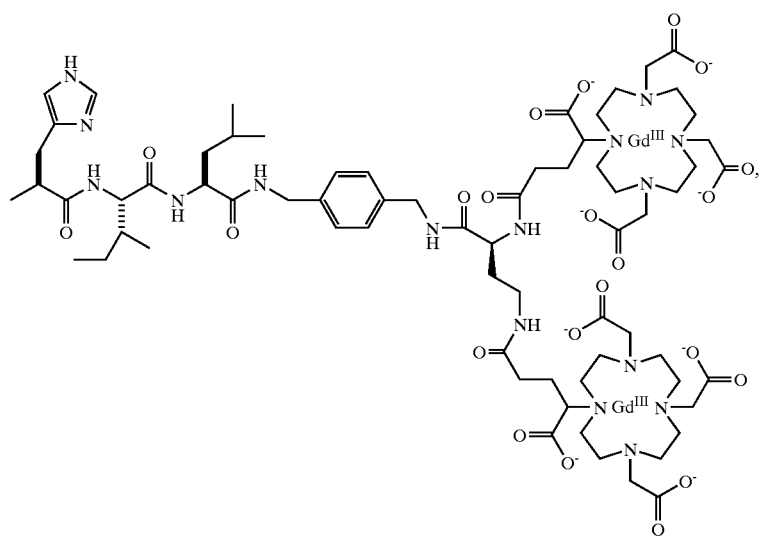
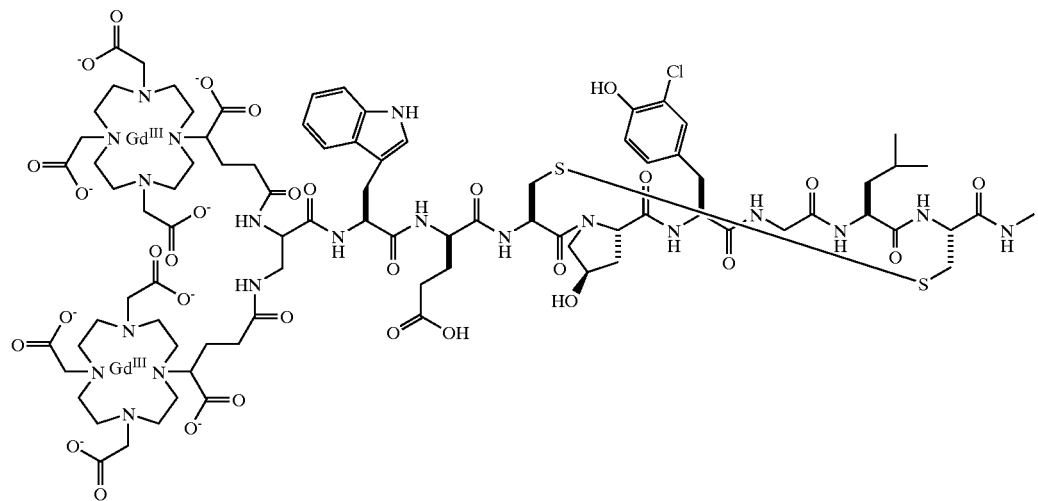
35

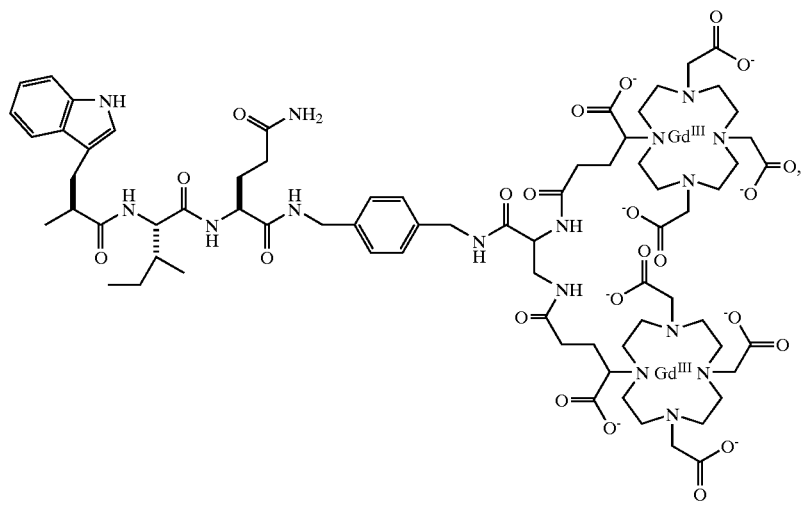
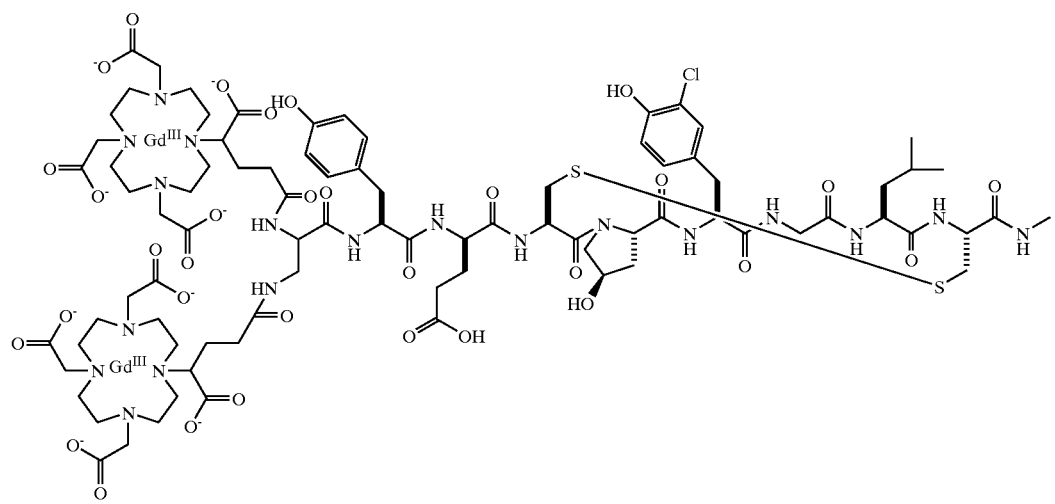
36
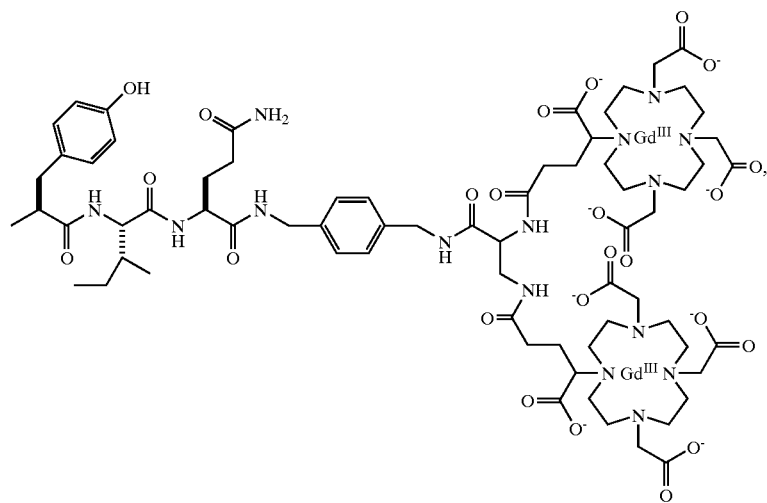

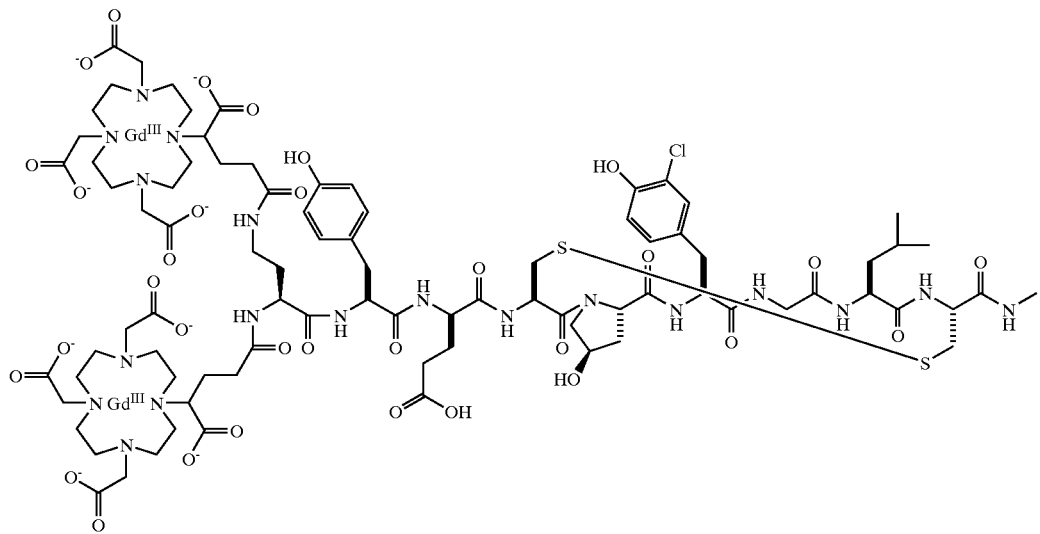
37
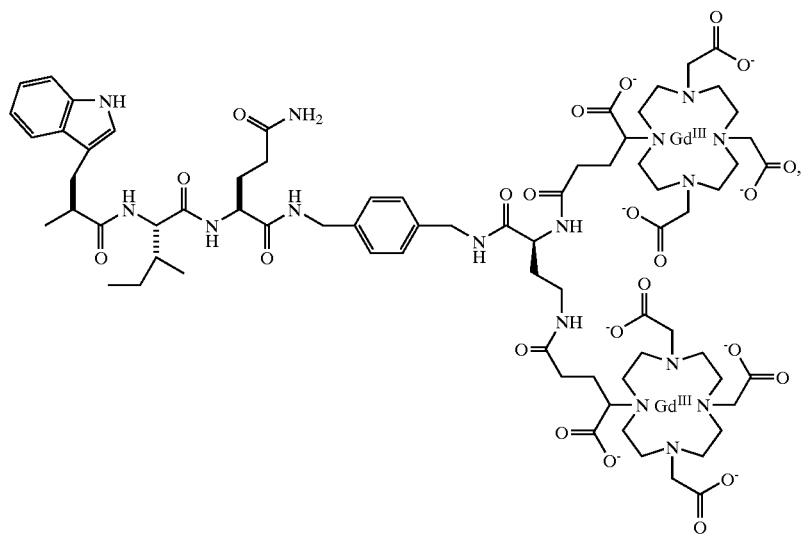
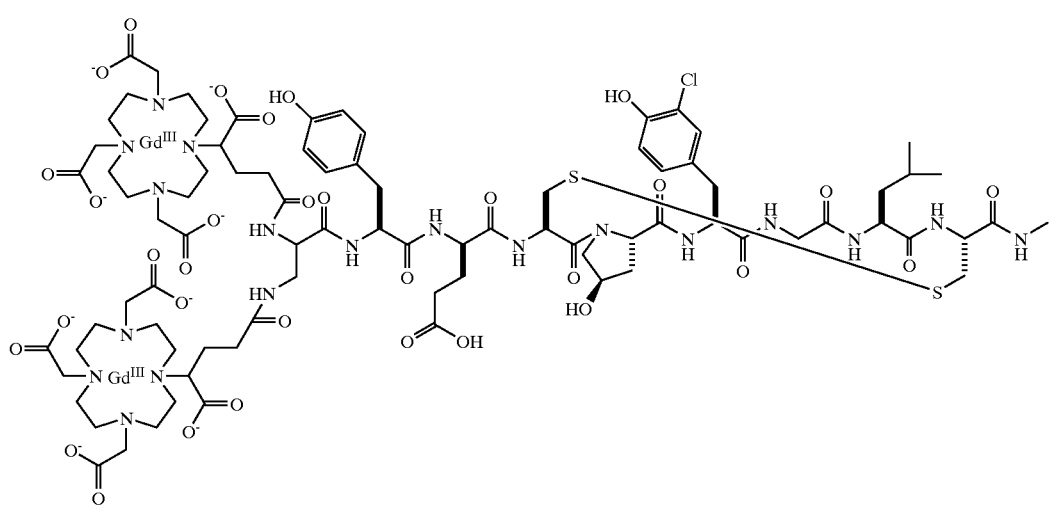
38

-continued
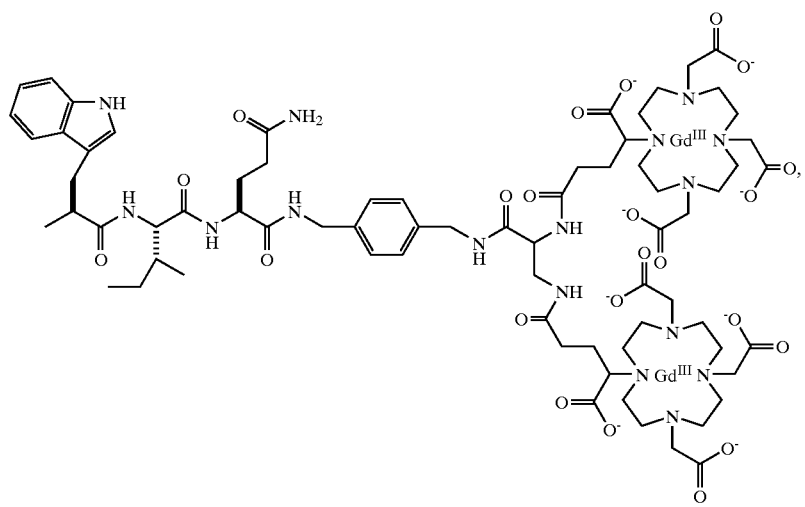
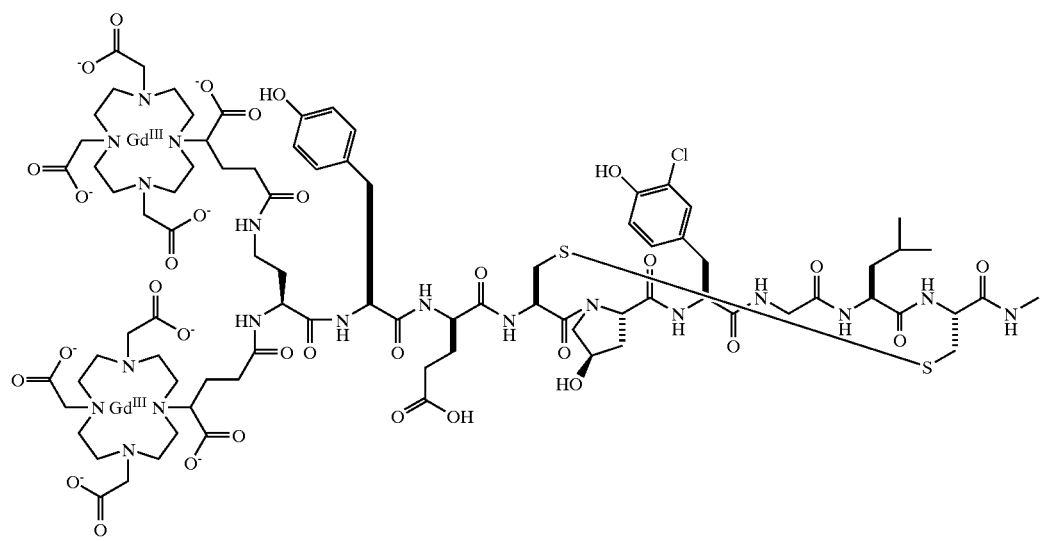
39
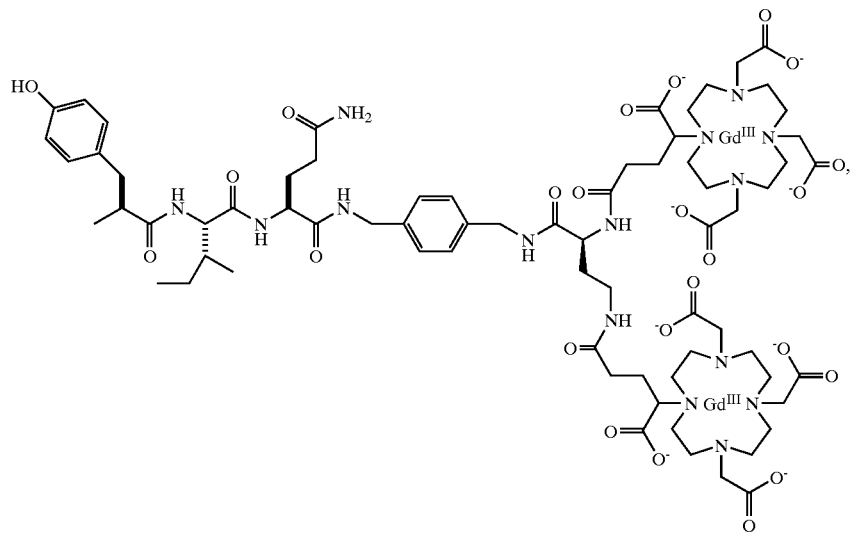

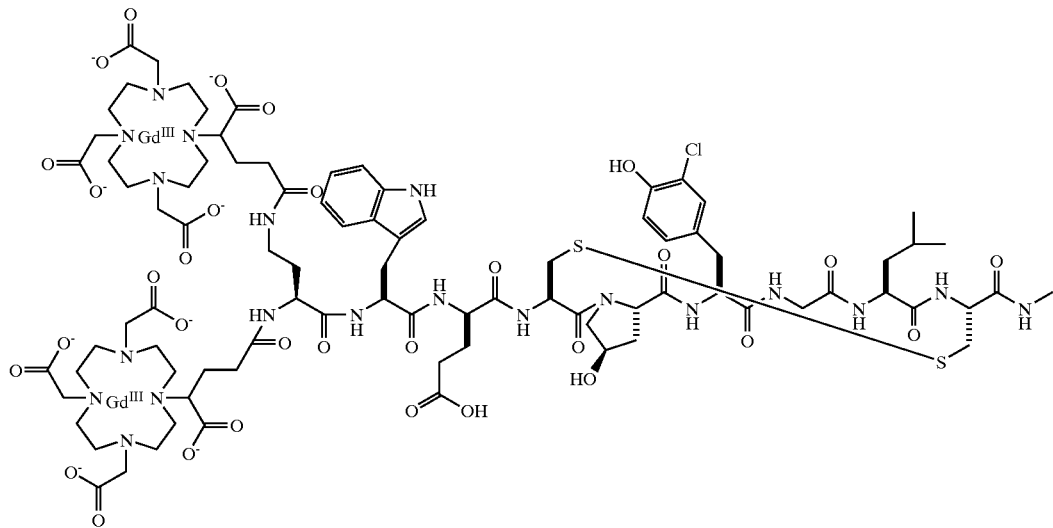
40
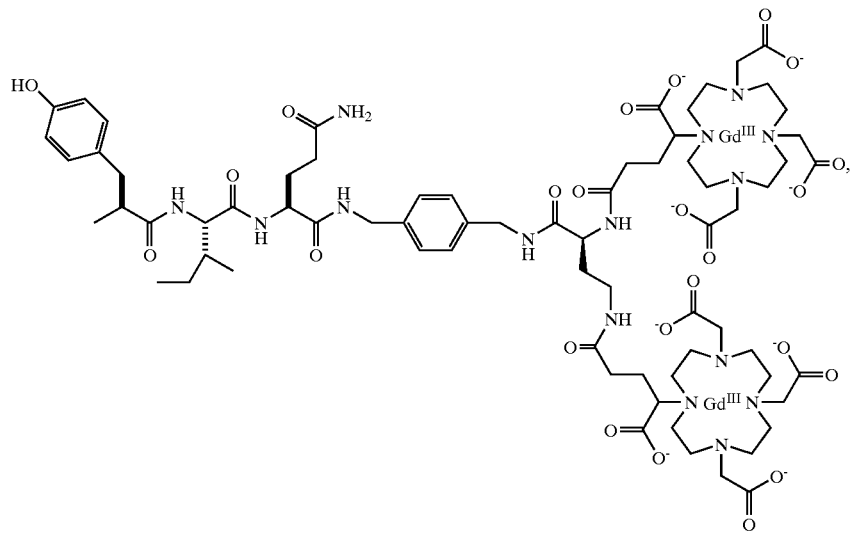
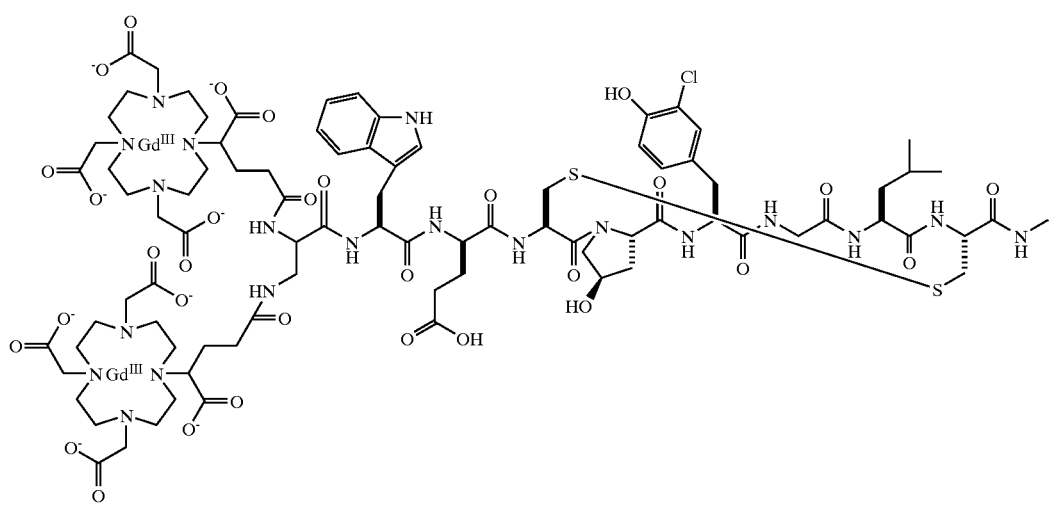
41

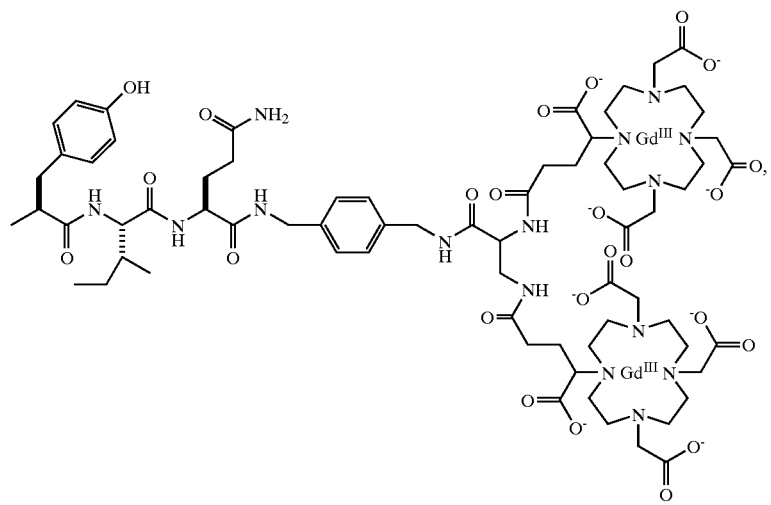
42
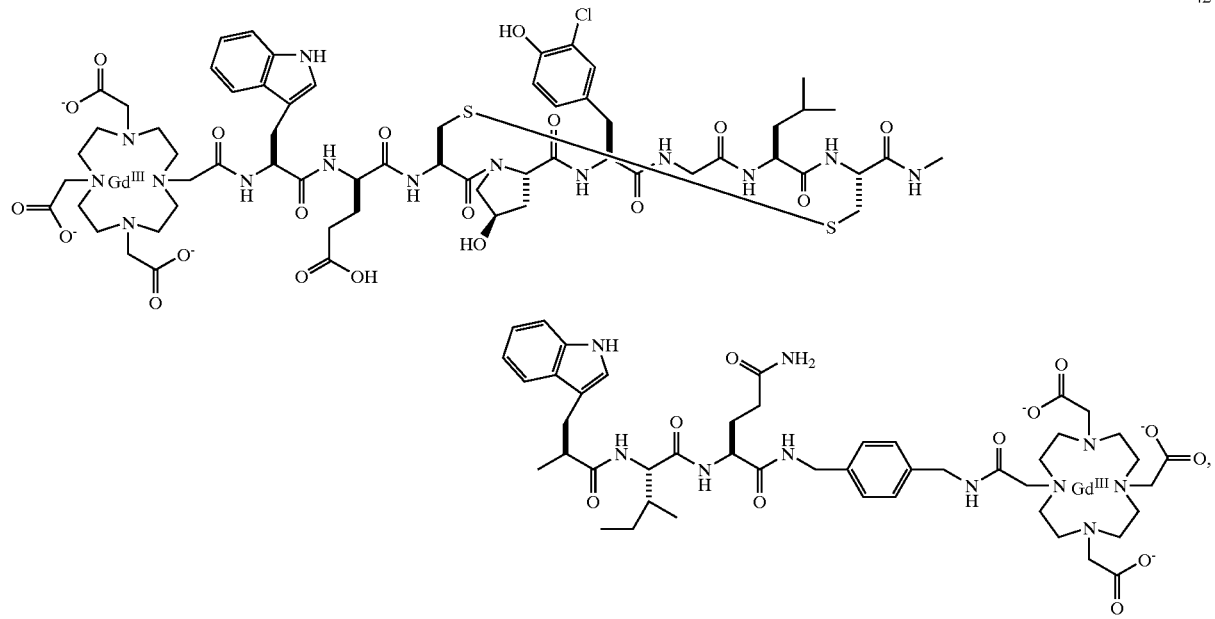
43
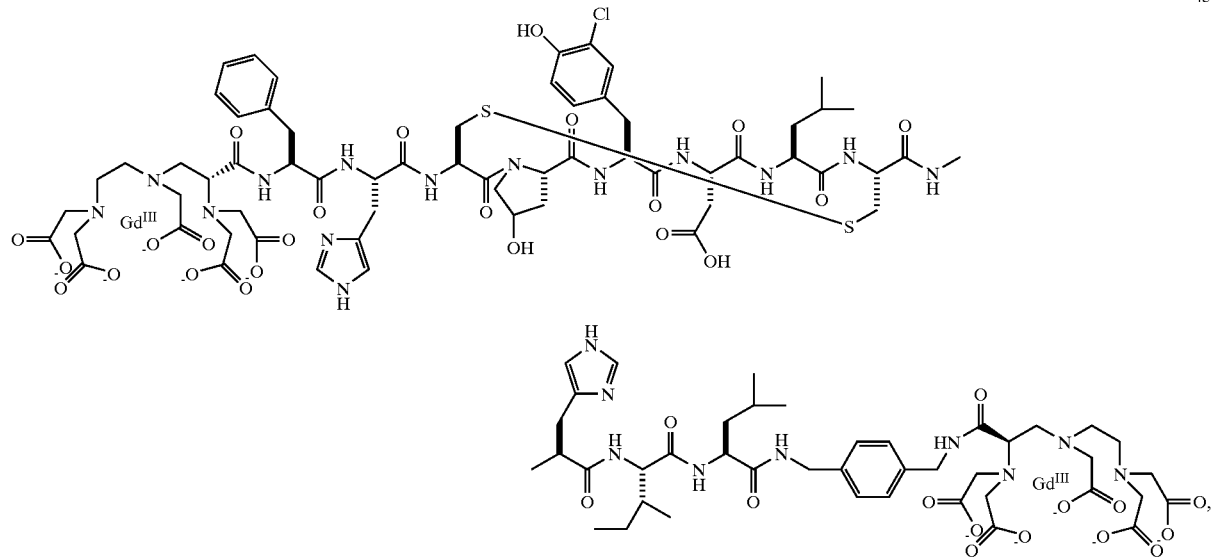

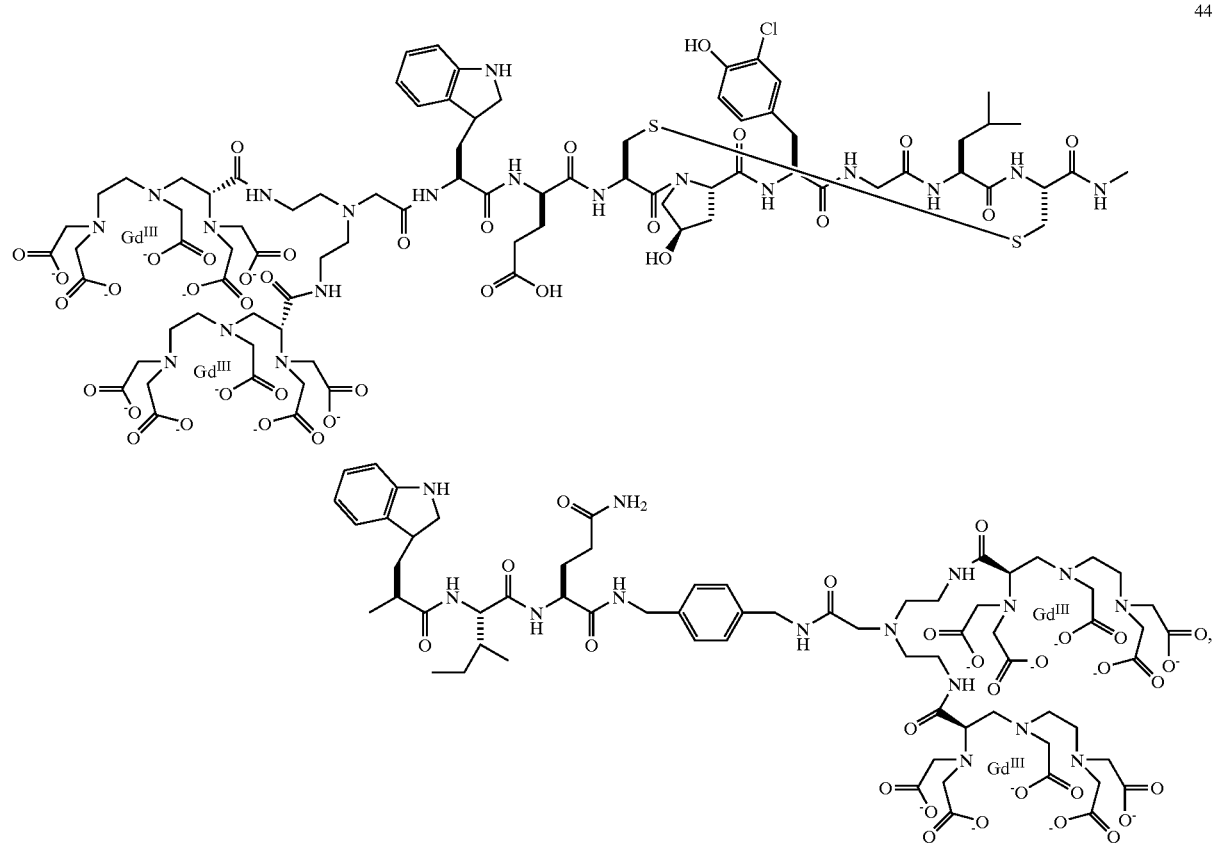
44
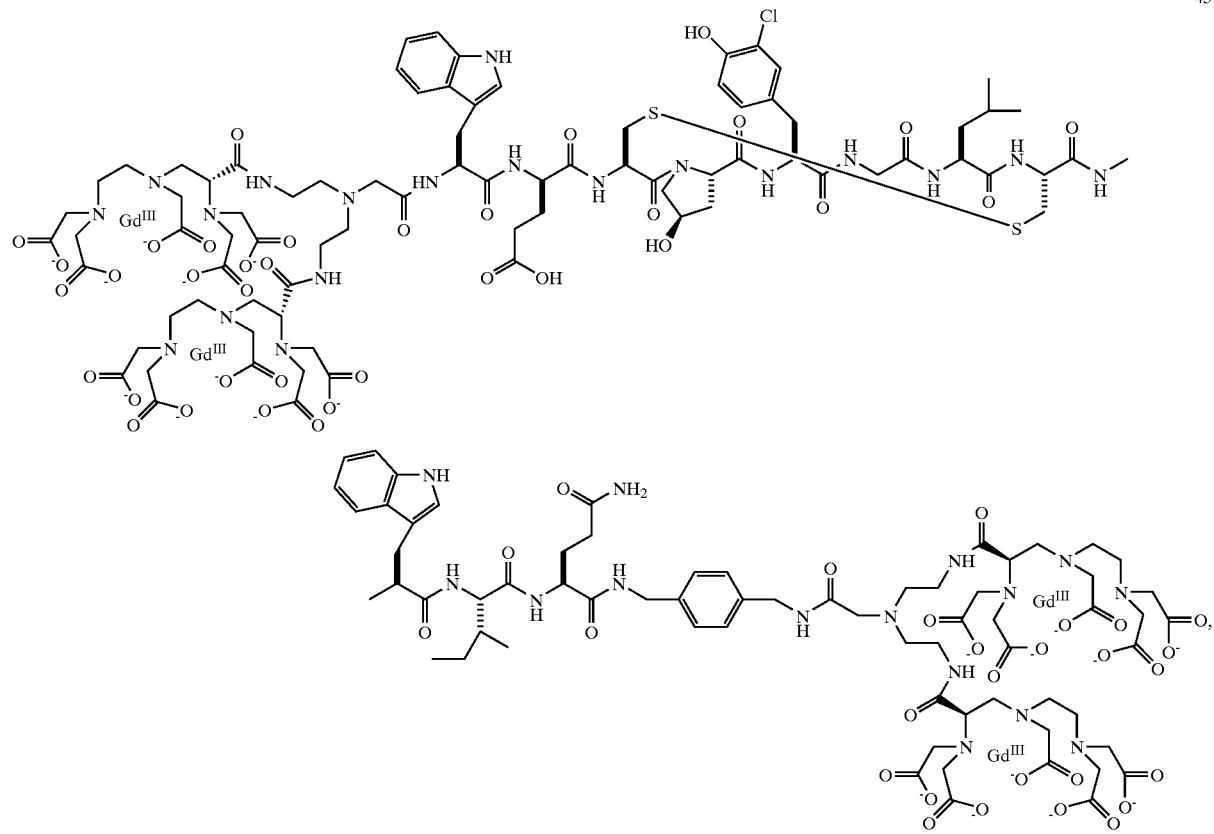
45

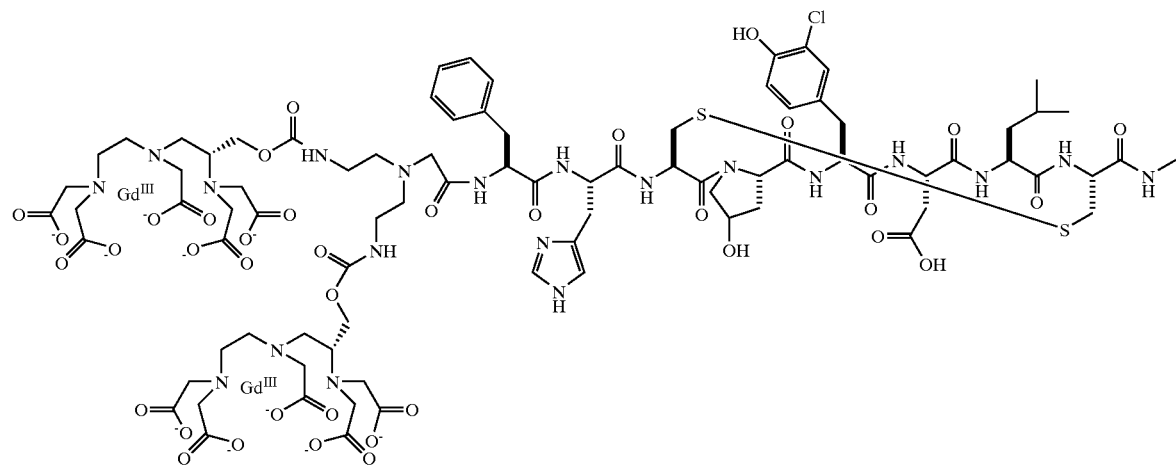
46
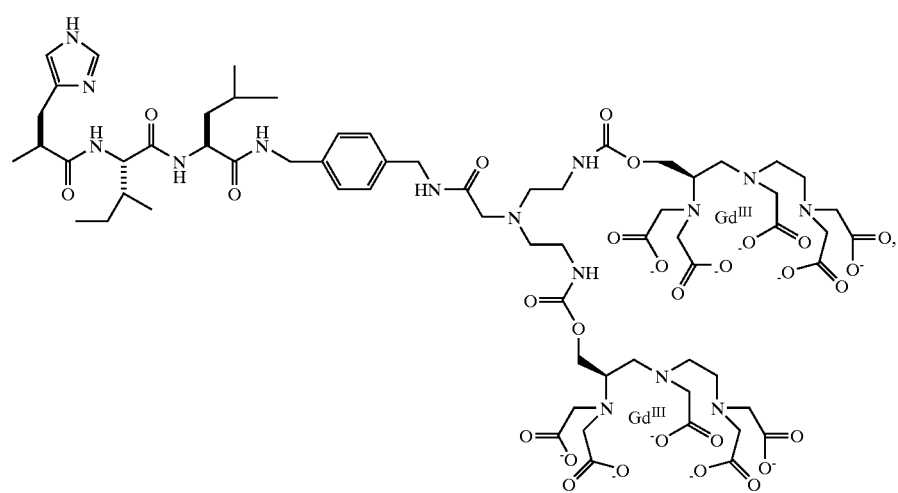
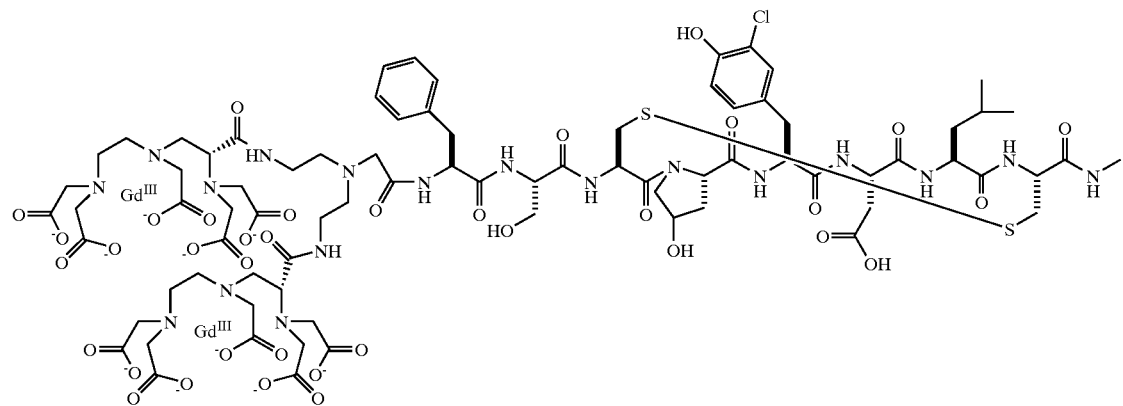
47

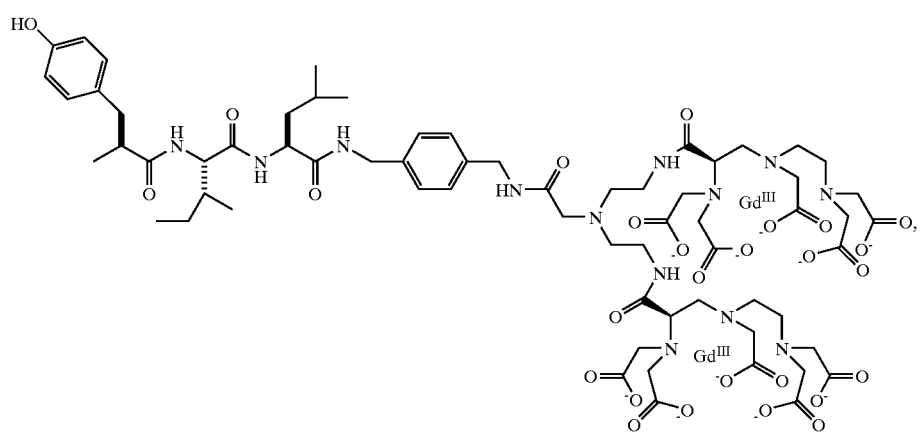
48
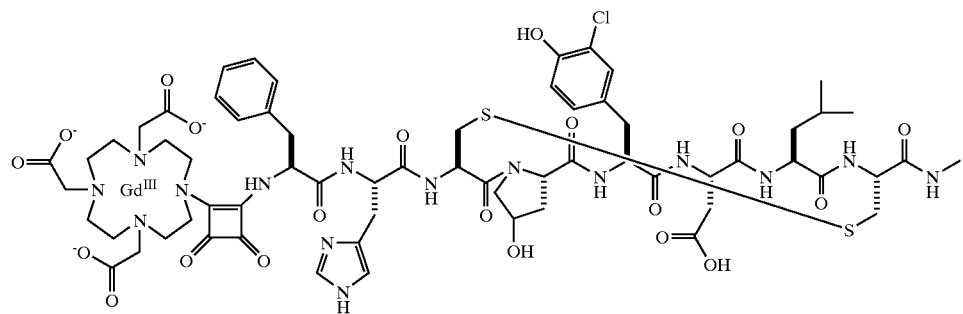
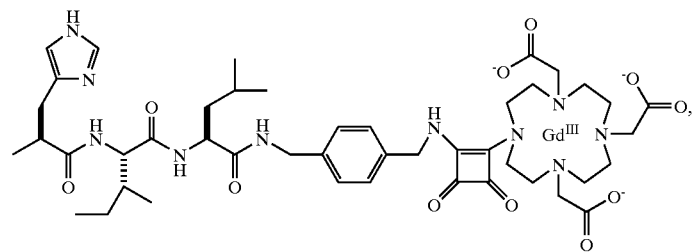
49
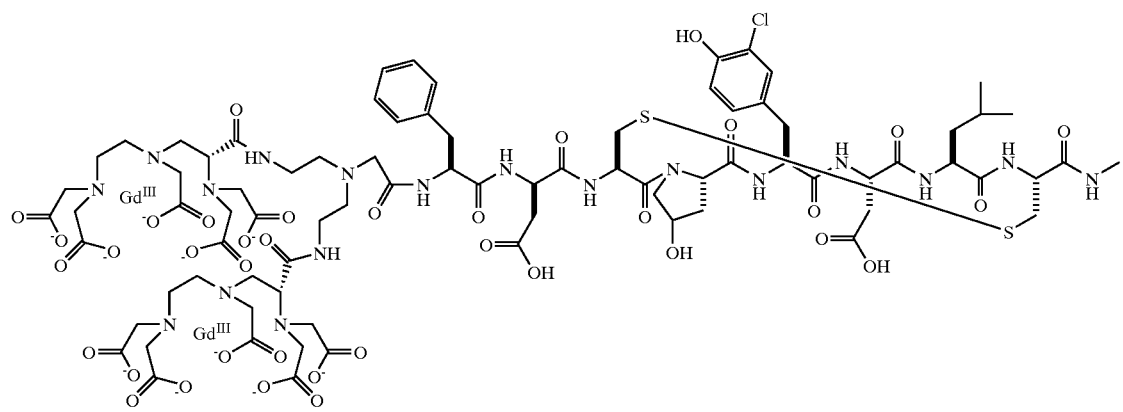

-continued
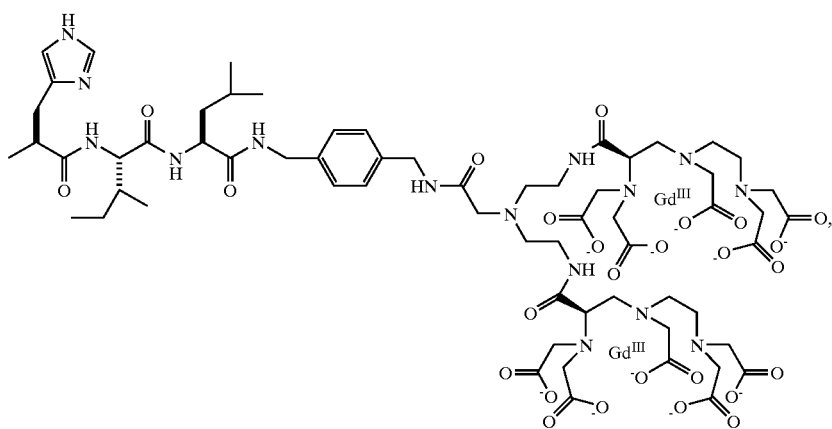
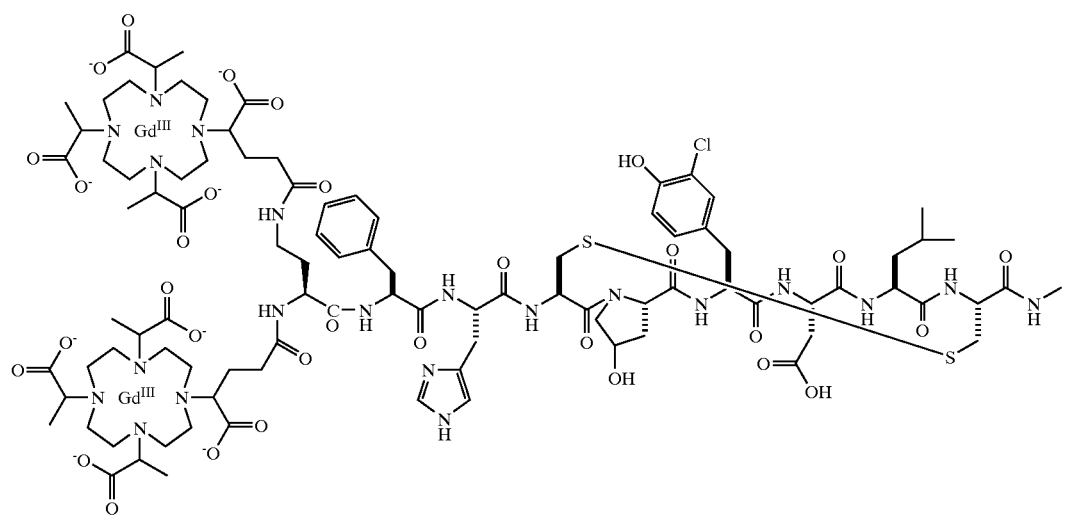
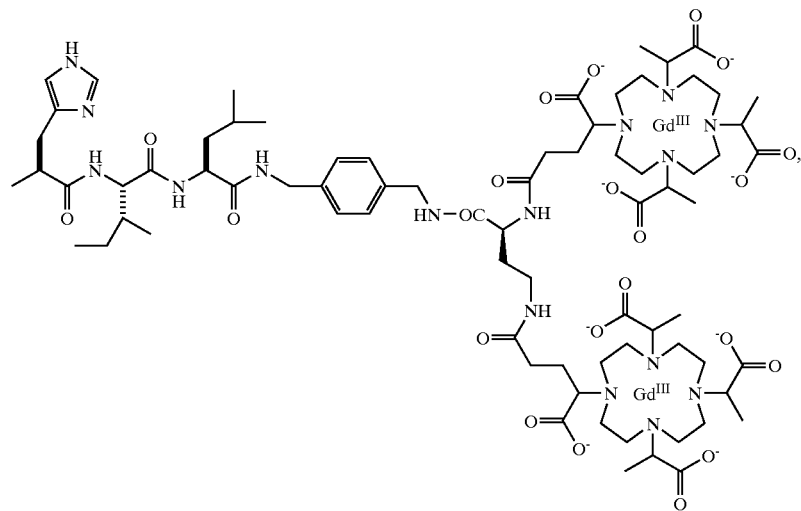

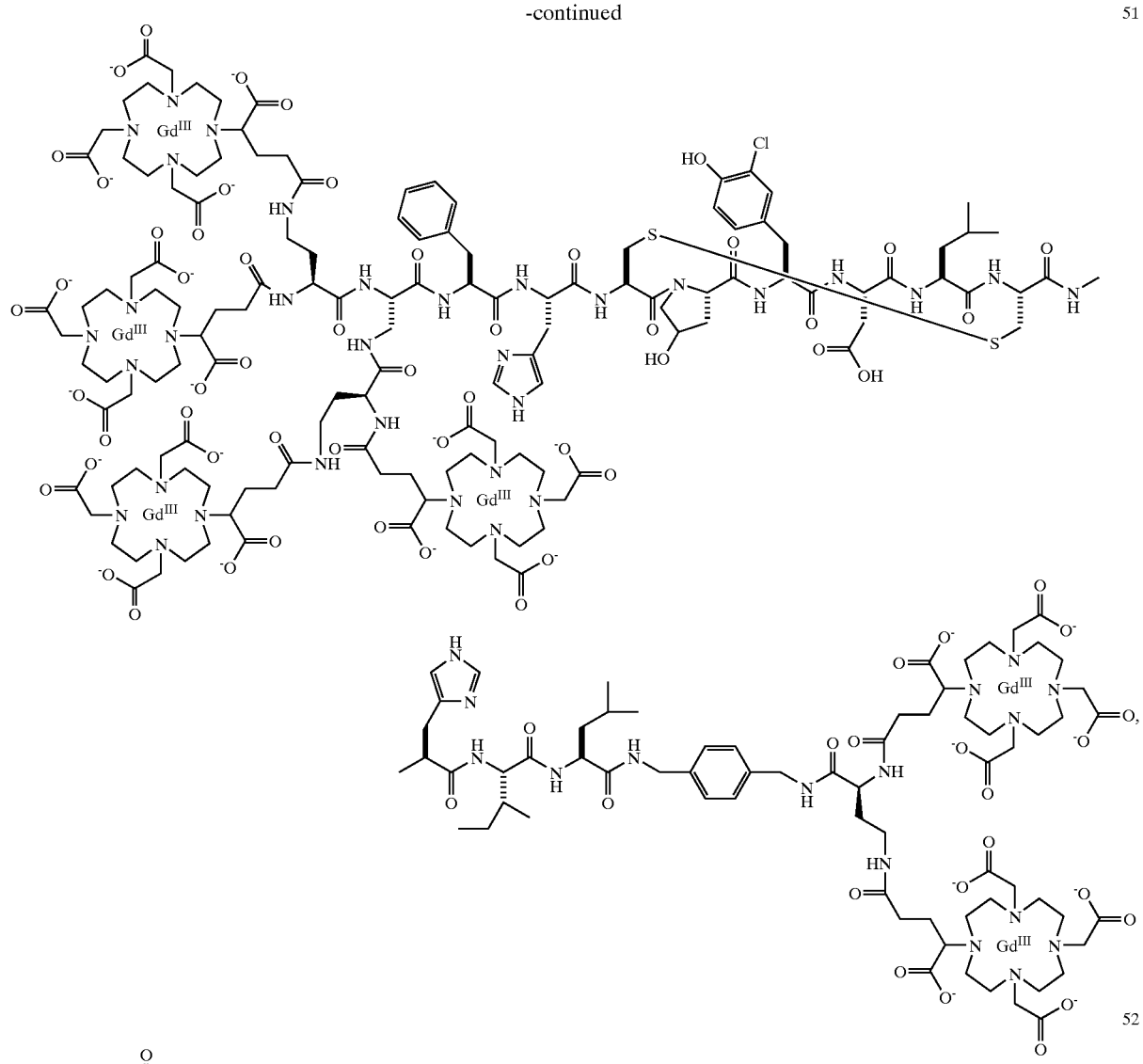
51
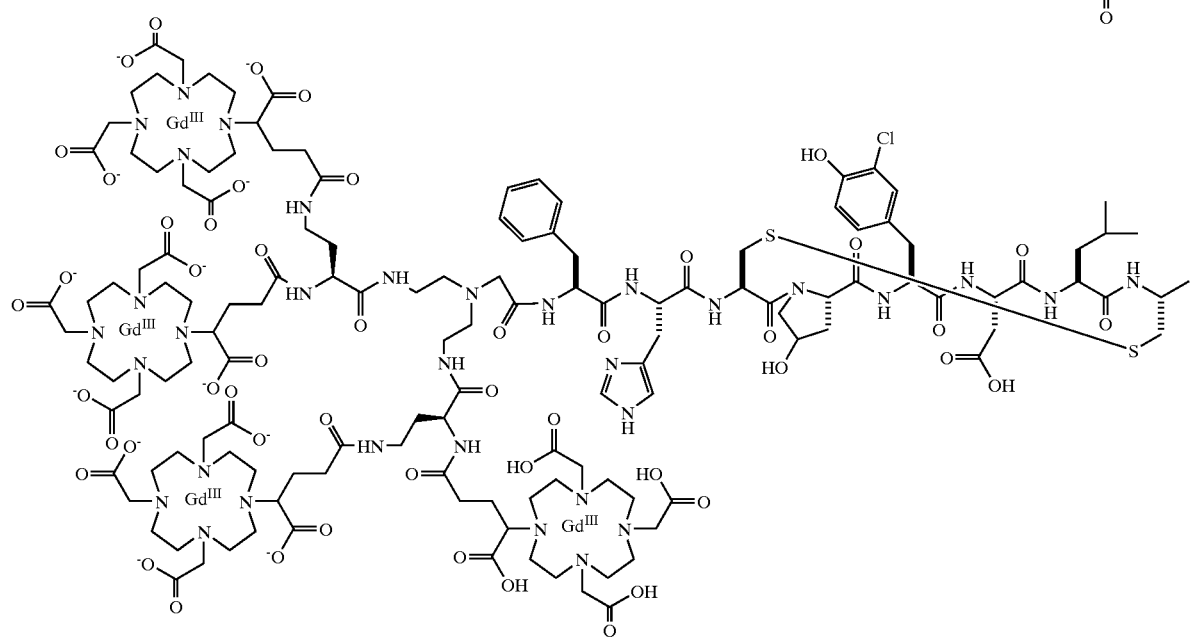
52

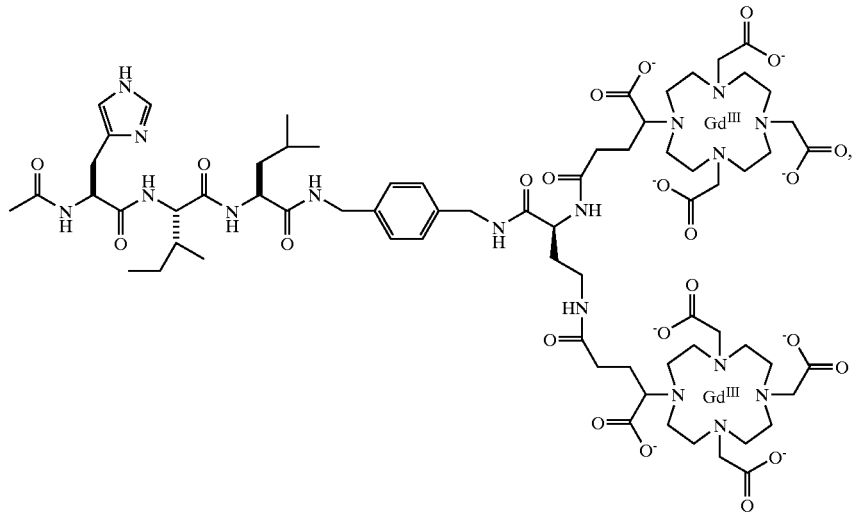
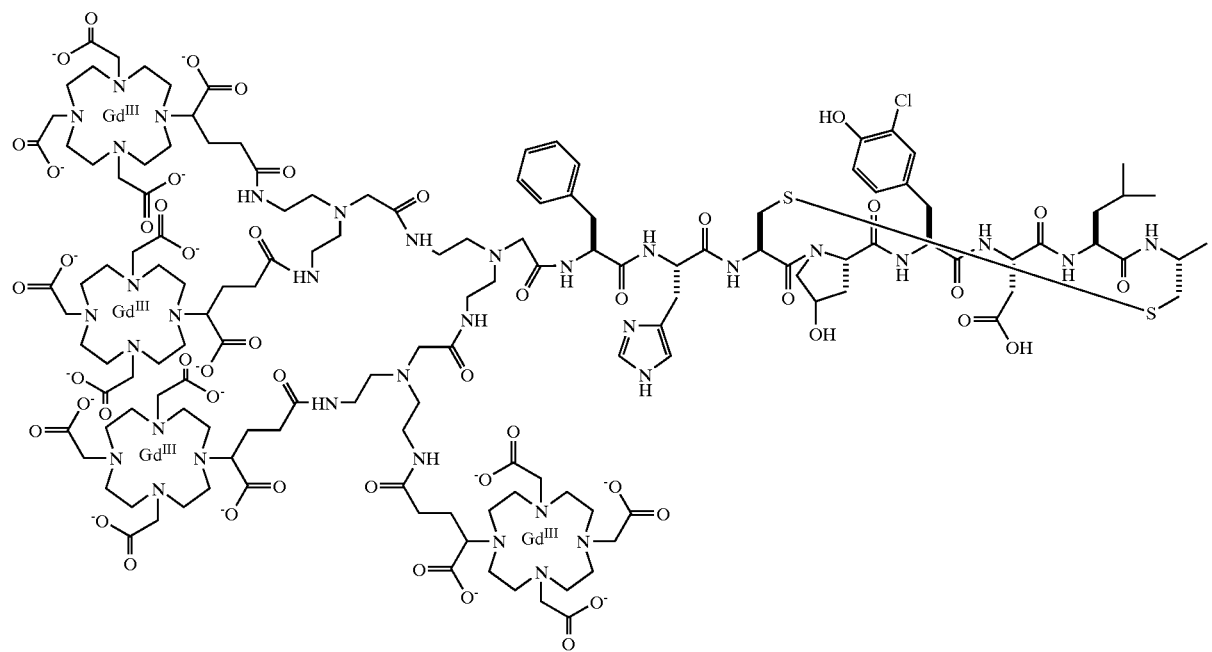
53
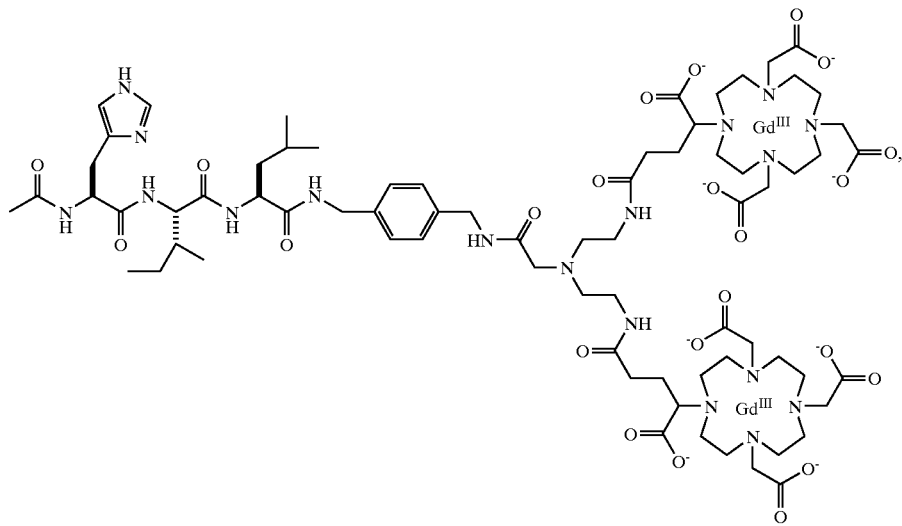

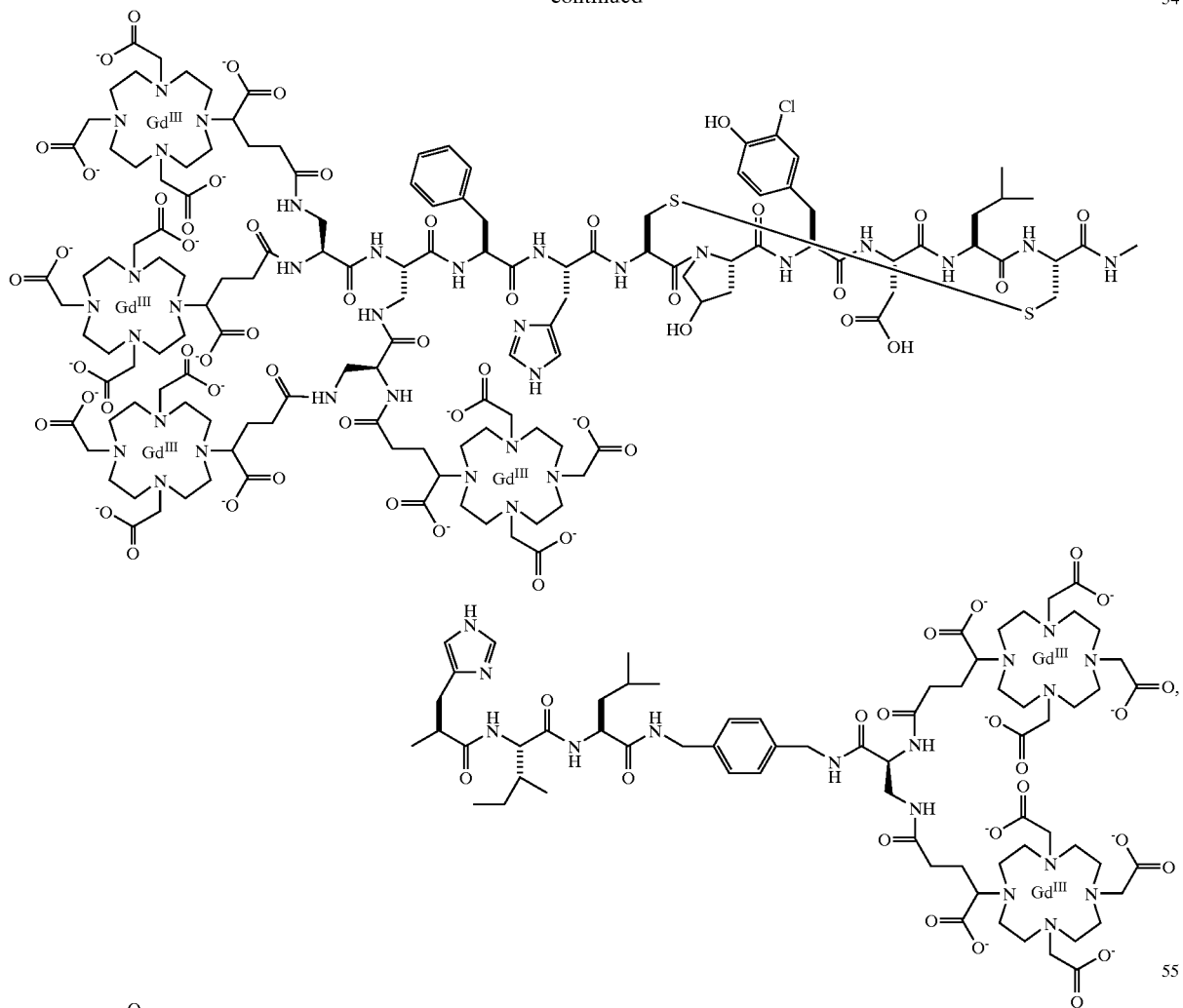
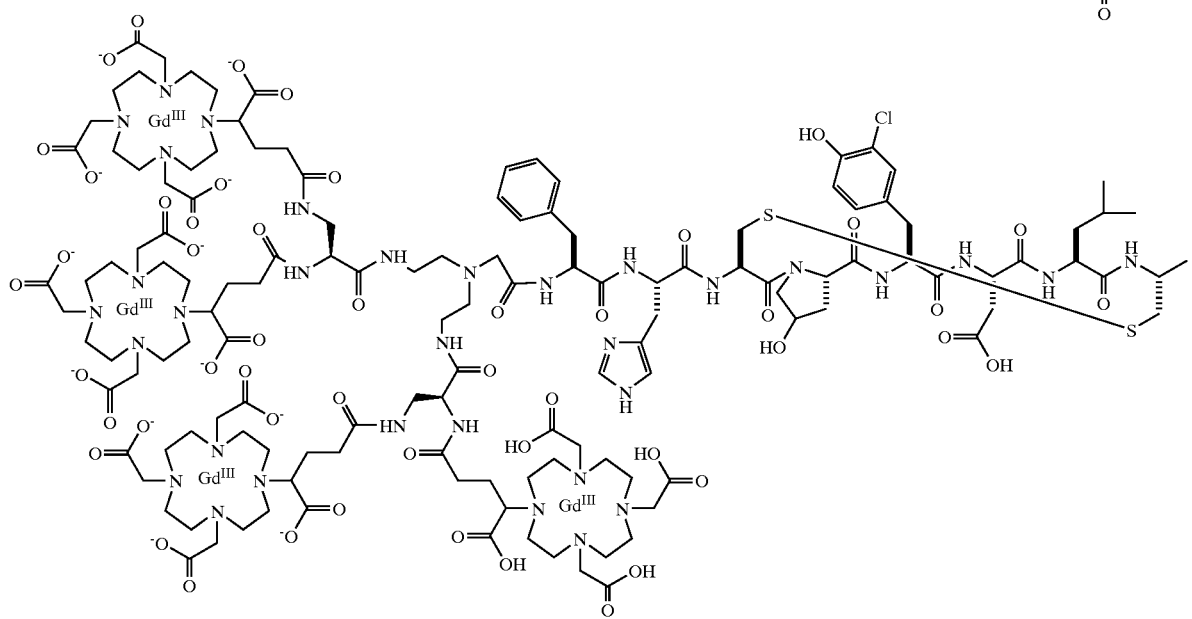

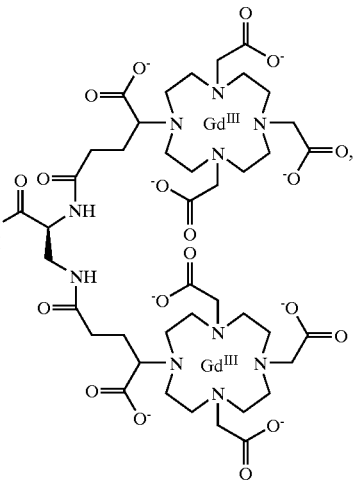

Properties of Contrast Agents

Compounds of this invention can be more stable with respect to degradation by endogenous enzymes than the parent peptide (i.e., the peptide without any attached chelates), a peptide with one or more chelates attached to the N-terminus, or a peptide with one or more chelates attached to the C-terminus. To estimate in vivo stability, test compounds can be incubated with rat liver homogenates. After selected intervals, the reactions can be quenched and centrifuged, and the supernatant can be analyzed by liquid chromatography-mass spectrometry to quantitate the amount of compound remaining.

Compounds of the invention also can bind a target such as human serum albumin or fibrin. For example, at least 10% (e.g., at least 50%, 80%, 90%, 92%, 94%, or 96%) of the contrast agent can be bound to the desired target at physiologically relevant concentrations of drug and target. The extent of binding of a contrast agent to a target, such as HSA or fibrin, can be assessed by a variety of equilibrium binding methods. For example, binding to HSA can be measured by ultrafiltration. For measuring binding to fibrin, a fibrin clot may be formed in a well of a microtiter plate and contacted with the targeting group. After an incubation time sufficient to establish equilibrium, the supernatant is removed by aspiration (the insoluble fibrin remains bound as a gelled clot to the bottom of the well). The concentration of unbound targeting group in the supernatant is then measured. In both methodologies, the concentration of bound contrast agent is determined as the difference between the total targeting group concentration initially present and the unbound targeting group concentration following the binding assay. The bound fraction is the concentration of bound targeting group divided by the concentration of total targeting group.

Compounds of the invention can exhibit high relaxivity as a result of target binding (e.g., to fibrin), which can lead to better image resolution. The increase in relaxivity upon binding is typically 1.5-fold or more (e.g., at least a 2, 3, 4, 5, 6, 7, 8, 9, or 10 fold increase in relaxivity). Targeted contrast agents having 7–8 fold, 9–10 fold, or even greater than 10 fold increases in relaxivity are particularly useful. Typically, relaxivity is measured using an NMR spectrometer. The preferred relaxivity of an MRI contrast agent at 20 MHz and 37° C. is at least 10 mM–1s–1 per paramagnetic metal ion (e.g., at least 15, 20, 25, 30, 35, 40, or 60 mM–1s–1 per paramagnetic metal ion. Contrast agents having a relaxivity greater than 60 mM–1s–1 at 20 MHz and 37° C. are particularly useful.

As described herein, targeted contrast agents can show an increase in clot uptake. Specificity of uptake of fibrin-targeted agents can be determined by comparing the uptake of the agent by blood clots to the uptake by blood. See Example 11 for more details. The specificity of fibrin-targeted contrast agents also can be demonstrated using MRI and observing enhancement of clot signal.

Use of Peptides and Contrast Agents of the Invention

Peptides of the invention can be used to improve therapies for treating thromboembolic disease. Current thrombolytic therapy has limitations, including a significant risk of bleeding, failure to restore blood flow, thrombotic reocclusion after cessation of therapy, and a lag between initiation of therapy and clot lysis. An improved therapeutic index can be achieved by conjugating a fibrin targeting peptide of the invention to a thrombolytic agent (e.g., a protein thrombolytic such as plasminogen activators of human or bacterial origin). Such conjugates can activate plasminogen locally or increase endogenous levels of tPA. For example, a fibrin targeting peptide can be conjugated to human plasminogen activators including recombinant tissue type plasminogen activator (tPA), prourokinase and urokinase (both single and two chain forms), bacterium derived plasminogen activator including streptokinase, staphylokinase, and animal derived plasminogen activators, including vampire bat plasminogen activator. In addition, fibrin targeting peptides can be conjugated to fibrinolytics such as copperhead snake fibrolase, which exhibits direct fibrinolytic activity. Such enzymes and proteins can be obtained commercially, extracted from natural sources or tissues, or prepared recombinantly.

The compositions of the invention can be linked or fused in known ways, using the same type of linkers discussed above with respect to constructing MRI contrast agents. Conjugation to a protein can be achieved by standard chemical techniques including the formation of amide, ester, disulfide, and thioether bonds. For example, a fibrin binding peptide can be covalently linked, either directly or through a linker, to a protein by forming an amide bond between the fibrin binding peptide or the linker and the lysine residues on the surface of the protein. These surface lysine residues are usually distant from the enzyme's catalytic site. Therefore, the tethered moieties do not interfere with the enzyme's catalytic activity. Multiple ligation can be achieved in a single step. The ratio of the fibrin targeting peptide to the thrombolytic or fibrinolytic agent can be controlled by adjusting the stoichiometry of the ligation chemistry. Multiple ligation is particularly useful in the case of a moderately strong fibrin binding ligand because higher binding affinity can be realized through the so called "avidity" effect. In particular, a coupling agent or an activated ester can be used to achieve amide bond formation between the lysine and the fibrin binding moiety or the linker. The below scheme shows an example of a hybrid molecule formed by chemical ligation of urokinase to multiple fibrin binding peptides via linker moieties. The number of surface lysine residues and the number of fibrin binding molecules are illustrative. Alternatively, the fibrin targeting peptide can be incorporated into the hybrid molecule using recombinant DNA technology.

the contrast between thrombus and background tissues. Methods of preparation for T2 techniques may also prove useful. Finally, preparations for magnetization transfer techniques may also improve contrast with agents of the invention.

Compositions of the invention, including peptides, peptides conjugated to thrombolytics, and peptide-targeted multimeric contrast agents, can be formulated as a pharmaceutical composition in accordance with routine procedures. As used herein, the compounds of the invention can include pharmaceutically acceptable derivatives thereof. "Pharmaceutically acceptable" means that the compound or composition can be administered to an animal without unaccept-

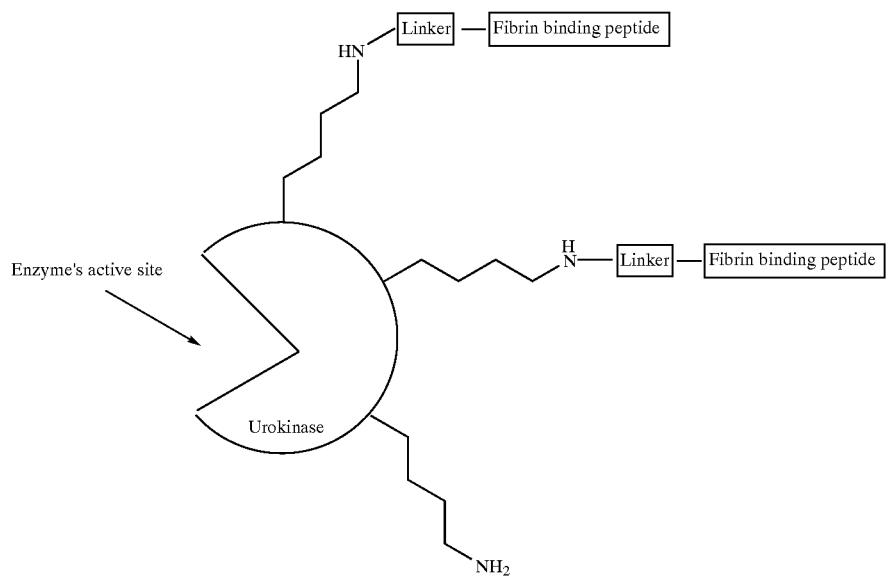

In some embodiments, peptides of the invention can be linked to a thrombolytic agent with a linker encompassing an enzymatic cleavage site, e.g., an enzymatic cleavage site normally cleaved by enzymes in the coagulation cascade, such as Factor Xa, thrombin, or plasmin cleavage sites, etc. The thrombolytic agent is not activated until it is cleaved from the clot binding compositions of the invention at the site of the clot, the risk of unwanted bleeding events at sites distant from the clot would be minimized. Furthermore, thrombolytic moieties can be linked to a peptide-targeted multimeric contrast agent such that a clot can be identified, imaged and dissolved.

Contrast agents prepared according to the disclosures herein may be used in the same manner as conventional MRI contrast agents and are useful for the diagnosis of deep vein thrombosis, pulmonary embolus, coronary thrombosis, carotid and intracranial thrombosis, atrial and ventricular thrombi, aortic arch thrombi, and high risk plaque. When imaging a thrombus, certain MR techniques and pulse sequences may be preferred to enhance the contrast of the thrombus compared to the background blood and tissues. These techniques include, but are not limited to, black blood angiography sequences that seek to make blood dark, such as fast spin echo sequences and flow-spoiled gradient echo sequences. These methods also include flow independent techniques that enhance the difference in contrast due to the T1 difference between contrast-enhanced thrombus and blood and tissue, such as inversion-recovery prepared or saturation-recovery prepared sequences that will increase able adverse effects. A "pharmaceutically acceptable derivative" means any pharmaceutically acceptable salt, ester, salt of an ester, or other derivative of a compound of this invention that, upon administration to a recipient, is capable of providing (directly or indirectly) a compound of this invention or an active metabolite or residue thereof. Other derivatives are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the compounds of this invention include counter ions derived from pharmaceutically acceptable inorganic and organic acids and bases known in the art.

Pharmaceutical compositions of the invention can be administered by any route, including both oral and parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, compositions of the invention can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions of this invention comprise the compounds of the present invention and pharmaceutically acceptable salts thereof, with any pharmaceutically acceptable ingredient, excipient, carrier, adjuvant or vehicle.

A contrast agent is preferably administered to the patient in the form of an injectable composition. The method of administering a contrast agent is preferably parenterally, meaning intravenously, intra-arterially, intrathecally, interstitially or intracavitarilly. Pharmaceutical compositions of this invention can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 $\mu$g/kg, preferably between 0.01 to 25.0 $\mu$g/kg of host body mass. The optimal dose will be determined empirically following the disclosure herein.

With respect to treatment of thrombolytic conditions, the quantity of material administered will depend on the seriousness of the thromboembolic condition and position and the size of the clot. The precise dose to be employed and the mode of administration can be decided according to the circumstances by the physician supervising treatment. In general, dosages of the combined composition/thrombolytic agent conjugate will follow the dosages that are routine for the thrombolytic agent alone, although the improved affinity for fibrin/clot binding added by the compositions disclosed herein may allow a decrease in the standard thrombolytic dosage. Particular thrombolytics contemplated for use in this therapy (with examples of dose and method of administration) are as follows:

The invention will be further described in the following examples, which do not limit the scope of the invention described in the claims.

EXAMPLES

Synthesis, characterization, and use of several high relaxivity contrast agent compositions of the invention will be further illustrated in the following examples. The specific parameters included in the following examples are intended to illustrate the practice of the invention, and they do not in any way limit the scope of the invention. Those skilled in the art will recognize, or be able to ascertain using no more than routine experimentation, many equivalents to the specific embodiments and methods described herein. Such experiments are intended to be encompassed by the scope of the claims.

Example 1

Synthesis of Peptide-Based MR Imaging Agents

The peptide with linker-subunit moiety bound to C-terminus (P-[linker-subunit moiety]). The unprotected peptide was prepared using standard Fmoc strategy and a diaminotrityl resin. The peptide was cyclized using thallium trifluoroacetate on the resin or in solution. After being cleaved from the resin, the unprotected peptide was purified by RP-HPLC (C-18 column, $H_2O/CH_3CN/TFA$).

Linker Moiety: To a solution of Boc-Dpr(Boc)-OH.DCHA (1 eq.) and pentafluorophenol (1.2 eq.) in dichloromethane was added PS-carbodiimide (1.2–1.5 eq.). The mixture was shaken for 3–5 h at room temperature. After LC-mass results indicated the reaction was complete, the resin was removed by filtration and the solvent was evaporated under reduced pressure to give the crude Linker Moiety (Boc-Dpr(Boc)-OPft (N-$\alpha$-Boc-N-$\beta$-Boc-L-diaminopropionic acid pentafluorophenyl ester, 356–128) as a white foam.

Precursor MR Imaging Agent: To a solution of P-[linker-subunit moiety] (1 eq.) and the Linker Moiety {Boc-Dpr(Boc)-Opft} (2.2 eq.) in DMF was added DIPEA (4–6 eq.). The mixture was stirred overnight at room temperature. After LC-mass results indicated the reaction was complete, the solvent was removed under reduced pressure. The crude product was then stirred in a mixture of TFA, water and anisole (90%/5%/5%) at room temperature for 3 h. Diethyl ether was added and a white precipitate formed, which was purified by RP-HPLC (C-18 column, $H_2O/CH_3CN/TFA$) to give the Precursor MR Imaging Agent (tetrakisamino-peptide as a white solid.

Precursor Chelate Moiety: DOTAGA-Opft. To a solution of DOTAGA-OH (1 eq.) and pentafluorophenol (1.2 eq.) in dichloromethane was added PS-carbodiimide (1.2–1.5 eq.). The mixture was shaken for 3–5 h at room temperature. After LC-mass results indicated the reaction was complete,

| | |
|---|---|
| Streptokinase | 1–3 megaunits over 30 minutes to 3 hrs |
| Anistreplase | 30 units; 2–5 minute injection |
| tPA (wild-type) | 50–150 mg; infusion over up to 6 hrs |
| Two-chain urokinase | (40–100 mg); infusion over up to 6 hrs |
| Single-chain urokinase (scuPA) | 3–12 megaunits (30–100 mg; infusion over up to 5 hrs |
| Hybrid plasminogen activators and derivatives | 20–100 mg; injection or infusion |
| Muteins of plasminogen activators | 10–100 mg; injection or infusion | the resin was removed by filtration and the solvent was evaporated under reduced pressure to give the crude Precursor Chelate Moiety as a white foam.

MR Imaging Agent. To a solution of the Precursor MR Imaging Agent (1 eq.) and Precursor Chelate Moiety (4.0 eq.) in DMF was added DIPEA (4.0 eq.). The mixture was stirred overnight at room temperature. After LC-mass results indicated the reaction was complete, the solvent was removed under reduced pressure.

The crude product was then stirred in a mixture of TFA, phenol, methylsulfonic acid, anisole and dichloromethane (90%/2.5%/2.5%/2.5%/2.5%) for 15 min. at room temperature. Diethyl ether was added and a white precipitate formed and was collected as the crude product.

The crude product was reacted with $GdCl_3 \cdot H_2O$ in deionized water to form the crude MR imaging agent, which was purified using RP-HPLC (C-18 column, Ethanol/50 mmol $AcONH_4$). Appropriate fractions were combined and the ethanol removed under reduced pressure, and then the combined fractions were treated with sodium acetate for salt exchange. After lyophilization the excess salts were removed using reverse-phase chromatography on a Waters Sep-Pak® C-18 cartridge with water and ethanol:water (50:50) eluants. Appropriate fractions were combined, the ethanol removed under reduced pressure, and the solution was lyophilized to give the desired peptide MR imaging agent as a white solid.

Similar methods were used to synthesize other MR imaging agents.

Example 2

Methods for Synthesis of A Chelate Precursor Moiety (Synthon #3)

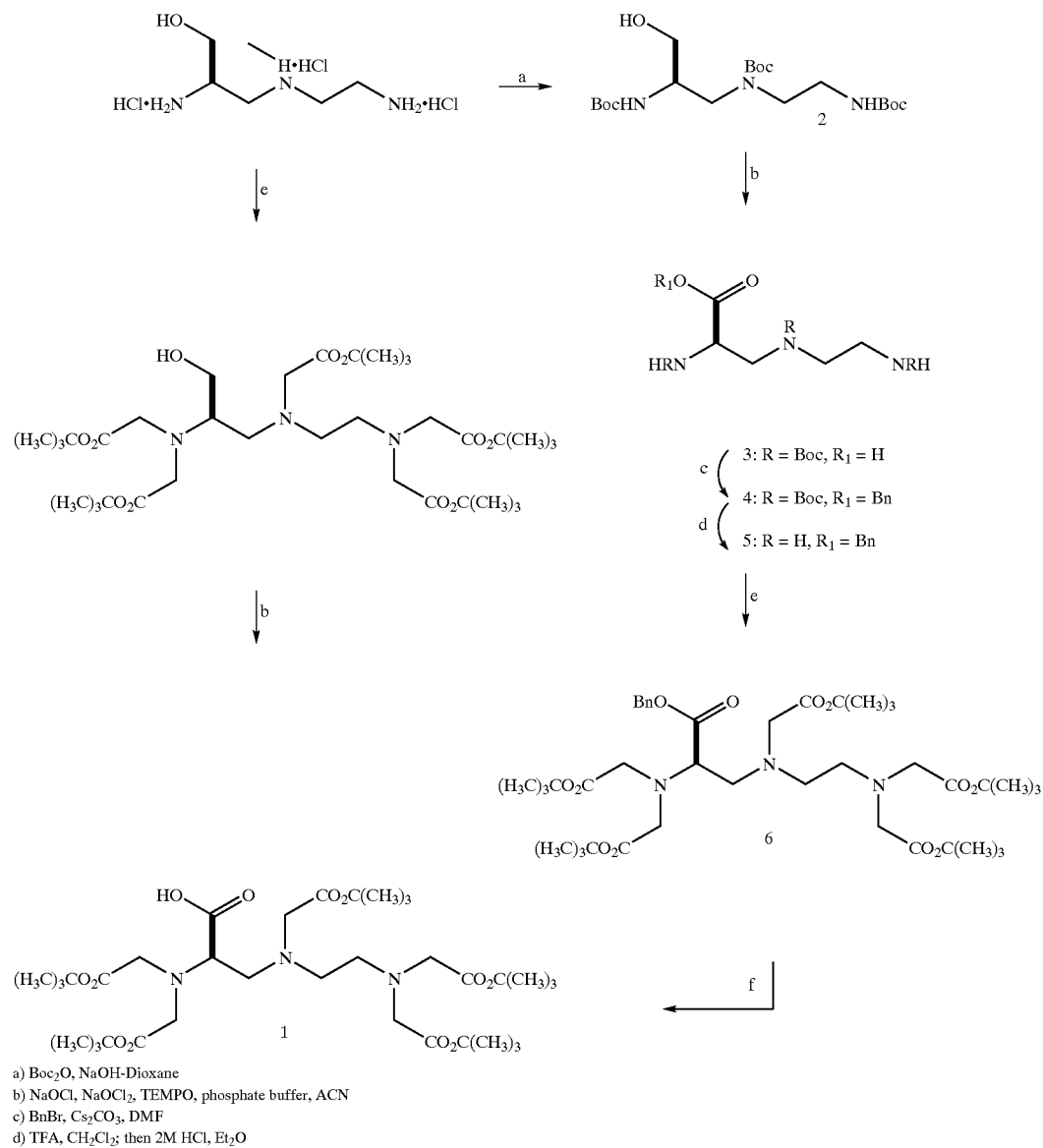

a) $Boc_2O$, NaOH-Dioxane
b) NaOCl, $NaOCl_2$, TEMPO, phosphate buffer, ACN
c) BnBr, $Cs_2CO_3$, DMF
d) TFA, $CH_2Cl_2$; then 2M HCl, $Et_2O$
e) t-butyl bromoacetate, DIPEA, DMF
f) $H_2$, Pd/C, EtOAc

Method A for Synthesis of Synthon #3

Step a - Protection of Amines

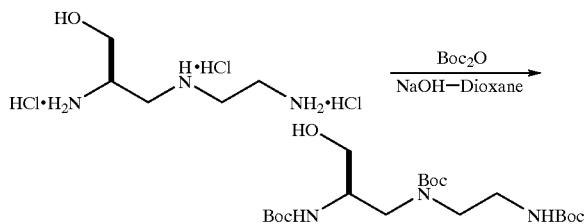

Hydroxymethyl-diethylenetriamine of the indicated stereochemistry trihydrochloride (25.15 g) (optically pure starting material: *Syn. Comm.* 29(14), 2377–2391 (1999), racemic starting material: *Coll. Czech. Chem. Comm.* 34, 630–634 (1969)) was dissolved in a deionized water/1,4-dioxane mixture and the pH of the solution was adjusted to between 8 and 9 with aqueous sodium hydroxide. Di-tert-butyl dicarbonate (3.5 equiv.) was dissolved in dioxane and added between 10 and 20° C. The reaction mixture was stirred between 12 and 20 hours at room temperature. The reaction mixture was then diluted with water, and extracted with ethyl acetate. The organic extract was extracted sequentially with water, saturated sodium bicarbonate, and saturated sodium chloride solutions. The organic extract was dried over sodium sulfate, filtered, and concentrated under in vacuo to provide an oil which was purified by silica gel chromatography with a mixture of ethyl acetate:hexane. The total yield of purified product was 30.11 g. $^1$H NMR (300 MHz): 5.18 (d, J=7.9 Hz, 1H), 4.76 (bs, 1H), 3.8–3.0 (m, 10H), 1.47–1.42 (2s, 27H). MS (m/Z): 456.4 [M+Na]$^+$.

Step b - Oxidation of Hydroxyl Group

[based on the oxidation procedure disclosed in Zhao et al. *J. Org. Chem.* 64, 2564-2566(1999)]

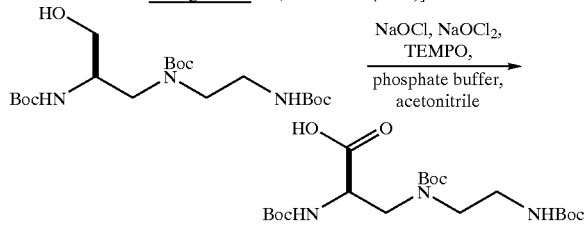

BOC-protected triamine (29.94 g) was dissolved in acetonitrile. Phosphate buffer, consisting of 21.6 g NaH$_2$PO$_4$, 21.6 g Na$_2$HPO$_4$ and enough deionized water to produce a 500 mL volume, was added (300 mL), followed by 2,2,6,6-tetramethylpiperidinyl-1-oxy (TEMPO) (0.07 equiv.). The mixture was stirred vigorously and warmed to 35° C. Sodium chlorite (2.0 equiv.) was dissolved in deionized water (100 mg/ml). The sodium chlorite solution and bleach (0.02 equiv., approx. 0.25% aqueous sodium hypochlorite) were added while maintaining a constant temperature. After addition of oxidant, the reaction was stirred for 24 hours. Additional TEMPO (0.07 equiv.) was added and the reaction mixture was stirred for 24 hours. The reaction was cooled to room temperature. Water was added and the pH was adjusted to 8 with 2.0 N aqueous NaOH. A cold solution of aqueous sodium sulfite was added (300 mL) while maintaining a constant pH. The solution was extracted with a small volume of methyl tert-butyl ether and set aside. The aqueous layer was acidified to pH 3–4 with 2.0 N aqueous HCl and extracted with two small volumes of methyl tert-butyl ether. The organic extract was combined with the one previously set aside and concentrated in vacuo. The product was used without purification in Step 3 below. $^1$H NMR (300 MHz): 5.8 (bs, 1H), 5.3 (m, 1H), 4.4 (M, 1H), 3.6–3.2 (m, 6H), 1.47–1.43 (2s, 27H). MS (m/Z): 470.2 [M+Na]$^+$.

Step c-Benzyl-Protection of Carboxylic acid

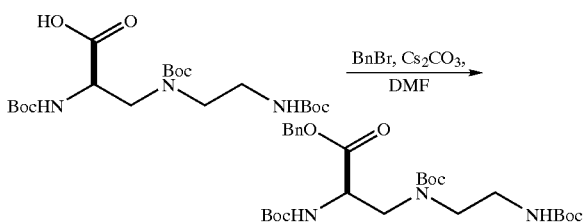

The carboxylic acid starting material (178 g) was dissolved in dry DMF. Cesium carbonate (2.0 equiv.) was added, and the solution was stirred for 30 minutes. Benzyl bromide (1.1 eq.) was added dropwise at room temperature. The reaction mixture was stirred under an inert atmosphere for 18 hours. The reaction mixture was diluted with water and extract twice with ethyl acetate. The organic layers were combined and washed sequentially with saturated sodium bicarbonate and sodium chloride solutions. The organic layer was concentrated to an oil (270 g) which was purified by silica gel chromatography using ethyl acetate:hexane. $^1$H NMR (300 MHz): 7.3 (s, 5H), 5.6 and 5.15 (2bs, 1H), 5.1 (s, 2H), 4.5 (bs, 1H), 4.0–4.1 (m, 1H), 3.5–3.2 (m, 6H), 1.45 and 1.4 (2s, 27H). MS (m/Z): 560.3 [M+Na]$^+$.

Steps d and e - Deprotection of Amines and Alkylation

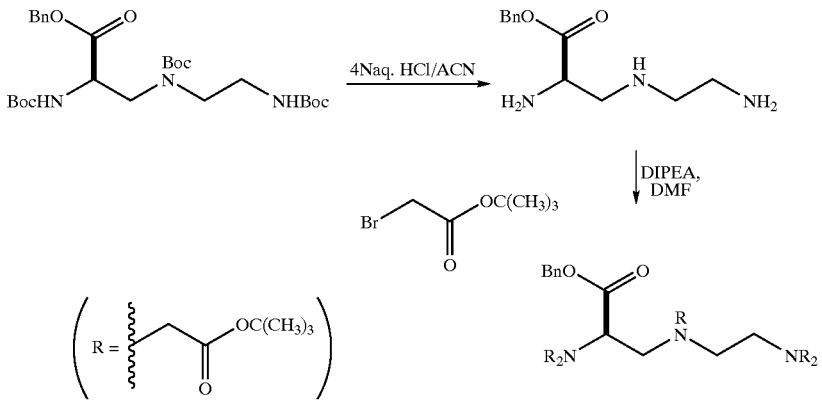

The BOC-protected triamine (250 g) was stirred in a solution of 1:1 acetonitrile:4 N aqueous HCl and allowed to stir for approximately 2.0 hours. The acetonitrile was removed in vacuo and the remaining solution was lyophilized to provide a residue that was immediately dissolved in DMF and diisopropylamine (a sufficient amount to raise the pH to 8). tert-Butyl bromoacetate was added (12.0 equiv.). After the addition was complete, the reaction mixture was warmed to 50° C. and stirred for 18 hours. Upon completion of reaction the volume of the reaction mixture was doubled by the addition of water, after which it was extracted twice with ethyl acetate. The organic extracts were combined and washed sequentially with water, saturated sodium bicarbonate, and saturated sodium chloride solutions. The organic solution was concentrated in vacuo to an oil which was purified by silica gel chromatography using ethyl acetate:hexane. The total yield of purified product was 190 g. MS (m/Z): 809.5 [M+Na]$^+$.

Step f-Deprotection of Carboxylate

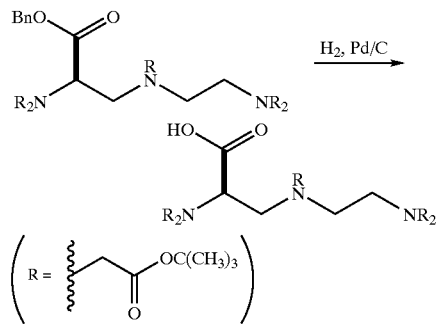

A stainless steel reactor was charged with benzyl ester (157 g), 10% palladium on carbon (19.8 g) and ethyl acetate and hydrogenated at 45 psi for 12 hours. Filtration through Celite® and concentration in vacuo gave an oil. The oil was dissolved in ethyl acetate/hexanes and purified by silica gel chromatography to provide the DTPA carboxylic acid penta-tert-butyl ester (yield: 82%). MS (m/Z): 719.5 [MH]$^+$. When this reagent is used in the synthesis of contrast agents using other chiral elements, no diastereomers are observed and therefore it is concluded that this material is essentially optically pure to the limit of detection by ordinary proton NMR.

Method B for Synthesis of Synthon #3

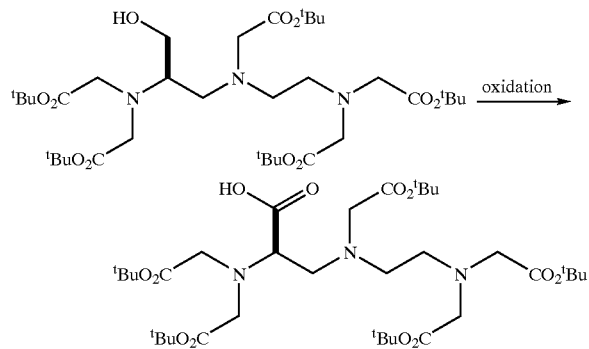

Alcohol (see *Syn. Comm.* 29(14), 2377–2391 (1999) for a synthesis from hydroxymethyl-diethylenetriamine) starting material (105.0 g), acetonitrile (1.0 L), phosphate buffer (1.0 L, prepared by dissolving 100 mg of NaH$_2$PO$_4$ and 10 mg of Na$_2$HPO$_4$ into 1.0 mL of water and then adjusting the pH to 4.5 with H$_3$PO$_4$) and TEMPO (7.0 g) were combined and warmed to between 45 and 50° C. A solution consisting of sodium chlorite (29.8 g dissolved in 298 mL of water) and sodium hypochlorite (744 µL) was added to the solution while maintaining a temperature of 45 to 50° C. The reaction mixture was stirred vigorously for 4 to 10 hours. The reaction mixture was cooled to room temperature and two layers were separated. The organic layer was isolated and combined with saturated aqueous sodium chloride and stirred for 15 minutes. The organic layer was isolated and concentrated in vacuo to give an oil (171 g) which was purified by column chromatography using hexane:isopropanol with 0.1% triethylamine throughout to provide 81 g of enriched product as an oil. MS (m/Z): 719.5 [MH]$^+$. The optical purity of material produced by this method did not differ from that above.

Example 3

Resins for Solid Phase Synthesis of Modified Peptides with C-terminal Amine Functional Groups The peptides have been prepared by solid-phase synthesis. In solid-phase synthesis, the linkers and resins are selected depending on the type of the peptides to be synthesized (e.g., the functional group required at the C-terminus, the protected or unprotected peptide) and the synthetic method to be used (e. g. Fmoc or BOC chemistry, manual or automated synthesis, the continuous flow or batch reactor). For example, in the synthesis of a peptide with a carboxylic group at the C-terminus, a protected-amino acid is attached to the different resins such as HMPB resins, 2-chlorotritylchloride resin and SUSRIN resin. On the other hand, in the synthesis of a peptide with an amino group at the C-terminus, a diamine can be attached to a trityl resin. The polystyrene (PS) resins can be used for batch synthesis, while polyethyleneglycol (PEG) modified resins are suitable for continuous flow and batch synthesis. Many trityl PS resins including 1,3-bis-(aminomethyl)-benzene trityl PS resin are commercially available. If the required trityl PS resin is not available, a similar procedure as described for PEG resins can be used to attach a diamine to a trityl PS resin.

The synthesis of 1,3-bis-(aminomethyl)-benzene trityl resin is discussed as an example. Other diamines can be attached to trityl resin in a similar manner.

Preparation of 1,3-bis-(aminomethyl)-benzene trityl PEG resin

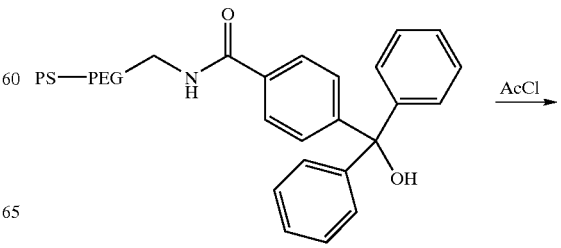

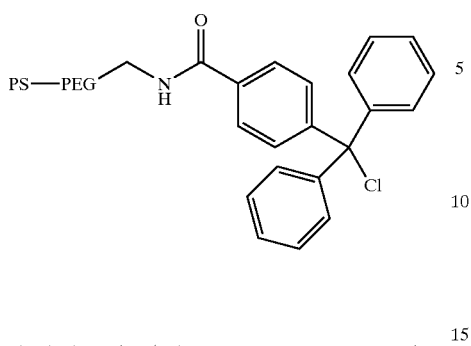

First, trityl alcohol resin (25 g, NovaSyn TGT resin, NovaBiochem) was placed in a funnel and washed sequentially with DMF, CH₂Cl₂, and toluene. After removing all solvent, the material was transferred to a flask equipped with a reflux condenser. Toluene (250 mL) and acetyl chloride (25 mL) were added and the slurry was heated to 70° C. and stirred for 1.0 hour. An additional portion of acetyl chloride (25 ml) was added and the slurry was stirred for 2.0 hours at 70° C. The slurry was filtered and the resin washed sequentially with toluene and CH₂Cl₂.

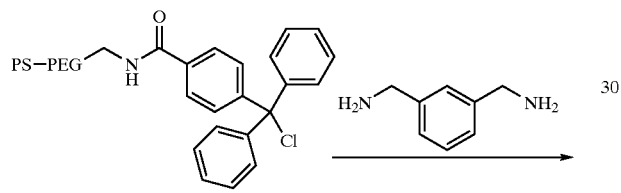

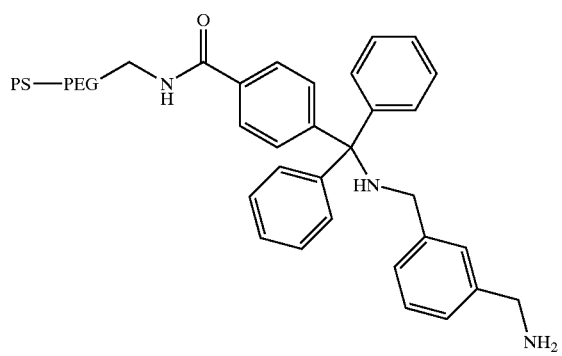

Second, freshly prepared trityl chloride resin and THF (250 mL) was placed in a flask. To the slurry was added 1,3-bis-(aminomethyl)-benzene (10 eq., based on a resin substitution of 0.23 mmol/g) and the mixture was stirred for 18.0 hours at room temperature. The slurry was filtered and the resin was washed sequentially with water, DMF, CH₂Cl₂, methanol, and CH₂Cl₂. The resin was dried under vacuo (room temperature, 1–5 mm Hg) to a constant weight (25.4 g). The substitution stoichiometry was conducted using a quantitative ninhydrin procedure.

Example 4

Synthesis of Covalent Conjugates (Synthon #1, #2, #4, and #5)

Method of the Synthesis of Synthon #1

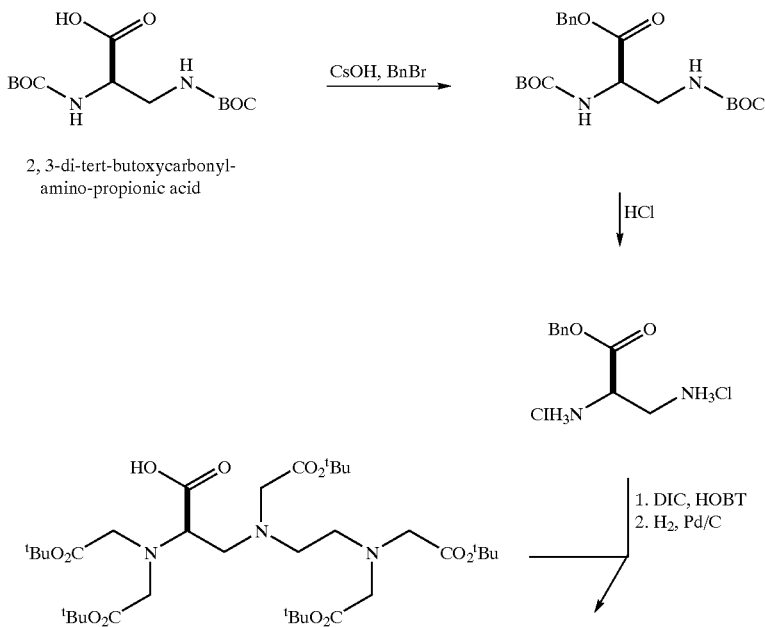

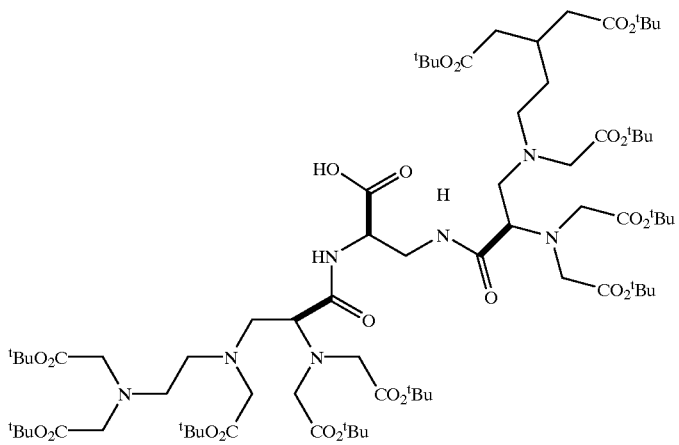

2,3-Bis-tert-butoxycarbonylamino propionic acid benzyl ester

A solution of cesium carbonate (6.5 g) and water was added to 2,3-bis-tert-butoxycarbonylamino propionic acid (3.04 g) in acetonitrile (25 ml). The mixture was stirred for 40 minutes at room temperature. The solvent was removed under vacuum. DMF (50 ml) was added to the solid residue. A solution of benzyl bromide (1.43 ml) and DMF (5.0 ml) was added over 15 minutes at room temperature. The mixture was stirred for 18 hours, and then the mixture was diluted with ethyl acetate (100 ml) and water (50 ml) and stirred for 15 minutes. The layers were separated and the organic layer was dried over sodium sulfate. The mixture was filtered, and the filtrate was concentrated under vacuum to give an oil (3.6 g). The oil was purified by column chromatography with ethyl acetate/hexane to provide an oil (1.8 g). MS (m/Z): $[M+Na]^+=417$. $^1$H NMR (300 MHz): 1.4 (s, 9H), 2.4 (m, 2H), 4.4 (m, 1H), 4.8 (m, 1H), 6.5 (m, 1H), 7.3 (m, 5H).

2,3-Diamino-propionic acid trihydrochloride

A solution of 2,3-bis-tert-butoxycarbonylamino propionic acid benzyl ester (1.8 g), 4N aqueous HCl (40 ml), and acetonitrile (50 ml) was stirred for 18 hours at room temperature. The solvent was removed under vacuum, and the mixture was diluted with ethyl acetate (100 ml) and water (50 ml) and stirred for 15 minutes. The layers were separated and the aqueous layer was evaporated to dryness (1.23 g of a foam/syrup). $^1$H NMR (300 MHz): 3.2–3.5 (m, 2H), 4.2–4.35 (m, 1H), 5.13–5.25 (q, 2H, J=11.8, 3.1 Hz).

2,3-Bis-carboxy-DTPA propionic acid benzyl ester

A solution of 2,3-diamino-propionic acid trihydrochloride (6.65 g), bb(CO)DTPE (40.0 g, "Synthon 3"), HOBt (8.5 g), DIC (9.0 ml), diisopropylethylamine (15.0 ml), $CH_2Cl_2$ (400 ml) and DMF (200 ml) was stirred for 48 hours. The mixture was diluted with methylene chloride (500 ml) and water (250 ml), and then stirred for 15 minutes. The layers were separated and the organic layer was washed with saturated sodium carbonate (250 ml), saturated sodium chloride (250 ml) and dried over sodium sulfate. The mixture was filtered and the filtrate was concentrated in vacuo to obtain an oil. The oil was purified by silica gel chromatography using ethyl acetate and hexanes to obtain 28.0 g of material. MS (m/Z): $[M+2]^+=798$; $[M+1]^+=1595$.

2,3-Bis-carboxy-DTPA propionic acid

Hydrogenation of 2,3-bis-carboxy-DTPA propionic acid benzyl ester (17.0 g) was performed in ethyl acetate/triethylamine (10:3) using 10% palladium on carbon (6.0 g) catalyst for 24 hours at 50 psi. The vessel was purged with nitrogen and the mixture was filtered through Celite®, and concentrated under reduced pressure to give 16.0 g of an oil. MS (m/Z): $[M+2]^+=753$; $[M+1]^+=1504$.

Method for Synthesis of Synthon #2

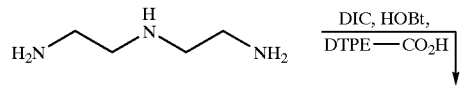

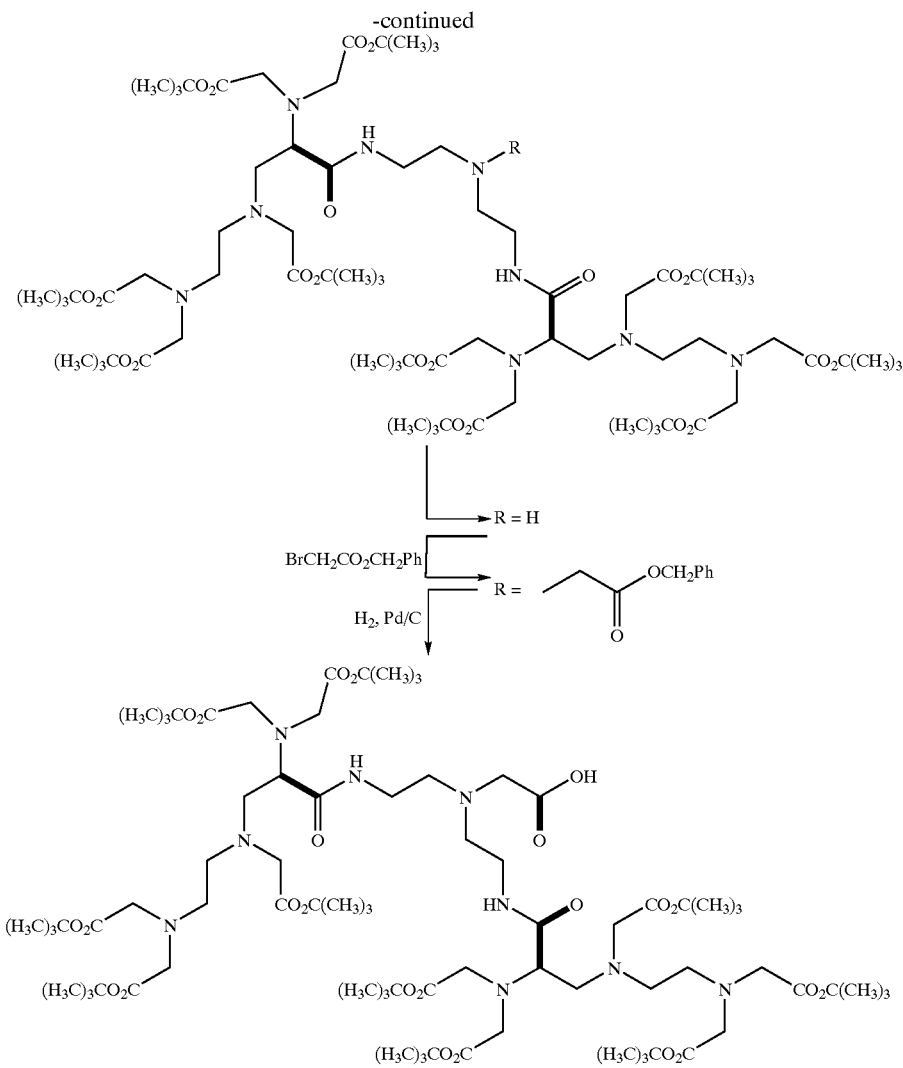

$N^1,N^3$-Bis[2-(bis-tert-butoxycarbonylmethyl-amino)-3-{[2-(bis-tert-butoxycarbonylmethyl-amino)-ethyl]-(tert-butoxycarbonylmethyl)-amino}-propionamide]-diethylenetriamine To a solution of diethylenetriamine (3.16 ml), acetonitrile (700 ml), and diisopropylethylamine (10.4 ml) was added pre-reacted (30 min) bb(CO)DTPE (42.0 g, "Synthon 3"), HOBt (7.9 g), EDC (11.2 g) and diisopropylethylamine (10 ml) in acetonitrile at room temperature. The reaction was stirred for 16.0 hours and then concentrated under reduced pressure. The oil was combined with ethyl acetate, extracted with water and saturated aqueous sodium chloride and then concentrated. The oil was purified by silica gel column chromatography using hexanes/isopropanol/triethylamine to provide 22.5 g of product. MS (m/Z): $[M+H]^+=1503$.

$N^1,N^3$-Bis[2-(bis-tert-butoxycarbonylmethyl-amino)-3-{[2-(bis-tert-butoxycarbonylmethyl-amino)-ethyl]-(tert-butoxycarbonylmethyl)-amino}-propionamide]-$N^2$-(benzyloxycarbonylmethyl)-diethylenetriamine Benzyl-2-bromoacetate (2.54 g) was added to a solution of the previous amine compound (13.5 g), acetonitrile (200 ml) and sodium carbonate (1.18 g). The mixture was warmed to 60° C. and stirred for 15 hours. The reaction mixture was cooled to room temperature and concentrated under reduced pressure. Ethyl acetate and water were added, the layers were separated. The organic layer was washed with saturated aqueous sodium chloride, then concentrated under reduced pressure to give an oil (14.5 g). MS (m/Z): $[M]^+=1651$.

$N^1,N^3$-Bis[2-(bis-tert-butoxycarbonylmethyl-amino)-3-{[2-(bis-tert-butoxycarbonylmethyl-amino)-ethyl]-(tert-butoxycarbonylmethyl)-amino}-propionamide]-$N^2$-(acetic acid)-diethylenetriamine The above benzyl ester (14 g) was hydrogenated in ethyl acetate/triethylamine (49:1) at 50 psi for 16.0 hours in the presence of 10% palladium on charcoal (3.5 g). The resulting mixture was filtered through Celite®, and concentrated in vacuo to provide 12.08 g of an oil. MS (m/Z): $[M+H]^+=1561$.

Synthesis of Synthon #4

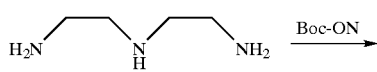

-continued

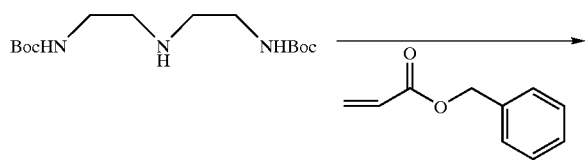

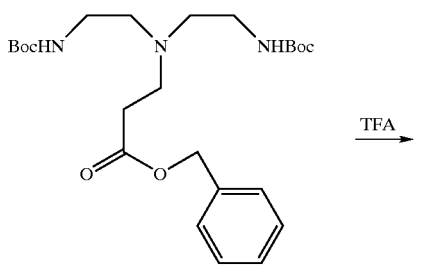

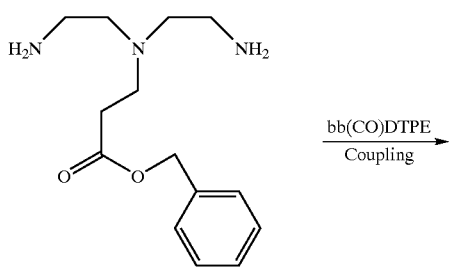

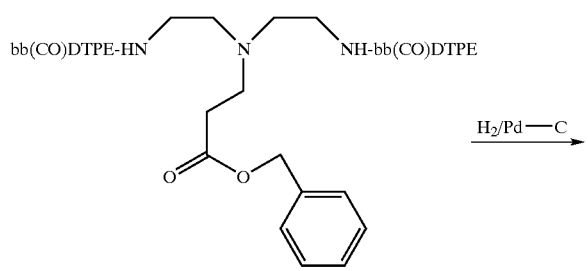

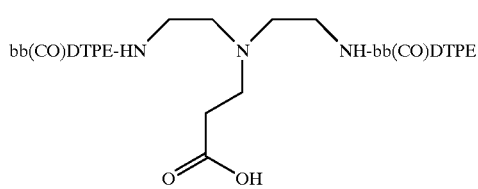

N$^1$,N$^3$-Bis-Butoxycarbonyl-Diethylenetriamine

To a solution of diethylenetriamine (2.12 g, 20.6 mmol) and triethylamine (30.0 g, 41.3 mmol) in THF (100 mL) was added Boc-ON (10.65 g, 43.3 mmol) at room temperature. The mixture was stirred for overnight. To the mixture was added 700 mL of ether and then extracted with phosphate buffer (pH=3, 100 mmol). The aqueous solution was basified to pH=11 and extracted with dichloromethane. The organic layer was separated and dried over anhydrous sodium sulfate. The salts were filtered and the solvent was removed under the reduced pressure to give the indicated compound as a colorless oil (5.55 g). MS (m/Z): [M+H]$^+$=304.1.

N$^1$,N$^3$-Bis-Butoxycarbonyl-N$^2$-(Benzyloxycarbonylethyl)-Diethylenetriamine To a solution of the compound above (1.0 g, 3.30 mmol) in methanol (40 mL) was added benzyl acrylate (1.07 g, 6.59 mmol) at room temperature. The mixture was refluxed for 3 days. The solvent was removed at reduced pressure to give a yellow liquid that contains the indicated compound and benzyl acrylate. MS (m/Z): [M+H]$^+$=466.1.

N$^2$-(Benzyloxycarbonylethyl)-Diethylenetriamine

To a mixture of the compound above and benzyl acrylate (1.0 g) in dichloromethane (25 mL) was added TFA (13.8 mL) at room temperature. The mixture was stirred for 3 h at room temperature and then to the mixture was added 1N HCl and water. The aqueous layer was separated and lyophilized to give the indicated compound (420 mg) as a sticky solid. MS [m/Z]: [M+H]+=266.2.

N$^1$,N$^3$-Bis[2-(Bis-Tert-Butoxycarbonylmethyl-Amino)-3-{[2-(Bis-Tert-Butoxycarbonylmethyl-Amino)-Ethyl]-(Tert-Butoxycarbonylmethyl)-Amino}-Propionamide]-N$^2$-(Benzyloxycarbonylethyl)-Diethylenetriamine To a solution of the above compound, "Synthon 3", HOBt and diisopropylethylamine, in CH$_2$Cl$_2$ and DMF is added DIC. The mixture is stirred for 48 h at room temperature. The mixture is diluted with dichloromethane and water, and then stirred for 15 minutes. The layers are separated and the organic layer is washed with saturated sodium carbonate, saturated sodium chloride and dried over sodium sulfate. The mixture is filtered and the filtrate is concentrated in vacuo to obtain an oil. The oil is purified by silica gel chromatography using ethyl acetate and hexanes to obtain the indicated compound.

N$^1$,N$^3$-Bis[2-(Bis-Tert-Butoxycarbonylmethyl-Amino)-3-{[2-(Bis-Tert-Butoxycarbonylmethyl-Amino)-Ethyl]-(Tert-Butoxycarbonylmethyl)-Amino}-Propionamide]-N$^2$-(Propionic Acid)-Diethylenetriamine A hydrogenation vessel is charged with the above compound, 10% palladium on carbon, ethyl acetate, and triethylamine. The vessel is purged with nitrogen then hydrogen. The mixture is shaken for 24 hours under a hydrogen atmosphere (50 psi). The vessel is purged with nitrogen and the mixture is filtered through Celite®, and the filtrate is concentrated under reduced pressure to give the product as an oil.

Synthesis of Synthon #5

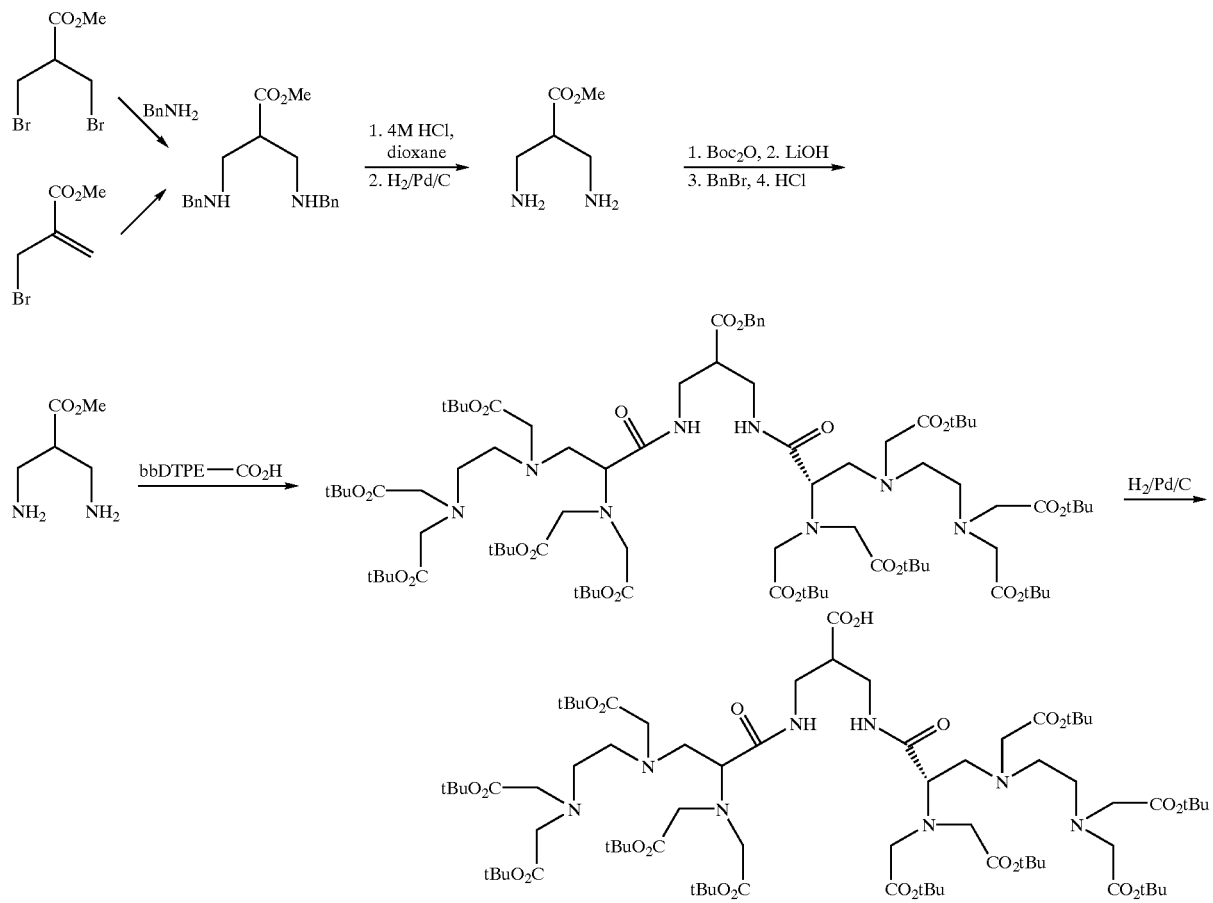

Methyl 3-(Benzylamino)-2-((Benzylamino)Methyl)-Proprionate

Methyl-2-(bromomethyl)-acrylate (1.00 g, 5.6 mmol, 1.0 eq.) dissolved in acetonitrile (20 mL) was added drop-wise with stirring at room temperature to a solution of benzylamine (1.83 mL, 16.8 mmol, 1.5 eq.) in anhydrous acetonitrile (10 mL). After 16 hours, ether (100 mL) was added, and the white solid (benzylamine hydrobromide) was filtered. The filtrate was concentrated under reduced pressure to give 1.90 g of a crude oil. The oil was dissolved in ethyl acetate (150 mL) and washed with $H_2O$ and NaCl brine. The organic layer was dried ($MgSO_4$), and evaporated under reduced pressure. The resulting clear oil was purified by flash chromatography (hexanes:ethyl acetate) to give 1.38 g (79%) of the product. $^1$H NMR (300 MHz, $CDCl_3$): δ 1.68 (s, 2H), 2.79–2.90 (m, 5H), 3.68 (s, 3H), 3.75 (s, 3H), 7.21–7.32 (m, 10H).

Methyl 3-(Amino)-2-(Aminomethyl)-Proprionate

Methyl 3-(benzylamino)-2-((benzylamino)methyl)-proprionate (2.27 g, 7.3 mmol, 1.0 eq) was dissolved in methylene chloride (20 mL) and 4.0 mL of a 4M solution of HCl in dioxane was added. The solution was stirred at room temperature for 20 minutes and solvents were then evaporated under reduced pressure to give a white powder that was dissolved in 50 mL MeOH. Catalyst (10% Palladium on carbon catalyst, 750 mg) was added at 0° C. under argon and the mixture was shaken at 45 psi $H_2$ for 18 hours, then filtered through Celite®. The product (1.47 g) was isolated following a MeOH was and evaporation under reduced pressure. $^1$H NMR (300 MHz, $D_2O$): δ 3.25–3.43 (m, 5H), 3.82 (s, 3H).

Methyl 3-(BOC-Amino)-2-(BOC-Aminomethyl)-Proprionate

Diamine (1.44 g) was reacted with di-tert-butyl dicarbonate (3.22 g, 14.8 mmol, 1.05 eq.) in dioxane/aqueous $Na_2CO_3$ at solution 0° C. for 1 hour and then room temperature for 18 hours. The mixture was then acidified (pH=4) with 0.5N $KHSO_4$ and dioxane was evaporated under reduced pressure. The aqueous portion was extracted with ethyl acetate, dried over $MgSO_4$ and concentrated under reduced pressure to give a crude oil that was purified by flash chromatography (hexanes:ethyl acetate) to give 1.86 g (80%) of the desired. NMR (300 MHz, $CDCl_3$): δ 1.41 (s, 18H), 2.66–2.78 (m, 1H), 3.10–3.27 (m, 2H), 3.50–3.62 (m, 2H), 3.68 (s, 3H), 5.17–5.27 (bt, 2H).

3-(BOC-Amino)-2-(BOC-Aminomethyl)-Propanoic Acid

Methyl ester (1.50 g) was dissolved in 15 mL of a 2:1 mixture of $THF/H_2O$. $LiOH \cdot H_2O$ (0.95 g) was added at 0° C. The mixture was stirred between 0° C. and room temperature for 44 hours. THF was evaporated under reduced pressure and the aqueous solution was extracted with EtOAc. The aqueous layer was made acidic (pH=3) with 0.5M aqueous KHSO$_4$ and extracted with EtOAc. Combined organic fractions were washed with 30 mL H$_2$O, and dried (MgSO$_4$). Solvents were evaporated under reduced pressure to give 1.32 g (92%) of the product. $^1$H NMR (300 MHz, CDCl$_3$): δ 1.40 (s, 18H), 2.66 (s, 1H), 3.27–3.47 (m, 4H), 5.42 (s, 1H).

Benzyl 3-(BOC-Amino)-2-(BOC-Aminomethyl)-Propionate

Acid (1.01 g) was reacted at room temperature with benzyl bromide (0.45 mL) in anhydrous DMF containing Cs$_2$CO$_3$ (2.07 g). DMF was evaporated under reduced pressure and the residue was partitioned between H$_2$O and EtOAc. The organic layer was washed with brine, and dried (MgSO$_4$). Solvent was evaporated under reduced pressure and the residue purified by flash chromatography on silica gel (Hexanes/EtOAc 95:5 to 9:1 to 85:15). Yield 1.16 g (90%). $^1$H NMR (300 MHz, CDCl$_3$): δ 1.42 (s, 18H), 2.79 (quint, 1H, 5.6 Hz), 3.1–3.3 (m, 2H), 3.5–3.65 (m, 2H), 5.13 (s, 2H), 5.15–5.28 (m, 1H), 7.30–7.40 (m, 5H). MS: 431.15 (M+1).

Benzyl 3-Amino-2-Aminomethyl-Propionate Dihydrochloride Salt

Benzyl 3-(BOC-amino)-2-(BOC-aminomethyl)-propionate (1.15 g) was dissolved in 5 mL 4M HCl solution in dioxane. The mixture was stirred at 0° C. for 6 hours and the dioxane was evaporated under reduced pressure. The residue was tritrated with ether and was filtered to give the unpurified diamine dihydrochloride salt (0.81 g) $^1$H NMR (300 MHz, MeOD): δ 3.1–3.3 (m, 5H+CHD$_2$OD), 3.55 (s, dioxane), 5.19 (s, 2H), 5.15–5.28 (m, 1H), 7.20–7.40 (m, 5H) MS: 209.00 (M+1).

Benzyl 3-(N-bb(CO)DTPE Carboxamide)-2-(N bb (CO)DTPE Carboxamide) Methyl-Propionate Acid (2.00 g, 2.8 mmol, 1.5 eq.) was dissolved in 5 mL anhydrous dichloromethane. The diamine (0.26 g), HOAt (0.32 g), and diisopropylethylamine (0.65 mL) were reacted 0° C. with HATU (0.88 g) for 2 hr. Tris amine resin (0.5 g), isocyanate resin (0.5 g), and HATU (0.42 g) were added and the reaction mixture was stirred for 16 h at room temperature. The resins were filtered and the filtrate was evaporated. The residue was partitioned between H$_2$O and EtOAc. The organic layer was washed with H$_2$O, saturated NaHCO$_3$, and brine (20 mL), and dried (MgSO$_4$). Solvent was evaporated under reduced pressure. The oil was purified by flash chromatography on silica gel (Hexanes/Acetone/Et$_3$N) and gave product (1.13 g). MS: 1607.95 (M+1) and 1629.95 (M+Na).

3-(N-bb(CO)DTPE Carboxamide)-2-(N bb(CO) DTPE Carboxamide) Methyl-Propionic Acid Benzyl ester (0.90 g, 0.56 mmol) was dissolved in 30 mL EtOAc and Et$_3$N (1 mL) was added. 10% Palladium catalyst on carbon (0.50 g) was added and the mixture was shaken for 15 h under 45 psi Hydrogen. The catalyst was filtered and the solvents evaporated to give the product (0.82 g). MS: 759.55 (M+2H/2).

Example 5-Synthesis of Fibrin-Binding MR Imaging Agents

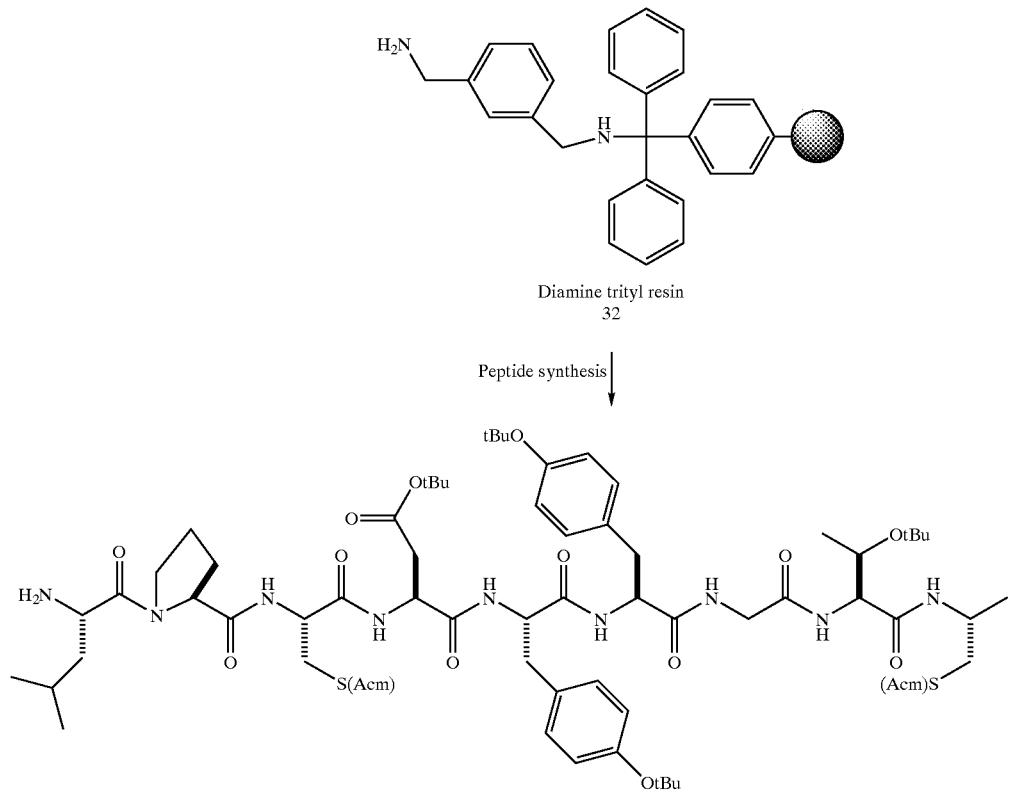

-continued
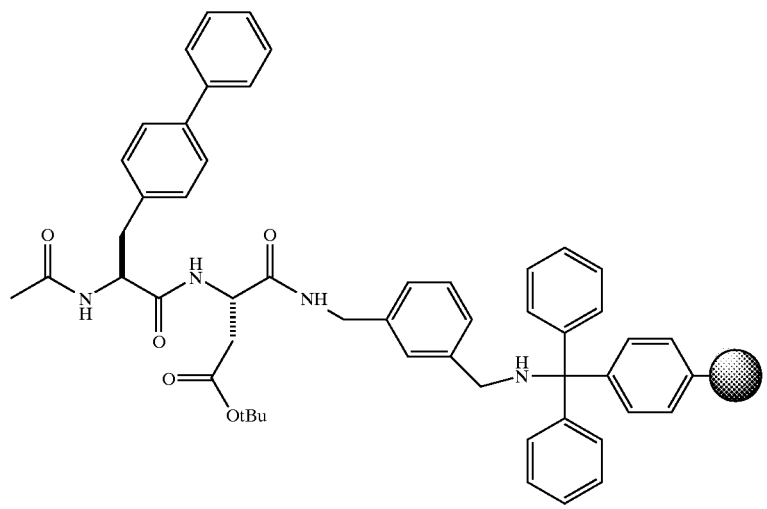
Cleavage | 1% TFA/DCM
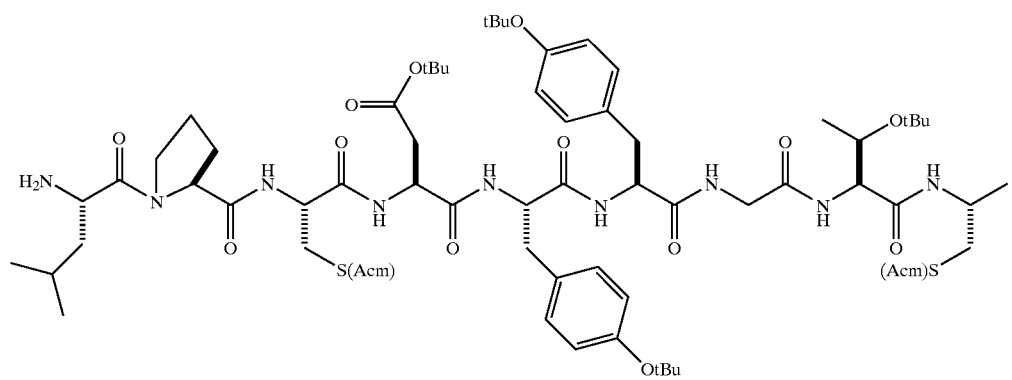
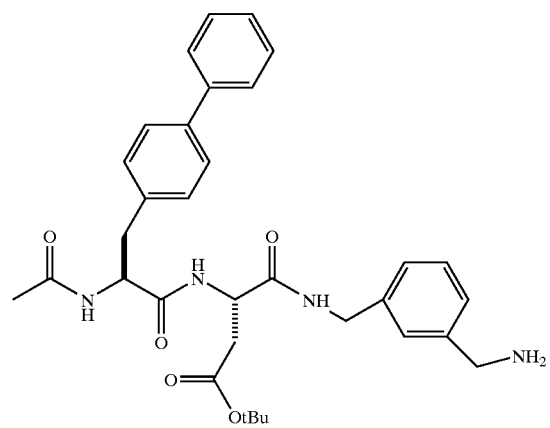
Cyclization | Tl(tfa)₃

-continued
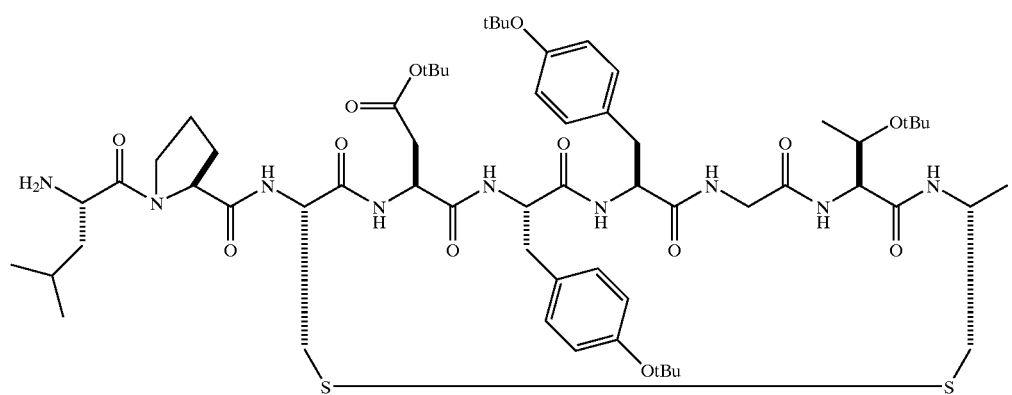
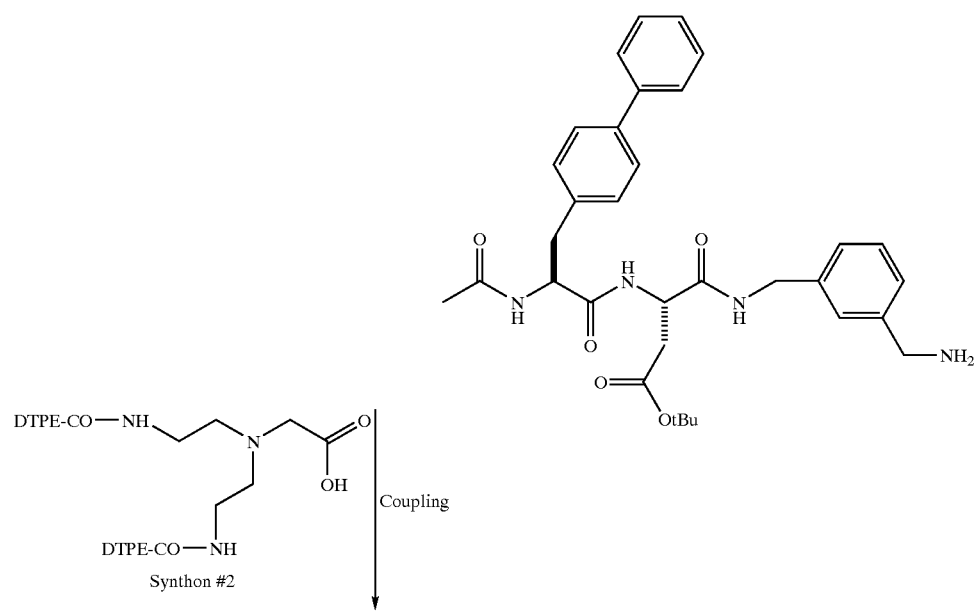
Synthon #2
Coupling
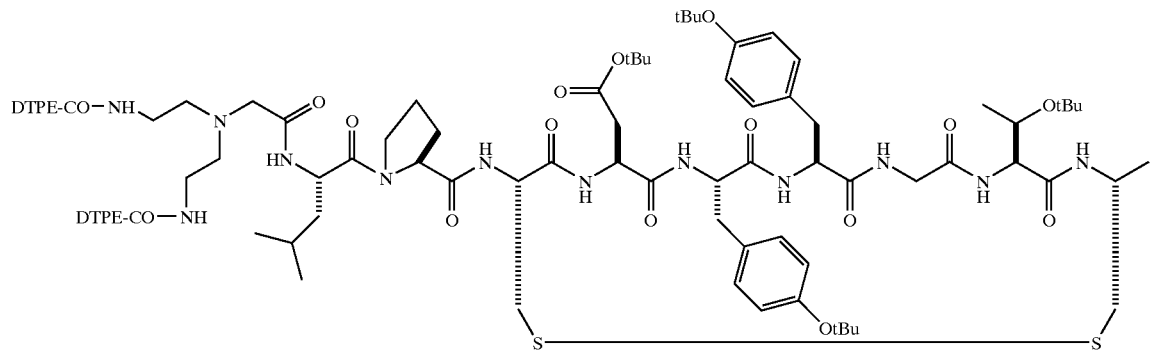

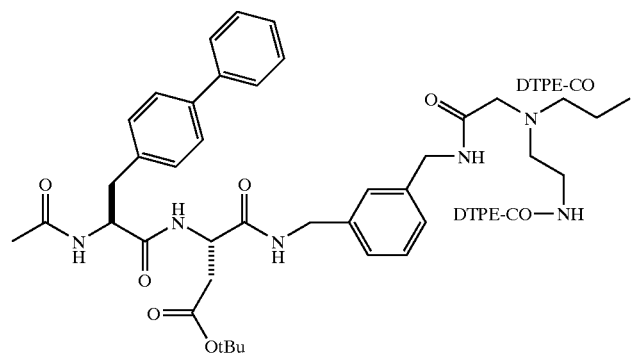
1) hydrolysis
2) GdCl₃, NaOH
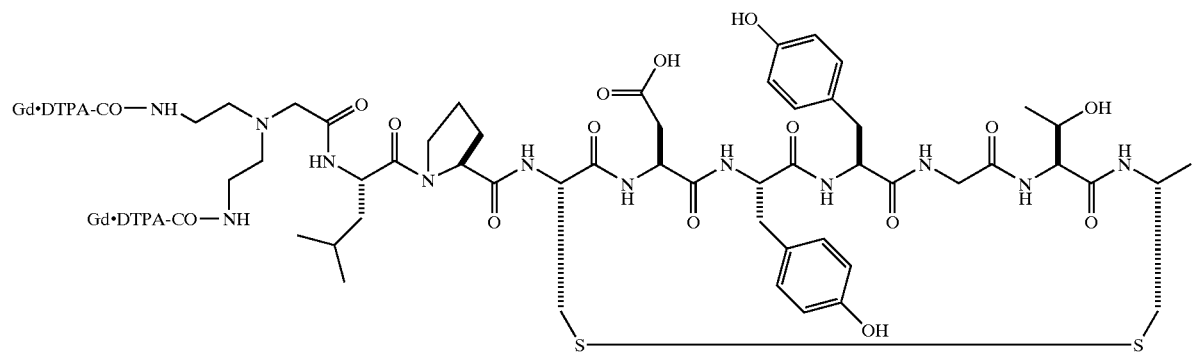
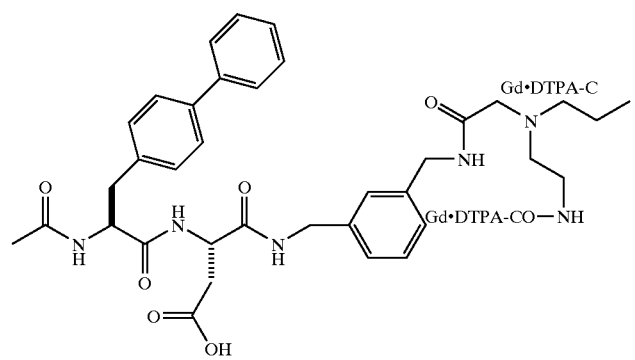

Peptide Construction: 3.39 g of the, 13-bis-(aminomethyl)-benzene trityl NovaSyn TGT resin (measured substitution=0.59 mmol) was placed in a standard peptide column and loaded onto a Peptide Synthesizer. Synthesis was carried out using a standard Fmoc strategy. Capping was carried out after coupling the first amino acid using acetic anhydride, 6% diisopropylethylamine in DMF. When the synthesis was complete, the resin was removed from the column and placed in a reaction vessel. The resin was rinsed once with $CH_2Cl_2$ and filtered. The resin was then treated with 1% trifluoroacetic acid in $CH_2Cl_2$ and placed on a mechanical shaker for 10 minutes. The mixture was filtered through the reaction vessel and the filtrate was collected. The pH of the combined filtrate was adjusted to approximately 8 with triethylamine, and the solution was concentrated under vacuum to an oil. Following precipitation with water, the white solid was filtered and rinsed with water and diethyl ether. The solid was dried by suction filtration, taken up in DMF and diluted with acetonitrile. The solution was cooled in an ice bath and was treated with 1.5 g of thallium trifluoroacetate for 2.0 hours. The pH of the solution was adjusted with triethylamine to pH 8 and then concentrated under vacuum. Water was added to the oil and the resulting precipitate was collected by suction filtration. The solid was washed with water and diethyl ether to give 2.7 g of crude modified peptide having a C-terminal amine functional group. An example synthesis of $H_2$N-Leu-Pro-Cys-Asp-Tyr-Tyr-Gly-Thr-Cys-Bip-Asp-CO-NHCH$_2$C$_6$H$_4$CH$_2$NH$_2$ (SEQ ID NO:21) was confirmed by an observed m/Z of 1792.8 [M+Na]$^+$. The modified peptide was purified by preparative HPLC. Fractions of similar purity (98–100%) were combined and lyophilized without neutralization.

Modified peptide (3.2 g) and covalent conjugate (Synthon #2 above) (3.95 g) were dissolved in dichloromethane. Diisopropylethylamine was added dropwise until the pH measured 9, and diisopropylcarbodiimide (2 eq.) and HOBt (2 eq.) were added simultaneously to the mixture. After stirring 2 minutes, diisopropylethylamine was added dropwise until the pH measured 9. The mixture was stirred at room temperature for two hours. Additional pre-activated Synthon #2 (with diisopropylcarbodiimide, diisopropylethylamine, and HOBt) was added in one portion. Solvents were removed in vacuo and the residue was dissolved in ethyl acetate, which was washed sequentially with 0.1 N hydrochloric acid, saturated sodium bicarbonate, and saturated aqueous sodium chloride. The organic layer was dried over sodium sulfate, filtered, and concentrated under reduced pressure to obtain a light yellow foam (7.8 g). The foam was dissolved in dichloromethane and purified by flash chromatography (dichloromethane: methanol eluent) to provide a white solid (5.6 g). The white solid was stirred in a mixture of TFA, water, and triethylsilane (90%/5%/5%, 30 ml) at room temperature. The mixture was heated to 40° C. and stirred for 2 hours. The solution was concentrated to a volume between 3–5 ml, then cooled to room temperature. Diethyl ether was added and a white precipitate formed. The mixture was allowed to stir for 10 minutes, and the solids were collected by filtration and washed with diethyl ether. The solids were dried under vacuum providing a white solid (4.0 g). The solid was dissolved in a mixture of water: acetonitrile (20 ml, 4:1 ratio) and purified by Prep HPLC to yield a white solid, precursor MR imaging agent (1.6 g).

Precursor MR imaging agent (1 g) was reacted with one equivalent of GdCl$_3$.6H$_2$O in distilled deionized water with the pH adjusted to ca. 6 by the addition of 1 M NaOH. The gadolinium complex was purified by reverse phase chromatography (Waters Sep-Pak® C-18) using distilled deionized water and 50:50 (v:v) methanol:water eluent. Appropriate fractions were combined and the methanol removed under reduced pressure at 50° C. and lyophilized to give 811 mg of the MR imaging agent.

Alternatively to the synthesis of 32 presented above, the peptide may be cyclized on a resin as illustrated in the following Scheme:

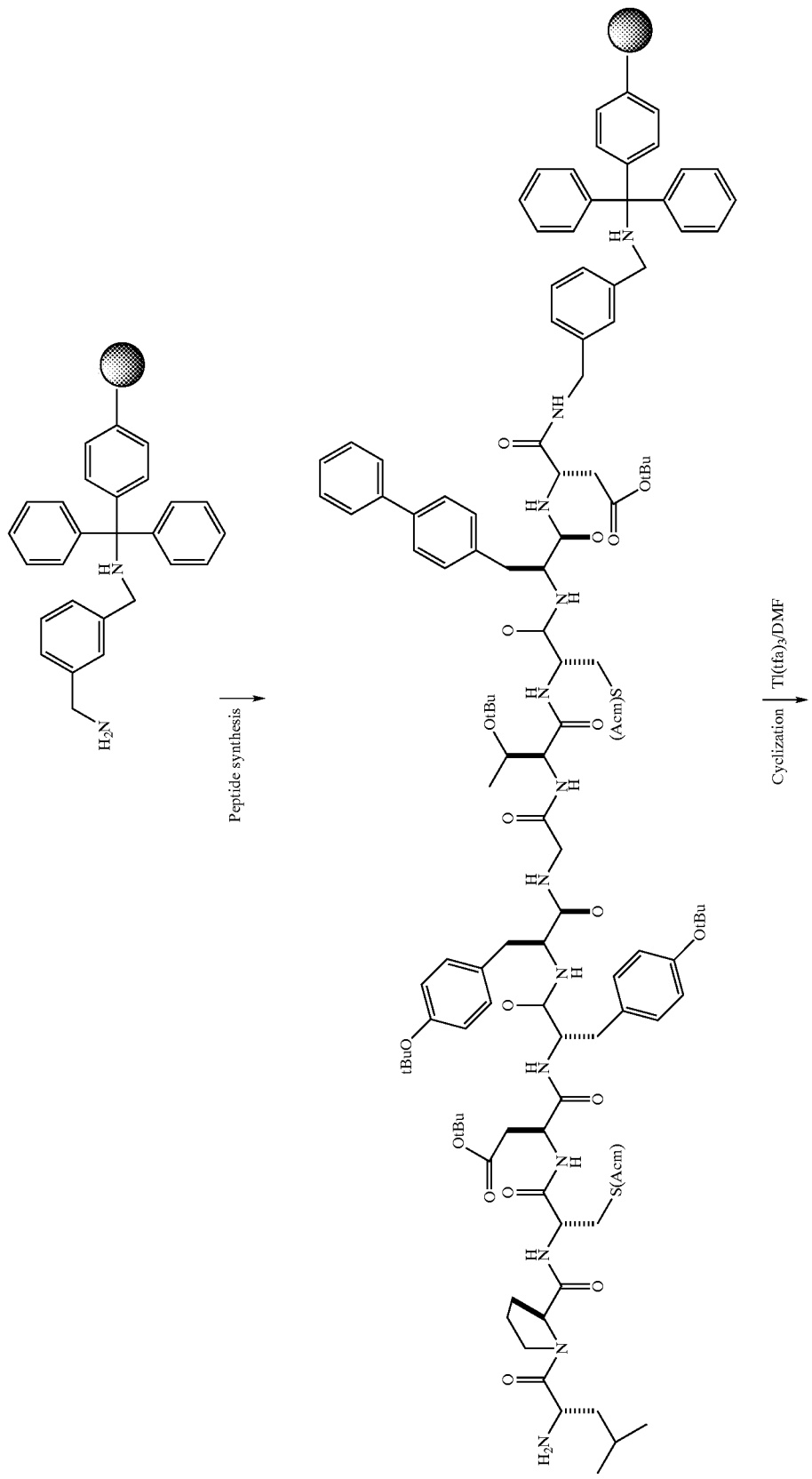

-continued
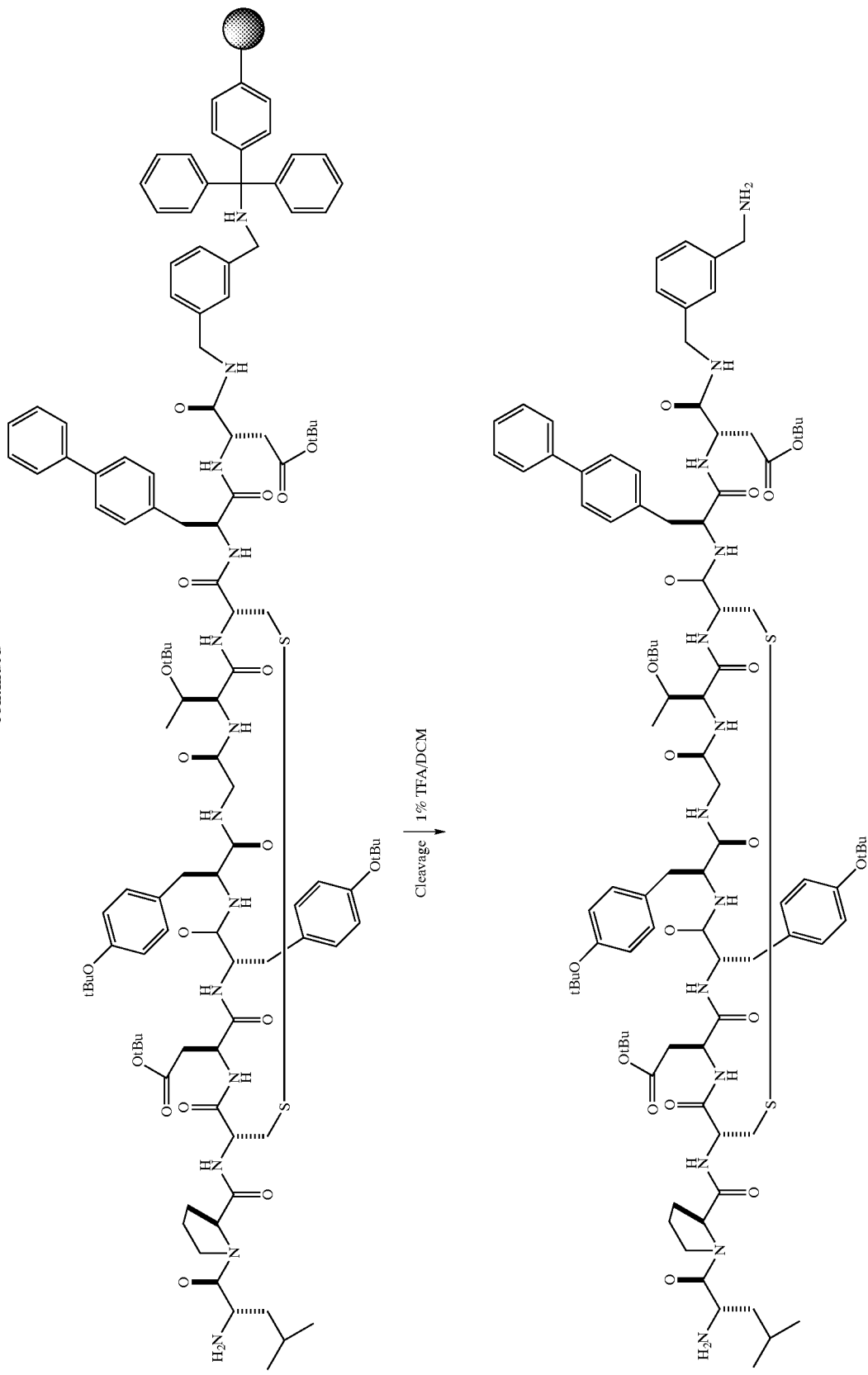

Example 6

MR Imaging Agents Prepared in Analogous Fashion

Each of the following MR imaging agents was synthesized analogously to the methods described above. Peptide, prepared using standard Fmoc strategy and cyclized using thallium trifluoroacetate was purified by HPLC and reacted with Synthon #2, diisopropylethylamine, diisopropylcarbodiimide (2 eq.) and HOBt (2 eq.) in dichloromethane. Solvents were removed in vacuo and the residue was dissolved in ethyl acetate, which was washed sequentially with 0.1 N hydrochloric acid, saturated sodium bicarbonate, and saturated aqueous sodium chloride. The organic layer was dried over sodium sulfate, filtered, and concentrated under reduced pressure to obtain a foam which was purified if necessary by flash chromatography or HPLC. The resulting white solid was stirred in a mixture of TFA, water, and triethylsilane (90%/5%/5%, 30 ml) at room temperature for 2–6 hours. Diethyl ether was added and a white precipitate formed, which was purified by Prep HPLC (CH3CN/H2O/AcONH4) to yield a white solid, precursor MR imaging agent.

Precursor MR imaging agent was reacted with one equivalent of $GdCl_3.6H_2O$ in deionized water (pH 6, NaOH). The gadolinium chelate was purified using reverse-phase chromatography on a Waters Sep-Pak® C-18 cartridge with water and methanol:water 50:50 eluant. Appropriate fractions were combined and the methanol removed under reduced pressure at 50° C. lyophilized to give the desired MR imaging agent. Table 3 provides mass spectrometry data confirming each of the compounds. See the detailed description for the structure of each of the compounds.

TABLE 3

MS data of Fibrin-Binding compounds

| Compound | Molecular Weight | MS $(M + 3H)^{3+}/3$ calcd | MS $(M + 3H)^{3+}/3$ obsd |
|---|---|---|---|
| 4 | 4016.884 | 1256.49467 | 1255.66 |
| 5 | 4025.96 | 1259.52 | 1259.9 |
| 6 | 4108.014 | 1286.87133 | 1284.53 |
| 7 | 4307.336 | 1353.312 | 1369.34 |
| 8 | 4076.064 | 1276.22133 | 1298.48 |
| 9 | 4233.208 | 1328.60267 | 1327.94 |
| 10 | 4221.199 | 1324.59967 | 1324.57 |
| 11 | 4142.146 | 1298.24867 | 1321.13 |
| 12 | 4123.378 | 1291.99267 | 1289.80 |
| 13 | 4325.675 | 1359.425 | 1333.3 |
| 14 | 4470.833 | 1407.811 | 1407.44 |
| 15 | 4363.362 | 1371.98733 | 1393.99 |
| 16 | 4511.483 | 1421.361 | 1444.57 |
| 17 | 4169.128 | 1307.24267 | 1329.85 |
| 18 | 4503.826 | 1418.80867 | 1419.25 |
| 19 | 4387.428 | 1380.00933 | 1379.12 |
| 20 | 4305.369 | 1352.65633 | 1351.6 |
| 21 | 4419.473 | 1390.691 | 1390.53 |
| 22 | 4277.356 | 1343.31867 | 1341.04 |
| 23 | 4357.829 | 1370.143 | 1370.63 |
| 24 | 4443.644 | 1398.748 | 1398.9 |
| 25 | 4448.209 | 1400.26967 | 1400.11 |
| 26 | 4326.731 | 1359.777 | 1359.9 |
| 27 | 4423.505 | 1392.035 | 1392.79 |
| 28 | 4343.375 | 1365.325 | 1364.7 |
| 29 | 4342.387 | 1364.99567 | 1364.7 |
| 30 | 4313.366 | 1355.322 | 1354.9 |
| 31 | 4342.387 | 1364.99567 | 1364.8 |
| 32 | 4319.303 | 1357.301 | 1357.6 |

Example 7

Synthesis of Fibrin-Binding Optical Contrast Agents

Each of the following optical contrast agents is synthesized analogously to the methods described above. Scheme X shows a general example wherein two identical optical dyes are added to the same peptide.

5-Carboxytetramethylrhodamine-containing compound (3A)

The peptide 1 (177 mg, 0.10 mmol) and 5-carboxytetramethylrhodamine succinimidyl ester A (111 mg, 0.21 mmol) are dissolved in dichloromethane (20 mL) and DMF (20 mL). Diidopropylethylamine is added dropwise until the pH measures 9. The mixture is stirred for overnight and then the solvents are removed under reduced pressure. The residue is purified by silica-gel flash column chromatograph (eluants:dichloromethane/methanol) to give compound 2A.

To compound 2A is added a solution of TFA, $H_2O$ and triethylsilane (ratio: 90/5/5, 5 mL). The mixture is shaken for 3 h at room temperature, and then the reaction mixture solution is poured into 50 mL of ether to precipitate the crude product. After the solvents are separated by centrifugation, the crude product is collected and then purified using reverse-phase HPLC to obtain compound 3A.

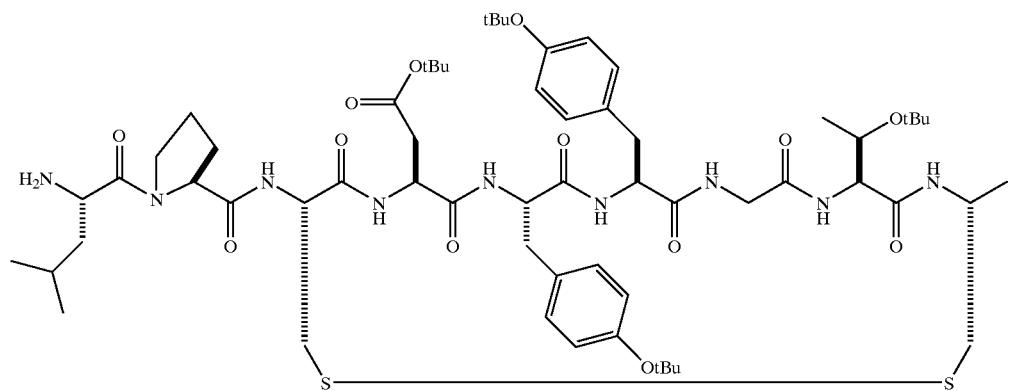
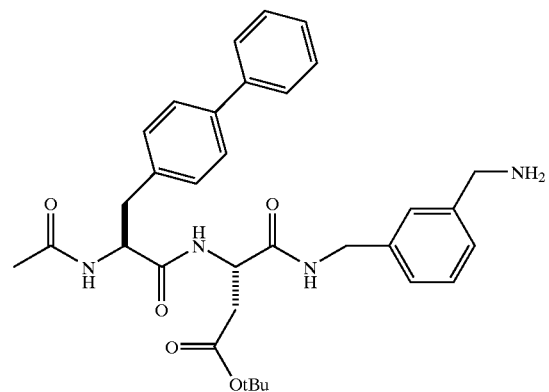
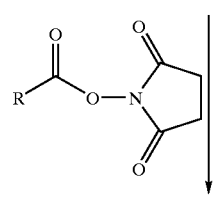
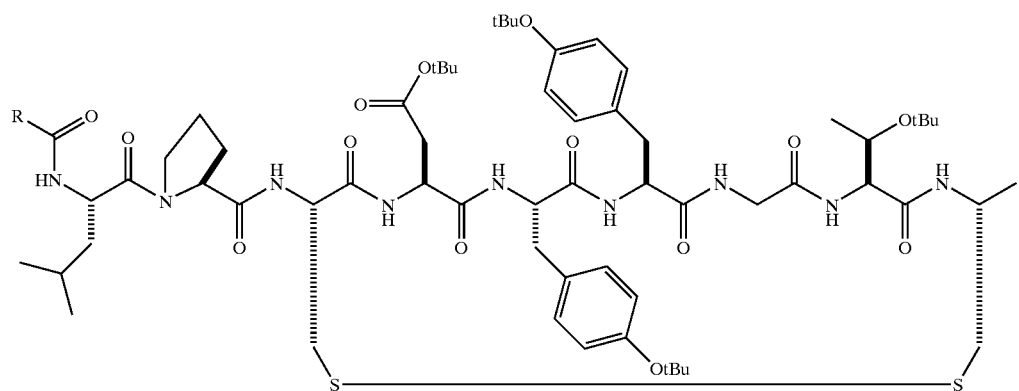

-continued
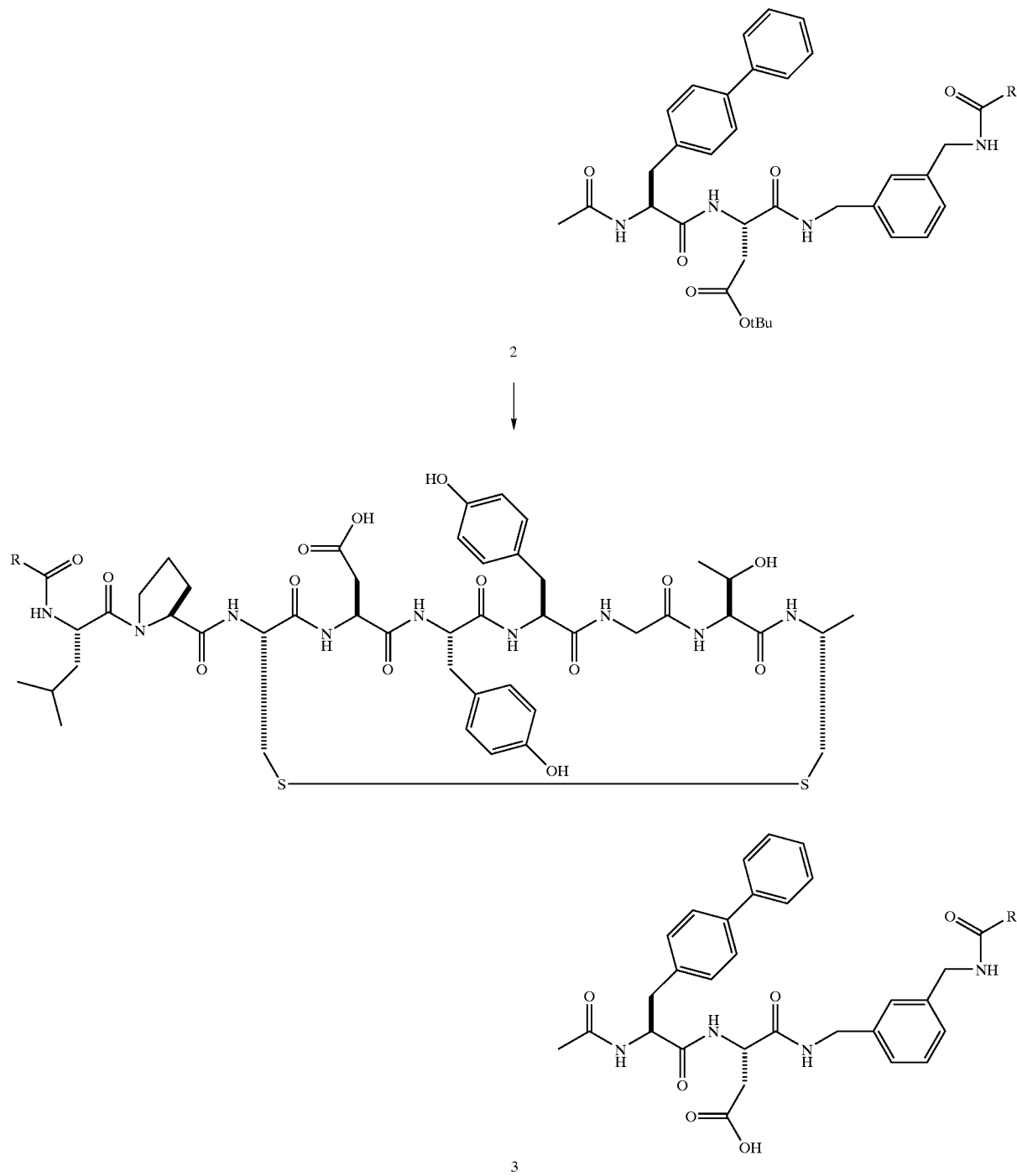
2
3
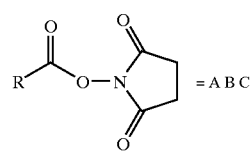 = A B C

5-Carboxyfluorescein-containing compound (3B)

In a similar procedure as described in the synthesis of 3A, 3B is synthesized using the peptide 1 (177 mg, 0.10 mmol) and 5-carboxyfluorescein succinimidyl ester B (99.4 mg, 0.21 mmol).

Texas Red®-X-containing compound (3C)

In a similar procedure as described in the synthesis of 3A, 3C is synthesized using the peptide 1 (177 mg, 0.10 mmol) and Texas Red®-X succinimidyl ester C (172 mg, 0.21 mmol).

Example 8

Measuring Binding of Contrast Agents to Targets

The extent of binding of a contrast agent according to the present invention to a target, such as HSA or fibrin, can be assessed by a variety of equilibrium binding methods. For example, binding to HSA can be measured by ultrafiltration. In a typical binding measurement using ultrafiltration, the contrast agent is mixed with 4.5% weight/volume HSA in a pH 7.4 buffer. The sample is loaded into a commercially available centrifugation apparatus equipped with a 30 kDa molecular weight cutoff filter (Millipore Ultrafree MC Low Binding Regenerated Cellulose 30 KDa mol. wt. cutoff catalog #UFC3LTK00), permeable to the targeting group, but not to HSA. A small portion (5–10%) of the sample volume is filtered by centrifugation at 2000×g for 20 min through the cutoff filter, and the concentration of unbound targeting group in the sample is measured in the filtrate.

For measuring binding to fibrin, a fibrin clot may be formed in a well of a microtiter plate and contacted with the targeting group. After an incubation time sufficient to establish equilibrium, the supernatant is removed by aspiration (the insoluble fibrin remains bound as a gelled clot to the bottom of the well). The concentration of unbound targeting group in the supernatant is then measured.

In both methodologies, the concentration of bound contrast agent is determined as the difference between the total targeting group concentration initially present and the unbound targeting group concentration following the binding assay. The bound fraction is the concentration of bound targeting group divided by the concentration of total targeting group.

Affinity of contrast agents to a soluble fibrin DD(E) fragment was examined as set forth above and is reported in Table 4. The compound numbers provided in Table 4 refer to the structures set forth in the detailed description. This data in multiple determinations has an error frequency of no more than 20% in this biological assay.

TABLE 4

Affinity of Compounds for Fibrin

| Compound | Kd, DD(E), $\mu$M |
|---|---|
| 4 | 33 |
| 5 | 12 |
| 6 | 13 |
| 7 | 12 |
| 12 | 5.0 |
| 13 | 5.1 |
| 14 | 4.9 |
| 32 | 4.7 |
| 15 | 4.0 |
| 16 | 3.5 |
| 17 | 6.2 |

TABLE 4-continued

Affinity of Compounds for Fibrin

| Compound | Kd, DD(E), $\mu$M |
|---|---|
| 18 | 5.9 |
| 8 | 8.6 |
| 9 | 6.1 |
| 10 | 9.6 |
| 11 | 13 |
| 27 | 0.7 |
| 28 | 5.3 |
| 29 | 0.8 |
| 30 | 3.7 |
| 19 | 10 |
| 20 | 1.2 |
| 21 | 9.1 |
| 22 | 3.5 |
| 31 | 0.8 |
| 23 | 0.25 |
| 24 | 0.7 |
| 25 | 5.6 |
| 42 | 0.07 |
| 43 | 0.08 |
| 44 | 0.09 |
| 45 | 0.1 |
| 33 | 0.1 |
| 35 | 0.11 |
| 46 | 0.15 |
| 47 | 0.18 |
| 48 | 0.199 |
| 49 | 0.22 |
| 50 | 0.3 |
| 34 | 0.39 |

Example 9

Stability of Contrast Agents

Stability was assayed using rat liver homogenate, which contains both intra- and extracellular enzymes and represents a particularly harsh chemical environment for peptide bonds. Freshly prepared rat liver homogenate (630 $\mu$L) was placed in a glass test tube and incubated at 37° C. in a water bath for 4 minutes. To the rat liver homogenate at 37° C. was added 70 $\mu$L of a 1 mM solution of test compound. At time points 0, 5, 15, 30, and 60 minutes, a 100 $\mu$L aliquot of the reaction mixture was removed and mixed with 100 $\mu$L of methanol in a microfuge tube to quench the reaction. The quenched reaction mixture was centrifuged for 3 minutes at 10,000 rpm to pellet the precipitated protein. The supernatant was analyzed by LC-MS to quantitate the amount of test compound remaining by comparing the area of the single ion MS peak to that of a series of standards. Half life (T1/2) was determined by plotting log percent signal remaining vs. time. The data were fit using an exponential curve fit, wherein T1/2=ln2/slope.

The stability data of the below compounds was tested. Compound 5, which has chelates at both the C- and N-termini of the peptide, had a dramatic increase in half-life resulting from resistance to exopeptidase hydrolysis. A comparable increase in half-life was not achieved through modification of one terminus with chelates, even when the other terminus was capped with an unnatural organic moiety as in, for example, compound 3 (containing a biphenyl group on the N-terminus).

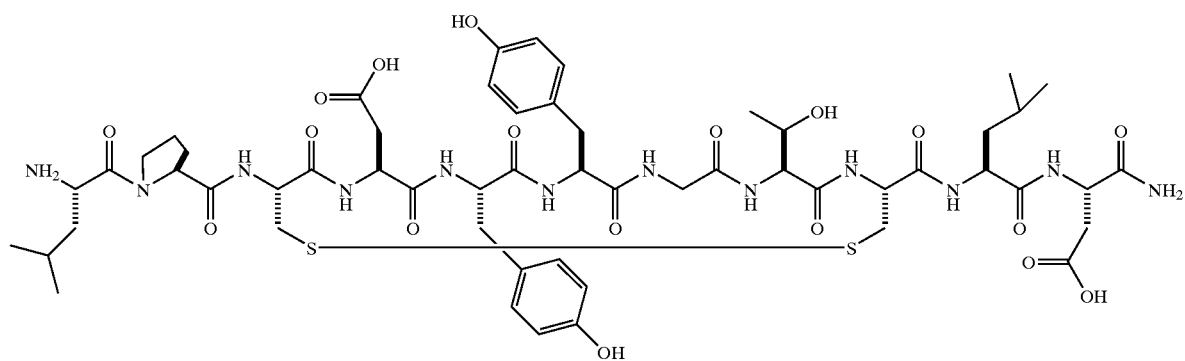
Structure 1: half-life=<2 min, free N- and amidated C-terminus
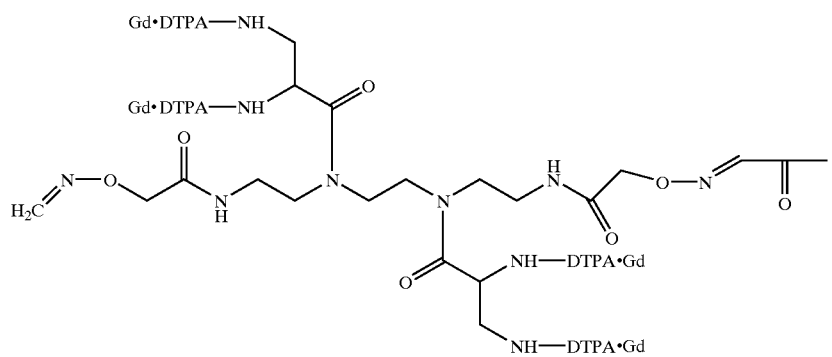
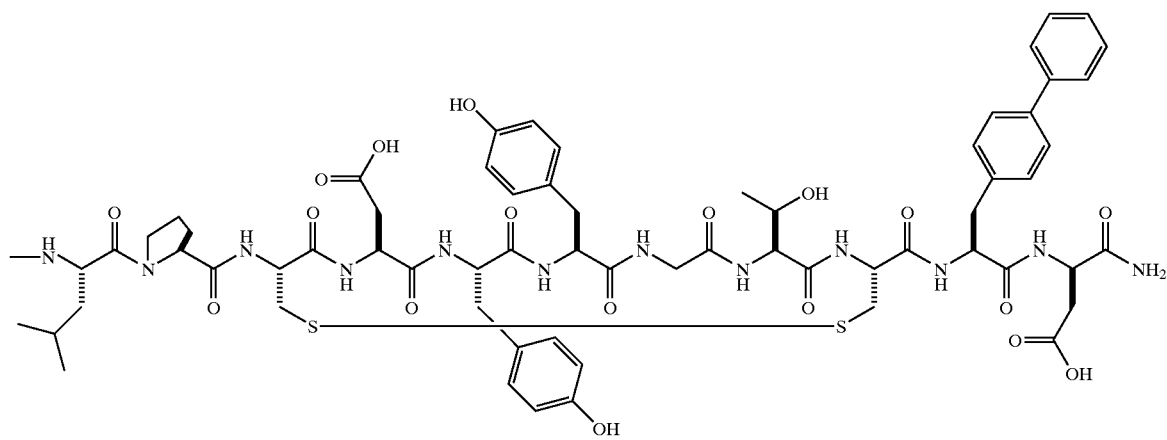
Structure 2: half-life=10 min, N-terminus conjugated to chelates and amidated C-terminus.

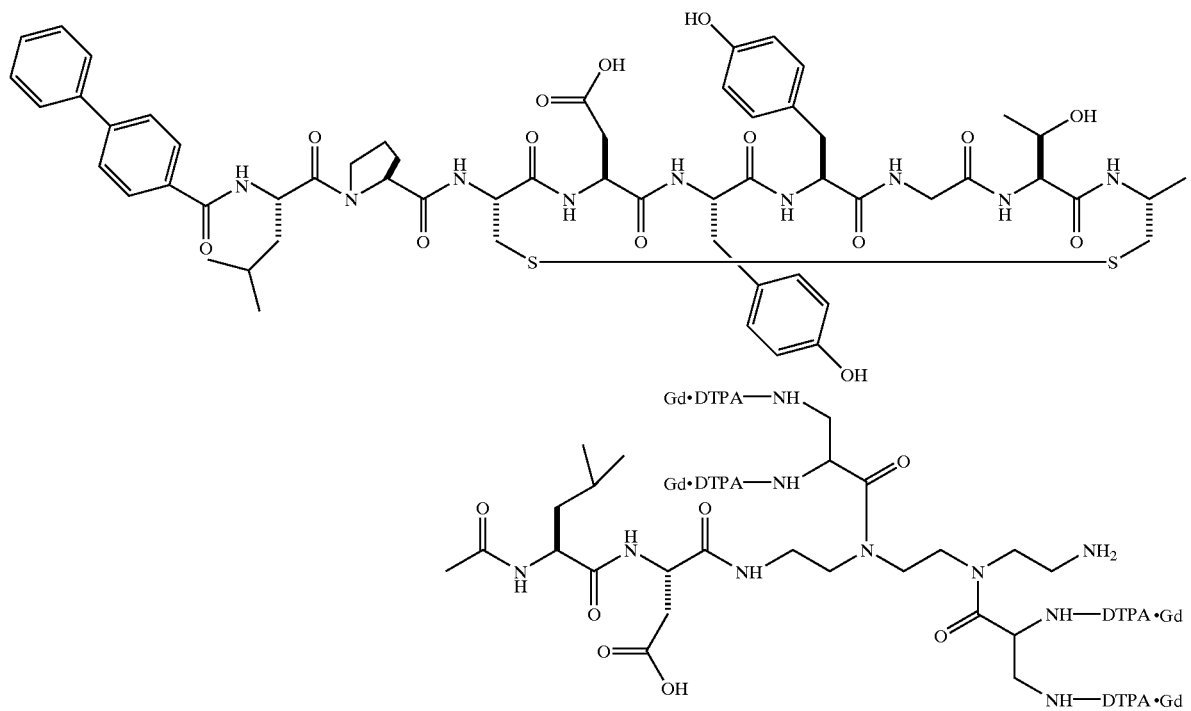

Structure 3: half-life=9 min, C-terminus conjugated to chelates and N-terminus acylated with para-(phenyl)benzoic acid.

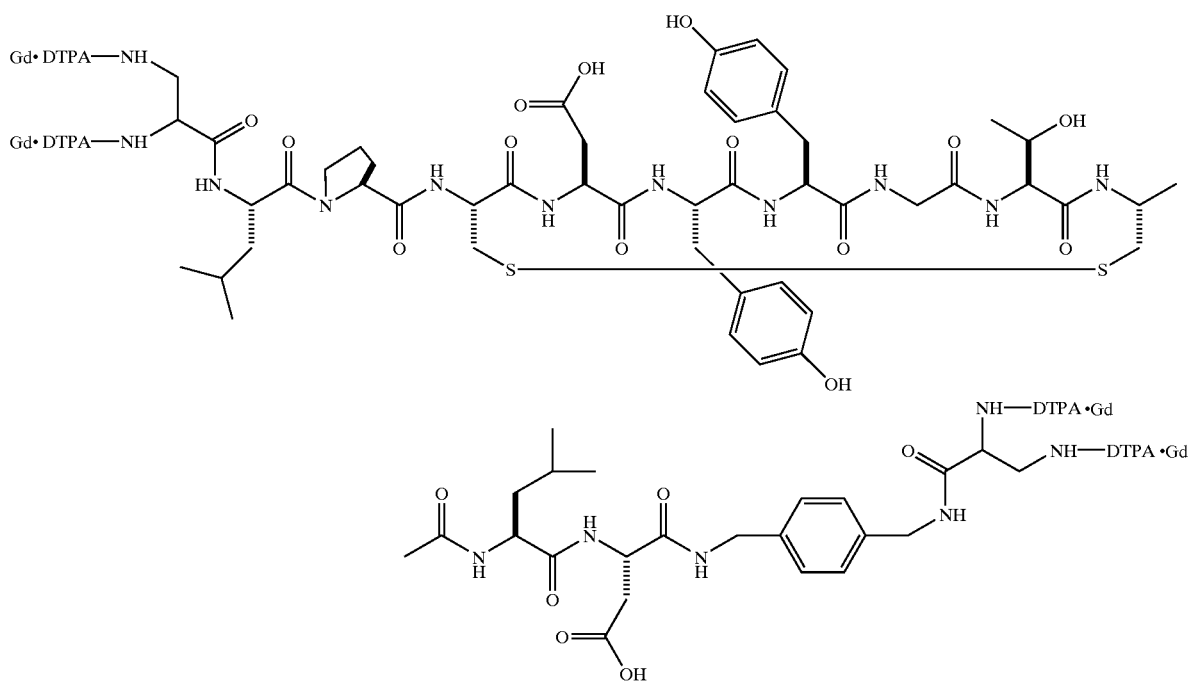

Structure 5: half-life=65 min, both N- and C-termini conjugated to chelates.

Surprisingly, the above data illustrate that the half-life of a peptide is most significantly increased by the addition of gadolinium chelates to both the C- and the N-termini.

Example 10

Relaxivity of Contrast Agents

The MRI contrast agents of the present invention were evaluated for relaxivity using a Bruker NMS-120 Minispec NMR spectrometer operating at 0.47 Tesla (20 MHz H-1 Larmor frequency) and 37° C. or a Konig-Brown relaxometer (20 MHz, H-1 Larmor frequency) operating at 35° C. T1 of water protons was determined by an inversion recovery pulse sequence using the instrument's software. Relaxivity was determined by measuring the T1 of multiple solutions of the target (for example, homodisperse gels of freshly polymerized fibrinogen, 10 mg/mL) containing zero, 20, 30, and 40 µM Gd(III), respectively. The samples are incubated at 37° C. for at least 15 minutes to ensure temperature equilibration before the T1 measurement is performed. The Gd(III) content of the samples is determined by inductively coupled plasma—mass spectrometry (ICP-MS). The relaxivity (per Gd(III) ion) is determined by plotting the relaxation rate (1/T1) in $s^{-1}$ versus the Gd(III) concentration in mM. The slope of a linear fit to the data gives the relaxivity. The relaxivity of the compounds in the absence of target is also determined in an analogous manner, except there is no target present.

Figure 2:
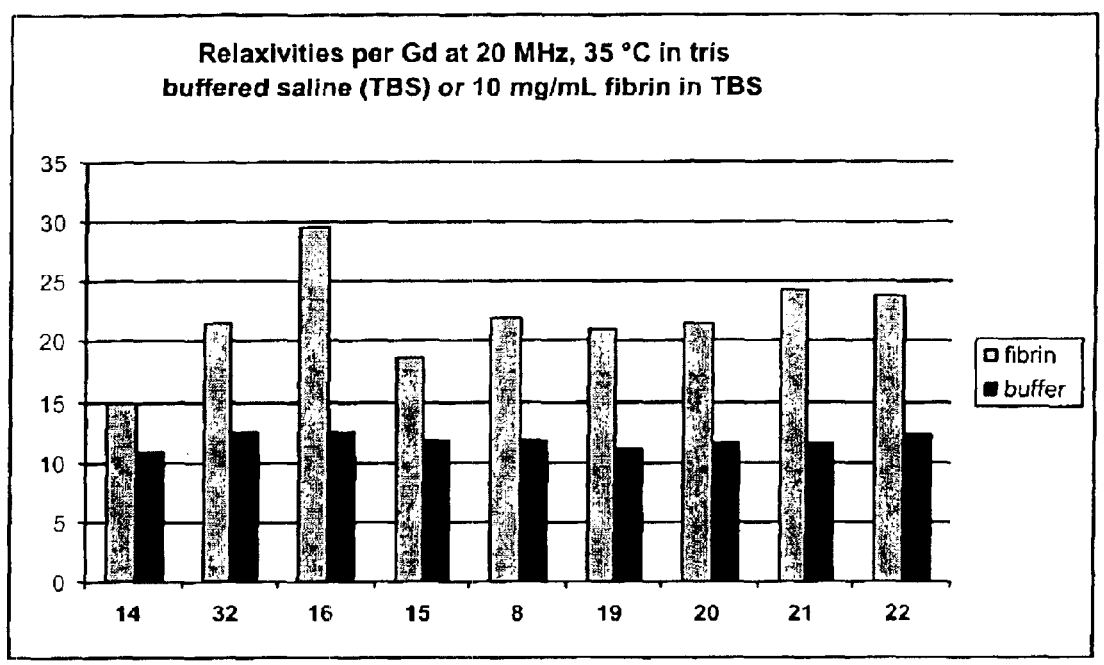
FIG. 2 depicts the relaxivities per Gd at 20 MHz, 35° C. in Tris buffered saline (TBS) or 10 mg/ml fibrin in TBS.

Compounds of the invention show increased relaxivity upon binding to fibrin (FIG. 2) as compared with the relaxivity in the absence of biological target.

Example 11

Clot Uptake of Contrast Agents

The uptake of a contrast agent into a thrombus (blood clot) was determined by the following method: A 600 g guinea pig (Hartley male) was anaesthetized. An incision was made in the abdomen and the inferior vena cava (IVC) isolated and the vessel was allowed to recover for 10 minutes. A 1 cm portion of the IVC was clamped and human thrombin (50 µL, 4 units) was injected into the vessel to promote thrombus formation. The lower clamp was opened and closed allowing partial blood flow to the segment. After 2–3 minutes the clips were removed. The thrombus was allowed to age in the animal for 30 minutes. At this point the contrast agent, compound 32 at a dose of 2 µmol/kg and trace radiolabeled with 70 µCi of $^{111}$In, was injected via the jugular vein. Immediately following injection of agent compound 32, a non-specific control comprising Gd(DTPA) at a dose of 2 µmol/kg mixed with 70 µCi $^{99m}$TcDTPA was injected via the jugular vein. After 30 minutes blood was drawn, the animal sacrificed, and the thrombus removed. The blood sample was weighed and counted using a Packard Cobra II gamma counter. The thrombus was also weighed and counted. Counts arising from $^{99m}$Tc were detected from 128–165 keV while counts arising from the decay of $^{111}$In were detected from 390–500 keV. Control experiments with only $^{99m}$Tc or $^{111}$In demonstrated radioactivity arising from $^{99m}$Tc was negligible at detection energies used for $^{111}$In and vice versa. The radioactive decay data were converted to % initial dose per gram of tissue, % ID/g, and the mean of three experiments is presented graphically. Radiolabeling with $^{111}$In was performed in advance: An appropriate radiochemical amount of $^{111}$InCl$_3$ (New England Nuclear) was added to the fibrin targeted contrast agent. The pH was adjusted to 4 by addition of 1 M HCl. The sample was heated at 45° C. for 1 hour. The pH was adjusted to neutral by addition of 1 M NaOH. The labeled agent compound 32 was >95% pure by γ-detected HPLC.

Figure 3:
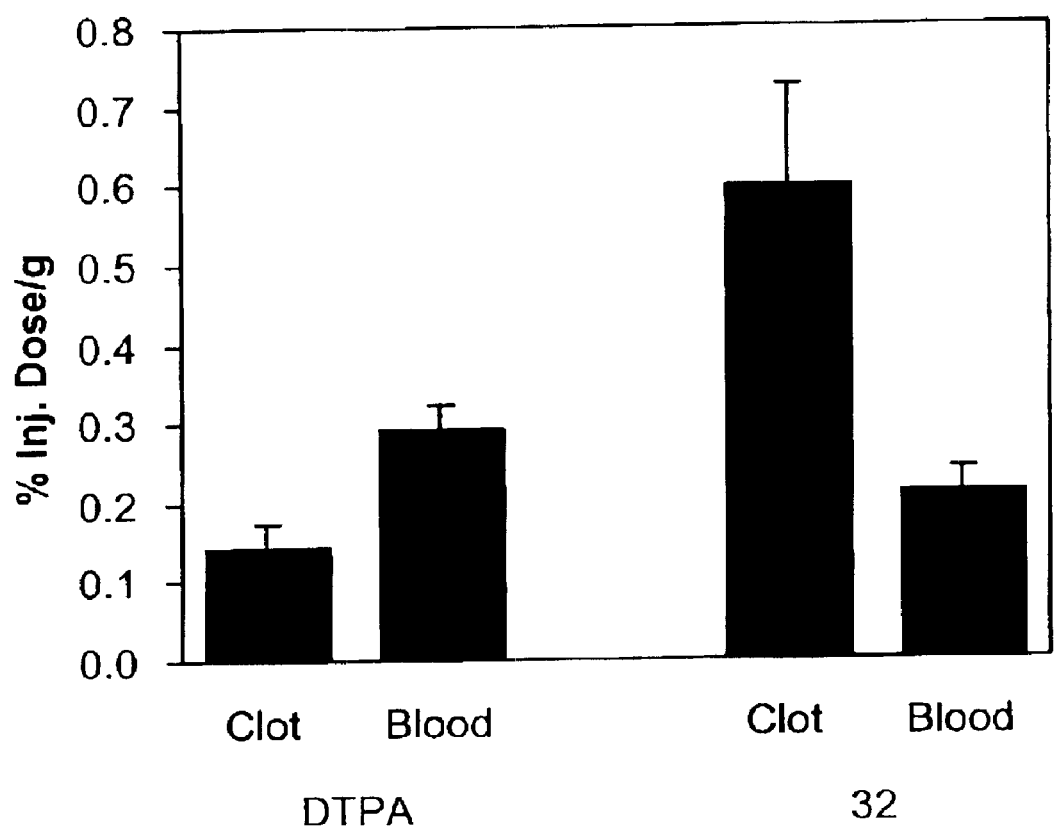
FIG. 3 depicts the accumulation of a contrast agent in the thrombus.

Fibrin-specific agents show a marked increase in clot uptake. FIG. 3 shows that an agent, compound 32, is accumulating in the thrombus. There is specific clot uptake compared to $^{99m}$TcDTPA and there is a higher concentration of the agent in the thrombus than in the surrounding blood.

Specificity of clot uptake also can be demonstrated using MRI. The procedure for in vivo imaging of a thrombus with an agent is as follows: A 600 g guinea pig (Hartley male) is anaesthetized. An incision is made in the throat and one of the jugular veins isolated. A 1 cm section of the jugular vein is isolated with vascular clamps. Freshly drawn blood from the animal (50 µL) is mixed with human thrombin (50 µL, 4 units) and is injected into the clamped segment of the vein. Four minutes after injection, the clamps are removed and the thrombus is allowed to age for 30 minutes. Agent, compound 32, is injected at a dose of 6 µmol/kg and the throat area of the guinea pig is imaged at 1.5 T using a spoiled gradient method TR=36, TE=5, flip angle=30°. The thrombus appears bright relative to the blood.

Example 12

Obtaining an MR Image of a Thrombus with a Targeted Contrast Agent with and without Black Blood A 2.5 kg female New Zealand White rabbit was anesthetized with a cocktail of Ketamine (50 mg/kg), Aceapromazine (2.5 mg/kg), and Rompon (5 mg/kg) and anesthesia maintained with sodium pentobarbital (approx.35 mg/kg as needed). An i.v. catheter (24 g) was placed into the ear vein and the ear artery. The jugular vein and carotid artery were isolated. A stenosis was created in the carotid artery by placing an 18 g needle on top of the vessel and then suturing it into place with 3–0 suture. The needle was then removed. A 5 mm portion of the artery was then segmented off distally to the stenosis with microvascular clips. The artery was then crushed twice along the 5 mm section. The proximal vascular clip was released to allow blood flow into the section for ca. 3 sec. The clip was reapplied and artery was crushed twice again along the 5 mm section. After 4 minutes, the clips were removed. A 5 mm segment of the jugular vein was isolated with microvascular clips. A thrombus was created by injecting 100 µL of a 3.7 units of thrombin, 0.06 M CaCl$_2$, rabbit whole blood mixture. After 4 minutes, the clips were removed.

The thrombi were allowed to age for 50 minutes. A 1.0 mL solution of the thrombus targeted agent (Structure III, 5 mM, 2 µmol/kg) was administered via the ear vein. After 10 minutes, the animal was placed inside a General Electric Signa LxCVi 1.5 tesla scanner and a first MRI data set was obtained using a 3D RF spoiled gradient echo sequence (SPGR: TR=39 ms, TE=3.1 ms, flip angle=40 degrees, field of view=8 cm, acquisition bandwith=31.25 kH). Chemical fat saturation was applied as well as 40 mm spatial inferior and superior saturation bands. Immediately following this scan (8 minutes later), a second MRI data set was acquired using the same parameters with the addition of 40 mm spatial inferior and superior saturation bands to generate a "black blood" image.

Figure 4:
FIG. 4A is an image of a thrombus.
FIG. 4B is an image of a thrombus with black blood.
Figure 4:

FIG. 4A shows the maximum intensity projection (MIP) of the first data set. The blood vessels are partially enhanced from time of flight effects. FIG. 4B shows the MIP of the second data set where the signal from in-flowing blood was suppressed (black blood) by the use of superior and inferior saturation bands. In FIGS. 4A and 4B, the identification of the stationary target (a thrombus) through use of the targeted contrast agent is clearly facilitated.

Example 13

Synthesis of an Optical Contrast Agent

NovaSyn TGR resin (0.20 mmol/g, 100 mg, 20 µmol) was washed with NMP/ether/NMP. The peptide was assembled by the standard solid phase method using the PyBOP/HOBt/DIEA activation. After the coupling of the final amino acid residue, the resin bound peptide was treated with a solution of piperidine in DMF (20% by volume, 2.0 mL) for 10 minutes to remove the Fmoc protecting group. The resin was washed thoroughly with NMP/ether/NMP, and was treated with a solution of fluorascein-5-isothiocyanate (23.4 mg, 60 μmol) and diisopropylethylamine (11.6 mg, 15.7 μL, 90 μmol) in DMF (1.5 mL) for 12 hours. The resin was washed thoroughly (NMP/ether/NMP), and treated with a solution of Tl(TFA)$_3$ (18.7 mg, 34.5 μmol) in DMF (1.5 mL) at 4° C. for three hours. The resin was washed after this treatment, and treated with a cocktail of TFA/TIS/water (95/2.5/2.5, 2.0 mL) for two hours. The crude peptide was precipitated by adding ether to the cleavage cocktail, and purified by preparative HPLC using a Vydac C-18 column. Structures A–N were formed in this manner and their fibrin DD(E) fragment affinities were determined (Table 5).

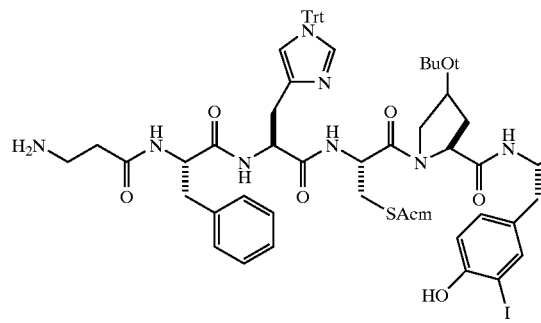

Peptide was assembled by standard procedure on NovaSyn TGR resin

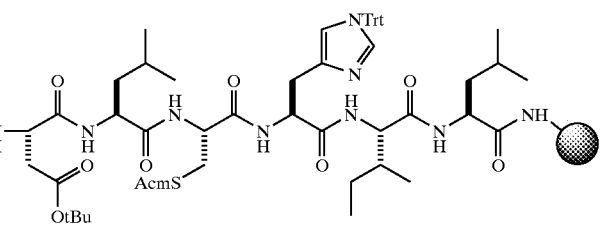

NovaSyn TGR resin, 0.20 mmol/g

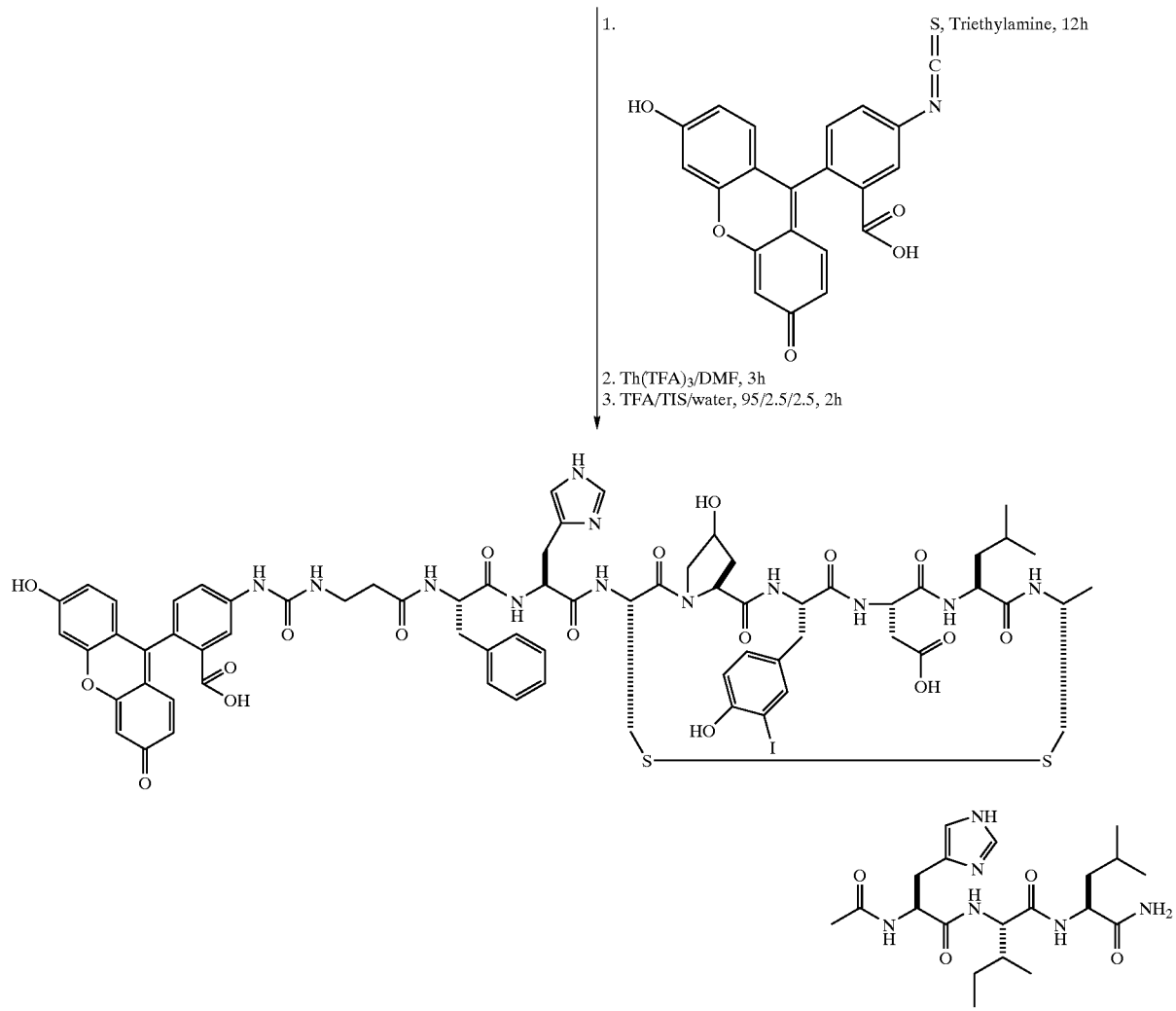

-continued
Structures
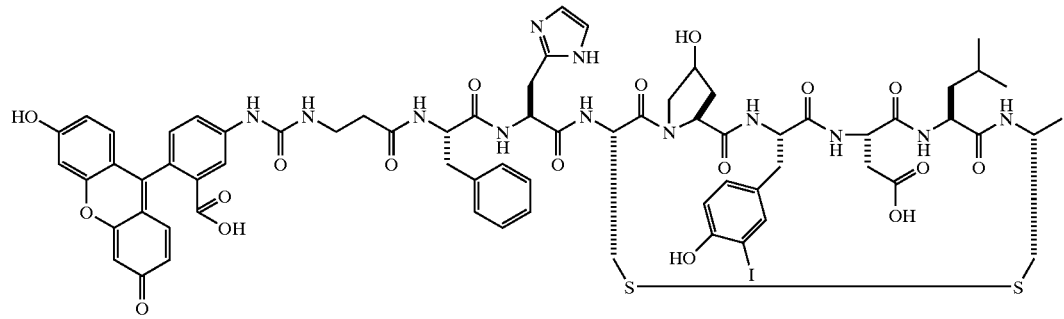
A
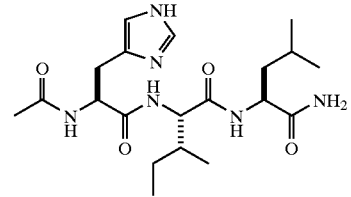
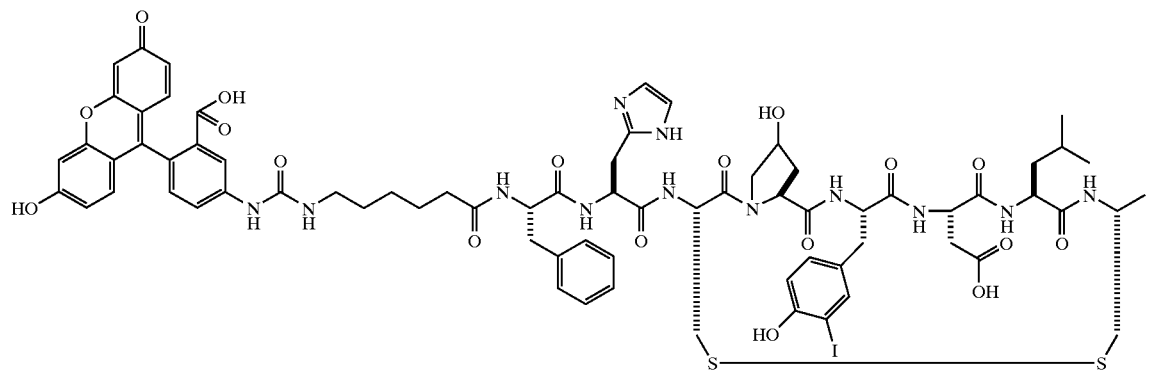
B
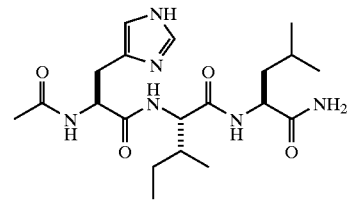
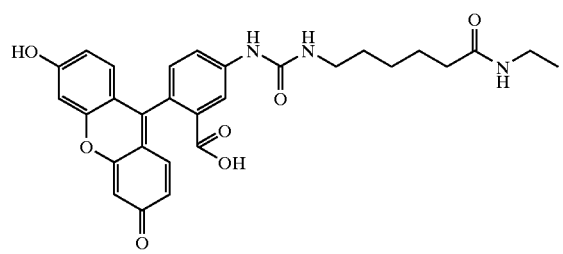
C
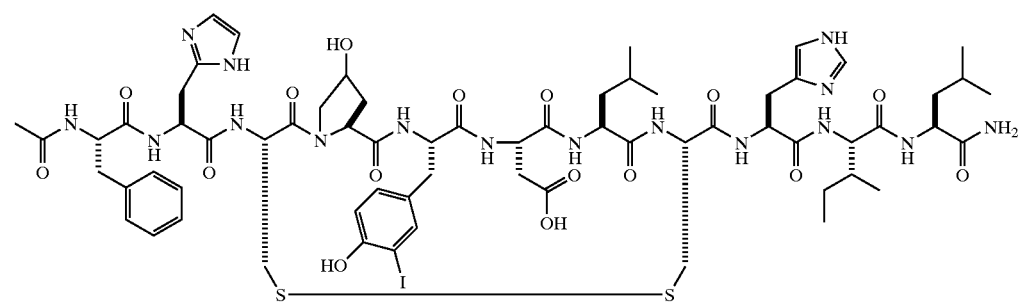

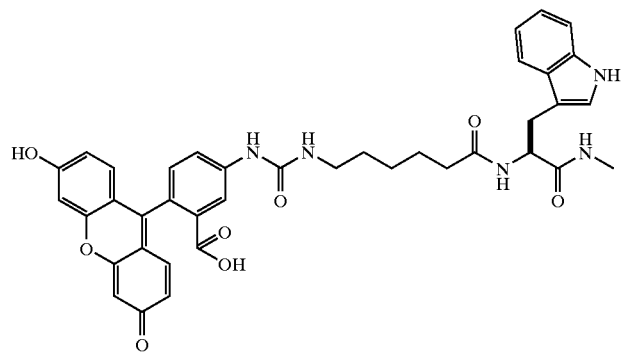
D
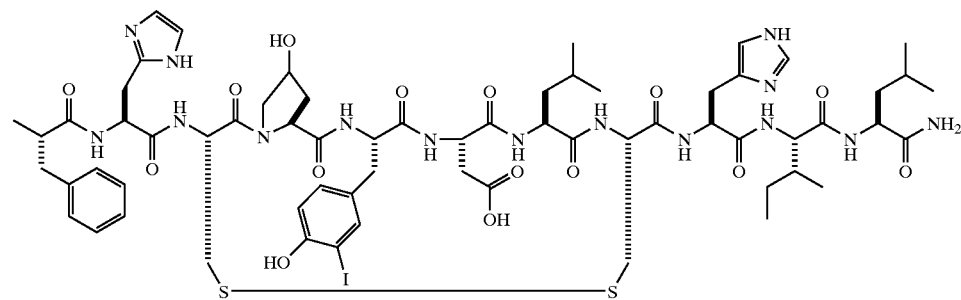
E
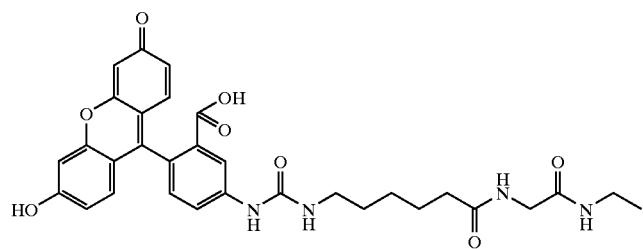
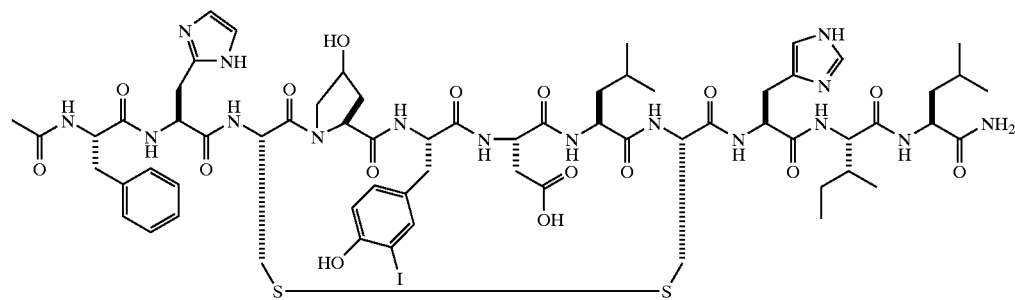
F
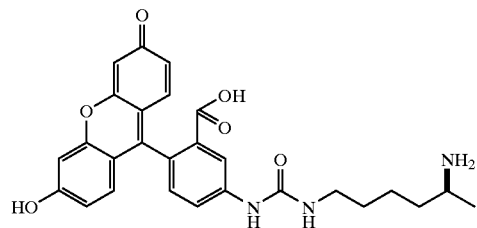

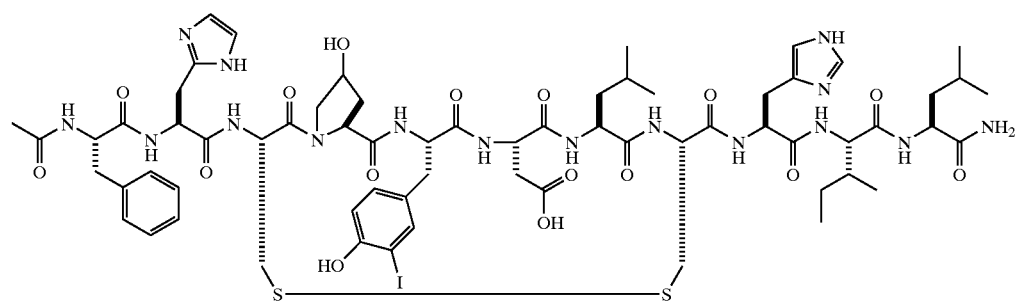
G
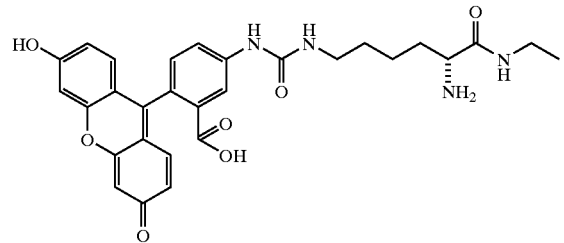
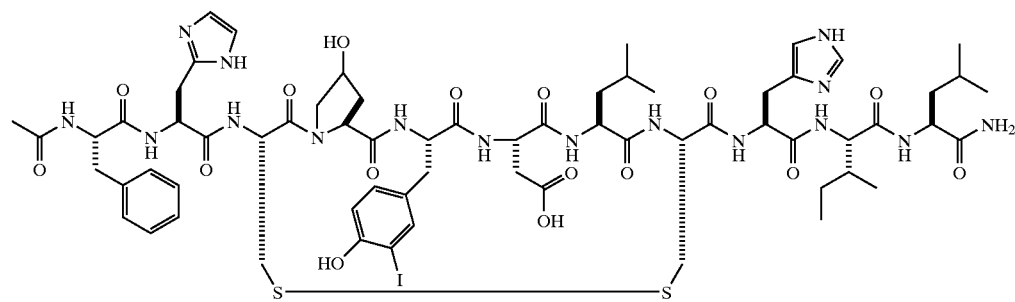
H
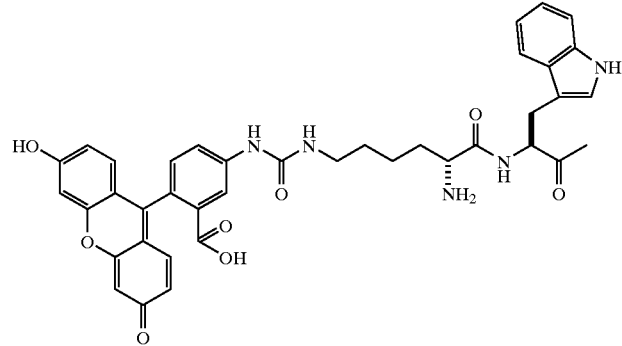
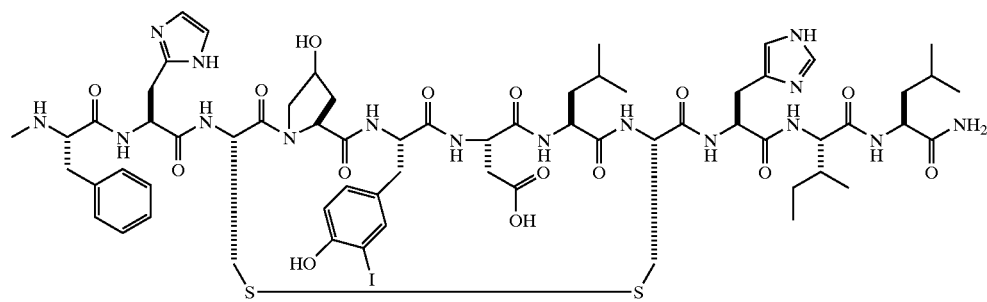

-continued
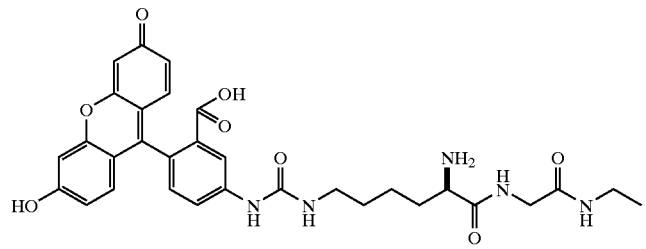
I
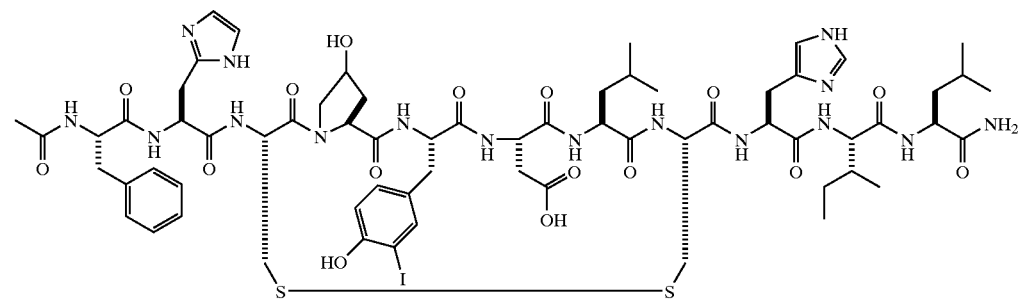
N
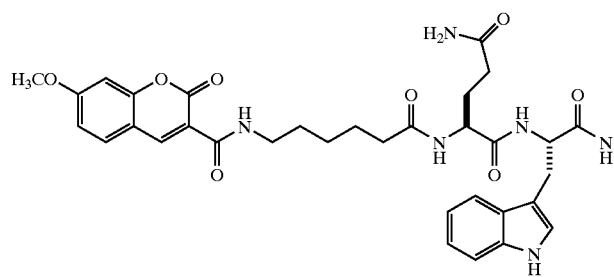
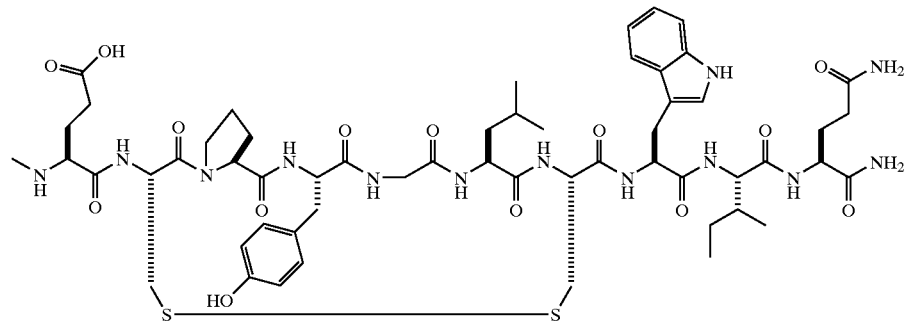
M
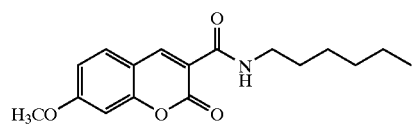
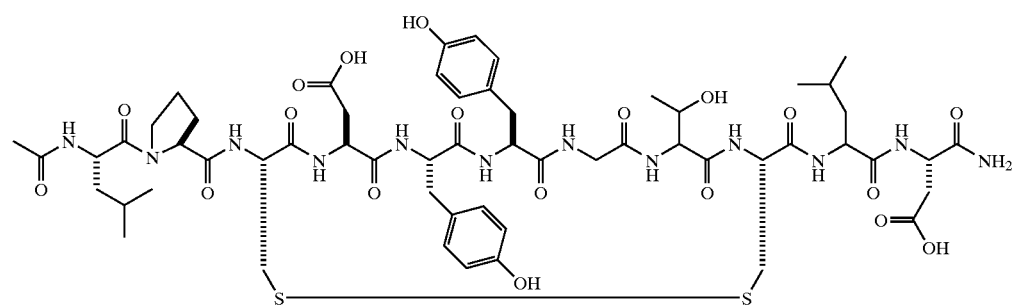

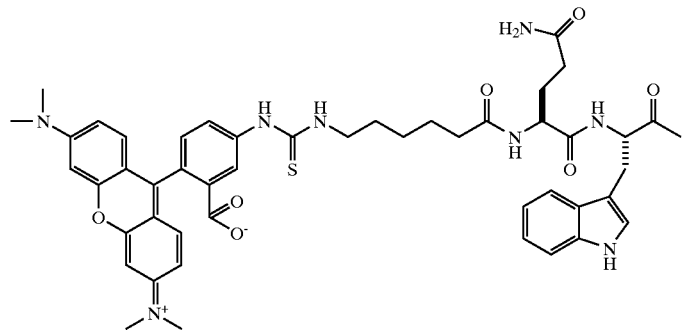
L
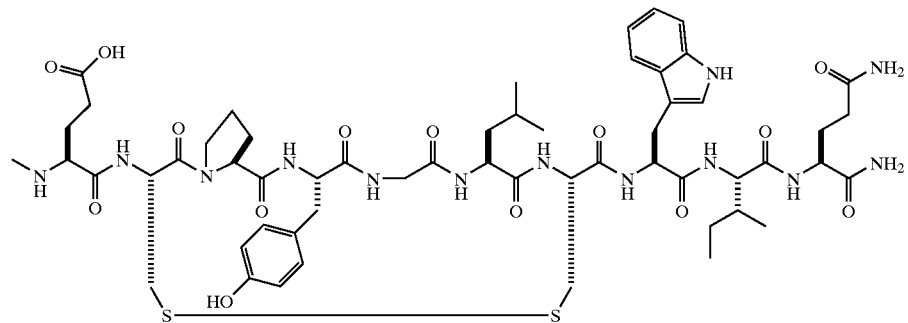
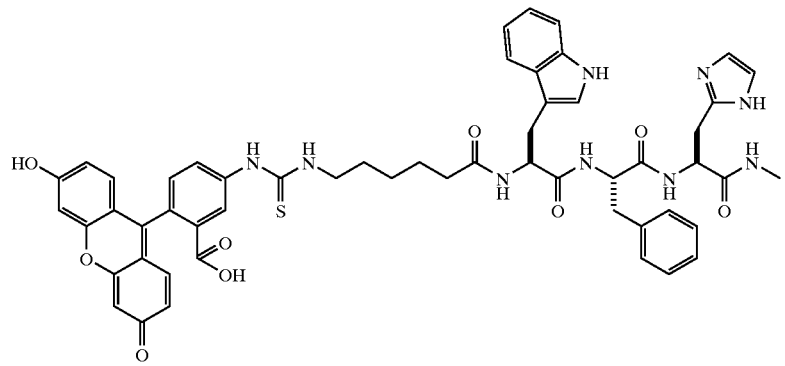
K
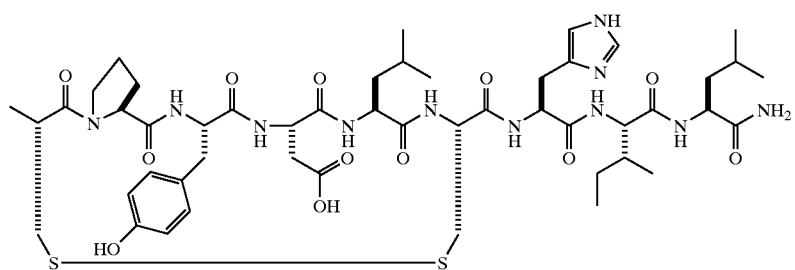

-continued

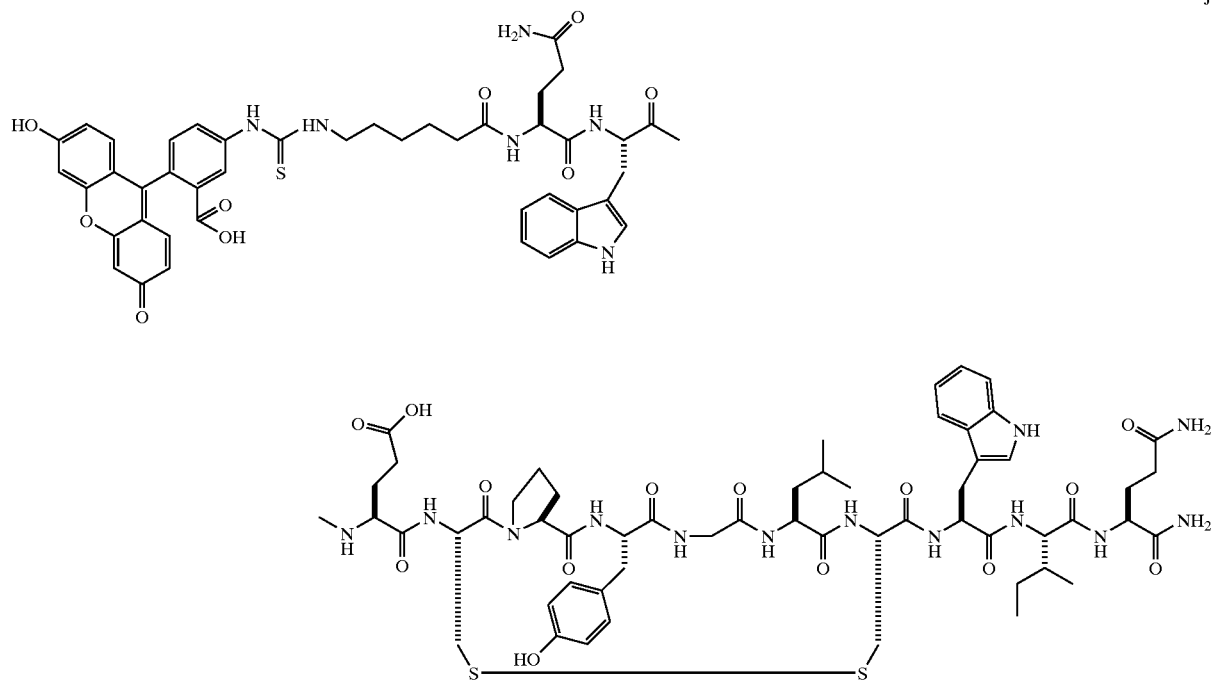

J

TABLE 5

Affinity of optical targeted contrast agents to fibrin.

| ID | Kd ($\mu$M) Vs. DD(E) | Fluor | $X_1$ | $X_2$ | $X_3$ | $X_4$ | $X_5$ | $X_6$ | $X_7$ | $X_8$ | $X_9$ | $X_{10}$ | $X_{11}$ | $X_{12}$ | $X_{13}$ |
|---|---|---|---|---|---|---|---|---|---|---|---|---|---|---|---|
| D | 0.061 | Fluor | Ahx | W | F | H | C | Hyp | Y(3-I) | D | L | C | H | I | |
| J | 0.055 | Fluor | Q | W | E | C | P | Y | G | L | C | W | I | Q | |
| K | 0.06 | Fluor | W | F | H | C | P | Y | D | L | C | H | I | L | |
| E | 0.09 | Fluor | Ahx | G | G | F | H | C | Hyp | Y(3-I) | D | L | C | H | I |
| C | 0.097 | Fluor | Ahx | G | F | H | C | Hyp | Y(3-I) | D | L | C | H | I | |
| B | 0.099 | Fluor | Ahx | F | H | C | Hyp | Y(3-I) | D | L | C | H | I | | |
| H | 0.119 | Fluor | K | W | F | H | C | Hyp | Y(3-I) | D | L | C | H | I | |
| G | 0.124 | Fluor | K | G | F | H | C | Hyp | Y(3-I) | D | L | C | H | I | |
| I | 0.127 | Fluor | K | G | G | F | H | C | Hyp | Y(3-I) | D | L | C | H | I |
| A | 0.136 | Fluor | beta-A | F | H | C | Hyp | Y(3-I) | D | L | C | H | I | | |
| F | 0.212 | Fluor | K | F | H | C | Hyp | Y(3-I) | D | L | C | H | I | | |

N-terminal labeling of the peptides with optical probes can modulate the binding affinity of the optical contrast agents. For example, when comparing fluorescein, 4-methoxycoumarin and tetramethylrhodamine derivatives of the peptide (QWECPYGLCWIQ (SEQ ID NO:27); Kd=3 $\mu$M) the following Kd's were observed (Table 6):

TABLE 6

| Compound | Fluorophore | Kd |
|---|---|---|
| J | Fluorescein | 0.06 |
| L | Tetramethylrhodamine | 2.0 |
| N | 4-Methoxycoumarin | 0.2 |

Example 14

Fibrin Targeted Urokinase

Fibrin targeted urokinase is prepared according to the following procedure. A fibrin binding peptide with a Gly-Gly dipeptide linker is prepared according to solid phase procedures. The N-terminus of the peptide is blocked with an acetyl group, and the C-terminal carboxylic acid is converted to a succinamidal active ester. Direct chemical ligation is achieved by mixing urokinase and the activated peptide in appropriate proportions in an aqueous buffer and gently agitating the solution for 30 minutes.

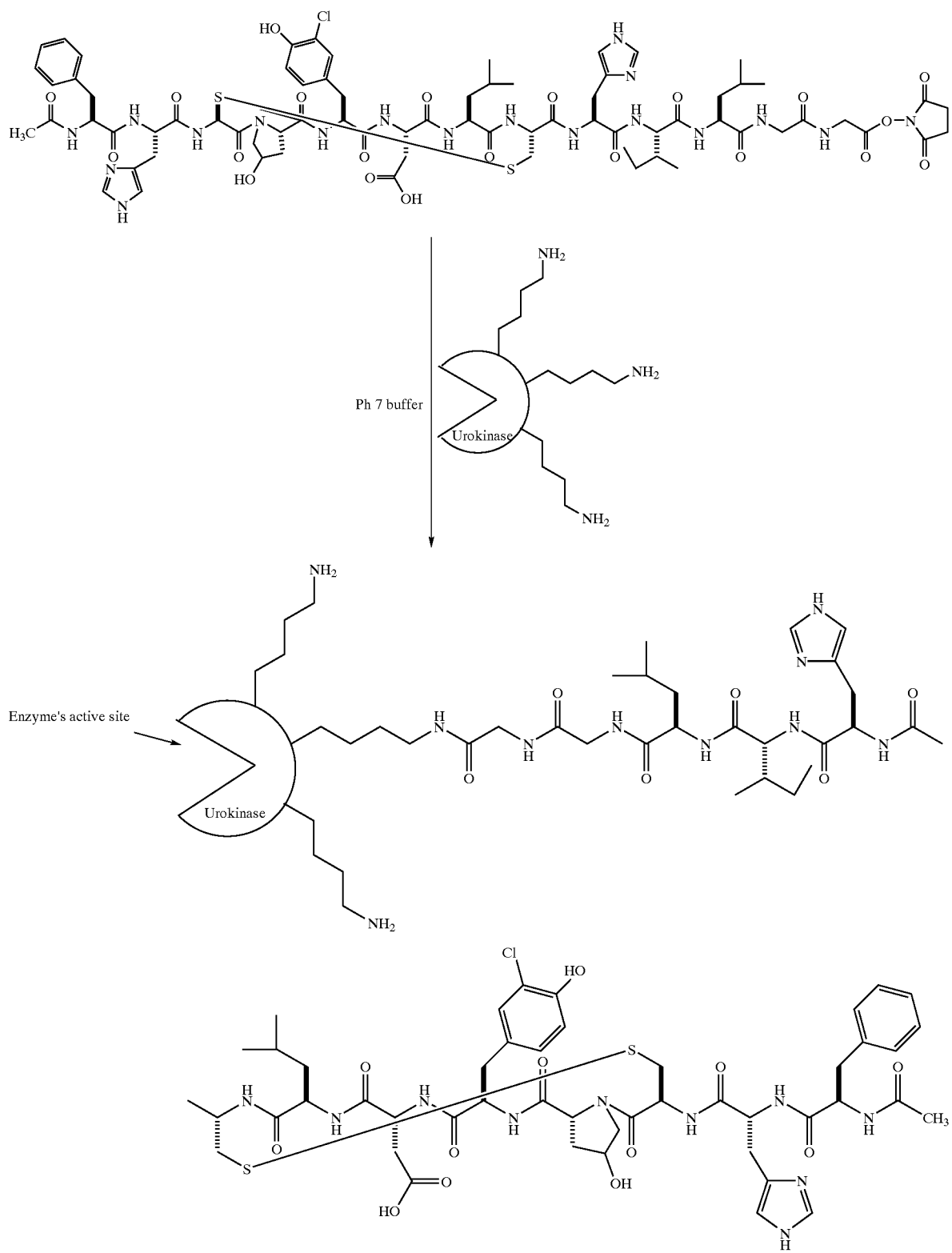
Fibrin targeted urokinase can be purified by HPLC. Binding to fibrin can be assessed. Compound 1 binds fibrin selectively versus fibrinogen.
The rabbit jugular vein model of Collen et al. (*J. Clin. Invest.* 1983, 71, 368–376) is used for thrombolysis assays. Compound (2 mg/kg) is administered by infusion of a bolus (consisting of 20% of the total dose) over 1 min, along with a heparin bolus (300 units/kg) over 1 min. The remainder of the dose is continuously infused over the next 60 min, and heparin (60 units/kg/hr) is continuously infused over the next 180 min. At 3 hours, the animals are sacrificed, and clots analyzed. Compound 1 is more potent in clot lysis than scuPA alone. At 3 hr, with 2 mg/kg of compound 1, there is less consumption of fibrinogen and α2-antiplasmin, relative to equivalent doses of scuPA alone, demonstrating that compound 1 was more fibrin specific than scuPA alone.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified peptide comprising the amino acid sequence: $P^*-Y^*-X_1^*-L^*$ (SEQ ID NO:1), wherein:

P* is a proline or its non-natural derivative 4-hydroxyproline;

Y* is a tyrosine or its non-natural derivative substituted at the 3 position with a moiety selected from the group consisting of F, Cl, Br, I, and $NO_2$;

provided that at least one of said P* or Y* is said non-natural derivative of the respective amino acid;

$X_1^*$ is G or a non-natural derivative of G selected from the group consisting of cyclohexylglycine, allylglycine, 2-indanylglycine, tert-butylglycine, N-(4-phenylbutyl) glycine, N-decylglycine, phenylglycine, propargylglycine, and the d isomer of glycine; or D or a non-natural derivative of D selected from the group consisting of β-connected aspartic acid (bD), N-methylaspartic acid, and the d isomer of aspartic acid; and L* is a leucine or a non-natural derivative of leucine selected from the group consisting of N-methylleucine, Norleucine, tert-leucine, and the d isomer of leucine.

2. A purified peptide according to claim 1, wherein $X_1^*$ is G or D and wherein L* is leucine.

3. A purified peptide comprising the amino acid sequence: $X_1-X_2-C-P^*-Y^*-X_3-L-C-X_4-X_5-X_6$ (SEQ ID NO:2), wherein:

P* is a proline or its non-natural derivative 4-hydroxyproline;

Y* is a tyrosine or its non-natural derivative substituted at the 3 position with a moiety selected from the group consisting of F, Cl, Br, I, and $NO_2$;

provided that at least one of said P* or Y* is said non-natural derivative of the respective amino acid;

$X_1$ is selected from the group consisting of W, Y, F, S, Bip, Hx, Dpr, Cy, Gu, Ad, Hfe, 3-Pal, 4-Pal, DopaMe2, nTyr, dW, dF, F(3/4*), and Y(3*), wherein F(3/4*) is a phenylalanine substituted at either the 3 or the 4 position with a moiety selected from the group consisting of $CH_3$, $CF_3$, $NH_2$, $CH_2NH_2$, CN, F, Cl, Br, I, Et, and OMe, and wherein Y(3*) is a tyrosine substituted at the 3 position with a moiety selected from the group consisting of F, Cl, Br, I, and $NO_2$;

$X_2$ is selected from the group consisting of E, H, dE, S, H(Bzl), 2-Pal, Dpr, and Th;

$X_3$ is selected from the group consisting of G and D;

$X_4$ is selected from the group consisting of H, F, Y, and W;

$X_5$ is selected from the group consisting of I, L, V, N, Bpa, Bal, Hfe, Nle, Tle, Nval, Phg, Cha, Taz, Fua, Th, 4-Pal, and F(3/4*), wherein F(3/4*) is a phenylalanine substituted at either the 3 or the 4 position with a moiety selected from the group consisting of $CF_3$, Et, iPr, and OMe; and $X_6$ is selected from the group consisting of N, Q, I, L, and V, or $X_6$ is not present.

4. A purified peptide according to claim 3, wherein P* is proline or 4-hydroxyproline, and Y* is tyrosine or said non-natural derivative of tyrosine substituted at the 3 position with Cl.

5. The purified peptide of claim 3 or 4, the peptide further capable of forming a disulfide bond under non-reducing conditions.

6. The purified peptide of claim 5, the peptide comprising a disulfide bond.

7. The purified peptide of claim 6, the peptide having a specific binding affinity for fibrin.

8. A purified peptide of claim 4 comprising an amino acid sequence selected from the group consisting of:

```
                              (SEQ ID NO:4)
W-dE-C-P(4-OH)-Y(3-Cl)-G-L-C-W-I-Q (SEQ ID NO:5)
Y-dE-C-P(4-OH)-Y(3-Cl)-G-L-C-Y-I-Q (SEQ ID NO:6)
Y-dE-C-P(4-OH)-Y(3-Cl)-G-L-C-W-I-Q (SEQ ID NO:7)
W-dE-C-P(4-OH)-Y(3-Cl)-G-L-C-Y-I-Q (SEQ ID NO:8)
W-dE-C-P(4-OH)-Y(3-Cl)-D-L-C-W-I-Q (SEQ ID NO:9)
Y-dE-C-P(4-OH)-Y(3-Cl)-D-L-C-Y-I-Q (SEQ ID NO:10)
Y-dE-C-P(4-OH)-Y(3-Cl)-D-L-C-W-I-Q (SEQ ID NO:11)
W-dE-C-P(4-OH)-Y(3-Cl)-D-L-C-Y-I-Q (SEQ ID NO:12)
F(4-OMe)-H-C-P(4-OH)-Y(3-Cl)-D-L-C-H-I-L (SEQ ID NO:13)
Y-H-C-P(4-OH)-Y(3-Cl)-G-L-C-W-I-Q (SEQ ID NO:14)
W-dE-C-P-Y(3-Cl)-G-L-C-W-I-Q (SEQ ID NO:15)
W-dE-C-P(4-OH)-Y-G-L-C-W-I-Q, and (SEQ ID NO:16)
F-H-C-P(4-OH)-Y(3-Cl)-D-L-C-H-I-L.
```

9. The purified peptide of claim 8, the peptide further capable of forming a disulfide bond under non-reducing conditions.

10. The purified peptide of claim 9, the peptide comprising a disulfide bond.

11. The purified peptide of claim 10, the peptide having a specific binding affinity for fibrin.

12. A compound comprising the peptide of claim 1 linked to a thrombolytic agent.

13. A purified peptide comprising the amino acid sequence: C-P*-Y*-X$_1$-L-C (SEQ ID NO:3), wherein:

X$_1$ is G or D,

P* is proline or its non-natural derivative 4-hydroxyproline;

Y* is tyrosine or its non-natural derivative substituted at the 3 position with a moiety selected from the group consisting of F, Cl, Br, I, and NO$_2$;

provided that at least one of P* or Y* is said non-natural derivative of the respective amino acid.

14. The purified peptide according to claim 13, the peptide further capable of forming a disulfide bond under non-reducing conditions.

15. The purified peptide according to claim 14, the peptide comprising a disulfide bond.

16. The purified peptide of claim 15, the peptide having a specific binding affinity for fibrin.

17. A compound comprising the peptide of claim 13, linked to a thrombolytic agent.

* * * * *

UNITED STATES PATENT AND TRADEMARK OFFICE
CERTIFICATE OF CORRECTION

PATENT NO. : 6,991,775 B2
APPLICATION NO. : 10/209172
DATED : January 31, 2006
INVENTOR(S) : Steffi K. Koerner et al.

It is certified that error appears in the above-identified patent and that said Letters Patent is hereby corrected as shown below:

Title Page, References Cited, Other Publications, Alexander et al. reference, please delete "Machine" and insert --Magnetic-- therefor;

Title Page, References Cited, Other Publications, Lanza et al. reference, please delete "and" and insert --with-- therefor;

Title Page (Page 2), References Cited, Other Publications, Restriction Requirement, please delete "Jul." and insert --Jan.-- therefor;

Title Page (Page 2), References Cited, Other Publications, Bligh et al. reference, please delete "Octadenate" and insert --Octadentate-- therefor;

Title Page (Page 2) References Cited, Other Publications, Mühler and Hochlaus reference, please delete "Hochlaus" and insert --Hochhaus-- therefor.

Signed and Sealed this

Nineteenth Day of September, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,991,775 B2 |
| APPLICATION NO. | : 10/209172 |
| DATED | : January 31, 2006 |
| INVENTOR(S) | : Steffi K. Koerner et al. |

It is certified that error appears in the above-identified patent and that said Letters Patent is hereby corrected as shown below:

Title Page, Assignee, please delete "Epix Medical, Inc." and insert --Epix Pharmaceuticals, Inc.--therefor.

Signed and Sealed this

Second Day of January, 2007

JON W. DUDAS
*Director of the United States Patent and Trademark Office*